US010987433B2

(12) United States Patent
Bennett et al.

(10) Patent No.: US 10,987,433 B2
(45) Date of Patent: Apr. 27, 2021

(54) COMPOSITIONS AND METHODS FOR CORRECTION OF HERITABLE OCULAR DISEASE

(71) Applicants: The Trustees of the University of Pennsylvania, Philadelphia, PA (US); Lloyd G. Mitchell, Bethesda, MD (US)

(72) Inventors: Jean Bennett, Bryn Mawr, PA (US); Jeannette Bennicelli, Philadelphia, PA (US); Scott J. Dooley, Philadelphia, PA (US); Lloyd G. Mitchell, Bethesda, MD (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 123 days.

(21) Appl. No.: 15/776,663

(22) PCT Filed: Nov. 18, 2016

(86) PCT No.: PCT/US2016/062941
§ 371 (c)(1),
(2) Date: May 16, 2018

(87) PCT Pub. No.: WO2017/087900
PCT Pub. Date: May 26, 2017

(65) Prior Publication Data
US 2018/0369412 A1 Dec. 27, 2018

Related U.S. Application Data

(60) Provisional application No. 62/257,500, filed on Nov. 19, 2015.

(51) Int. Cl.
| | |
|---|---|
| *C03C 17/06* | (2006.01) |
| *A61K 48/00* | (2006.01) |
| *C12N 15/86* | (2006.01) |
| *C12N 15/00* | (2006.01) |
| *C12N 15/11* | (2006.01) |

(52) U.S. Cl.
CPC ........ *A61K 48/005* (2013.01); *A61K 48/0075* (2013.01); *C12N 15/00* (2013.01); *C12N 15/11* (2013.01); *C12N 15/86* (2013.01); *C12N 2740/10043* (2013.01); *C12N 2750/14143* (2013.01)

(58) Field of Classification Search
CPC .................................................. A61K 48/005
See application file for complete search history.

(56) References Cited

U.S. PATENT DOCUMENTS

| | | | |
|---|---|---|---|
| 6,013,487 A | 1/2000 | Mitchell | |
| 6,280,978 B1 | 8/2001 | Mitchell et al. | |
| 7,943,374 B2 | 5/2011 | Hildinger | |
| 8,053,232 B2 | 11/2011 | Puttaraju et al. | |
| 8,076,461 B2 | 12/2011 | Pearce et al. | |
| 8,173,377 B2 | 5/2012 | Agris et al. | |
| 8,236,557 B2 | 8/2012 | Dongsheng et al. | |
| 8,323,910 B2 | 12/2012 | Agris et al. | |
| 8,697,355 B2 | 4/2014 | Agris et al. | |
| 8,735,366 B2 | 5/2014 | Bauer et al. | |
| 2013/0059901 A1 | 3/2013 | Bauer et al. | |
| 2013/0071951 A1 | 3/2013 | Agris et al. | |
| 2014/0087444 A1 | 3/2014 | Bennett et al. | |
| 2014/0243388 A1 | 8/2014 | Hastings | |
| 2015/0202269 A1 | 7/2015 | Beltran et al. | |
| 2015/0252358 A1 | 9/2015 | Maeder et al. | |

FOREIGN PATENT DOCUMENTS

| | | |
|---|---|---|
| EP | 2151248 | 2/2010 |
| WO | WO-97/22250 | 6/1997 |
| WO | WO-98/14275 | 4/1998 |
| WO | WO-2001/049745 | 7/2001 |
| WO | WO-2003/003014 | 1/2003 |
| WO | WO-2003/069311 | 8/2003 |
| WO | WO-2003/072739 | 9/2003 |
| WO | WO-2003/104412 | 12/2003 |
| WO | WO-2003/104416 | 12/2003 |
| WO | WO-2004/006678 | 1/2004 |
| WO | WO-2004/038380 | 5/2004 |
| WO | WO-2005/023990 | 3/2005 |
| WO | WO-2005/070023 | 8/2005 |
| WO | WO-2005/070948 | 8/2005 |
| WO | WO-2006/026611 | 3/2006 |

(Continued)

OTHER PUBLICATIONS

Gérard et al. (Molecular Therapy—Nucleic Acids (2015) 4, e250; doi:10.1038/mtna.2015.24 [published online Sep. 1, 2015]). (Year: 2015).*

Collin, R. et al., Antisense Oligonucleotide (AON)-based Therapy for Leber Congenital Amaurosis Caused by a Frequent Mutation in CEP290, Molecular Therapy Nucleic Acids, Mar. 27, 2012; vol. 1: e14, 1-7.

Garanto, A. et al., Species-Dependent Splice Recognition of a Cryptic Exon Resulting from a Recurrent Intronic CEP290 Mutation that Causes Congenital Blindness, International Journal of Molecular Sciences, Mar. 9, 2015; 16(3):5285-5298.

(Continued)

*Primary Examiner* — Scott Long
(74) *Attorney, Agent, or Firm* — Howson & Howson LLP

(57) ABSTRACT

A nucleic acid trans-splicing molecule is provided that can replace an exon in a targeted mammalian ocular gene carrying a defect or mutation causing an ocular disease with an exon having the naturally-occurring sequence without the defect or mutation. A method of treating an ocular disease, e.g., Stargardt's Disease, caused by a defect or mutation in a target gene, e.g., ABCA4 comprising: administering to the ocular cells of a subject having an ocular disease a composition comprising a recombinant AAV comprising a nucleic acid trans-splicing molecule as described above.

17 Claims, 5 Drawing Sheets
Specification includes a Sequence Listing.

(56) References Cited

FOREIGN PATENT DOCUMENTS

| WO | WO-2009/103562 | 8/2009 |
|---|---|---|
| WO | WO-2010/012472 | 2/2010 |
| WO | WO-2014/170480 | 10/2014 |

OTHER PUBLICATIONS

Garanto, A. et al., In Vitro and In Vivo Rescue of Aberrant Splicing in CEP290-associated LCA by Antisense Oligonucleotide Delivery, Human Molecular Genetics, Jun. 15, 2015; 25(12): 2552-2563. (Epub Apr. 22, 2016).

Gerard, X. et al, Intravitreal Injection of Splice-switching Oligonucleotides to Manipulate Splicing in Retinal Cells, Molecular Therapy, Sep. 1, 2015, vol. 4: e250, 1-8.

Koller, U.A. et al., A Novel Screening System Improves Genetic Correction by Internal Exon Replacement, Nucleic Acids Research, Sep. 1, 2011; 39(16): e108, 11 pages. (Epub Jun. 11, 2017).

Communication issued in related European Patent Application No. EP16867296.2, dated Mar. 1, 2019.

Supplementary European Search Report issued in related European Patent Application No. EP16867296.2, dated Feb. 15, 2019.

Zhang, N. et al., Protein misfolding and the pathogenesis of ABCA4-associated retinal degenerations, Human Molecular Genetics, Feb. 2015, 24(11):3320-3237.

Maia-Lopes, S. et al., ABCA4 mutations in Portuguese Stargardt patients: identification of new mutations and their phenotypic analysis, Molecular Vision, Mar. 2009, 15:584-591.

Bennicelli, J. et al, CEP290 Minigene Model of Common Splice Site Mutation in Leber Congenital Amaurosis, Poster presented at American Society of Gene and Cell Therapy, 15th Annual Meeting, May 2012.

Bennicelli, J. et al, CEP290 Minigene Model of Common Splice Site Mutation in Leber Congenital Amaurosis, Molecular Therapy, May 2012, 20:Abstract.

Havens, M. A. et al., Targeting RNA Splicing for Disease Therapy, Wiley Interdiscip Rev RNA, May 2013, 4(3):247-266.

Bacchi, N. et al., Splicing-Correcting Therapeutic Approaches for Retinal Dystrophies: Where Endogenous Gene Regulation and Specificity Matter, Investigative Ophthalmology & Visual Science, May 2014, 55:3285-3294.

Written Opinion dated Feb. 16, 2017 issued in International Patent Application No. PCT/US2016/062941, filed Nov. 18, 2016.

International Search Report dated Feb. 16, 2017 issued in International Patent Application No. PCT/US2016/062941, filed Nov. 18, 2016.

Applicants' Response and Amendment filed Jan. 8, 2020 in European Patent Application No. EP16867296.2.

Communication pursuant to Article 94(3) EPC issued in European Patent Application No. EP16867296.2, dated Sep. 2, 2020.

* cited by examiner

*ABCA4*
*3' RTM*
*Ex27-50*

| 5' ITR | Photoreceptor Specific Promoter-Enhancer | ABCA4 Intron 26 Binding Domain | Spacer | 3' Splice Site | ABCA4 cDNA Ex27-50 | bGH poly(A) | 3' ITR |

*AAV ABCA4*
*5' RTM*
*Ex1-22*

| 5' ITR | Photoreceptor Specific Promoter-Enhancer | ABCA4 cDNA Ex1-22 | 5' Splice Site | Spacer | ABCA4 Intron 26 Binding Domain | bGH poly(A) | 3' ITR |

FIG. 1

COMPOSITIONS AND METHODS FOR CORRECTION OF HERITABLE OCULAR DISEASE

CROSS-REFERENCE TO RELATED APPLICATIONS

This application is a national stage of International Patent Application No. PCT/US2016/062941, filed Nov. 18, 2016, which claims the benefit of the priority of U.S. Provisional Patent Application No. 62/257,500, filed Nov. 19, 2015, which applications are incorporated herein by reference.

INCORPORATION-BY-REFERENCE OF MATERIAL SUBMITTED IN ELECTRONIC FORM

Applicant hereby incorporates by reference the Sequence Listing material filed in electronic form herewith. This file is labeled "UPN-15-7313PCT_ST25.txt".

BACKGROUND

A number of inherited retinal diseases are caused by mutations, generally multiple mutations, located throughout portions of large ocular genes. As one example, Stargardt disease, also known as Stargardt 1 (STGD1), is an autosomal recessive form of retinal dystrophy that is usually characterized by a progressive loss of central vision. Worldwide prevalence of STGD1 is estimated at 1/8,000-1/10,000. The disease typically presents within the first two decades of life. Although disease progression and severity varies widely, STGD1 is usually characterized by a progressive loss of central vision causing blurry vision and, occasionally, an increasing difficulty to adapt in the dark. STGD1 may progress rapidly over a few months or gradually over several years leading to a severe decrease in visual acuity. Most affected individuals also have impaired color vision or photophobia. There is no treatment currently available for STGD1.

STGD1 has been linked to mutations in the ABCA4 gene, which has a sequence of 6822 nucleotides that encodes an adenosine triphosphate (ATP)-binding cassette transporter (ABCR) of sub-family A number 4, which is expressed specifically in the cones and rods of the retina. Defects in ABCR function cause the accumulation of all-trans-retinal and its cytotoxic derivatives (e.g., diretinoid-pyridinium-ethanolamine) (lipofuscin pigments) in photoreceptors and retinal pigment epithelial (RPE) cells, ultimately causing RPE cell death and the subsequent loss of photoreceptors. Mutations in ABCA4 have been linked to a spectrum of phenotypes ranging from STGD1, to a juvenile onset macular degeneration, fundus flavimaculatus, to cone-rod dystrophy, and a form of retinitis pigmentosa. ABCA4 mutations also contribute to age-related macular degeneration (AMD) and severe early-onset retinal dystrophy.

Similar retinal diseases are caused by defects in other large ocular genes, including CEP290 (7440 nucleotides) which defects or mutations cause Leber's congenital amaurosis, among other ocular disorders, and MYO7A (7465 nucleotides), which defects or mutations cause Usher's disease.

The occurrences and locations of multiple mutations in such large ocular genes has made strategies for repairing the mutations very challenging. There remains a need for effective compositions and therapeutic methods for treating such ocular disorders.

SUMMARY

In one aspect, a composition comprises a pre-RNA trans-splicing molecule (RTM) that can replace an exon or multiple exons in a targeted mammalian ocular gene carrying a defect or mutation causing an ocular disease with an exon(s) having the naturally-occurring sequence without the defect or mutation.

In another aspect, a recombinant nucleic acid molecule and vectors capable of expressing the RTMs described herein are provided.

In still another aspect, ocular cells expressing the RTM are provided for use in ex vivo repair and reimplantation to the subject from which the ocular cells were extracted.

In another aspect, a proviral plasmid comprises a modular recombinant AAV genome comprising in operative association comprising a 5' AAV2 ITR sequence, a suitable promoter operative in a mammalian ocular cell, an RNA trans-splicing molecule that can replace an exon in a targeted mammalian ocular gene carrying a defect or mutation causing an ocular disease with an exon having the naturally-occurring sequence without the defect or mutation, wherein the RTM is operatively linked to, and under the regulatory control of, the promoter; and a 3' AAV2 ITR sequence. The modular AAV genome is present in a plasmid backbone comprising the elements necessary for replication in a host cell.

In yet another aspect, a cell culture comprises bacterial or mammalian host cells transfected with the plasmids or nucleic acid constructs described herein.

In another aspect, a recombinant AAV infectious particle comprises an RTM or nucleic acid construct described herein.

In another embodiment, a recombinant AAV infectious particle is produced by culturing a packaging cell carrying a proviral plasmid as described herein and carrying an RTM in the presence of sufficient viral sequences to permit packaging of the ocular gene nucleic acid sequence expression cassette viral genome into an infectious AAV envelope or capsid.

In one aspect, a kit is provided that comprises an RTM as described herein, a recombinant nucleic acid construct as described herein, or a proviral plasmid as described herein.

In another aspect, a method of treating an ocular disease caused by a defect or mutation in a target gene comprising administering to the ocular cells of a mammalian subject having the ocular disease a composition comprising an rAAV particle carrying an RNA trans-splicing molecule (RTM) that can replace an exon in a targeted mammalian ocular gene carrying a defect or mutation causing an ocular disease with an exon having the naturally-occurring sequence without the defect or mutation. These methods include ex vivo methods including contacting the RTMs with specific target pre-mRNA expressed within ocular cells under conditions in which a portion of the RTM is trans-spliced to a portion of the target pre-mRNA to form a chimeric RNA molecule which contains sequence in which the genetic defect in the specific target ocular gene is corrected for return to the subject's eye.

In another aspect, the method of treatment involves administering via sub-retinal injection to the ocular cells an rAAV particle comprising the RTM, wherein the ocular cell infected with the rAAV employs the RTM to replace the defective gene in vivo by trans-splicing.

Other aspects and embodiments are are described in the following detailed description.

BRIEF DESCRIPTION OF THE FIGURES

FIG. 1 shows a diagram of an AAV genome encoding RNA trans-splicing molecules targeting mutations in ABCA4.

DETAILED DESCRIPTION

Figure 2A:
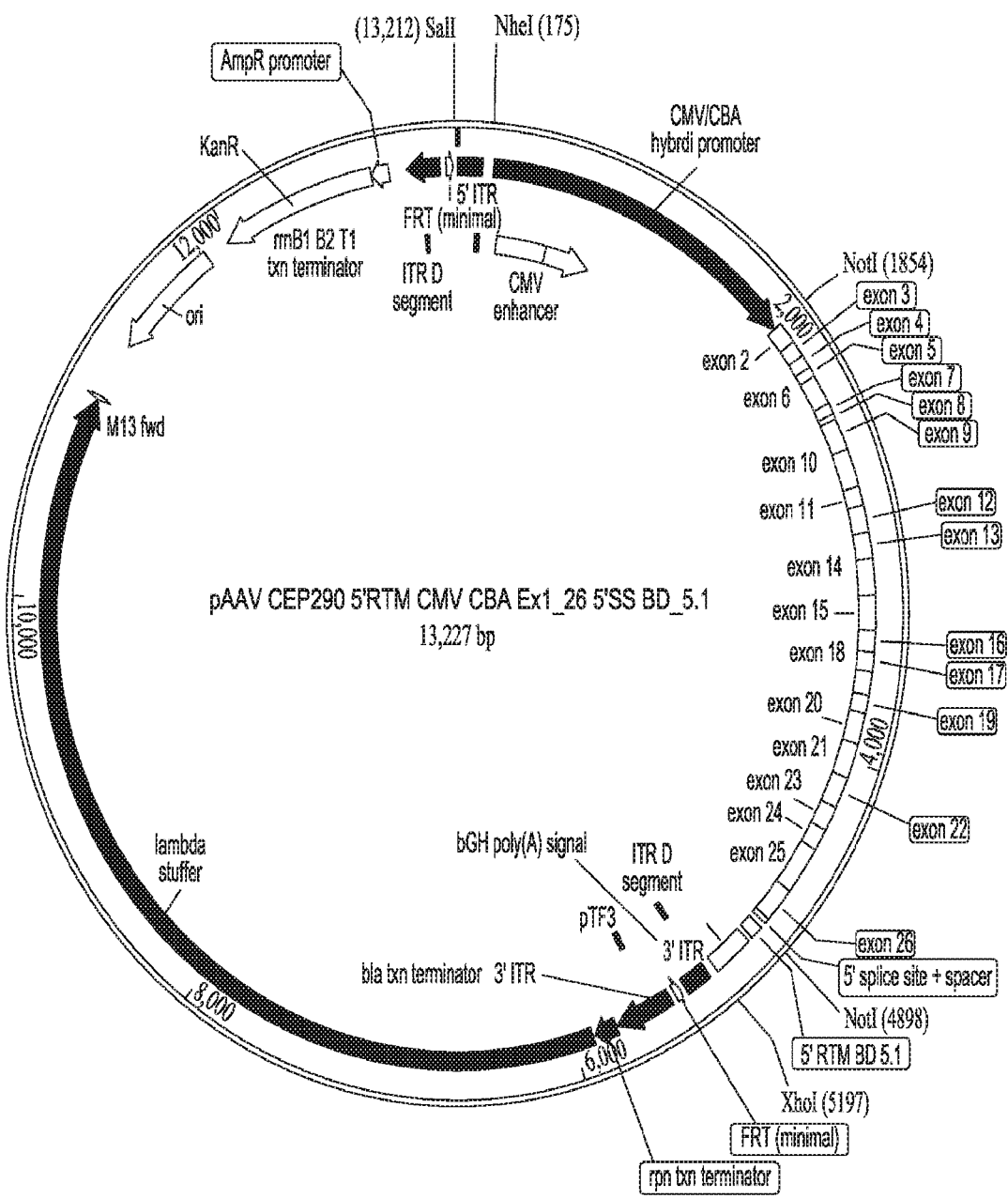
FIG. 2A is a 5'RTM model for CEP290 (Exons 1 to 26) inserted into the p618 plasmid.

The compositions and methods described herein employ gene therapy using adeno-associated virus (AAV) as a means for treating heritable ocular genetic disorders. More specifically, the methods and compositions described herein employ the use of pre-mRNA trans-splicing as a gene therapy, both ex vivo and in vivo, for the treatment of ocular diseases caused by defects in large genes. In one embodiment, these compositions and methods overcome the problem caused by the packaging limit for nucleic acids into AAV being limited to 4700 nucleotides. When including sequences necessary for producing an effective rAAV therapeutic and expressing the RNA-trans-splicing molecule (RTM), the effective size constraint for the RTM containing the ocular gene sequences is about 4000 nucleotides. These methods and compositions are particularly desirable for treatment of ocular disorders caused by defects in genes exceeding the size necessary for incorporation and expression in an AAV, such as ABCA4, CEP290 and MYO7A, among other genes.

Definitions

Unless defined otherwise, technical and scientific terms used herein have the same meaning as commonly understood by one of ordinary skill in the art to which this invention belongs and by reference to published texts, which provide one skilled in the art with a general guide to many of the terms used in the present application. The definitions used herein are provided for clarity only and are not intended to limit the claimed invention.

As used herein, the term "mammalian subject" or "subject" includes any mammal in need of these methods of treatment or prophylaxis, including particularly humans. Other mammals in need of such treatment or prophylaxis include dogs, cats, or other domesticated animals, horses, livestock, laboratory animals, including non-human primates, etc. The subject may be male or female. In one embodiment, the subject has, or is at risk of developing an ocular disorder. In another embodiment, the subject has shown clinical signs of an ocular disorder, particular a disorder related to a defect or mutation in the genes ABCA4, CEP290, or MYO7A.

The term "ocular disorder" includes, without limitation, Stargardt disease (autosomal dominant or autosomal recessive), retinitis pigmentosa, rod-cone dystrophy, Leber's congenital amaurosis, Usher's syndrome, Bardet-Biedl Syndrome, Best disease, retinoschisis, untreated retinal detachment, pattern dystrophy, cone-rod dystrophy, achromatopsia, ocular albinism, enhanced S cone syndrome, diabetic retinopathy, age-related macular degeneration, retinopathy of prematurity, sickle cell retinopathy, Congenital Stationary Night Blindness, glaucoma, or retinal vein occlusion. In another embodiment, the subject has, or is at risk of developing glaucoma, Leber's hereditary optic neuropathy, lysosomal storage disorder, or peroxisomal disorder.

Clinical signs of ocular disease include, but are not limited to, decreased peripheral vision, decreased central (reading) vision, decreased night vision, loss of color perception, reduction in visual acuity, decreased photoreceptor function, pigmentary changes. In another embodiment, the subject has been diagnosed with STGD1. In another embodiment, the subject has been diagnosed with a juvenile onset macular degeneration, fundus flavimaculatus. In another embodiment, the subject has been diagnosed with cone-rod dystrophy. In another embodiment, the subject has been diagnosed with retinitis pigmentosa. In another embodiment, the subject has been diagnosed with age-related macular degeneration (AMD). In another embodiment, the subject has been diagnosed with LCA10. In yet another embodiment, the subject has not yet shown clinical signs of these ocular pathologies.

As used herein, the term "treatment" or "treating" is defined as one or more of reducing onset or progression of an ocular disease, preventing disease, reducing the severity of the disease symptoms, or retarding their progression, removing the disease symptoms, delaying onset of disease or monitoring progression of disease or efficacy of therapy in a given subject.

As used herein, the term "selected cells" refers to an ocular cell, which is any cell associated with the function of, the eye. In one embodiment, the ocular cell is a photoreceptor cell. In another embodiment, the term refers to rod, cone and photosensitive ganglion cells, retinal pigment epithelium (RPE) cells, Mueller cells, bipolar cells, horizontal cells, amacrine cells. Some genes are expressed in the eye as well as in other organs. For example, CEP290 is expressed in kidney epithelium and in the central nervous system; MYO7A is expressed in cochlear hair cells. "Selected cells" may also include these extra-ocular cells.

As used herein, the term "host cell" may refer to the packaging cell line in which the rAAV is produced from the plasmid. In the alternative, the term "host cell" may refer to the target cell in which expression of the transgene is desired.

An RNA trans-splicing molecule (RTM) has three main elements: (a) an anti-sense binding domain (BD) which is the element that confers specificity by tethering the RTM to its target pre-mRNA; (b) a 3' and/or 5' splice site; and (c) a coding sequence to be trans-spliced, which can re-write most of the targeted pre-mRNA by replacing one or numerous exons anywhere in a message.

Codon optimization refers to modifying a nucleic acid sequence to change individual nucleic acids without any resulting change in the encoded amino acid. This process may be performed on any of the sequences described in this specification to enhance expression or stability. Codon optimization may be performed in a manner such as that described in, e.g., U.S. Pat. Nos. 7,561,972; 7,561,973; and 7,888,112, incorporated herein by reference, and conversion of the sequence surrounding the translational start site to a consensus Kozak sequence. See, Kozak et al, *Nucleic Acids Res.* 15 (20): 8125-8148, incorporated herein by reference.

The term "homologous" refers to the degree of identity between sequences of two nucleic acid sequences. The homology of homologous sequences is determined by comparing two sequences aligned under optimal conditions over the sequences to be compared. The sequences to be compared herein may have an addition or deletion (for example, gap and the like) in the optimum alignment of the two sequences. Such a sequence homology can be calculated by creating an alignment using, for example, the ClustalW algorithm (Nucleic Acid Res., 22(22): 4673 4680 (1994). Commonly available sequence analysis software, more specifically, Vector NTI, GENETYX, BLAST or analysis tools provided by public databases may also be used.

The term "pharmaceutically acceptable" means approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, or vehicle with which the synthetic is administered. Examples of suitable pharmaceutical carriers are described in "Remington's Pharmaceutical sciences" by E. W. Martin.

The terms "a" or "an" refers to one or more, for example, "a gene" is understood to represent one or more such genes. As such, the terms "a" (or "an"), "one or more," and "at least one" are used interchangeably herein.

As used herein, the term "about" means a variability of ±0.1 to 10% from the reference given, unless otherwise specified.

With regard to the following description, it is intended that each of the compositions herein described, is useful, in another embodiment, in the methods of treatment described herein. In addition, it is also intended that each of the compositions herein described as useful in the methods, is itself an embodiment. While various embodiments in the specification are presented using "comprising" language, which is inclusive of other components or steps, under other circumstances, a related embodiment is also intended to be interpreted and described using "consisting of" or "consisting essentially of" language, which is exclusive of all or any components or steps which significantly change the embodiment.

Pre-mRNA Trans-Splicing Methods and Molecules

Within a cell, a pre-mRNA intermediate exists that includes non-coding nucleic acid sequences, i.e., introns, and nucleic acid sequences that encode the amino acids forming the gene product. The introns are interspersed between the exons of a gene in the pre-mRNA, and are ultimately excised from the pre-mRNA molecule, when the exons are joined together by a protein complex known as the spliceosome. Using spliceosome activity, one may introduce an alternative exon via the introduction of a second nucleic acid. Spliceosome mediated RNA trans-splicing (SMaRT) has been described as employing an engineered pre-mRNA trans-splicing molecule (RTM) that binds specifically to target pre-mRNA in the nucleus and triggers trans-splicing in a process mediated by the spliceosome. This methodology is described in, for example, Puttaraju M, et al 1999 Nat Biotechnol., 17:246-252; Gruber C et al, 2013 December, Mol. Oncol. 7(6):1056; Avale M E, 2013 July, Hum. Mol. Genet., 22(13):2603-11; Rindt H et al, 2012 December, Cell Mol. Life Sci., 69(24):4191; US Patent Application Publication Nos. 2006/0246422 and 20130059901, and U.S. Pat. Nos. 6,083,702; 6,013,487; 6,280,978; 7,399,753; and 8,053,232. These documents are incorporated herein by reference.

A pre-RNA trans-splicing molecule (RTM) useful as or in the compositions described herein is a molecule that can replace an exon (or multiple exons) in a targeted ocular gene. The design of the RTM permits replacement of the defective or mutated portion of the pre-mRNA exon(s) with a nucleic acid sequence, i.e., the exon (s) having a normal sequence without the defect or mutation. The "normal" sequence can be a wild-type naturally-occurring sequence or a corrected sequence with some other modification, e.g., codon-modified, that is not disease-causing.

The RTM useful in the compositions and methods herein comprises a binding domain that targets binding of the molecule to a pre-mRNA of a target ocular gene expressed within a mammalian ocular cell; a splicing domain containing motifs necessary for a trans-splicing reaction to occur; and a coding domain from an ocular gene. The coding domain contains a nucleotide sequence from the wild-type or corrected cDNA, usually one or more exons, that are necessary to repair the targeted mutation or defects that cause ocular disease. The RTM in one embodiment contains multiple binding domains. The RTM in one embodiment contains multiple splicing domains. The RTM in one embodiment contains multiple coding domains. In one embodiment, RTMs are designed to replace target sequences located on the 3' portion of the targeted gene. In one embodiment, RTMs are designed to replace target sequences located on the 5' portion of the targeted gene. In still other embodiments, RTMs are designed to replace an internal target sequence in the gene. The RTMs function to repair the defective gene in the subject's cell by replacing the defective exon and subsequently removing the defective portion of the target pre-mRNA, leaving a functional gene capable of transcribing a function gene product in the cell. The design and assembly of such RTMs follow the descriptions of this technology set out in the patents and references cited throughout this specification and incorporated herein by reference.

As one example, a 3' pre-mRNAABCA4 trans-splicing molecule operates as follows: A chimeric mRNA is created through a trans-splicing reaction mediated by the spliceosome between the 5' splice site of the endogenous target pre-mRNA, ABCA4, and the 3' splice site of the rAAV-delivered pre-trans-splicing RNA molecule. The RTM molecule binds through specific base pairing to an intron of the endogenous target pre-mRNA and replaces the whole 3' sequence of the endogenous gene upstream of the targeted intron with the wild type coding sequence of the RTM. The operation of the 5' and double trans-splicing RTMs can be observed in FIG. 1 of U.S. Pat. No. 8,053,232, incorporated herein by reference.

A 3' RTM comprises a binding domain which binds to the target pre-mRNA 5' to the mutation or defect, an optional spacer, a 3' splice site, and a coding domain that encodes all exons of the ocular target gene that are 3' to the binding of the binding domain to the target. A 5' RTM comprising a binding domain binds to the target pre-mRNA 3' to the mutation or defect, a 5' splice site, an optional spacer and a coding domain that encodes all exons of the ocular target gene that are 5' to the binding of the binding domain to the target. A double trans-splicing RTM contains the elements of the 3' RTM and a second binding domain that targets a sequence of the ocular gene and which binds to the target intro 3' to the mutation or defect in the target pre-mRNA and a 5'splice site.

For delivery via a recombinant AAV as described herein, in one embodiment, the entire RTM is a nucleic acid sequence of up to 3000 nucleotide bases in length.

Targeted Ocular Genes

The targeted ocular gene is one that contains one or multiple defects or mutations that cause an ocular disease. In one embodiment described herein, the targeted ocular gene is a mammalian gene with defects known to cause inherited retinal disorders.

The wildtype sequences of the ocular genes and encoded proteins and/or the genomic and chromosomal sequences are available from publically available databases and their accession numbers are provided herein. In addition to these published sequences, all corrections later obtained or naturally occurring conservative and non-disease-causing variants sequences that occur in the human or other mammalian population are also included. Additionally conservative nucleotide replacements or those causing codon optimizations are also included. The sequences as provided by the database accession numbers may also be used to search for homologous sequences in the same or another mammalian organism.

It is anticipated that the target ocular gene nucleic acid sequences and the resulting protein truncates or amino acid fragments identified herein may tolerate certain minor modifications at the nucleic acid level to include, for example, modifications to the nucleotide bases which are silent, e.g., preference codons. In other embodiments, nucleic acid base modifications which change the amino acids, e.g. to improve expression of the resulting peptide/protein are anticipated. Also included as likely modification of fragments are allelic variations, caused by the natural degeneracy of the genetic code.

Also included as modification of the selected ocular genes are analogs, or modified versions, of the encoded protein fragments provided herein. Typically, such analogs differ from the specifically identified proteins by only one to four codon changes. Conservative replacements are those that take place within a family of amino acids that are related in their side chains and chemical properties.

The nucleic acid sequence encoding a normal ocular gene may be derived from any mammal which natively expresses that gene, or homolog thereof. In another embodiment, the ocular gene sequence is derived from the same mammal that the composition is intended to treat. In another embodiment, the ocular gene sequence is derived from a human. In other embodiments, certain modifications are made to the gene sequence in order to enhance the expression in the target cell. Such modifications include codon optimization.

In one embodiment, the gene is ABCA4, which is indicated in the diseases discussed in the background above. The genomic sequence of the DNA for this gene can be found in the NCBI Reference Sequence for Chromosome 1 (135313 bp) at NG_009073.1. The mRNA for the gene as well as the locations of the exons are indicated in the NCBI report. The DNA sequence of ABCA4 provided as NCBI Reference Sequence: NM_000350.2. The amino acid sequence is provided as NCBI Reference Sequence: NP000341.2. TABLE 1 lists mutations in ABCA4 and their locations in certain introns or exons of the nucleotide sequence. TABLE 1 also identifies the associated ocular disease, specific mutation, exon location of mutation, target cells, target intron and it published sequence for designing the binding domain sequence and the exon and its published sequence for use in the coding domain, as well as the 3' or 5' direction of the RTM created to contain these components. It should be understood that the binding domain may include sequences complementary to more than target intron sequences, as described below in detail with respect to RTM binding domains. In one embodiment, the RTM is designed to correct ABCA4 mutations p.Leu541Pro and p.Ala1038Val, among others.

In another embodiment, the gene is CEP290. Leber congenital amaurosis comprises a group of early-onset childhood retinal dystrophies characterized by vision loss, nystagmus, and severe retinal dysfunction. Patients usually present at birth with profound vision loss and pendular nystagmus. Electroretinogram (ERG) responses are usually nonrecordable. Other clinical findings may include high hypermetropia, photodysphoria, oculodigital sign, keratoconus, cataracts, and a variable appearance to the fundus. LCA10 is caused by mutation in the CEP290 gene on chromosome 12q21 and may account for as many as 21% of cases of LCA. Mutations in CEP290 can also result in extra-ocular findings, including kidney and CNS abnormalities, and thus can result in syndromes (Senior Loken syndrome, Joubert syndrome, Bardet-Biedl).

The genomic sequence of the DNA for this gene can be found in the NCBI Reference Sequence for Chromosome 12 from nt. 88049013-88142216 (93,204 bp) at NC_000012.12. The mRNA and the exons are identified in NCBI report. The DNA sequence of CEP290 provided as NCBI Reference Sequence: NM_025114.3. The amino acid sequence is provided as NCBI Reference Sequence: NP0789390.3. The mRNA contains 54 exons and 59 introns (due to alternative splicing). Many mutations of CEP290 and their locations in the nucleotide sequence are known. TABLE 2 lists mutations in CEP290 and their locations in certain introns or exons of the nucleotide sequence. TABLE 2 also identifies the associated ocular disease, specific mutation, exon location of mutation, target cells, the intron and it published sequence for designing the binding domain sequence and the exon and its published sequence for use in the coding domain as well as the 3' or 5' direction of the RTM created to contain these components. It should be understood that the binding domain may include sequences complementary to more than target intron sequences, as described below in detail with respect to RTM binding domains. In one embodiment an RTM is designed to correct the exons carry the mutations c2991+1655A to G and Ser1056 to A. In another embodiment, an RTM is designed to target Intron 26 of CEP290.

In another embodiment, the gene is MYO7A. Mutations in this gene are related to Usher Syndrome. Usher syndrome is a condition characterized by hearing loss and progressive vision loss. The loss of vision is caused by an eye disease called retinitis pigmentosa (RP), which affects the layer of light-sensitive retina. Vision loss occurs as the light-sensing cells of the retina gradually deteriorate. Over time, these blind spots enlarge and merge to produce tunnel vision. In some cases of Usher syndrome, vision is further impaired by clouding of the lens of the eye (cataracts). Many people with retinitis pigmentosa retain some central vision throughout their lives, however. The loss of hearing is caused by disease in cochlear hair cells, which also gradually deteriorate. Usher syndrome type I can result from mutations in the CDH23, MYO7A, PCDH15, USH1C, or USH1G gene.

More than 250 mutations in the MYO7A gene have been identified in people with Usher syndrome type 1B. Many of these genetic changes alter a single protein building block (amino acid) in critical regions of the myosin VIIA protein. Other mutations introduce a premature stop signal in the instructions for the myosin VIIA protein. As a result, an abnormally small version of this protein is made. Some mutations insert or delete small amounts of DNA in the MYO7A gene, which alters the protein. All of these changes cause the production of a nonfunctional myosin VIIA protein that adversely affects the development and function of cells in the inner ear and retina, resulting in Usher syndrome.

The genomic sequence of the DNA for this gene can be found in the NCBI Reference Sequence for Chromosome 11 from nt. 77,128,255 to 77,215,240 (86,986 bp) at NC_000011.9. The DNA sequence of MYO7A provided as NCBI Reference Sequence: NM_000260.3. The amino acid sequence is provided as NCBI Reference Sequence: NP 000251.1. The DNA sequence, amino acid sequence, exon sequences and intron sequences are provided for MYO7A online at haps://grenada.lumc.nl/LOVD2/Usher_montpellier/refseq/MYO7A_codingDNA.html, last modified Feb. 17, 2010. The mRNA contains 49 exons and 61 introns. Many mutations of MYO7A may be found on the CCHMC Molecular Genetics Laboratory Mutation Database, LOVD v.2.0. See also, TABLE 3 which lists mutations in MYO7A identifying ocular disease, specific mutation, exon location of mutation, target cells, the intron and it published sequence for designing the binding domain sequence and the exon and its published sequence for use in the coding domain as well as the 3' or 5' direction of the RTM created to contain these components. It should be understood that the binding domain may include sequences complementary to more than target intron sequences, as described below in detail with respect to RTM binding domains.

RTM Binding Domains

Each RTM comprises one or more binding domains (BD). In one embodiment, the target binding domain is a nucleic acid sequence, complementary to and in antisense orientation to a sequence of the target pre-mRNA, e.g., ABCA4, to suppress target cis-splicing while enhancing trans-splicing between the RTM and the target. The binding domains generally bind to the target gene 5' to the mutation or defect in the target pre-mRNA. In one embodiment, the binding domain comprises a part of a sequence complementary to an intron of the targeted gene. In another embodiment, the binding domain comprises a part of a sequence complementary to an exon of the targeted gene. In another embodiment, the binding domain comprises a part of a sequence complementary to an intron of the targeted gene and a part of a sequence complementary to an exon of the targeted gene. In one embodiment the binding domain comprises part of the respective intron upstream of the exon that is primarily functioning as the binding domain. In one embodiment herein, the binding domain is a nucleic acid sequence complementary to the intron closest to the exon sequence that is being corrected. In still another embodiment, the binding domain is targeted to an intron sequence in close proximity to the 3' or 5' splice signals of a target intron. In still another embodiment, a binding domain BD sequence can base-pair to the target sequence in two sequences within the target gene, part intron and part exon. The binding domains shown in TABLES 1 to 3 should be understood to encompass any of these regions for a suitable binding domain.

The BD thus binds specifically to the endogenous target pre-mRNA which carries the mutation(s), to anchor the pre-mRNA closely in space to the coding domain of the RTM to permit trans-splicing to occur at the correct position in the target gene. The spliceosome processing machinery of the nucleus then causes successful trans-splicing of the corrected exon for the mutated exon causing the disease.

For use in the RTMs described herein suitable target binding domains may include from 20 up to 50 nucleotides in length. In another embodiment, the target binding domains may include a nucleic acid sequence up to 100 nucleotides in length. In another embodiment, the target binding domains may include a nucleic acid sequence up to 300 nucleotides in length. In another embodiment, the target binding domains may include a nucleic acid sequence up to 500 nucleotides in length. In another embodiment, the target binding domains may include a nucleic acid sequence up to 750 nucleotides in length. In another embodiment, the target binding domains may include a nucleic acid sequence up to 1000 nucleotides in length. In another embodiment, the target binding domains may include a nucleic acid sequence up to 2000 nucleotides or more in length. In certain embodiments, the RTMs contain binding domains that contain sequences on the target pre-mRNA that bind in more than one place. The binding domain may contain any number of nucleotides necessary to stably bind to the target pre-mRNA to permit trans-splicing to occur with the coding domain. In one embodiment, the binding domains are selected using mFOLD structural analysis for accessible loops. Bearing in mind the packaging limitations of the rAAV, the target BD in one embodiment is between about 30 to about 250 nucleotides in length. In one embodiment the binding domains may comprise between and including 70 and 200 nucleotides. In one embodiment the binding domains may comprise between and including 20 and 500 nucleotides. The specificity of the RTM may be increased significantly by increasing the length of the target binding domain. Other lengths may be used depending upon the lengths of the other components of the RTM.

The binding domain may be 100% complementary to the targeted genes' exon, or have sufficient complementarity to be able to hybridize stably with the target pre-mRNA. The degree of complementarity is selected by one of skill in the art based on the need to keep the RTM and the nucleic acid construct containing the necessary sequences for expression and for inclusion in the rAAV within a 3000 or up to 4000 bp limit. The selection of this sequence and strength of hybridization depends on the complementarity and the length of the nucleic acid (See, for example, Sambrook et al., 1989, Molecular Cloning, A Laboratory Manual, 2d Ed., Cold Spring Harbor Laboratory Press, Cold Spring Harbor, N.Y.).

In one embodiment, a suitable RTM binding domain for ABCA4 is a sequence of from 70-200 nucleotides complementary to the target Intron 22 (see Table 1) or to part of the target intron and part of the exon. In another embodiment a suitable RTM binding domain is a sequence from e.g., 70-200 nucleotides complementary to the target Intron 22 or to part of the target intron and part of the exon. Given the teachings herein and TABLE 1, one may select other intron and/or exon targets or portions of introns and their flanking exons to prepare the binding domain based upon the mutation selected and the intron to be targeted. The binding domains of TABLE 1 may be greater than 200 nucleotides in length, as taught herein.

In one embodiment, a suitable RTM binding domain for CEP290 is a sequence of from 70-200 nucleotides complementary to the target Intron 26. Given the teachings herein including TABLE 2, select other intron targets or portions of introns and their flanking exons to prepare the binding domain based upon the mutation selected and the intron to be targeted. The binding domains of TABLE 2 may be greater than 200 nucleotides in length, as taught herein.

In one embodiment, a suitable RTM binding domain for MYO7A is a sequence of from 70-200 nucleotides complementary to the target Intron 32. Given the teachings herein including TABLE 3, select other intron targets or portions of introns and their flanking exons to prepare the binding domain based upon the mutation selected and the intron to be targeted. The binding domains of TABLE 2 may be greater than 200 nucleotides in length, as taught herein.

One of skill in the art may readily select portions of other ocular target genes for correction following the teachings herein.

RTM Splicing Domains

The splicing domains of the 3' RTM comprise a strong conserved branch point or branch site (BP) sequence, a polypyrimidine tract (PPT), and a 3' splice acceptor (AG or YAG) site and/or a 5' splice donor (GU) site. The splicing domains of the 5' RTM do not contain the branch point or PPT, but comprise a 5' splice acceptor/or 3' splice donor. Splicing domains may be selected by one of skill in the art (see also, the RTM technology documents cited herein).

Briefly, the splicing domain provides essential consensus motifs that are recognized by the spliceosome. The use of BP and PPT follows consensus sequences required for performance of the two phosphoryl transfer reaction involved in cis-splicing and, presumably, also in trans-splicing. In one embodiment a branch point consensus sequence in mammals is YNYURAC (Y=pyrimidine; N=any nucleotide). The underlined A is the site of branch formation. A polypyrimidine tract is located between the branch point and the splice site acceptor and is important for different branch point utilization and 3' splice site recognition. Consensus sequences for the 5' splice donor site and the 3' splice region used in RNA splicing are well known in the art. In addition, modified consensus sequences that maintain the ability to function as 5' donor splice sites and 3' splice regions may be used. Briefly, in one embodiment, the 5' splice site consensus sequence is the nucleic acid sequence AG/GURAGU (where/indicates the splice site). In another embodiment the endogenous splice sites that correspond to the exon proximal to the splice site can be employed to maintain any splicing regulatory signals. In one embodiment, the ABCA4 5'RTM containing as a coding region the sequence encoding exon 1-22 with a binding domain complementary to a region in intron 22 uses the endogenous intron 22 5' splice site. In another embodiment, the ABCA4 3'RTM encoding exons 27-50 with a binding domain complementary to intron 26 uses the endogenous intron 26 3' splice site.

In one embodiment a suitable 5' splice site with spacer is: 5'-GTA AGA GAG CTC GTT GCG ATA TTA T-3' SEQ ID NO: 5. In one embodiment a suitable 5' splice site is AGGT.

In one embodiment, a suitable 3' RTM BP is 5'-TACTAAC-3'. In one embodiment, a suitable 3' splice site is: 5'-TAC TAA CTG GTA CCT CTT CTT TTT TTT CTG CAG-3' SEQ ID NO: 6 or 5'-CAGGT-3'. In one embodiment, a suitable 3'RTM PPT is 5'-TGG TAC CTC TTC TTT TTT TTC TG-3' SEQ ID NO: 7.

RTM Target Gene Coding Sequence

The coding domain of the RTMs described herein includes part of the wild type coding sequence to be trans-spliced to the target pre-mRNA. In one embodiment, the coding domain is a single exon of the target gene, which contains the normal wildtype sequence lacking the disease-causing mutations, e.g., Exon 27 of ABCA4. In another embodiment, the coding domain comprises multiple exons which contain multiple mutations causing disease, e.g., Exons 1-22 of ABCA4. Depending upon the location of the exon to be corrected, the RTM may contain multiple exons located at the 5' or 3' end of the target gene, or the RTM may be designed to replace an exon in the middle of the gene. For use and delivery in the rAAV, the entire coding sequence of the ocular gene is not useful as the coding domain of RTM, unless this technique is directed to a small ocular gene less than 3000 nucleotides in length. As described herein, to replace an entire large gene, two RTMs, a 3' and a 5' RTM can be employed in different rAAV particles.

RTMs described herein can comprise coding domains encoding for one or more exons identified herein and characterized by containing a gene mutation or defect relating to the associated disease, e.g., Exon 27 of ABCA4 may be the coding domain for an RTM designed for the treatment of Stargardt's disease. In TABLEs 1 to 3 herein, the names of the targeted genes and the exons containing likely mutations causing disease are identified.

In one embodiment, the coding domain of a 5' RTM is designed to replace the exons in the 5' portion of the targeted gene. In another embodiment, the coding domain of a 3' RTM is designed to replace the exons in the 3' portion of a gene. In another embodiment, the coding domain is one or a multiple exons located internally in the gene and the coding domain is located in a double trans-splicing RTMs.

Thus, for example, three possible types of RTMs are useful for treatment of disease caused by defects in e.g., ABCA4: A 5' trans-splicing RTMs which include a 5' splice site. After trans-splicing, the 5' RTM will have changed the 5' region of the target mRNA; a 3' RTM which include a 3' splice site that is used to trans-splice and replace the 3' region of the target mRNA; and a double trans-splicing RTMs, which carry multiple binding domains along with a 3' and a 5' splice site. After trans-splicing, this RTM replaces an internal exon in the processed target mRNA. In other embodiments, the coding domain can include an exon that comprises naturally occurring or artificially introduced stop-codons in order to reduce gene expression; or the RTM can contains other sequences which produce an RNAi-like effect.

For use in treating Stargardt's disease, suitable coding regions of ABCA4 are Exons 1-22 or 27-50, in separate RTMs. For use in treating LCA10, suitable coding regions of CEP290 are Exons 1-26 or exons 27-54 in separate RTMs. For use in treating Usher Syndrome, suitable coding regions of MYO7A are Exons 1-18 or 33-49, in separate RTMs.

Still other coding domains can be constructed by one of skill in the art to replace the entirety of the genes in fragments provided by a 5' RTM and 3'RTM, and/or a double splicing RTM, given the teachings provided herein.

Optional Components or Modifications of the RTM

An optional spacer region may be used to separate the splicing domain from the target binding domain in the RTM. The spacer region may be designed to include features such as (i) stop codons which would function to block translation of any unspliced RTM and/or (ii) sequences that enhance trans-splicing to the target pre-mRNA. The spacer may be between 3 to 25 nucleotides or more depending upon the lengths of the other components of the RTM and the rAAV limitations. In one embodiment a suitable 5' RTM spacer is AGA TCT CGT TGC GAT ATT AT SEQ ID NO: 8. In one embodiment a suitable 3' spacer is: 5'-GAG AAC ATT ATT ATA GCG TTG CTC GAG-3' SEQ ID NO: 9.

Still other optional components of the RTMs include mini introns, and intronic or exonic enhancers or silencers that would regulate the trans-splicing (See, e.g., the descriptions in the RTM technology publications cited herein.)

In another embodiment, the RTM further comprises at least one safety sequence incorporated into the spacer, binding domain, or elsewhere in the RTM to prevent non-specific trans-splicing. This is a region of the RTM that covers elements of the 3' and/or 5' splice site of the RTM by relatively weak complementarity, preventing non-specific trans-splicing. The RTM is designed in such a way that upon hybridization of the binding/targeting portion(s) of the RTM, the 3' and/or 5' splice site is uncovered and becomes fully active. Such "safety" sequences comprise a complementary stretch of cis-sequence (or could be a second, separate, strand of nucleic acid) which binds to one or both sides of the RTM branch point, pyrimidine tract, 3' splice site and/or 5' splice site (splicing elements), or could bind to parts of the splicing elements themselves. The binding of the "safety" may be disrupted by the binding of the target binding region of the RTM to the target pre-mRNA, thus exposing and activating the RTM splicing elements (making them available to trans-splice into the target pre-mRNA). In another embodiment, the RTM has 3'UTR sequences or ribozyme sequences added to the 3 or 5' end.

In an embodiment, splicing enhancers such as, for example, sequences referred to as exonic splicing enhancers may also be included in the structure of the synthetic RTMs. Additional features can be added to the RTM molecule, such as polyadenylation signals to modify RNA expression/stability, or 5' splice sequences to enhance splicing, additional binding regions, "safety"-self complementary regions, additional splice sites, or protective groups to modulate the stability of the molecule and prevent degradation. In addition, stop codons may be included in the RTM structure to prevent translation of unspliced RTMs. Further elements such as a 3' hairpin structure, circularized RNA, nucleotide base modification, or synthetic analogs can be incorporated into RTMs to promote or facilitate nuclear localization and spliceosomal incorporation, and intra-cellular stability.

The binding of the RTM nucleic acid molecule to the target pre-mRNA is mediated by complementarity (i.e. based on base-pairing characteristics of nucleic acids), triple helix formation or protein-nucleic acid interaction (as described in documents cited herein). In one embodiment, the RTM nucleic acid molecules consist of DNA, RNA or DNA/RNA hybrid molecules, wherein the DNA or RNA is either single or double stranded. Also comprised are RNAs or DNAs, which hybridize to one of the aforementioned RNAs or DNAs preferably under stringent conditions like, for example, hybridization at 60° C. in 2.5×SSC buffer and several washes at 37° C. at a lower buffer concentration like, for example, 0.5×SSC buffer and which encode proteins exhibiting lipid phosphate phosphatase activity and/or association with plasma membranes. When RTMs are synthesized in vitro (synthetic RTMs), such RTMs can be modified at the base moiety, sugar moiety, or phosphate backbone, for example, to improve stability of the molecule, hybridization to the target mRNA, transport into the cell, stability in the cells to enzymatic cleavage, etc. For example, modification of a RTM to reduce the overall charge can enhance the cellular uptake of the molecule. In addition modifications can be made to reduce susceptibility to nuclease or chemical degradation. The nucleic acid molecules may be synthesized in such a way as to be conjugated to another molecule, e.g., a peptide, hybridization triggered cross-linking agent, transport agent, hybridization-triggered cleavage agent, etc.

Various other well-known modifications to the nucleic acid molecules can be introduced as a means of increasing intracellular stability and half-life (see also above for oligonucleotides). Possible modifications are known to the art (see documents cited herein). Modifications, which may be made to the structure of the synthetic RTMs include but are not limited to backbone modifications such as described in the cited RTM technology documents.

RTMs Useful in Ocular Treatment

Thus, for use in the methods of treating ocular diseases, an RTM comprises a binding domain BD sequence that targets a selected intron of an ocular gene and which binds to the target intron 5' to the mutation or defect in the target pre-mRNA; an optional spacer; a 3' splice site; and a target gene coding sequence that encodes an exon of the ocular gene that is 3' to the binding of the BD to the target. This target gene coding sequence corrects the defects or mutations in the target gene. In another embodiment, the RTM also comprises a second binding domain BD sequence that targets a selected intron of the ocular gene and which binds to the target intron 3' to the mutation or defect in the target pre-mRNA; and a 5' splice site for use in replacing an internal exonic sequence. In still another embodiment, the RTM comprises a binding domain BD sequence that targets a selected intron of an ocular gene and which binds to the target intron 3' to the mutation or defect in the target pre-mRNA; a 5' splice site; an optional spacer; and a target gene coding sequence that encodes an exon of the ocular gene that is 5' to the binding of the BD to the target for correcting the defects or mutations in the target gene. In other embodiments, the sequence of the RTM or its components are codon optimized for use in mammalian cells or human cells. In order to fit into the rAAV vector for delivery to the ocular cells, the RTM nucleic acid sequence is less than 4000 kb in length.

As one example, RNA trans-splicing as a treatment of ABCA4-mediated disease, requires constructing and packaging an RTM into AAV. Therefore the RTM is designed to be a nucleic acid molecule of approximately 4,000 nucleic acids in length. As splicing generally occurs between complete exons, in one embodiment, the RTM coding sequence begins at the first nucleotide of the exon following the targeted intron for a 3' RTM. In another embodiment, the RTM coding sequence ends on the last nucleotide of the exon preceding the targeted intron for a 5' RTM. Because the spectrum of patients with Stargardt Disease (or in cone-rod dystrophy, autosomal recessive RP, and age-related macular degeneration) have mutations throughout ABCA4, broad correction of as much of the gene as possible is highly desirable.

Thus, in an embodiment described in the Examples below a 3' RTM and a 5' RTM are designed to replace exons 1-22 and 27-50 of ABCA4, and thus all of the mutations within those exons. The binding domains employed are sequence complementary to introns 22 and 26, respectively. In still other embodiments, the RTM for ABCA4 may replace only certain exons carrying critical mutations.

An important consideration for the process of designing an RTM is the identification of putative binding domains that are accessible and specific. Larger introns offer more time for an RTM to bind before the spliceosome processes out an intron lariat. By comparison of predicted pre-mRNA folding, candidate binding regions are designed to bind regions in ABCA4 intron 22 and intron 26.

In one embodiment of an RTM, wherein the ocular gene is ACA4, the selected intron is Intron 22 for the 5' RTM or Intron 26 for the 3' RTM. In another embodiment, wherein the target ocular gene is CEP290, the selected intron for the 5' RTM is Intron 26 or for the 3' RTM is Intron 37. In still another embodiment in which the target gene is MYO7A, the 5'RTM contains a binding sequence complementary to at least a portion of Intron 18 or a 3'RTM contains a binding sequence complementary to at least a portion of Intron 6. Still other suitable RTMs may be designed according to the teachings herein taking into account the mutations and locations provided in TABLEs 1 to 3.

Recombinant AAV Molecules

A variety of known nucleic acid vectors may be used in these methods to design and assemble the components of the RTM and the recombinant adeno-associated virus (AAV), intended to deliver the RTM to the ocular cells. A wealth of publications known to those of skill in the art discusses the use of a variety of such vectors for delivery of genes (see, e.g., Ausubel et al., Current Protocols in Molecular Biology, John Wiley & Sons, New York, 1989; Kay, M. A. et al, 2001 Nat. Medic., 7(1):33 to 40; and Walther W. and Stein U., 2000 Drugs, 60(2):249 to 71). In one embodiment described herein the vector is a recombinant AAV carrying a the RTM and driven by a promoter that expresses RTM in selected ocular cells of the affected subject. Methods for assembly of the recombinant vectors are well-known (see, e.g., International Patent Publication No. WO 00/15822, published Mar. 23, 2000 and other references cited herein).

In certain embodiments described herein, the RTM(s) carrying the ocular gene binding and coding sequences is delivered to the selected cells, e.g., photoreceptor cells, in need of treatment by means of an adeno-associated virus vector. More than 30 naturally occurring serotypes of AAV are available. Many natural variants in the AAV capsid exist, allowing identification and use of an AAV with properties specifically suited for ocular cells. AAV viruses may be engineered by conventional molecular biology techniques, making it possible to optimize these particles for cell specific delivery of the RTM nucleic acid sequences, for minimizing immunogenicity, for tuning stability and particle lifetime, for efficient degradation, for accurate delivery to the nucleus, etc.

The expression of the RTMs described herein can be achieved in the selected cells through delivery by recombinantly engineered AAVs or artificial AAV's that contain sequences encoding the desired RTM. The use of AAVs is a common mode of exogenous delivery of DNA as it is relatively non-toxic, provides efficient gene transfer, and can be easily optimized for specific purposes. Among the serotypes of AAVs isolated from human or non-human primates (NHP) and well characterized, human serotype 2 has been widely used for efficient gene transfer experiments in different target tissues and animal models. Other AAV serotypes include, but are not limited to, AAV1, AAV3, AAV4, AAV5, AAV6, AAV7, AAV8 and AAV9. Unless otherwise specified, the AAV ITRs, and other selected AAV components described herein, may be readily selected from among any AAV serotype, including, without limitation, AAV1, AAV2, AAV3, AAV4, AAV5, AAV6, AAV7, AAV8, AAV9 or other known and unknown AAV serotypes. These ITRs or other AAV components may be readily isolated using techniques available to those of skill in the art from an AAV serotype. Such AAV may be isolated or obtained from academic, commercial, or public sources (e.g., the American Type Culture Collection, Manassas, Va.). Alternatively, the AAV sequences may be obtained through synthetic or other suitable means by reference to published sequences such as are available in the literature or in databases such as, e.g., GenBank, PubMed, or the like.

See, e.g., WO 2005/033321 or WO2014/124282 for a discussion of various AAV serotypes, which is incorporated herein by reference.

Desirable AAV fragments for assembly into vectors include the cap proteins, including the vp1, vp2, vp3 and hypervariable regions, the rep proteins, including rep 78, rep 68, rep 52, and rep 40, and the sequences encoding these proteins. These fragments may be readily utilized in a variety of vector systems and host cells. Such fragments may be used alone, in combination with other AAV serotype sequences or fragments, or in combination with elements from other AAV or non-AAV viral sequences. As used herein, artificial AAV serotypes include, without limitation, AAV with a non-naturally occurring capsid protein. Such an artificial capsid may be generated by any suitable technique, using a selected AAV sequence (e.g., a fragment of a vp1 capsid protein) in combination with heterologous sequences which may be obtained from a different selected AAV serotype, non-contiguous portions of the same AAV serotype, from a non-AAV viral source, or from a non-viral source. An artificial AAV serotype may be, without limitation, a pseudotyped AAV, a chimeric AAV capsid, a recombinant AAV capsid, or a "humanized" AAV capsid. Pseudotyped vectors, wherein the capsid of one AAV is replaced with a heterologous capsid protein, are useful in the invention. In one embodiment, AAV2/5 a useful pseudotyped vector. In another embodiment, the AAV is AAV2/8.

In one embodiment, the vectors useful in compositions and methods described herein contain, at a minimum, sequences encoding a selected AAV serotype capsid, e.g., an AAV2 capsid, or a fragment thereof. In another embodiment, useful vectors contain, at a minimum, sequences encoding a selected AAV serotype rep protein, e.g., AAV2 rep protein, or a fragment thereof. Optionally, such vectors may contain both AAV cap and rep proteins. In vectors in which both AAV rep and cap are provided, the AAV rep and AAV cap sequences can both be of one serotype origin, e.g., all AAV2 origin. Alternatively, vectors may be used in which the rep sequences are from an AAV serotype which differs from that which is providing the cap sequences. In one embodiment, the rep and cap sequences are expressed from separate sources (e.g., separate vectors, or a host cell and a vector). In another embodiment, these rep sequences are fused in frame to cap sequences of a different AAV serotype to form a chimeric AAV vector, such as AAV2/8 described in U.S. Pat. No. 7,282,199, which is incorporated by reference herein.

A suitable recombinant adeno-associated virus (AAV) is generated by culturing a host cell which contains a nucleic acid sequence encoding an adeno-associated virus (AAV) serotype capsid protein, or fragment thereof, as defined herein; a functional rep gene; a minigene composed of, at a minimum, AAV inverted terminal repeats (ITRs) and the RTM nucleic acid sequence; and sufficient helper functions to permit packaging of the minigene into the AAV capsid protein. The components required to be cultured in the host cell to package an AAV minigene in an AAV capsid may be provided to the host cell in trans. Alternatively, any one or more of the required components (e.g., minigene, rep sequences, cap sequences, and/or helper functions) may be provided by a stable host cell which has been engineered to contain one or more of the required components using methods known to those of skill in the art.

In one embodiment, the AAV comprises a promoter (or a functional fragment of a promoter). The selection of the promoter to be employed in the rAAV may be made from among a wide number of constitutive or inducible promoters that can express the selected transgene in the desired target cell. See, e.g., the list of promoters identified in International Patent Publication No. WO2014/12482, published Aug. 14, 2014, incorporated herein by reference. In one embodiment, the promoter is "cell specific". The term "cell-specific" means that the particular promoter selected for the recombinant vector can direct expression of the selected transgene in a particular cell or ocular cell type. In one embodiment, the promoter is specific for expression of the transgene in photoreceptor cells. In another embodiment, the promoter is specific for expression in the rods and/or cones. In another embodiment, the promoter is specific for expression of the transgene in RPE cells. In another embodiment, the promoter is specific for expression of the transgene in ganglion cells. In another embodiment, the promoter is specific for expression of the transgene in Mueller cells. In another embodiment, the promoter is specific for expression of the transgene in bipolar cells. In another embodiment, the transgene is expressed in any of the above noted ocular cells.

In another embodiment, promoter is the native promoter for the target ocular gene to be expressed. Useful promoters include, without limitation, the rod opsin promoter, the red-green opsin promoter, the blue opsin promoter, the cGMP-β-phosphodiesterase promoter, the mouse opsin promoter (Beltran et al 2010 cited above), the rhodopsin promoter (Mussolino et al, Gene Ther, July 2011, 18(7):637-45); the alpha-subunit of cone transducin (Morrissey et al, BMC Dev, Biol, January 2011, 11:3); beta phosphodiesterase (PDE) promoter; the retinitis pigmentosa (RP1) promoter (Nicord et al, J. Gene Med, December 2007, 9(12): 1015-23); the NXNL2/NXNL1 promoter (Lambard et al, PLoS One, October 2010, 5(10):e13025), the RPE65 promoter; the retinal degeneration slow/peripherin 2 (Rds/perph2) promoter (Cai et al, Exp Eye Res. 2010 August; 91(2):186-94); and the VMD2 promoter (Kachi et al, Human Gene Therapy, 2009 (20:31-9)). Each of these documents is incorporated by reference herein.

Other conventional regulatory sequences contained in the mini-gene or rAAV are also disclosed in documents such as WO2014/124282 and others cited and incorporated by reference herein. One of skill in the art may make a selection among these, and other, expression control sequences without departing from the scope described herein The desired AAV minigene is composed of, at a minimum, the RTM described herein and its regulatory sequences, and 5' and 3' AAV inverted terminal repeats (ITRs). In one embodiment, the ITRs of AAV serotype 2 are used. In another embodiment, the ITRs of AAV serotype 5 or 8 are used. However, ITRs from other suitable serotypes may be selected. It is this minigene which is packaged into a capsid protein and delivered to a selected host cell.

The minigene, rep sequences, cap sequences, and helper functions required for producing the rAAV may be delivered to the packaging host cell in the form of any genetic element which transfers the sequences carried thereon. The selected genetic element may be delivered by any suitable method, including those described herein. The methods used to construct any embodiment described herein are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present invention. See, e.g., K. Fisher et al, 1993 J. Virol., 70:520 to 532 and U.S. Pat. No. 5,478,745, among others. These publications are incorporated by reference herein.

In another aspect, the RTM minigene is prepared in a proviral plasmid, such as those disclosed in International Patent Publication No. WO2012/158757, incorporated herein by reference. Such a proviral plasmid contains a modular recombinant AAV genome comprising in operative association comprising: a wildtype 5' AAV2 ITR sequence flanked by unique restriction sites that permit ready removal or replacement of said ITR; a promoter comprising a 49 nucleic acid cytomegalovirus sequence upstream of a cytomegalovirus (CMV)-chicken beta actin sequence, or a photoreceptor-specific promoter/enhancer, the promoter flanked by unique restriction sites that permit ready removal or replacement of the entire promoter sequence, and the upstream sequence flanked by unique restriction sites that permit ready removal or replacement of only the upstream CMV or enhancer sequence, from the promoter sequence. The RTM described herein is inserted into the site of a multi-cloning polylinker, wherein the RTM is operatively linked to, and under the regulatory control of, the promoter. A bovine growth hormone polyadenylation sequence flanked by unique restriction sites that permit ready removal or replacement of said polyA sequence; and a wildtype 3' AAV2 ITR sequence flanked by unique restriction sites that permit ready removal or replacement of the 3' ITR; are also part of this plasmid. The plasmid backbone comprises the elements necessary for replication in bacterial cells, e.g., a kanamycin resistance gene, and is itself flanked by transcriptional terminator/insulator sequences. As described in the publication immediately referenced, in one embodiment, the plasmid is that designated as p618 comprising the RTM.

In one embodiment, a proviral plasmid comprises (a) a modular recombinant AAV genome comprising in operative association comprising: (i) a wildtype 5' AAV2 ITR sequence flanked by unique restriction sites that permit ready removal or replacement of said ITR; (ii) a promoter comprising (A) a 49 nucleic acid cytomegalovirus sequence upstream of a cytomegalovirus (CMV)-chicken beta actin sequence, or (B) a photoreceptor-specific promoter/enhancer, or (C) a neuronal cell-specific promoter/enhancer. The promoter is flanked by unique restriction sites that permit ready removal or replacement of the entire promoter sequence, and the upstream sequence flanked by unique restriction sites that permit ready removal or replacement of only the upstream CMV or enhancer sequence, from the promoter sequence. Also part of this proviral plasmid is a multi-cloning polylinker sequence that permits insertion of an RTM sequence including any of those described herein, wherein the RTM is operatively linked to, and under the regulatory control of, the promoter; a bovine growth hormone polyadenylation sequence flanked by unique restriction sites that permit ready removal or replacement of said polyA sequence; and a wildtype 3' AAV2 ITR sequence flanked by unique restriction sites that permit ready removal or replacement of the 3' ITR. The proviral plasmid also contains a plasmid backbone comprising the elements necessary for replication in bacterial cells, and further comprising a kanamycin resistance gene, said plasmid backbone flanked by transcriptional terminator/insulator sequences. The proviral plasmid described herein may also contain in the plasmid backbone a non-coding lambda phage 5.1 kb stuffer sequence to increase backbone length and prevent reverse packaging of non-functional AAV genomes.

Figure 3A:
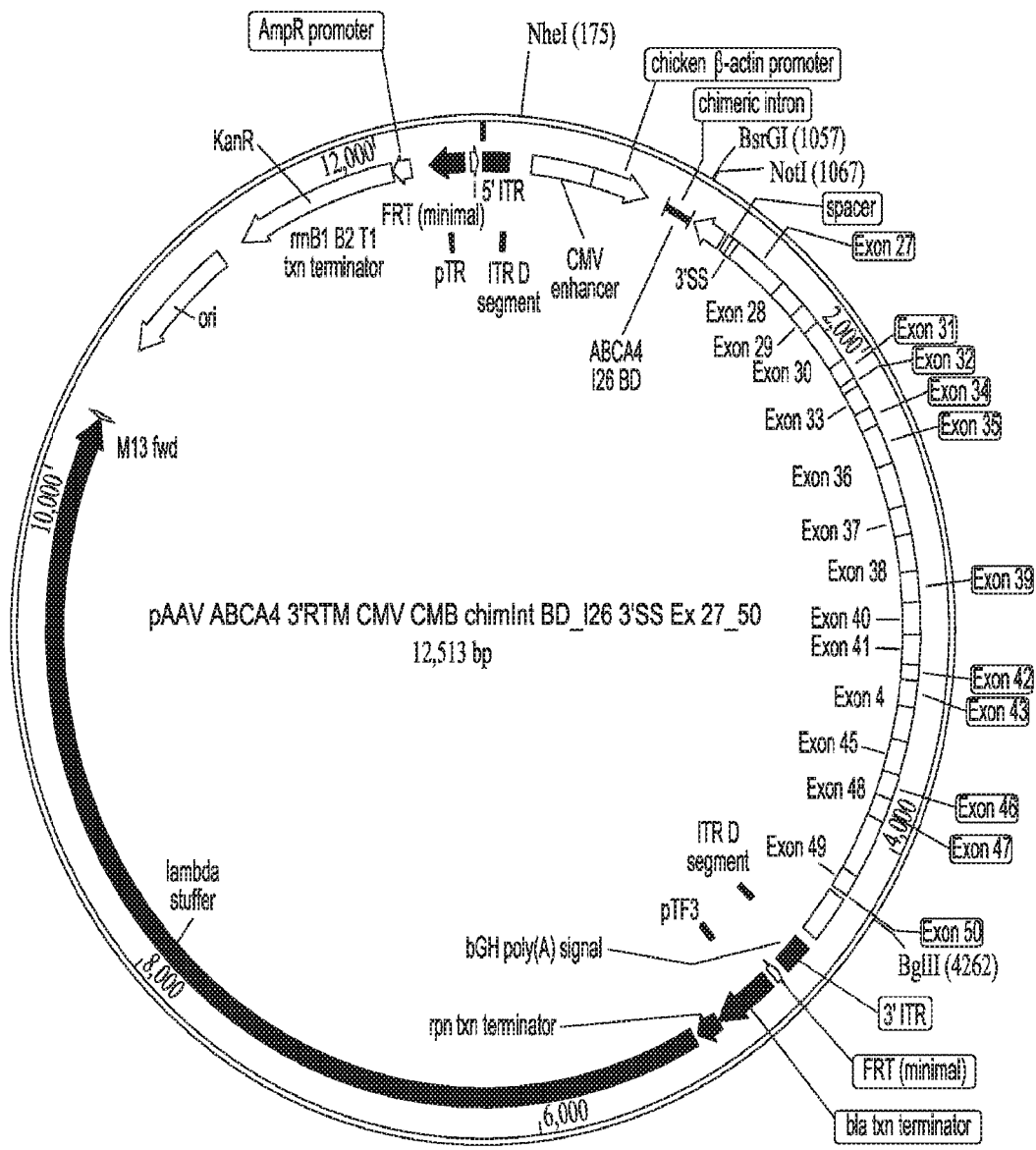
FIG. 3A is a 3'RTM prophetic model for ABCA4 (Exons 27-50) inserted into a modified shorter-intron p618 plasmid.
Figure 3B:
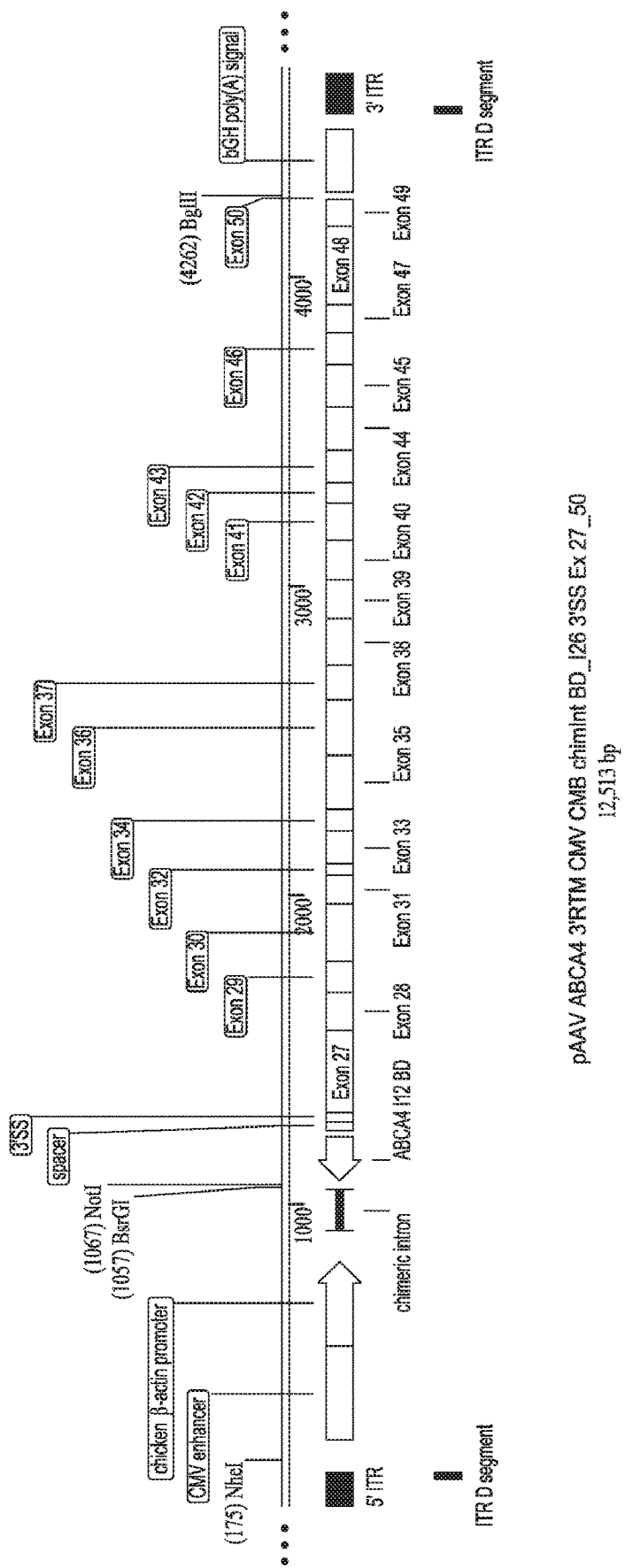
FIG. 3B is a linearized map of the focusing on the provirus containing the RTM of FIG. 3A, i.e., the plasmid bases only between the 5' and 3' AAV ITRs.

In yet a further aspect, the promoter of the proviral plasmid is modified to reduce the size of the promoter to permit larger RTM sequences to be inserted in the rAAV. In one embodiment, the CMV/CBA hybrid promoter, which normally includes a non-coding exon and intron totaling about 1,000 base pairs, is replaced with a 130 bp chimeric intron (chimera between introns from human β-globin and immunoglobulin heavy chain genes), as illustrated in FIGS. 3A and 3B.

These proviral plasmids are then employed in currently conventional packaging methodologies to generate a recombinant virus expressing the RTM transgene carried by the proviral plasmids. Suitable production cell lines are readily selected by one of skill in the art. For example, a suitable host cell can be selected from any biological organism, including prokaryotic (e.g., bacterial) cells, and eukaryotic cells, including, insect cells, yeast cells and mammalian cells. Briefly, the proviral plasmid is transfected into a selected packaging cell, where it may exist transiently. Alternatively, the minigene or gene expression cassette with its flanking ITRs is stably integrated into the genome of the host cell, either chromosomally or as an episome. Suitable transfection techniques are known and may readily be utilized to deliver the recombinant AAV genome to the host cell. Typically, the proviral plasmids are cultured in the host cells which express the cap and/or rep proteins. In the host cells, the minigene consisting of the RTM with flanking AAV ITRs is rescued and packaged into the capsid protein or envelope protein to form an infectious viral particle. Thus a recombinant AAV infectious particle is produced by culturing a packaging cell carrying the proviral plasmid in the presence of sufficient viral sequences to permit packaging of the gene expression cassette viral genome into an infectious AAV envelope or capsid.

As other aspects of this invention are all of the components of the rAAV particle construction including the cell culture comprising host cells transfected with the proviral plasmid or any similar plasmid and the recombinant AAV infectious particle comprising an RTM as described herein.

TABLES 1, 2 and 3 as referred to above are provided below.

TABLE 1

| Target Ocular Gene | Ocular Disease | Mutation | Exon | Target Cells | Intron/SEQ |
|---|---|---|---|---|---|
| ABCA4 | STGD | c.2T > C (p.Met1?) | ex1 | Photoreceptors | Int 22 (NG_009073.1) |
| ABCA4 | STGD | c.20T > A (p.Ile7Lys) | ex1 | Photoreceptors | Int 22 (NG_009073.1) |
| ABCA4 | STGD | c.32T > C (p.Leu11Pro) | ex1 | Photoreceptors | Int 22 (NG_009073.1) |
| ABCA4 | STGD | c.38_46del9 (p.Lys13_Tip15del) | ex1 | Photoreceptors | Int 22 (NG_009073.1) |
| ABCA4 | STGD | c.45G > A (p.Trp15*) | ex1 | Photoreceptors | Int 22 (NG_009073.1) |
| ABCA4 | STGD, CRD | c.52C > T (p.Arg18Trp) | ex1 | Photoreceptors | Int 22 (NG_009073.1) |
| ABCA4 | STGD | c.61C > T (p.Gln21*) | ex1 | Photoreceptors | Int 22 (NG_009073.1) |
| ABCA4 | STGD, CRD | c.70C > T (p.Arg24Cys) | ex2 | Photoreceptors | Int 22 (NG_009073.1) |
| ABCA4 | STGD | c.71G > A (p.Arg24His) | ex2 | Photoreceptors | Int 22 (NG_009073.1) |
| ABCA4 | STGD | c.91T > C (p.Trp31Arg) | ex2 | Photoreceptors | Int 22 (NG_009073.1) |
| ABCA4 | STGD | c.108delT (p.Leu37fs) | ex2 | Photoreceptors | Int 22 (NG_009073.1) |
| ABCA4 | STGD | c.123G > A (p.Trp41*) | ex2 | Photoreceptors | Int 22 (NG_009073.1) |
| ABCA4 | STGD | c.122G > A (p.Trp41*) | ex2 | Photoreceptors | Int 22 (NG_009073.1) |
| ABCA4 | STGD | c.160T > G (p.Cys54Gly) | ex2 | Photoreceptors | Int 22 (NG_009073.1) |
| ABCA4 | STGD | c.160 + 1G > A (—) | int2 | Photoreceptors | Int 22 (NG_009073.1) |
| ABCA4 | STGD | c.160 + 2T > C (—) | int2 | Photoreceptors | Int 22 (NG_009073.1) |
| ABCA4 | STGD | c.161 − 1G > A (—) | int2 | Photoreceptors | Int 22 (NG_009073.1) |
| ABCA4 | STGD, AMD | c.161G > A (p.Cys54Tyr) | ex3 | Photoreceptors | Int 22 (NG_009073.1) |
| ABCA4 | STGD | c.161G > T (p.Cys54Phe) | ex3 | Photoreceptors | Int 22 (NG_009073.1) |
| ABCA4 | STGD | c.164A > C (p.His55Pro) | ex3 | Photoreceptors | Int 22 (NG_009073.1) |
| ABCA4 | STGD | c.164A > G (p.His55Arg) | ex3 | Photoreceptors | Int 22 (NG_009073.1) |
| ABCA4 | STGD | c.174C > G (p.Asn58Lys) | ex3 | Photoreceptors | Int 22 (NG_009073.1) |
| ABCA4 | STGD | c.178G > A (p.Ala60Thr) | ex3 | Photoreceptors | Int 22 (NG_009073.1) |
| ABCA4 | STGD | c.184C > T (p.Pro62Ser) | ex3 | Photoreceptors | Int 22 (NG_009073.1) |
| ABCA4 | STGD | c.190G > C (p.Ala64Pro) | ex3 | Photoreceptors | Int 22 (NG_009073.1) |
| ABCA4 | STGD, CRD | c.194G > A (p.Gly65Glu) | ex3 | Photoreceptors | Int 22 (NG_009073.1) |
| ABCA4 | STGD, AMD | c.203C > T (p.Pro68Leu) | ex3 | Photoreceptors | Int 22 (NG_009073.1) |
| ABCA4 | STGD, CRD | c.203C > G (p.Pro68Arg) | ex3 | Photoreceptors | Int 22 (NG_009073.1) |
| ABCA4 | STGD | c.214G > A (p.Gly72Arg) | ex3 | Photoreceptors | Int 22 (NG_009073.1) |
| ABCA4 | STGD | c.223T > G (p.Cys75Gly) | ex3 | Photoreceptors | Int 22 (NG_009073.1) |
| ABCA4 | STGD | c.230T > A (p.Val77Glu) | ex3 | Photoreceptors | Int 22 (NG_009073.1) |
| ABCA4 | STGD | c.247_250delCAAA (p.Gln83fs) | ex3 | Photoreceptors | Int 22 (NG_009073.1) |
| ABCA4 | CRD, STGD | c.250_251insCAAA (p.Ser84fs) | ex3 | Photoreceptors | Int 22 (NG_009073.1) |
| ABCA4 | STGD | c.286A > G (p.Asn96Asp) | ex3 | Photoreceptors | Int 22 (NG_009073.1) |
| ABCA4 | STGD | c.286A > C (p.Asn96His) | ex3 | Photoreceptors | Int 22 (NG_009073.1) |
| ABCA4 | STGD | c.286A > T (p.Asn96Tyr) | ex3 | Photoreceptors | Int 22 (NG_009073.1) |
| ABCA4 | STGD | c.288C > A (p.Asn96Lys) | ex3 | Photoreceptors | Int 22 (NG_009073.1) |
| ABCA4 | STGD | c.288C > G (p.Asn96Lys) | ex3 | Photoreceptors | Int 22 (NG_009073.1) |
| ABCA4 | STGD | c.296_297insA (p.Asn99fs) | ex3 | Photoreceptors | Int 22 (NG_009073.1) |
| ABCA4 | STGD | c.298T > C (p.Ser100Pro) | ex3 | Photoreceptors | Int 22 (NG_009073.1) |
| ABCA4 | STGD | c.302 + 1G > A (—) | int3 | Photoreceptors | Int 22 (NG_009073.1) |
| ABCA4 | STGD | c.302 + 4A > C (—) | int3 | Photoreceptors | Int 22 (NG_009073.1) |
| ABCA4 | STGD | c.317A > T (p.Tyr106Phe) | ex4 | Photoreceptors | Int 22 (NG_009073.1) |
| ABCA4 | STGD | c.318T > G (p.Tyr106*) | ex4 | Photoreceptors | Int 22 (NG_009073.1) |
| ABCA4 | STGD | c.319C > T (p.Arg107*) | ex4 | Photoreceptors | Int 22 (NG_009073.1) |
| ABCA4 | STGD | c.400C > T (p.Gln134*) | ex4 | Photoreceptors | Int 22 (NG_009073.1) |
| ABCA4 | STGD | c.323A > T (p.Asp108Val) | ex4 | Photoreceptors | Int 22 (NG_009073.1) |

TABLE 1-continued

| | | | | | |
|---|---|---|---|---|---|
| ABCA4 | STGD | c.327dupT (p.Gln110fs) | ex4 | Photoreceptors | Int 22 (NG_009073.1) |
| ABCA4 | STGD | c.355_356delAG (p.Ser119fs) | ex4 | Photoreceptors | Int 22 (NG_009073.1) |
| ABCA4 | STGD | c.428C > T (p.Pro143Leu) | ex4 | Photoreceptors | Int 22 (NG_009073.1) |
| ABCA4 | STGD | c.454C > T (p.Arg152*) | ex5 | Photoreceptors | Int 22 (NG_009073.1) |
| ABCA4 | STGD, FFM | c.455G > A (p.Arg152Gln) | ex5 | Photoreceptors | Int 22 (NG_009073.1) |
| ABCA4 | STGD | c.466A > G (p.Ile156Val) | ex5 | Photoreceptors | Int 22 (NG_009073.1) |
| ABCA4 | CRD | c.481G > A (p.Glu161Lys) | ex5 | Photoreceptors | Int 22 (NG_009073.1) |
| ABCA4 | STGD | c.514G > A (p.Gly172Ser) | ex5 | Photoreceptors | Int 22 (NG_009073.1) |
| ABCA4 | STGD | c.560G > A (p.Arg187His) | ex5 | Photoreceptors | Int 22 (NG_009073.1) |
| ABCA4 | STGD | c.564delA (p.Glu189fs) | ex5 | Photoreceptors | Int 22 (NG_009073.1) |
| ABCA4 | STGD | c.570G > C (p.Gln190His) | ex5 | Photoreceptors | Int 22 (NG_009073.1) |
| ABCA4 | STGD | c.571 − 2A > G (—) | int5 | Photoreceptors | Int 22 (NG_009073.1) |
| ABCA4 | STGD | c.571 − 2A > T (—) | int5 | Photoreceptors | Int 22 (NG_009073.1) |
| ABCA4 | STGD | c.571 − 1G > T (—) | int5 | Photoreceptors | Int 22 (NG_009073.1) |
| ABCA4 | STGD | c.574G > A (p.Ala192Thr) | ex6 | Photoreceptors | Int 22 (NG_009073.1) |
| ABCA4 | STGD | c.618C > G (p.Ser206Arg) | ex6 | Photoreceptors | Int 22 (NG_009073.1) |
| ABCA4 | STGD | c.618C > A (p.Ser206Arg) | ex6 | Photoreceptors | Int 22 (NG_009073.1) |
| ABCA4 | STGD, AMD, CRD | c.634C > T (p.Arg212Cys) | ex6 | Photoreceptors | Int 22 (NG_009073.1) |
| ABCA4 | STGD | c.635G > A (p.Arg212His) | ex6 | Photoreceptors | Int 22 (NG_009073.1) |
| ABCA4 | STGD | c.655A > T (p.Arg219*) | ex6 | Photoreceptors | Int 22 (NG_009073.1) |
| ABCA4 | STGD | c.656G > C (p.Arg219Thr) | ex6 | Photoreceptors | Int 22 (NG_009073.1) |
| ABCA4 | STGD | c.658C > T (p.Arg220Cys) | ex6 | Photoreceptors | Int 22 (NG_009073.1) |
| ABCA4 | STGD | c.664delG (p.Ala222fs) | ex6 | Photoreceptors | Int 22 (NG_009073.1) |
| ABCA4 | STGD, AMD | c.666_678del13 (p.Lys223fs) | ex6 | Photoreceptors | Int 22 (NG_009073.1) |
| ABCA4 | STGD | c.667A > C (p.Lys223Gln) | ex6 | Photoreceptors | Int 22 (NG_009073.1) |
| ABCA4 | STGD | c.671delC (p.Thr224fs) | ex6 | Photoreceptors | Int 22 (NG_009073.1) |
| ABCA4 | STGD | c.677G > T (p.Arg226Leu) | ex6 | Photoreceptors | Int 22 (NG_009073.1) |
| ABCA4 | STGD | c.688T > A (p.Cys230Ser) | ex6 | Photoreceptors | Int 22 (NG_009073.1) |
| ABCA4 | STGD | c.700C > T (p.Gln234*) | ex6 | Photoreceptors | Int 22 (NG_009073.1) |
| ABCA4 | STGD | c.730_731delCT (p.Leu244fs) | ex6 | Photoreceptors | Int 22 (NG_009073.1) |
| ABCA4 | STGD | c.731T > C (p.Leu244Pro) | ex6 | Photoreceptors | Int 22 (NG_009073.1) |
| ABCA4 | STGD | c.735T > G (p.Tyr245*) | ex6 | Photoreceptors | Int 22 (NG_009073.1) |
| ABCA4 | STGD | c.736G > A (p.Ala246Thr) | ex6 | Photoreceptors | Int 22 (NG_009073.1) |
| ABCA4 | STGD | c.740A > G (p.Asn247Ser) | ex6 | Photoreceptors | Int 22 (NG_009073.1) |
| ABCA4 | STGD | c.740A > T (p.Asn247Ile) | ex6 | Photoreceptors | Int 22 (NG_009073.1) |
| ABCA4 | STGD | c.746A > G (p.Asp249Gly) | ex6 | Photoreceptors | Int 22 (NG_009073.1) |
| ABCA4 | STGD | c.760T > C (p.Phe254Leu) | ex6 | Photoreceptors | Int 22 (NG_009073.1) |
| ABCA4 | STGD | c.763C > T(p.Arg255Cys) | ex6 | Photoreceptors | Int 22 (NG_009073.1) |
| ABCA4 | STGD, AMD, CRD | c.768G > T (p.(=)) | ex6 | Photoreceptors | Int 22 (NG_009073.1) |
| ABCA4 | AMD | c.769 − 5T > G (—) | int6 | Photoreceptors | Int 22 (NG_009073.1) |
| ABCA4 | STGD | c.769 − 1G > T (—) | int6 | Photoreceptors | Int 22 (NG_009073.1) |
| ABCA4 | STGD | c.770T > G (p.Leu257Arg) | ex7 | Photoreceptors | Int 22 (NG_009073.1) |
| ABCA4 | STGD | c.832delT (p.Ser278fs) | ex7 | Photoreceptors | Int 22 (NG_009073.1) |
| ABCA4 | STGD | c.839T > G (p.Met280Arg) | ex7 | Photoreceptors | Int 22 (NG_009073.1) |
| ABCA4 | ARRP | c.859 − 45_952delinsTCTGACC (—) | int7/ex8 | Photoreceptors | Int 22 (NG_009073.1) |
| ABCA4 | STGD | c.868C > T (p.Arg290Trp) | ex8 | Photoreceptors | Int 22 (NG_009073.1) |
| ABCA4 | STGD | c.872C > T (p.Pro291Leu) | ex8 | Photoreceptors | Int 22 (NG_009073.1) |
| ABCA4 | STGD | c.880C > T (p.Gln294*) | ex8 | Photoreceptors | Int 22 (NG_009073.1) |
| ABCA4 | STGD | c.885delC (p.Leu296fs) | ex8 | Photoreceptors | Int 22 (NG_009073.1) |
| ABCA4 | STGD | c.899C > A (p.Thr300Asn) | ex8 | Photoreceptors | Int 22 (NG_009073.1) |
| ABCA4 | STGD | c.926C > G (p.Pro309Arg) | ex8 | Photoreceptors | Int 22 (NG_009073.1) |
| ABCA4 | STGD | c.982G > T (p.Glu328*) | ex8 | Photoreceptors | Int 22 (NG_009073.1) |
| ABCA4 | STGD | c.983A > T (p.Glu328Val) | ex8 | Photoreceptors | Int 22 (NG_009073.1) |
| ABCA4 | STGD | c.997C > T (p.Arg333Trp) | ex8 | Photoreceptors | Int 22 (NG_009073.1) |
| ABCA4 | STGD | c.998G > A (p.Arg333Gln) | ex8 | Photoreceptors | Int 22 (NG_009073.1) |
| ABCA4 | STGD | c.1007C > G (p.Ser336Cys) | ex8 | Photoreceptors | Int 22 (NG_009073.1) |
| ABCA4 | STGD | c.1015T > G (p.Trp339Gly) | ex8 | Photoreceptors | Int 22 (NG_009073.1) |
| ABCA4 | STGD | c.1018T > G (p.Tyr340Asp) | ex8 | Photoreceptors | Int 22 (NG_009073.1) |
| ABCA4 | STGD | c.1018T > C (p.Tyr340His) | ex8 | Photoreceptors | Int 22 (NG_009073.1) |
| ABCA4 | STGD | c.1029_1030insT (p.Asn344*) | ex8 | Photoreceptors | Int 22 (NG_009073.1) |
| ABCA4 | STGD | c.1025_1038del14 (p.Asp342fs) | ex8 | Photoreceptors | Int 22 (NG_009073.1) |
| ABCA4 | STGD | c.1037A > C (p.Lys346Thr) | ex8 | Photoreceptors | Int 22 (NG_009073.1) |
| ABCA4 | CRD | c.1066A > T (p.Lys356*) | ex8 | Photoreceptors | Int 22 (NG_009073.1) |
| ABCA4 | STGD | c.1086T > A (p.Tyr362*) | ex8 | Photoreceptors | Int 22 (NG_009073.1) |
| ABCA4 | STGD | c.110T > A (p.Asn380Lys) | ex9 | Photoreceptors | Int 22 (NG_009073.1) |
| ABCA4 | STGD, CRD | c.1220C > T (p.Ala407Val) | ex9 | Photoreceptors | Int 22 (NG_009073.1) |
| ABCA4 | STGD | c.1222C > T (p.Arg408*) | ex9 | Photoreceptors | Int 22 (NG_009073.1) |
| ABCA4 | STGD | c.1225delA(p.Arg409fs) | ex9 | Photoreceptors | Int 22 (NG_009073.1) |

TABLE 1-continued

| | | | | | |
|---|---|---|---|---|---|
| ABCA4 | STGD | c.1239 + 1G > C (—) | int9 | Photoreceptors | Int 22 (NG_009073.1) |
| ABCA4 | STGD | c.1240 − 2A > G (—) | int9 | Photoreceptors | Int 22 (NG_009073.1) |
| ABCA4 | STGD | c.1245C > A (p.Asn415Lys) | ex10 | Photoreceptors | Int 22 (NG_009073.1) |
| ABCA4 | STGD | c.1253T > C (p.Phe418Ser) | ex10 | Photoreceptors | Int 22 (NG_009073.1) |
| ABCA4 | STGD | c.1268A > G (p.His423Arg) | ex10 | Photoreceptors | Int 22 (NG_009073.1) |
| ABCA4 | STGD | c.1268A > C (p.His423Pro) | ex10 | Photoreceptors | Int 22 (NG_009073.1) |
| ABCA4 | STGD, ARRP | c.1271T > C (p.Val424Ala) | ex10 | Photoreceptors | Int 22 (NG_009073.1) |
| ABCA4 | STGD | c.1294G > A (p.Glu432Lys) | ex10 | Photoreceptors | Int 22 (NG_009073.1) |
| ABCA4 | STGD | c.1317G > A (p.Trp439*) | ex10 | Photoreceptors | Int 22 (NG_009073.1) |
| ABCA4 | STGD | c.1325T > C (p.Phe442Ser) | ex10 | Photoreceptors | Int 22 (NG_009073.1) |
| ABCA4 | STGD | c.1335C > G (p.Ser445Arg) | ex10 | Photoreceptors | Int 22 (NG_009073.1) |
| ABCA4 | STGD | c.1344delG (p.Met448fs) | ex10 | Photoreceptors | Int 22 (NG_009073.1) |
| ABCA4 | CRD | IVS10 − 38t > c | in10 | Photoreceptors | Int 22 (NG_009073.1) |
| ABCA4 | STGD | c.1357G > T (p.Asp453Tyr) | ex11 | Photoreceptors | Int 22 (NG_009073.1) |
| ABCA4 | STGD | c.1374delA (p.Thr459fs) | ex11 | Photoreceptors | Int 22 (NG_009073.1) |
| ABCA4 | STGD | c.1381A > T (p.Lys461*) | ex11 | Photoreceptors | Int 22 (NG_009073.1) |
| ABCA4 | STGD | c.1390_1391delTT (p.Leu464fs) | ex11 | Photoreceptors | Int 22 (NG_009073.1) |
| ABCA4 | STGD, AMD | c.1411G > A (p.Glu471Lys) | ex11 | Photoreceptors | Int 22 (NG_009073.1) |
| ABCA4 | STGD | c.1494C > A (p.Asp498Glu) | ex11 | Photoreceptors | Int 22 (NG_009073.1) |
| ABCA4 | STGD | c.1506_1514del9 (p.Phe503_Ile505del) | ex11 | Photoreceptors | Int 22 (NG_009073.1) |
| ABCA4 | STGD | c.1513_1517del5 (p.Ile505*) | ex11 | Photoreceptors | Int 22 (NG_009073.1) |
| ABCA4 | STGD | c.1522C > T (p.Arg508Cys) | ex11 | Photoreceptors | Int 22 (NG_009073.1) |
| ABCA4 | STGD | c.1531C > T (p.Arg511Cys) | ex11 | Photoreceptors | Int 22 (NG_009073.1) |
| ABCA4 | STGD | c.1554 + 1G > A (—) | int11 | Photoreceptors | Int 22 (NG_009073.1) |
| ABCA4 | STGD | c.1555-1seG > A (—) | int11 | Photoreceptors | Int 22 (NG_009073.1) |
| ABCA4 | STGD | c.1569T > G (p.Asp523Glu) | ex12 | Photoreceptors | Int 22 (NG_009073.1) |
| ABCA4 | STGD | c.1574T > G (p.Phe525Cys) | ex12 | Photoreceptors | Int 22 (NG_009073.1) |
| ABCA4 | STGD | c.1574T > C (p.Phe525Ser) | ex12 | Photoreceptors | Int 22 (NG_009073.1) |
| ABCA4 | STGD | c.1609C > T (p.Arg537Cys) | ex12 | Photoreceptors | Int 22 (NG_009073.1) |
| ABCA4 | STGD | c.1610G > A (p.Arg537His) | ex12 | Photoreceptors | Int 22 (NG_009073.1) |
| ABCA4 | STGD | c.1613C > A (p.Ala538Asp) | ex12 | Photoreceptors | Int 22 (NG_009073.1) |
| ABCA4 | STGD | c.1613C > T (p.Ala538Val) | ex12 | Photoreceptors | Int 22 (NG_009073.1) |
| ABCA4 | STGD, CRD, RP | c.1622T > C (p.Leu541Pro) | ex12 | Photoreceptors | Int 22 (NG_009073.1) |
| ABCA4 | STGD | c.1645G > C (p.Ala549Pro) | ex12 | Photoreceptors | Int 22 (NG_009073.1) |
| ABCA4 | STGD, AMD | c.1648G > A (p.Gly550Arg) | ex12 | Photoreceptors | Int 22 (NG_009073.1) |
| ABCA4 | STGD | c.1654G > A (p.Val552Ile) | ex12 | Photoreceptors | Int 22 (NG_009073.1) |
| ABCA4 | STGD | c.1659C > G (p.Phe553Leu) | ex12 | Photoreceptors | Int 22 (NG_009073.1) |
| ABCA4 | STGD | c.1699G > A (p.Val567Met) | ex12 | Photoreceptors | Int 22 (NG_009073.1) |
| ABCA4 | STGD | c.1714C > T (p.Arg572*) | ex12 | Photoreceptors | Int 22 (NG_009073.1) |
| ABCA4 | STGD | c.1715G > A (p.Arg572Gln) | ex12 | Photoreceptors | Int 22 (NG_009073.1) |
| ABCA4 | STGD | c.1715G > C (p.Arg572Pro) | ex12 | Photoreceptors | Int 22 (NG_009073.1) |
| ABCA4 | STGD | c.1745A > G (p.Asn582Ser) | ex12 | Photoreceptors | Int 22 (NG_009073.1) |
| ABCA4 | ARRP, CRD, STGD | c.1760 + 2T > G (—) | int12 | Photoreceptors | Int 22 (NG_009073.1) |
| ABCA4 | CRD | c.1789C > T (p.Pro597Ser) | ex13 | Photoreceptors | Int 22 (NG_009073.1) |
| ABCA4 | STGD | c.1798G > T (p.Asp600Tyr) | ex13 | Photoreceptors | Int 22 (NG_009073.1) |
| ABCA4 | STGD | c.1804C > T (p.Arg602Trp) | ex13 | Photoreceptors | Int 22 (NG_009073.1) |
| ABCA4 | STGD | c.1805G > A (p.Arg602Gln) | ex13 | Photoreceptors | Int 22 (NG_009073.1) |
| ABCA4 | STGD | c.1811T > G (p.Ile604Ser) | ex13 | Photoreceptors | Int 22 (NG_009073.1) |
| ABCA4 | STGD | c.1817G > C (p.Gly606Ala) | ex13 | Photoreceptors | Int 22 (NG_009073.1) |
| ABCA4 | STGD | c.1817G > A (p.Gly606Asp) | ex13 | Photoreceptors | Int 22 (NG_009073.1) |
| ABCA4 | STGD | c.1819G > T (p.Gly607Trp) | ex13 | Photoreceptors | Int 22 (NG_009073.1) |
| ABCA4 | STGD | c.1819G > A (p.Gly607Arg) | ex13 | Photoreceptors | Int 22 (NG_009073.1) |
| ABCA4 | STGD | c.1819G > C (p.Gly607Arg) | ex13 | Photoreceptors | Int 22 (NG_009073.1) |
| ABCA4 | STGD | c.1822T > A (p.Phe608Ile) | ex13 | Photoreceptors | Int 22 (NG_009073.1) |
| ABCA4 | STGD | c.1822T > C (p.Phe608Leu) | ex13 | Photoreceptors | Int 22 (NG_009073.1) |
| ABCA4 | STGD | c.1823T > A (p.Phe608Tyr) | ex13 | Photoreceptors | Int 22 (NG_009073.1) |
| ABCA4 | STGD | c.1843G > T (p.Val615Phe) | ex13 | Photoreceptors | Int 22 (NG_009073.1) |
| ABCA4 | STGD | c.1846G > A (p.Glu616Lys) | ex13 | Photoreceptors | Int 22 (NG_009073.1) |
| ABCA4 | ARRP, STGD | c.1847delA (p.Glu616fs) | ex13 | Photoreceptors | Int 22 (NG_009073.1) |
| ABCA4 | STGD | c.1848_1857del10 (p.Ile619fs) | ex13 | Photoreceptors | Int 22 (NG_009073.1) |
| ABCA4 | STGD | c.1852G > A (p.Gly618Arg) | ex13 | Photoreceptors | Int 22 (NG_009073.1) |
| ABCA4 | CRD | c.1853G > A (p.Gly618Glu) | ex13 | Photoreceptors | Int 22 (NG_009073.1) |
| ABCA4 | STGD | c.1868A > G (p.Gln623Arg) | ex13 | Photoreceptors | Int 22 (NG_009073.1) |
| ABCA4 | STGD, ARRP | c.1894delA (p.Ile632fs) | ex13 | Photoreceptors | Int 22 (NG_009073.1) |
| ABCA4 | STGD | c.1903C > A (p.Gln635Lys) | ex13 | Photoreceptors | Int 22 (NG_009073.1) |
| ABCA4 | STGD | c.1903C > T (p.Gln635*) | ex13 | Photoreceptors | Int 22 (NG_009073.1) |
| ABCA4 | STGD | c.1906C > T (p.Gln636*) | ex13 | Photoreceptors | Int 22 (NG_009073.1) |
| ABCA4 | STGD | c.1908G > T (p.Gln636His) | ex13 | Photoreceptors | Int 22 (NG_009073.1) |

TABLE 1-continued

| Gene | Disease | Variant | Location | Tissue | Intron target |
|---|---|---|---|---|---|
| ABCA4 | STGD | c.1917C > A (p.Tyr639*) | ex13 | Photoreceptors | Int 22 (NG_009073.1) |
| ABCA4 | STGD | c.1917C > T (p.Tyr639(=)) | ex13 | Photoreceptors | Int 22 (NG_009073.1) |
| ABCA4 | STGD | c.1922G > C (p.Cys641Ser) | ex13 | Photoreceptors | Int 22 (NG_009073.1) |
| ABCA4 | STGD | c.1927G > A (p.Val643Met) | ex13 | Photoreceptors | Int 22 (NG_009073.1) |
| ABCA4 | STGD | c.1928T > G (p.Val643Gly) | ex13 | Photoreceptors | Int 22 (NG_009073.1) |
| ABCA4 | STGD, AMD | c.1933G > A (p.Asp645Asn) | ex13 | Photoreceptors | Int 22 (NG_009073.1) |
| ABCA4 | STGD, ARRP | c.1937 + 1G > A (—) | int13 | Photoreceptors | Int 22 (NG_009073.1) |
| ABCA4 | STGD | c.1937 + 2T > C (—) | int13 | Photoreceptors | Int 22 (NG_009073.1) |
| ABCA4 | STGD | c.1938 − 2A > G (—) | int13 | Photoreceptors | Int 22 (NG_009073.1) |
| ABCA4 | STGD | c.1938 − 1G > A (—) | int13 | Photoreceptors | Int 22 (NG_009073.1) |
| ABCA4 | STGD | c.1957C > T (p.Arg653Cys) | ex14 | Photoreceptors | Int 22 (NG_009073.1) |
| ABCA4 | STGD | c.1964T > G (p.Phe655Cys) | ex14 | Photoreceptors | Int 22 (NG_009073.1) |
| ABCA4 | STGD | c.1977G > A (p.Met659Ile) | ex14 | Photoreceptors | Int 22 (NG_009073.1) |
| ABCA4 | STGD | c.1982_1983insG (p.Ala662fs) | ex14 | Photoreceptors | Int 22 (NG_009073.1) |
| ABCA4 | STGD | c.1988G > A (p.Trp663*) | ex14 | Photoreceptors | Int 22 (NG_009073.1) |
| ABCA4 | STGD | c.1995C > A (p.Tyr665*) | ex14 | Photoreceptors | Int 22 (NG_009073.1) |
| ABCA4 | STGD | c.2005_2006delAT (p.Met669fs) | ex14 | Photoreceptors | Int 22 (NG_009073.1) |
| ABCA4 | STGD | c.2041C > T (p.Arg681*) | ex14 | Photoreceptors | Int 22 (NG_009073.1) |
| ABCA4 | STGD | c.2057T > C (p.Leu686Ser) | ex14 | Photoreceptors | Int 22 (NG_009073.1) |
| ABCA4 | STGD | c.2069G > T (p.Gly690Val) | ex14 | Photoreceptors | Int 22 (NG_009073.1) |
| ABCA4 | STGD | c.2090G > A (p.Trp697*) | ex14 | Photoreceptors | Int 22 (NG_009073.1) |
| ABCA4 | STGD | c.2099G > A (p.Trp700*) | ex14 | Photoreceptors | Int 22 (NG_009073.1) |
| ABCA4 | STGD | c.2147C > T (p.Thr716Met) | ex14 | Photoreceptors | Int 22 (NG_009073.1) |
| ABCA4 | STGD, AMD | c.2160 + 1G > C (—) | int14 | Photoreceptors | Int 22 (NG_009073.1) |
| ABCA4 | STGD | c.2243G > A (p.Cys748Tyr) | ex15 | Photoreceptors | Int 22 (NG_009073.1) |
| ABCA4 | STGD | c.2285C > A (p.Ala762Glu) | ex15 | Photoreceptors | Int 22 (NG_009073.1) |
| ABCA4 | STGD | c.2291G > A (p.Cys764Tyr) | ex15 | Photoreceptors | Int 22 (NG_009073.1) |
| ABCA4 | STGD | c.2292delT (p.Cys764*) | ex15 | Photoreceptors | Int 22 (NG_009073.1) |
| ABCA4 | STGD | c.2294G > A (p.Ser765Asn) | ex15 | Photoreceptors | Int 22 (NG_009073.1) |
| ABCA4 | STGD | c.2295T > G (p.Ser765Arg) | ex15 | Photoreceptors | Int 22 (NG_009073.1) |
| ABCA4 | STGD, ARRP, CRD | c.2300T > A (p.Val767Asp) | ex15 | Photoreceptors | Int 22 (NG_009073.1) |
| ABCA4 | STGD | c.2337C > A (p.Cys779*) | ex15 | Photoreceptors | Int 22 (NG_009073.1) |
| ABCA4 | STGD | c.2382 + 1G > A (—) | int15 | Photoreceptors | Int 22 (NG_009073.1) |
| ABCA4 | STGD | c.2385C > G (p.Ser795Arg) | ex16 | Photoreceptors | Int 22 (NG_009073.1) |
| ABCA4 | STGD | c.2385_2400del16 (p.Ser795fs) | ex16 | Photoreceptors | Int 22 (NG_009073.1) |
| ABCA4 | STGD | c.2390T > C (p.Leu797Pro) | ex16 | Photoreceptors | Int 22 (NG_009073.1) |
| ABCA4 | STGD | c.2401G > A (p.Ala801Thr) | ex16 | Photoreceptors | Int 22 (NG_009073.1) |
| ABCA4 | STGD | c.2409_2410delAT (p.Phe804fs) | ex16 | Photoreceptors | Int 22 (NG_009073.1) |
| ABCA4 | STGD, AMD | c.2453G > A (p.Gly818Glu) | ex16 | Photoreceptors | Int 22 (NG_009073.1) |
| ABCA4 | STGD, AMD | c.2461T > A (p.Trp821Arg) | ex16 | Photoreceptors | Int 22 (NG_009073.1) |
| ABCA4 | STGD | c.2471T > C (p.Ile824Thr) | ex16 | Photoreceptors | Int 22 (NG_009073.1) |
| ABCA4 | STGD | c.2486C > T (p.Thr829Met) | ex16 | Photoreceptors | Int 22 (NG_009073.1) |
| ABCA4 | STGD | c.2519T > G (p.Met840Arg) | ex16 | Photoreceptors | Int 22 (NG_009073.1) |
| ABCA4 | STGD | c.2536G > C (p.Asp846His) | ex16 | Photoreceptors | Int 22 (NG_009073.1) |
| ABCA4 | STGD | c.2546T > C (p.Val849Ala) | ex16 | Photoreceptors | Int 22 (NG_009073.1) |
| ABCA4 | STGD | c.2552G > A (p.Gly851Asp) | ex16 | Photoreceptors | Int 22 (NG_009073.1) |
| ABCA4 | STGD | c.2560G > A (p.Ala854Thr) | ex16 | Photoreceptors | Int 22 (NG_009073.1) |
| ABCA4 | STGD | c.2564G > A (p.Trp855*) | ex16 | Photoreceptors | Int 22 (NG_009073.1) |
| ABCA4 | STGD | c.2565G > A (p.Trp855*) | ex16 | Photoreceptors | Int 22 (NG_009073.1) |
| ABCA4 | STGD | c.2570seT > C (p.Leu857Pro) | ex16 | Photoreceptors | Int 22 (NG_009073.1) |
| ABCA4 | STGD | c.2570delT (p.Asp858fs) | ex16 | Photoreceptors | Int 22 (NG_009073.1) |
| ABCA4 | STGD | c.2587 + 1G > A (—) | int16 | Photoreceptors | Int 22 (NG_009073.1) |
| ABCA4 | STGD, AMD, CRD, ARRP | c.2588G > C (p.Gly863Ala) | ex17 | Photoreceptors | Int 22 (NG_009073.1) |
| ABCA4 | STGD | c.2609C > T (p.Pro870Leu) | ex17 | Photoreceptors | Int 22 (NG_009073.1) |
| ABCA4 | STGD | c.2616_2617delCT (p.Phe873fs) | ex17 | Photoreceptors | Int 22 (NG_009073.1) |
| ABCA4 | STGD | c.2617T > C (p.Phe873Leu) | ex17 | Photoreceptors | Int 22 (NG_009073.1) |
| ABCA4 | STGD | c.2627A > C (p.Gln876Pro) | ex17 | Photoreceptors | Int 22 (NG_009073.1) |
| ABCA4 | STGD | c.2644G > A (p.Gly882Ser) | ex17 | Photoreceptors | Int 22 (NG_009073.1) |
| ABCA4 | STGD | c.2690C > T (p.Thr897Ile) | ex18 | Photoreceptors | Int 22 (NG_009073.1) |
| ABCA4 | STGD | c.2701A > G (p.Thr901Ala) | ex18 | Photoreceptors | Int 22 (NG_009073.1) |
| ABCA4 | STGD | c.2791G > A (p.Val931Met) | ex19 | Photoreceptors | Int 22 (NG_009073.1) |
| ABCA4 | STGD | c.2798A > T (p.Asn933Ile) | ex19 | Photoreceptors | Int 22 (NG_009073.1) |
| ABCA4 | STGD | c.2804T > C (p.Val935Ala) | ex19 | Photoreceptors | Int 22 (NG_009073.1) |
| ABCA4 | STGD | c.2819C > G (p.Pro940Arg) | ex19 | Photoreceptors | Int 22 (NG_009073.1) |

TABLE 1-continued

| Gene | Disease | Mutation | Location | Cell Type | Reference |
|---|---|---|---|---|---|
| ABCA4 | STGD | c.2826delC (p.Arg943fs) | ex19 | Photoreceptors | Int 22 (NG_009073.1) |
| ABCA4 | STGD, CRD, AMD, ARRP | c.2827C > T (p.Arg943Trp) | ex19 | Photoreceptors | Int 22 (NG_009073.1) |
| ABCA4 | STGD | c.2828G > A (p.Arg943Gln) | ex19 | Photoreceptors | Int 22 (NG_009073.1) |
| ABCA4 | STGD | c.2829delG (p.Pro994fs) | ex19 | Photoreceptors | Int 22 (NG_009073.1) |
| ABCA4 | STGD | c.2860T > G (p.Tyr954Asp) | ex19 | Photoreceptors | Int 22 (NG_009073.1) |
| ABCA4 | STGD | c.2861A > C (p.Tyr954Ser) | ex19 | Photoreceptors | Int 22 (NG_009073.1) |
| ABCA4 | STGD | c.2870A > G (p.Gln957Arg) | ex19 | Photoreceptors | Int 22 (NG_009073.1) |
| ABCA4 | STGD | c.2876C > T (p.Thr959Ile) | ex19 | Photoreceptors | Int 22 (NG_009073.1) |
| ABCA4 | STGD | c.2883delC (p.Leu962fs) | ex19 | Photoreceptors | Int 22 (NG_009073.1) |
| ABCA4 | STGD | c.2888delG (p.Gly963fs) | ex19 | Photoreceptors | Int 22 (NG_009073.1) |
| ABCA4 | STGD | c.2893A > T (p.Asn965Tyr) | ex19 | Photoreceptors | Int 22 (NG_009073.1) |
| ABCA4 | STGD, AMD | c.2894A > G (p.Asn965Ser) | ex19 | Photoreceptors | Int 22 (NG_009073.1) |
| ABCA4 | STGD | c.2906A > G (p.Lys969Arg) | ex19 | Photoreceptors | Int 22 (NG_009073.1) |
| ABCA4 | STGD | c.2908A > C (p.Thr970Pro) | ex19 | Photoreceptors | Int 22 (NG_009073.1) |
| ABCA4 | STGD | c.2909C > T (p.Thr970Ile) | ex19 | Photoreceptors | Int 22 (NG_009073.1) |
| ABCA4 | STGD | c.2912C > A (p.Thr971Asn) | ex19 | Photoreceptors | Int 22 (NG_009073.1) |
| ABCA4 | STGD | c.2915C > A (p.Thr972Asn) | ex19 | Photoreceptors | Int 22 (NG_009073.1) |
| ABCA4 | STGD | c.2919 − 2A > G (—) | int19 | Photoreceptors | Int 22 (NG_009073.1) |
| ABCA4 | STGD | c.2920T > C (p.Ser974Pro) | ex20 | Photoreceptors | Int 22 (NG_009073.1) |
| ABCA4 | STGD | c.2932G > T (p.Gly978Cys) | ex20 | Photoreceptors | Int 22 (NG_009073.1) |
| ABCA4 | STGD | c.2933G > A (p.Gly978Asp) | ex20 | Photoreceptors | Int 22 (NG_009073.1) |
| ABCA4 | STGD | c.2947A > G (p.Thr983Ala) | ex20 | Photoreceptors | Int 22 (NG_009073.1) |
| ABCA4 | STGD | c.2948C > T (p.Thr983Ile) | ex20 | Photoreceptors | Int 22 (NG_009073.1) |
| ABCA4 | STGD | c.2966T > C (p.Val989Ala) | ex20 | Photoreceptors | Int 22 (NG_009073.1) |
| ABCA4 | STGD | c.2967delT (p.Gly991fs) | ex20 | Photoreceptors | Int 22 (NG_009073.1) |
| ABCA4 | STGD | c.2971G > C (p.Gly991Arg) | ex20 | Photoreceptors | Int 22 (NG_009073.1) |
| ABCA4 | STGD | c.2971G > T (p.Gly991*) | ex20 | Photoreceptors | Int 22 (NG_009073.1) |
| ABCA4 | STGD | c.2977_2984del8 (p.Asp993fs) | ex20 | Photoreceptors | Int 22 (NG_009073.1) |
| ABCA4 | STGD | c.3041T > G (p.Leu1014Arg) | ex20 | Photoreceptors | Int 22 (NG_009073.1) |
| ABCA4 | STGD | c.3043T > A (p.Phe1015Ile) | ex20 | Photoreceptors | Int 22 (NG_009073.1) |
| ABCA4 | STGD | c.3050 + 5G > A (—) | int20 | Photoreceptors | Int 22 (NG_009073.1) |
| ABCA4 | STGD | c.3055A > G (p.Thr1019Ala) | ex21 | Photoreceptors | Int 22 (NG_009073.1) |
| ABCA4 | STGD | c.3056C > T (p.Thr1019Met) | ex21 | Photoreceptors | Int 22 (NG_009073.1) |
| ABCA4 | STGD | c.3064G > A (p.Glu1022Lys) | ex21 | Photoreceptors | Int 22 (NG_009073.1) |
| ABCA4 | STGD, CRD | c.3085C > T (p.Gln1029*) | ex21 | Photoreceptors | Int 22 (NG_009073.1) |
| ABCA4 | STGD | c.3091A > G (p.Lys1031Glu) | ex21 | Photoreceptors | Int 22 (NG_009073.1) |
| ABCA4 | STGD | c.3106G > A (p.Glu1036Lys) | ex21 | Photoreceptors | Int 22 (NG_009073.1) |
| ABCA4 | STGD, CRD, ARRP, AMD | c.3113C > T (p.Ala1038Val) | ex21 | Photoreceptors | Int 22 (NG_009073.1) |
| ABCA4 | STGD | c.3148G > A (p.Gly1050Ser) | ex21 | Photoreceptors | Int 22 (NG_009073.1) |
| ABCA4 | STGD | c.3149G > A (p.Gly1050Asp) | ex21 | Photoreceptors | Int 22 (NG_009073.1) |
| ABCA4 | STGD | c.3163C > T (p.Arg1055Trp) | ex21 | Photoreceptors | Int 22 (NG_009073.1) |
| ABCA4 | STGD | c.3187T < C (p.Ser1063Pro) | ex21 | Photoreceptors | Int 22 (NG_009073.1) |
| ABCA4 | STGD | c.3204A > T (p.Arg1068Ser) | ex22 | Photoreceptors | Int 22 (NG_009073.1) |
| ABCA4 | STGD | c.3204A > C (p.Arg1068Ser) | ex22 | Photoreceptors | Int 22 (NG_009073.1) |
| ABCA4 | STGD | c.3202_3204delAGA (p.Arg1068del) | ex22 | Photoreceptors | Int 22 (NG_009073.1) |
| ABCA4 | STGD | c.3205A > G (p.Lys1069Glu) | ex22 | Photoreceptors | Int 22 (NG_009073.1) |
| ABCA4 | STGD | c.3205_3206dupAA (p.Leu1070fs) | ex22 | Photoreceptors | Int 22 (NG_009073.1) |
| ABCA4 | STGD | c.3211_3212insGT (p.Ser1071fs) | ex22 | Photoreceptors | Int 22 (NG_009073.1) |
| ABCA4 | STGD | c.3212C > T (p.Ser1071Leu) | ex22 | Photoreceptors | Int 22 (NG_009073.1) |
| ABCA4 | STGD | c.3215T > C (p.Val1072Ala) | ex22 | Photoreceptors | Int 22 (NG_009073.1) |
| ABCA4 | STGD | c.3233G > A (p.Gly1078Glu) | ex22 | Photoreceptors | Int 22 (NG_009073.1) |
| ABCA4 | STGD | c.3241A > G (p.Lys1081Glu) | ex22 | Photoreceptors | Int 22 (NG_009073.1) |
| ABCA4 | STGD, CRD | c.3259G > A (p.Glu1087Lys) | ex22 | Photoreceptors | Int 22 (NG_009073.1) |
| ABCA4 | STGD | c.3261A > C (p.Glu1087Asp) | ex22 | Photoreceptors | Int 22 (NG_009073.1) |
| ABCA4 | STGD | c.3272G > A (p.Gly1091Glu) | ex22 | Photoreceptors | Int 22 (NG_009073.1) |
| ABCA4 | STGD | c.3278A > G (p.Asp1093Gly) | ex22 | Photoreceptors | Int 22 (NG_009073.1) |
| ABCA4 | STGD | c.3279C > A (p.Asp1093Glu) | ex22 | Photoreceptors | Int 22 (NG_009073.1) |
| ABCA4 | STGD | c.3289A > T (p.Arg1097*) | ex22 | Photoreceptors | Int 22 (NG_009073.1) |
| ABCA4 | STGD | c.3292C > T (p.Arg1098Cys) | ex22 | Photoreceptors | Int 22 (NG_009073.1) |
| ABCA4 | STGD | c.3295T > C (p.Ser1099Pro) | ex22 | Photoreceptors | Int 22 (NG_009073.1) |
| ABCA4 | STGD | c.3296C > G (p.Ser1099*) | ex22 | Photoreceptors | Int 22 (NG_009073.1) |
| ABCA4 | STGD | c.3296C > A (p.Ser1099*) | ex22 | Photoreceptors | Int 22 (NG_009073.1) |
| ABCA4 | STGD | c.3303G > A (p.Trp1101*) | ex22 | Photoreceptors | Int 22 (NG_009073.1) |

TABLE 1-continued

| | | | | | |
|---|---|---|---|---|---|
| ABCA4 | STGD | c.3305A > T (p.Asp1102Val) | ex22 | Photoreceptors | Int 22 (NG_009073.1) |
| ABCA4 | STGD, AMD | c.3322C > T (p.Arg1108Cys) | ex22 | Photoreceptors | Int 22 (NG_009073.1) |
| ABCA4 | STGD | c.3323G > T (p.Arg1108Leu) | ex22 | Photoreceptors | Int 22 (NG_009073.1) |
| ABCA4 | STGD | c.3323G > A (p.Arg1108His) | ex22 | Photoreceptors | Int 22 (NG_009073.1) |
| ABCA4 | STGD | c.3329 − 2seA > G (—) | int22 | Photoreceptors | Int 22 (NG_009073.1) |
| ABCA4 | STGD | c.3329 − 2seA > T (—) | int22 | Photoreceptors | Int 22 (NG_009073.1) |
| ABCA4 | STGD | c.3335C > A (p.Thr1112Asn) | ex23 | Photoreceptors | |
| ABCA4 | STGD | c.3350C > T (p.Thr1117Ile) | ex23 | Photoreceptors | |
| ABCA4 | STGD, CRD | c.3364G > A (p.Glu1122Lys) | ex23 | Photoreceptors | |
| ABCA4 | STGD | c.3366G > C (p.Glu1122Asp) | ex23 | Photoreceptors | |
| ABCA4 | STGD | c.3377T > C (p.Leu1126Pro) | ex23 | Photoreceptors | |
| ABCA4 | STGD | c.3385C > T (p.Arg1129Cys) | ex23 | Photoreceptors | |
| ABCA4 | STGD | c.3385C > G (p.Arg1129Gly) | ex23 | Photoreceptors | |
| ABCA4 | STGD, AMD | c.3386G > T (p.Arg1129Leu) | ex23 | Photoreceptors | |
| ABCA4 | STGD | c.3393delC (p.Ile1132fs) | ex23 | Photoreceptors | |
| ABCA4 | STGD | c.3412seC > T (p.Leu1138Phe) | ex23 | Photoreceptors | |
| ABCA4 | STGD | c.3449_3451delGCT (p.Cys1150del) | ex23 | Photoreceptors | |
| ABCA4 | ARRP | c.3523 − 28T > C | in23 | Photoreceptors | |
| ABCA4 | STGD | c.3522 + 5delG (—) | int23 | Photoreceptors | |
| ABCA4 | STGD | c.3523 − 2A > T (—) | int23 | Photoreceptors | |
| ABCA4 | STGD | c.3523 − 1G > A (—) | int23 | Photoreceptors | |
| ABCA4 | STGD | c.3531C > A (p.Cys1177*) | ex24 | Photoreceptors | |
| ABCA4 | STGD | c.3539_3554del16 (p.Ser1180fs) | ex24 | Photoreceptors | |
| ABCA4 | STGD | c.3543delT (p.Lys1182fs) | ex24 | Photoreceptors | |
| ABCA4 | STGD | c.3547seG > T (p.Gly1183Cys) | ex24 | Photoreceptors | |
| ABCA4 | STGD | c.3602T > G (p.Leu1201Arg) | ex24 | Photoreceptors | |
| ABCA4 | STGD | c.3607G > A (p.Gly1203Arg) | ex24 | Photoreceptors | |
| ABCA4 | STGD | c.3607 + 1G > A (—) | int24 | Photoreceptors | |
| ABCA4 | STGD | c.3608G > A (p.Gly1203Glu) | ex25 | Photoreceptors | |
| ABCA4 | STGD | c.3610G > A (p.Asp1204Asn) | ex25 | Photoreceptors | |
| ABCA4 | STGD | c.3626T > C (p.Met1209Thr) | ex25 | Photoreceptors | |
| ABCA4 | STGD | c.3655G > C (p.Ala1219Pro) | ex25 | Photoreceptors | |
| ABCA4 | STGD | c.3703A > G (p.Asn1235Asp) | ex25 | Photoreceptors | |
| ABCA4 | STGD | c.3749T > C (p.Leu1250Pro) | ex25 | Photoreceptors | |
| ABCA4 | STGD | c.3754G > T (p.Glu1252*) | ex25 | Photoreceptors | |
| ABCA4 | STGD | c.3758C > T (p.Thr1253Met) | ex25 | Photoreceptors | |
| ABCA4 | STGD | c.3808G > T (p.Glu1270*) | ex25 | Photoreceptors | |
| ABCA4 | STGD | c.3812A > G (p.Glu1271Gly) | ex25 | Photoreceptors | |
| ABCA4 | STGD | c.3814 − 2A > G (—) | int25 | Photoreceptors | |
| ABCA4 | STGD | c.3819_3820insT (p.Leu1274fs) | ex26 | Photoreceptors | |
| ABCA4 | STGD | c.3835_3840del6 (p.Asp1279_Ser1280del) | ex26 | Photoreceptors | |
| ABCA4 | STGD | c.3846delA (p.Gly1283fs) | ex26 | Photoreceptors | |
| ABCA4 | CRD | c.3862 + 1G > A (—) | int26 | Photoreceptors | |
| ABCA4 | STGD | c.3874C > T (p.Gln1292*) | ex27 | Photoreceptors | Int 26 (NG_009073.1) |
| ABCA4 | STGD | c.3898C > T (p.Arg1300*) | ex27 | Photoreceptors | Int 26 (NG_009073.1) |
| ABCA4 | STGD | c.3899G > A (p.Arg1300Gln) | ex27 | Photoreceptors | Int 26 (NG_009073.1) |
| ABCA4 | STGD | c.3943C > T (p.Gln1315*) | ex27 | Photoreceptors | Int 26 (NG_009073.1) |
| ABCA4 | STGD | c.3970delG (p.Ala1324fs) | ex27 | Photoreceptors | Int 26 (NG_009073.1) |
| ABCA4 | STGD | c.3994C > T (p.Gln1332*) | ex27 | Photoreceptors | Int 26 (NG_009073.1) |
| ABCA4 | STGD | c.4034_4035insCA (p.Gly1347fs) | ex27 | Photoreceptors | Int 26 (NG_009073.1) |
| ABCA4 | CRD | c.4035insCA | ex27 | Photoreceptors | Int 26 (NG_009073.1) |
| ABCA4 | STGD | c.4036_4037delAC (p.Thr1346fs) | ex27 | Photoreceptors | Int 26 (NG_009073.1) |
| ABCA4 | STGD | c.4073T > C (p.Leu1358Pro) | ex27 | Photoreceptors | Int 26 (NG_009073.1) |
| ABCA4 | STGD | c.4128G > A (p.?) | ex27 | Photoreceptors | Int 26 (NG_009073.1) |
| ABCA4 | STGD, AMD | c.4139C > T (p.Pro1380Leu) | ex28 | Photoreceptors | Int 26 (NG_009073.1) |
| ABCA4 | STGD | c.4163T > C (p.Leu1388Pro) | ex28 | Photoreceptors | Int 26 (NG_009073.1) |
| ABCA4 | STGD | c.4169T > C (p.Leu1390Pro) | ex28 | Photoreceptors | Int 26 (NG_009073.1) |
| ABCA4 | STGD | c.4195G > A (p.Glu1399Lys) | ex28 | Photoreceptors | Int 26 (NG_009073.1) |
| ABCA4 | STGD | c.4200C > A (p.Tyr1400*) | ex28 | Photoreceptors | Int 26 (NG_009073.1) |
| ABCA4 | STGD | c.4203C > A (p.(=)) | ex28 | Photoreceptors | Int 26 (NG_009073.1) |
| ABCA4 | STGD | c.4203C > T (p.(=)) | ex28 | Photoreceptors | Int 26 (NG_009073.1) |

TABLE 1-continued

| | | | | | |
|---|---|---|---|---|---|
| ABCA4 | STGD | c.4216C > T (p.His1406Tyr) | ex28 | Photoreceptors | Int 26 (NG_009073.1) |
| ABCA4 | STGD | c.4217A > G (p.His1406Arg) | ex28 | Photoreceptors | Int 26 (NG_009073.1) |
| ABCA4 | STGD, AMD | c.4222T > C (p.Trp1408Arg) | ex28 | Photoreceptors | Int 26 (NG_009073.1) |
| ABCA4 | STGD | c.4223G > T (p.Trp1408Leu) | ex28 | Photoreceptors | Int 26 (NG_009073.1) |
| ABCA4 | STGD | c.4224G > A (p.Trp1408*) | ex28 | Photoreceptors | Int 26 (NG_009073.1) |
| ABCA4 | STGD, AMD | c.4232_4233insTATG (p.Gln1412fs) | ex28 | Photoreceptors | Int 26 (NG_009073.1) |
| ABCA4 | STGD | c.4234C > T (p.Gln1412*) | ex28 | Photoreceptors | Int 26 (NG_009073.1) |
| ABCA4 | STGD | c.4248C > A (p.Phe1416Leu) | ex28 | Photoreceptors | Int 26 (NG_009073.1) |
| ABCA4 | STGD | c.4253 + 4C > T (—) | int28 | Photoreceptors | Int 26 (NG_009073.1) |
| ABCA4 | STGD | c.4253 + 5G > T (—) | int28 | Photoreceptors | Int 26 (NG_009073.1) |
| ABCA4 | STGD | c.4253 + 5G > A (—) | int28 | Photoreceptors | Int 26 (NG_009073.1) |
| ABCA4 | STGD | c.4254 − 15_4261del23 (—) | int28 | Photoreceptors | Int 26 (NG_009073.1) |
| ABCA4 | STGD | c.4254 − 2A > G (—) | int28 | Photoreceptors | Int 26 (NG_009073.1) |
| ABCA4 | AMD | c.4283C > T (p.Thr1428Met) | ex29 | Photoreceptors | Int 26 (NG_009073.1) |
| ABCA4 | STGD | c.4286T > C (p.Val1429Ala) | ex29 | Photoreceptors | Int 26 (NG_009073.1) |
| ABCA4 | STGD | c.4289T > C (p.Leu1430Pro) | ex29 | Photoreceptors | Int 26 (NG_009073.1) |
| ABCA4 | CRD | c.4297G > A (p.Val1433Ile) | ex29 | Photoreceptors | Int 26 (NG_009073.1) |
| ABCA4 | STGD | c.4316G > A (p.Gly1439Asp) | ex29 | Photoreceptors | Int 26 (NG_009073.1) |
| ABCA4 | STGD | c.4318T > G (p.Phe1440Val) | ex29 | Photoreceptors | Int 26 (NG_009073.1) |
| ABCA4 | STGD | c.4319T > C (p.Phe1440Ser) | ex29 | Photoreceptors | Int 26 (NG_009073.1) |
| ABCA4 | STGD | c.4326C > A (p.Asn1442Lys) | ex29 | Photoreceptors | Int 26 (NG_009073.1) |
| ABCA4 | STGD | c.4328G > A (p.Arg1443His) | ex29 | Photoreceptors | Int 26 (NG_009073.1) |
| ABCA4 | STGD | c.4342G > A (p.Gly1448Arg) | ex29 | Photoreceptors | Int 26 (NG_009073.1) |
| ABCA4 | STGD | c.4342G > C (p.Gly1448Arg) | ex29 | Photoreceptors | Int 26 (NG_009073.1) |
| ABCA4 | STGD | c.4346G > A (p.Trp1449*) | ex29 | Photoreceptors | Int 26 (NG_009073.1) |
| ABCA4 | STGD | c.4352 + 1G > A (—) | int29 | Photoreceptors | Int 26 (NG_009073.1) |
| ABCA4 | STGD | c.4353 − 1G > T (—) | int29 | Photoreceptors | Int 26 (NG_009073.1) |
| ABCA4 | STGD | c.4363T > C (p.Cys1455Arg) | ex30 | Photoreceptors | Int 26 (NG_009073.1) |
| ABCA4 | STGD | c.4417C > A (p.Leu1473Met) | ex30 | Photoreceptors | Int 26 (NG_009073.1) |
| ABCA4 | STGD | c.4436G > A (p.Trp1479*) | ex30 | Photoreceptors | Int 26 (NG_009073.1) |
| ABCA4 | STGD | c.4437G > A (p.Trp1479*) | ex30 | Photoreceptors | Int 26 (NG_009073.1) |
| ABCA4 | STGD | c.4450C > T (p.Pro1484Ser) | ex30 | Photoreceptors | Int 26 (NG_009073.1) |
| ABCA4 | STGD | c.4457C > T (p.Pro1486Leu) | ex30 | Photoreceptors | Int 26 (NG_009073.1) |
| ABCA4 | STGD, AMD | c.4462T > C (p.Cys1488Arg) | ex30 | Photoreceptors | Int 26 (NG_009073.1) |
| ABCA4 | STGD | c.4463G > A (p.Cys1488Tyr) | ex30 | Photoreceptors | Int 26 (NG_009073.1) |
| ABCA4 | STGD | c.4463G > T (p.Cys1488Phe) | ex30 | Photoreceptors | Int 26 (NG_009073.1) |
| ABCA4 | CRD | c.4469G > A (p.Cys1490Tyr) | ex30 | Photoreceptors | Int 26 (NG_009073.1) |
| ABCA4 | STGD | c.4506C > T (p.(=)) | ex30 | Photoreceptors | Int 26 (NG_009073.1) |
| ABCA4 | STGD | c.4506C > A (p.Cys1502*) | ex30 | Photoreceptors | Int 26 (NG_009073.1) |
| ABCA4 | STGD | c.4517C > T (p.Ala1506Val) | ex30 | Photoreceptors | Int 26 (NG_009073.1) |
| ABCA4 | STGD | c.4522G > T (p.Gly1508Cys) | ex30 | Photoreceptors | Int 26 (NG_009073.1) |
| ABCA4 | STGD | c.4535C > G (p.Pro1512Arg) | ex30 | Photoreceptors | Int 26 (NG_009073.1) |
| ABCA4 | STGD | c.4535C > T (p.Pro1512Leu) | ex30 | Photoreceptors | Int 26 (NG_009073.1) |
| ABCA4 | STGD | c.4537delC (p.Gln1513fs) | ex30 | Photoreceptors | Int 26 (NG_009073.1) |
| ABCA4 | STGD | c.4537_4538insC (p.Gln1513fs) | ex30 | Photoreceptors | Int 26 (NG_009073.1) |
| ABCA4 | STGD | c.4538A > G (p.Gln1513Arg) | ex30 | Photoreceptors | Int 26 (NG_009073.1) |
| ABCA4 | CRD | c.4538A > C (p.Gln1513Pro) | ex30 | Photoreceptors | Int 26 (NG_009073.1) |
| ABCA4 | CRD, ARRP, STGD, AMD | c.4539 + 1G > T (—) | int30 | Photoreceptors | Int 26 (NG_009073.1) |
| ABCA4 | STGD | c.4539 + 3seA > G (—) | int30 | Photoreceptors | Int 26 (NG_009073.1) |
| ABCA4 | STGD | c.4540 − 2A > G (—) | int30 | Photoreceptors | Int 26 (NG_009073.1) |
| ABCA4 | AMD | c.4549C > A (p.Arg1517Ser) | ex31 | Photoreceptors | Int 26 (NG_009073.1) |
| ABCA4 | STGD | c.4574T > C (p.Leu1525Pro) | ex31 | Photoreceptors | Int 26 (NG_009073.1) |
| ABCA4 | STGD, AMD | c.4577C > T (p.Thr1526Met) | ex31 | Photoreceptors | Int 26 (NG_009073.1) |
| ABCA4 | STGD, AMD | c.4594G > A (p.Asp1532Asn) | ex31 | Photoreceptors | Int 26 (NG_009073.1) |
| ABCA4 | STGD | c.4610C > T (p.Thr1537Met) | ex31 | Photoreceptors | Int 26 (NG_009073.1) |
| ABCA4 | STGD | c.4635 − 1G > T (—) | int31 | Photoreceptors | Int 26 (NG_009073.1) |
| ABCA4 | STGD | c.4639A > T (p.Lys1547*) | ex32 | Photoreceptors | Int 26 (NG_009073.1) |
| ABCA4 | STGD | c.4670A > G (p.Tyr1557Cys) | ex33 | Photoreceptors | Int 26 (NG_009073.1) |
| ABCA4 | STGD | c.4667 + 1G > A (—) | int32 | Photoreceptors | Int 26 (NG_009073.1) |
| ABCA4 | STGD | c.4667 + 2T > C (—) | int32 | Photoreceptors | Int 26 (NG_009073.1) |
| ABCA4 | CRD, STGD, AMD | c.4685T > C (p.Ile1562Thr) | ex33 | Photoreceptors | Int 26 (NG_009073.1) |
| ABCA4 | STGD | c.4710delC (p.Ile1571fs) | ex33 | Photoreceptors | Int 26 (NG_009073.1) |
| ABCA4 | AMD | c.4715C > T (p.Thr1572Met) | ex33 | Photoreceptors | Int 26 (NG_009073.1) |
| ABCA4 | STGD | c.4720G > T (p.Glu1574*) | ex33 | Photoreceptors | Int 26 (NG_009073.1) |

TABLE 1-continued

| | | | | | |
|---|---|---|---|---|---|
| ABCA4 | STGD | c.4720delG (p.Glu1574fs) | ex33 | Photoreceptors | Int 26 (NG_009073.1) |
| ABCA4 | AMD | c.4732G > A (p.Gly1578Arg) | ex33 | Photoreceptors | Int 26 (NG_009073.1) |
| ABCA4 | STGD | c.4734_4737del4 (p.Phe1579*) | ex33 | Photoreceptors | Int 26 (NG_009073.1) |
| ABCA4 | STGD | c.4734delG (p.Leu1580*) | ex33 | Photoreceptors | Int 26 (NG_009073.1) |
| ABCA4 | STGD | c.4735_4739delinsCC (p.Phe1579_Leu1580delinsPro) | ex33 | Photoreceptors | Int 26 (NG_009073.1) |
| ABCA4 | STGD | c.4739T > C (p.Leu1580Ser) | ex33 | Photoreceptors | Int 26 (NG_009073.1) |
| ABCA4 | STGD | c.4739delT(p.Leu1580*) | ex33 | Photoreceptors | Int 26 (NG_009073.1) |
| ABCA4 | STGD | C.4748T > C (p.Leu1583Pro) | ex33 | Photoreceptors | Int 26 (NG_009073.1) |
| ABCA4 | STGD | c.4771G > A (p.Gly1591Arg) | ex33 | Photoreceptors | Int 26 (NG_009073.1) |
| ABCA4 | STGD | c.4771G > C (p.Gly1591Arg) | ex33 | Photoreceptors | Int 26 (NG_009073.1) |
| ABCA4 | STGD | c.4773 + 1G > A (—) | int33 | Photoreceptors | Int 26 (NG_009073.1) |
| ABCA4 | STGD | c.4773 + 1G > T (—) | int33 | Photoreceptors | Int 26 (NG_009073.1) |
| ABCA4 | STGD | c.4773 + 2T > C (—) | int33 | Photoreceptors | Int 26 (NG_009073.1) |
| ABCA4 | STGD, CRD, ARRP, AMD | C.4773 + 48C > T (—) | int33 | Photoreceptors | Int 26 (NG_009073.1) |
| ABCA4 | STGD | c.4774 − 2A > C (—) | int33 | Photoreceptors | Int 26 (NG_009073.1) |
| ABCA4 | STGD, AMD | c.4793C > A (p.Ala1598Asp) | ex34 | Photoreceptors | Int 26 (NG_009073.1) |
| ABCA4 | STGD | c.4838delA (p.Asp1613fs) | ex34 | Photoreceptors | Int 26 (NG_009073.1) |
| ABCA4 | STGD | c.4848 + 1seG > A (—) | int34 | Photoreceptors | Int 26 (NG_009073.1) |
| ABCA4 | STGD | c.4848 + 2T > C (—) | int34 | Photoreceptors | Int 26 (NG_009073.1) |
| ABCA4 | STGD | c.4848 + 2T > A (—) | int34 | Photoreceptors | Int 26 (NG_009073.1) |
| ABCA4 | STGD | c.4849G > A (p.?) | ex35 | Photoreceptors | Int 26 (NG_009073.1) |
| ABCA4 | STGD | c.4854G > A (p.Trp1618*) | ex35 | Photoreceptors | Int 26 (NG_009073.1) |
| ABCA4 | STGD | c.4859_4864delinsTCCT (p.Asn1620fs) | ex35 | Photoreceptors | Int 26 (NG_009073.1) |
| ABCA4 | STGD | c.4867G > A (p.Gly1623Ser) | ex35 | Photoreceptors | Int 26 (NG_009073.1) |
| ABCA4 | STGD | c.4875T > A (p.His1625Gln) | ex35 | Photoreceptors | Int 26 (NG_009073.1) |
| ABCA4 | STGD | c.4892T > C (p.Leu1631Pro) | ex35 | Photoreceptors | Int 26 (NG_009073.1) |
| ABCA4 | STGD | c.4909G > A (p.Ala1637Thr) | ex35 | Photoreceptors | Int 26 (NG_009073.1) |
| ABCA4 | AMD, CRD | c.4918C > T (p.Arg1640Trp) | ex35 | Photoreceptors | Int 26 (NG_009073.1) |
| ABCA4 | STGD, AMD | c.4919G > A (p.Arg1640Gln) | ex35 | Photoreceptors | Int 26 (NG_009073.1) |
| ABCA4 | STGD | c.4926C > G (p.Ser1642Arg) | ex35 | Photoreceptors | Int 26 (NG_009073.1) |
| ABCA4 | STGD, AMD | c.4947delC (p.Glu1650fs) | ex35 | Photoreceptors | Int 26 (NG_009073.1) |
| ABCA4 | STGD | c.4954T > G (p.Tyr1652Asp) | ex35 | Photoreceptors | Int 26 (NG_009073.1) |
| ABCA4 | STGD | c.4956T > G (p.Tyr1652*) | ex35 | Photoreceptors | Int 26 (NG_009073.1) |
| ABCA4 | STGD | c.4999C > A (p.Gln1667Lys) | ex35 | Photoreceptors | Int 26 (NG_009073.1) |
| ABCA4 | STGD | c.5018 + 2T > C (—) | intr35 | Photoreceptors | Int 26 (NG_009073.1) |
| ABCA4 | STGD | c.5018 + 2T > A (—) | intr35 | Photoreceptors | Int 26 (NG_009073.1) |
| ABCA4 | CRD | c.5019 − 2_5019 − 1del (—) | intr35 | Photoreceptors | Int 26 (NG_009073.1) |
| ABCA4 | STGD | c.5041_5055del15 (p.Val1681_Cys1685del) | ex36 | Photoreceptors | Int 26 (NG_009073.1) |
| ABCA4 | STGD | c.5056G > A (p.Val1686Met) | ex36 | Photoreceptors | Int 26 (NG_009073.1) |
| ABCA4 | STGD | c.5059A > T (p.Ile1687Phe) | ex36 | Photoreceptors | Int 26 (NG_009073.1) |
| ABCA4 | STGD | c.5065T > C (p.Ser1689Pro) | ex36 | Photoreceptors | Int 26 (NG_009073.1) |
| ABCA4 | STGD | c.5077G > A (p.Val1693Ile) | ex36 | Photoreceptors | Int 26 (NG_009073.1) |
| ABCA4 | STGD | c.5087G > A (p.Ser1696Asn) | ex36 | Photoreceptors | Int 26 (NG_009073.1) |
| ABCA4 | STGD | c.5107C > G (p.Gln1703Glu) | ex36 | Photoreceptors | Int 26 (NG_009073.1) |
| ABCA4 | STGD | c.5110delG(p.Glu1704fs) | ex36 | Photoreceptors | Int 26 (NG_009073.1) |
| ABCA4 | STGD | c.5113C > T (p.Arg1705Trp) | ex36 | Photoreceptors | Int 26 (NG_009073.1) |
| ABCA4 | STGD | c.5114G > T (p.Arg1705Leu) | ex36 | Photoreceptors | Int 26 (NG_009073.1) |
| ABCA4 | STGD | c.5114G > A (p.Arg1705Gln) | ex36 | Photoreceptors | Int 26 (NG_009073.1) |
| ABCA4 | STGD | c.5138A > G (p.Gln1713Arg) | ex36 | Photoreceptors | Int 26 (NG_009073.1) |
| ABCA4 | STGD | c.5161_5162delAC (p.Thr1721fs) | ex36 | Photoreceptors | Int 26 (NG_009073.1) |
| ABCA4 | STGD | c.5172G > T (p.Trp1724Cys) | ex36 | Photoreceptors | Int 26 (NG_009073.1) |
| ABCA4 | STGD | c.5177C > A (p.Thr1726Asn) | ex36 | Photoreceptors | Int 26 (NG_009073.1) |
| ABCA4 | STGD | c.5186T > C (p.Leu1729Pro) | ex36 | Photoreceptors | Int 26 (NG_009073.1) |
| ABCA4 | AMD, STGD, CRD | c.5196 + 1G > A (—) | int36 | Photoreceptors | Int 26 (NG_009073.1) |
| ABCA4 | AMD, STGD, CRD | c.5196 + 2T > C (—) | int36 | Photoreceptors | Int 26 (NG_009073.1) |
| ABCA4 | STGD | c.5196 + 2T > G (—) | int36 | Photoreceptors | Int 26 (NG_009073.1) |
| ABCA4 | STGD | c.5196 + 1_5196 + 4del4 (—) | int36 | Photoreceptors | Int 26 (NG_009073.1) |
| ABCA4 | STGD | c.5196 + 1_5196 + 6del6 (—) | int36 | Photoreceptors | Int 26 (NG_009073.1) |

TABLE 1-continued

| Gene | Disease | Variant | Location | Cell type | Reference |
|---|---|---|---|---|---|
| ABCA4 | CRD | c.5197 − 3seG > A (—) | int36 | Photoreceptors | Int 26 (NG_009073.1) |
| ABCA4 | STGD | c.5197 − 3seG > C (—) | int36 | Photoreceptors | Int 26 (NG_009073.1) |
| ABCA4 | STGD | c.5206T > C (p.Ser1736Pro) | ex37 | Photoreceptors | Int 26 (NG_009073.1) |
| ABCA4 | STGD | c.5222_5232del11 (p.Leu1741fs) | ex37 | Photoreceptors | Int 26 (NG_009073.1) |
| ABCA4 | STGD | c.5242G > A (p.Gly1748Arg) | ex37 | Photoreceptors | Int 26 (NG_009073.1) |
| ABCA4 | STGD | c.5248C > T (p.Gln1750*) | ex37 | Photoreceptors | Int 26 (NG_009073.1) |
| ABCA4 | STGD | c.5281_5289del9 (p.Pro1761_Leu1763del) | ex37 | Photoreceptors | Int 26 (NG_009073.1) |
| ABCA4 | STGD | c.5285C > A (p.Ala1762Asp) | ex37 | Photoreceptors | Int 26 (NG_009073.1) |
| ABCA4 | STGD | c.5288T > C (p.Leu1763Pro) | ex37 | Photoreceptors | Int 26 (NG_009073.1) |
| ABCA4 | STGD | c.5288delT (p.Val1764fs) | ex37 | Photoreceptors | Int 26 (NG_009073.1) |
| ABCA4 | STGD | c.5300T > C (p.Leu1767Pro) | ex37 | Photoreceptors | Int 26 (NG_009073.1) |
| ABCA4 | STGD | c.5312 + 1G > A (—) | int37 | Photoreceptors | Int 26 (NG_009073.1) |
| ABCA4 | STGD | c.5312 + 3A > T (—) | int37 | Photoreceptors | Int 26 (NG_009073.1) |
| ABCA4 | STGD | c.5316G > A (p.Trp1772*) | ex38 | Photoreceptors | Int 26 (NG_009073.1) |
| ABCA4 | STGD | c.5317insA (p.Ala1773fs) | ex38 | Photoreceptors | Int 26 (NG_009073.1) |
| ABCA4 | STGD | c.5318C > A (p.Ala1773Glu) | ex38 | Photoreceptors | Int 26 (NG_009073.1) |
| ABCA4 | STGD | c.5318C > T (p.Ala1773Val) | ex38 | Photoreceptors | Int 26 (NG_009073.1) |
| ABCA4 | STGD | c.5327C > T (p.Pro1776Leu) | ex38 | Photoreceptors | Int 26 (NG_009073.1) |
| ABCA4 | STGD | c.5337C > G (p.Tyr1779*) | ex38 | Photoreceptors | Int 26 (NG_009073.1) |
| ABCA4 | STGD | c.5337C > A (p.Tyr1779*) | ex38 | Photoreceptors | Int 26 (NG_009073.1) |
| ABCA4 | STGD | c.5338C > G (p.Pro1780Ala) | ex38 | Photoreceptors | Int 26 (NG_009073.1) |
| ABCA4 | CRD | c.5381C > A (p.Ala1794Asp) | ex38 | Photoreceptors | Int 26 (NG_009073.1) |
| ABCA4 | STGD | c.5395A > G (p.Asn1799Asp) | ex38 | Photoreceptors | Int 26 (NG_009073.1) |
| ABCA4 | STGD | c.5413A > G (p.Asn1805Asp) | ex38 | Photoreceptors | Int 26 (NG_009073.1) |
| ABCA4 | STGD, AMD | c.5451G > T (p.Glu1817Asp) | ex38 | Photoreceptors | Int 26 (NG_009073.1) |
| ABCA4 | STGD | c.5459G > C (p.Arg1820Pro) | ex38 | Photoreceptors | Int 26 (NG_009073.1) |
| ABCA4 | STGD | c.5460 + 1G > A (—) | int38 | Photoreceptors | Int 26 (NG_009073.1) |
| ABCA4 | STGD | c.5460 + 5G > A (—) | int38 | Photoreceptors | Int 26 (NG_009073.1) |
| ABCA4 | CRD | c.5461-10T > C (—) | int38 | Photoreceptors | Int 26 (NG_009073.1) |
| ABCA4 | STGD | c.5512C > T (p.His1838Tyr) | ex39 | Photoreceptors | Int 26 (NG_009073.1) |
| ABCA4 | STGD | c.5512C > G (p.His1838Asp) | ex39 | Photoreceptors | Int 26 (NG_009073.1) |
| ABCA4 | STGD | c.5527C > T (p.Arg1843Trp) | ex39 | Photoreceptors | Int 26 (NG_009073.1) |
| ABCA4 | STGD | c.5537T > C (p.Ile1846Thr) | ex39 | Photoreceptors | Int 26 (NG_009073.1) |
| ABCA4 | STGD | c.5578C > T (p.Arg1860Trp) | ex39 | Photoreceptors | Int 26 (NG_009073.1) |
| ABCA4 | STGD | Splice Site (c.5584 + 5G > A) | int39 | Photoreceptors | Int 26 (NG_009073.1) |
| ABCA4 | STGD | c.5584 + 6T > C (—) | int39 | Photoreceptors | Int 26 (NG_009073.1) |
| ABCA4 | ARRP | C.5584 +− 70 C > T | int39 | Photoreceptors | Int 26 (NG_009073.1) |
| ABCA4 | STGD, AMD | c.5585-1G > A (—) | int39 | Photoreceptors | Int 26 (NG_009073.1) |
| ABCA4 | STGD | c.5593C > T (p.His1865Tyr) | ex40 | Photoreceptors | Int 26 (NG_009073.1) |
| ABCA4 | STGD | c.5603A > T (p.Asn1868Ile) | ex40 | Photoreceptors | Int 26 (NG_009073.1) |
| ABCA4 | STGD | c.5629_5643dup (Lys1877_Ala1881dup) | ex40 | Photoreceptors | Int 26 (NG_009073.1) |
| ABCA4 | STGD | c.5644A > G (p.Met1882Val) | ex40 | Photoreceptors | Int 26 (NG_009073.1) |
| ABCA4 | STGD | c.5646G > A (p.Met1882Ile) | ex40 | Photoreceptors | Int 26 (NG_009073.1) |
| ABCA4 | STGD | c.5651T > A (p.Val1884Glu) | ex40 | Photoreceptors | Int 26 (NG_009073.1) |
| ABCA4 | STGD | c.5653G > A (p.Glu1885Lys) | ex40 | Photoreceptors | Int 26 (NG_009073.1) |
| ABCA4 | STGD | c.5657G > A (p.Gly1886Glu) | ex40 | Photoreceptors | Int 26 (NG_009073.1) |
| ABCA4 | STGD | c.5668_5670del (p.Phe1890del) | ex40 | Photoreceptors | Int 26 (NG_009073.1) |
| ABCA4 | STGD | c.5682G > C (p.(=)) | ex40 | Photoreceptors | Int 26 (NG_009073.1) |
| ABCA4 | STGD | c.5687T > A (p.Val1896Asp) | ex40 | Photoreceptors | Int 26 (NG_009073.1) |
| ABCA4 | AMD | c.5693G > A (p.Arg1898His) | ex40 | Photoreceptors | Int 26 (NG_009073.1) |
| ABCA4 | STGD, AMD, CRD | c.5714 + 5G > A (—) | int40 | Photoreceptors | Int 26 (NG_009073.1) |
| ABCA4 | STGD | c.5715 − 2delA (—) | int40 | Photoreceptors | Int 26 (NG_009073.1) |
| ABCA4 | STGD | c.5761G > A (p.Val1921Met) | ex41 | Photoreceptors | Int 26 (NG_009073.1) |
| ABCA4 | STGD | c.5761G > T (p.Val1921Leu) | ex41 | Photoreceptors | Int 26 (NG_009073.1) |
| ABCA4 | STGD | c.5762_5763dup (p.Ala1922fs) | ex41 | Photoreceptors | Int 26 (NG_009073.1) |
| ABCA4 | STGD | c.5810T > C (p.Ile1937Thr) | ex41 | Photoreceptors | Int 26 (NG_009073.1) |
| ABCA4 | STGD | c.5814A > G(p.(=)) | ex41 | Photoreceptors | Int 26 (NG_009073.1) |
| ABCA4 | STGD | c.5819T > C (p.Leu1940Pro) | ex41 | Photoreceptors | Int 26 (NG_009073.1) |
| ABCA4 | STGD | c.5821C > T (p.His1941Tyr) | ex41 | Photoreceptors | Int 26 (NG_009073.1) |
| ABCA4 | STGD | c.5836 − 2A > G (—) | int41 | Photoreceptors | Int 26 (NG_009073.1) |
| ABCA4 | STGD | c.5836 − 2del (—) | int41 | Photoreceptors | Int 26 (NG_009073.1) |
| ABCA4 | STGD | c.5843C > T (p.Pro1948Leu) | ex42 | Photoreceptors | Int 26 (NG_009073.1) |

TABLE 1-continued

| | | | | | |
|---|---|---|---|---|---|
| ABCA4 | STGD | c.5844A > G (p.(=)) | ex42 | Photoreceptors | Int 26 (NG_009073.1) |
| ABCA4 | STGD | c.5881G > A (p.Gly1961Arg) | ex42 | Photoreceptors | Int 26 (NG_009073.1) |
| ABCA4 | STGD, AMD, ARRP, CRD | c.5882G > A (p.Gly1961Glu) | ex42 | Photoreceptors | Int 26 (NG_009073.1) |
| ABCA4 | STGD | c.5885T > A (p.Val1962Asp) | ex42 | Photoreceptors | Int 26 (NG_009073.1) |
| ABCA4 | ARRP | c.5888delG (p.Arg1963fs) | ex42 | Photoreceptors | Int 26 (NG_009073.1) |
| ABCA4 | STGD | c.5898 + 1G > T (—) | int42 | Photoreceptors | Int 26 (NG_009073.1) |
| ABCA4 | STGD | c.5898 + 1G > A (—) | int42 | Photoreceptors | Int 26 (NG_009073.1) |
| ABCA4 | STGD | c.5898 + 3delG (—) | int42 | Photoreceptors | Int 26 (NG_009073.1) |
| ABCA4 | STGD | c.5905delG (p.Gly1969fs) | ex43 | Photoreceptors | Int 26 (NG_009073.1) |
| ABCA4 | AMD | c.5908C > T (p.Leu1970Phe) | ex43 | Photoreceptors | Int 26 (NG_009073.1) |
| ABCA4 | STGD | c.5912T > G (p.Leu1971Arg) | ex43 | Photoreceptors | Int 26 (NG_009073.1) |
| ABCA4 | STGD | c.5914G > A (p.Gly1972Arg) | ex43 | Photoreceptors | Int 26 (NG_009073.1) |
| ABCA4 | ARRP, CRD | c.5917delG (p.Val1973*) | ex43 | Photoreceptors | Int 26 (NG_009073.1) |
| ABCA4 | STGD | c.5923G > C (p.Gly1975Arg) | ex43 | Photoreceptors | Int 26 (NG_009073.1) |
| ABCA4 | STGD | c.5929G > A (p.Gly1977Ser) | ex43 | Photoreceptors | Int 26 (NG_009073.1) |
| ABCA4 | STGD | c.5932delA (p.Thr1979fs) | ex43 | Photoreceptors | Int 26 (NG_009073.1) |
| ABCA4 | STGD | c.5936C > T (p.Thr1979Ile) | ex43 | Photoreceptors | Int 26 (NG_009073.1) |
| ABCA4 | STGD | c.5961_5964del4 (p.Asp1988fs) | ex43 | Photoreceptors | Int 26 (NG_009073.1) |
| ABCA4 | STGD | c.6005 + 1G > T (—) | int43 | Photoreceptors | Int 26 (NG_009073.1) |
| ABCA4 | STGD, AMD, CRD | c.6079C > T (p.Leu2027Phe) | ex44 | Photoreceptors | Int 26 (NG_009073.1) |
| ABCA4 | CRD | c.6088C > T (p.Arg2030*) | ex44 | Photoreceptors | Int 26 (NG_009073.1) |
| ABCA4 | STGD | c.6089G > A (p.Arg2030Gln) | ex44 | Photoreceptors | Int 26 (NG_009073.1) |
| ABCA4 | STGD | c.6104T > C (p.Leu2035Pro) | ex44 | Photoreceptors | Int 26 (NG_009073.1) |
| ABCA4 | STGD | c.6112C > T (p.Arg2038Trp) | ex44 | Photoreceptors | Int 26 (NG_009073.1) |
| ABCA4 | STGD | c.6118C > T (p.Arg2040*) | ex44 | Photoreceptors | Int 26 (NG_009073.1) |
| ABCA4 | STGD | c.6122G > A (p.Gly2041Asp) | ex44 | Photoreceptors | Int 26 (NG_009073.1) |
| ABCA4 | STGD | c.6140T > A (p.Ile2047Asn) | ex44 | Photoreceptors | Int 26 (NG_009073.1) |
| ABCA4 | STGD | c.6147 + 2T > A (—) | int44 | Photoreceptors | Int 26 (NG_009073.1) |
| ABCA4 | STGD, ARRP, AMD | c.6148G > C (p.Val2050Leu) | ex45 | Photoreceptors | Int 26 (NG_009073.1) |
| ABCA4 | STGD | c.6166A > T (p.Lys2056*) | ex45 | Photoreceptors | Int 26 (NG_009073.1) |
| ABCA4 | STGD | c.6179T > G (p.Leu2060Arg) | ex45 | Photoreceptors | Int 26 (NG_009073.1) |
| ABCA4 | STGD | c.6190G > C (p.Ala2064Pro) | ex45 | Photoreceptors | Int 26 (NG_009073.1) |
| ABCA4 | STGD | c.6212A > T (p.Tyr2071Phe) | ex45 | Photoreceptors | Int 26 (NG_009073.1) |
| ABCA4 | STGD | c.6220G > A (p.Gly2074Ser) | ex45 | Photoreceptors | Int 26 (NG_009073.1) |
| ABCA4 | STGD | c.6229C > T (p.Arg2077Trp) | ex45 | Photoreceptors | Int 26 (NG_009073.1) |
| ABCA4 | STGD | c.6229C > G (p.Arg2077Gly) | ex45 | Photoreceptors | Int 26 (NG_009073.1) |
| ABCA4 | STGD | c.6238_6239del (p.Ser2080fs) | ex45 | Photoreceptors | Int 26 (NG_009073.1) |
| ABCA4 | STGD, AMD | c.6286G > A (p.Glu2096Lys) | ex46 | Photoreceptors | Int 26 (NG_009073.1) |
| ABCA4 | STGD | c.6300delG (p.Met2101fs) | ex46 | Photoreceptors | Int 26 (NG_009073.1) |
| ABCA4 | STGD | c.6306C > A (p.Asp2102Glu) | ex46 | Photoreceptors | Int 26 (NG_009073.1) |
| ABCA4 | STGD | c.6316C > T (p.Arg2106Cys) | ex46 | Photoreceptors | Int 26 (NG_009073.1) |
| ABCA4 | STGD | c.6317_6323del7 (p.Arg2107fs) | ex46 | Photoreceptors | Int 26 (NG_009073.1) |
| ABCA4 | STGD | c.6319C > T (p.Arg2107Cys) | ex46 | Photoreceptors | Int 26 (NG_009073.1) |
| ABCA4 | STGD, AMD | c.6320G > A (p.Arg2107His) | ex46 | Photoreceptors | Int 26 (NG_009073.1) |
| ABCA4 | STGD | c.6320G > C (p.Arg2107Pro) | ex46 | Photoreceptors | Int 26 (NG_009073.1) |
| ABCA4 | STGD | c.6329G > A (p.Trp2110*) | ex46 | Photoreceptors | Int 26 (NG_009073.1) |
| ABCA4 | STGD | c.6339C > G (p.Ile2113Met) | ex46 | Photoreceptors | Int 26 (NG_009073.1) |
| ABCA4 | STGD | c.6352delA (p.Arg2118fs) | ex46 | Photoreceptors | Int 26 (NG_009073.1) |
| ABCA4 | STGD | c.6383A > G (p.His2128Arg) | ex46 | Photoreceptors | Int 26 (NG_009073.1) |
| ABCA4 | STGD | c.6386 + 2C > G (—) | int46 | Photoreceptors | Int 26 (NG_009073.1) |
| ABCA4 | STGD | c.6387 − 1G > T (—) | int46 | Photoreceptors | Int 26 (NG_009073.1) |
| ABCA4 | STGD | c.6391G > A (p.Glu2131Lys) | ex47 | Photoreceptors | Int 26 (NG_009073.1) |
| ABCA4 | STGD | c.6410G > A (p.Cys2137Tyr) | ex47 | Photoreceptors | Int 26 (NG_009073.1) |
| ABCA4 | STGD | c.6411T > A (p.Cys2137*) | ex47 | Photoreceptors | Int 26 (NG_009073.1) |
| ABCA4 | STGD | c.6415C > T (p.Arg2139Trp) | ex47 | Photoreceptors | Int 26 (NG_009073.1) |
| ABCA4 | STGD | c.6419T > A (p.Leu2140Gln) | ex47 | Photoreceptors | Int 26 (NG_009073.1) |
| ABCA4 | STGD | c.6437G > A (p.Gly2146Asp) | ex47 | Photoreceptors | Int 26 (NG_009073.1) |
| ABCA4 | STGD | c.6445C > T (p.Arg2149*) | ex47 | Photoreceptors | Int 26 (NG_009073.1) |
| ABCA4 | STGD | c.6446G > T (p.Arg2149Leu) | ex47 | Photoreceptors | Int 26 (NG_009073.1) |
| ABCA4 | STGD | c.6448T > C (p.Cys2150Arg) | ex47 | Photoreceptors | Int 26 (NG_009073.1) |
| ABCA4 | CRD | c.6449G > A (p.Cys2150Tyr) | ex47 | Photoreceptors | Int 26 (NG_009073.1) |

TABLE 1-continued

| | | | | | |
|---|---|---|---|---|---|
| ABCA4 | STGD | c.6479A > G (p.Lys2160Arg) | ex47 | Photoreceptors | Int 26 (NG_009073.1) |
| ABCA4 | STGD | c.6479 + 1G > A (—) | int47 | Photoreceptors | Int 26 (NG_009073.1) |
| ABCA4 | STGD | c.6479 + 1G > C (—) | int47 | Photoreceptors | Int 26 (NG_009073.1) |
| ABCA4 | AMD | c.6498C > G (p.Ile2166Met) | ex48 | Photoreceptors | Int 26 (NG_009073.1) |
| ABCA4 | STGD | c.6498C > T (p.Ile2166p.(=)) | ex48 | Photoreceptors | Int 26 (NG_009073.1) |
| ABCA4 | STGD | c.6515A > G (p.Lys2172Arg) | ex48 | Photoreceptors | Int 26 (NG_009073.1) |
| ABCA4 | STGD, AMD | c.6519_6529del11 (p.Lys2175fs) | ex48 | Photoreceptors | Int 26 (NG_009073.1) |
| ABCA4 | ARRP | c.6529G > A (p.Asp2177Asn) | ex48 | Photoreceptors | Int 26 (NG_009073.1) |
| ABCA4 | STGD | c.6543_6578del36 (p.Leu2182_Phe2193del) | ex48 | Photoreceptors | Int 26 (NG_009073.1) |
| ABCA4 | STGD | 6548_6549insTGAA (p.Pro2184fs) | ex48 | Photoreceptors | Int 26 (NG_009073.1) |
| ABCA4 | STGD | c.6559C > T (p.Gln2187*) | ex48 | Photoreceptors | Int 26 (NG_009073.1) |
| ABCA4 | STGD | c.6560A > C (p.Gln2187Pro) | ex48 | Photoreceptors | Int 26 (NG_009073.1) |
| ABCA4 | STGD | c.6563T > C (p.Phe2188Ser) | ex48 | Photoreceptors | Int 26 (NG_009073.1) |
| ABCA4 | AMD | c.6568delC (p.Gln2190fs) | ex48 | Photoreceptors | Int 26 (NG_009073.1) |
| ABCA4 | CRD | c.6601_6602delAG (p.Arg2201fs) | ex48 | Photoreceptors | Int 26 (NG_009073.1) |
| ABCA4 | STGD | c.6609C > A (p.Tyr2203*) | ex48 | Photoreceptors | Int 26 (NG_009073.1) |
| ABCA4 | STGD | c.6658C > T (p.Gln2220*) | ex48 | Photoreceptors | Int 26 (NG_009073.1) |
| ABCA4 | STGD | c.6662T > C (p.Leu2221Pro) | ex48 | Photoreceptors | Int 26 (NG_009073.1) |
| ABCA4 | STGD | c.6686T > C (p.Leu2229Pro) | ex48 | Photoreceptors | Int 26 (NG_009073.1) |
| ABCA4 | STGD | c.6707_6714del (p.Val2236fs) | ex48 | Photoreceptors | Int 26 (NG_009073.1) |
| ABCA4 | STGD | c.6709_6710insG (p.Thr2237fs) | ex48 | Photoreceptors | Int 26 (NG_009073.1) |
| ABCA4 | STGD | c.6710_6711insA (p.Gln2238fs) | ex48 | Photoreceptors | Int 26 (NG_009073.1) |
| ABCA4 | STGD | c.6712C > T (p.Gln2238*) | ex48 | Photoreceptors | Int 26 (NG_009073.1) |
| ABCA4 | STGD | c.6718A > G (p.Thr2240Ala) | ex48 | Photoreceptors | Int 26 (NG_009073.1) |
| ABCA4 | STGD | c.6721C > G (p.Leu2241Val) | ex48 | Photoreceptors | Int 26 (NG_009073.1) |
| ABCA4 | STGD | c.6729 + 1G > A (—) | int48 | Photoreceptors | Int 26 (NG_009073.1) |
| ABCA4 | STGD | c.6729 + 5_6729 + 19del15 (—) | int48 | Photoreceptors | Int 26 (NG_009073.1) |
| ABCA4 | STGD | c.6730 − 10_6730 − 2del9 (—) | int48 | Photoreceptors | Int 26 (NG_009073.1) |
| ABCA4 | STGD | c.6730 − 16_6757del (—) | int48/ex49 | Photoreceptors | Int 26 (NG_009073.1) |
| ABCA4 | STGD | c.6748delA (p.Lys2250fs) | ex49 | Photoreceptors | Int 26 (NG_009073.1) |
| ABCA4 | STGD | c.6757A > G (p.Thr2253Ala) | ex49 | Photoreceptors | Int 26 (NG_009073.1) |
| ABCA4 | STGD, AMD | c.6764G > T (p.Ser2255Ile) | ex49 | Photoreceptors | Int 26 (NG_009073.1) |
| ABCA4 | STGD | c.6788G > T (p.Arg2263Leu) | ex49 | Photoreceptors | Int 26 (NG_009073.1) |
| ABCA4 | STGD | c.6817 − 1G > A ( ) | int49 | Photoreceptors | Int 26 (NG_009073.1) |

| Target Ocular Gene | RTM Binding Domain Seq | Exon/Seq | Splice Site Seq |
|---|---|---|---|
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |

TABLE 1-continued

| | | | |
|---|---|---|---|
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |

TABLE 1-continued

| | | | |
|---|---|---|---|
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |

TABLE 1-continued

| | | | |
|---|---|---|---|
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |

TABLE 1-continued

| | | | |
|---|---|---|---|
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |

TABLE 1-continued

| | | | |
|---|---|---|---|
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |

TABLE 1-continued

| Gene | Description | Target | End |
|---|---|---|---|
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |

TABLE 1-continued

| | | | |
|---|---|---|---|
| ABCA4 | ~30-250 nts complementary to target intron | | |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |

TABLE 1-continued

| | | | |
|---|---|---|---|
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |

TABLE 1-continued

| | | | |
|---|---|---|---|
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron (NM_000350.2) | Ex 1-22 [c.1A p.Met1] through [c.3328G p.Ser1109 + 1] | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron (NM_000350.2) | Ex 1-22 [c.1A p.Met1] through [c.3328G p.Ser1109 + 1] | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |

TABLE 1-continued

| | | | |
|---|---|---|---|
| ABCA4 | ~30-250 nts complementary to target intron (NM_000350.2) | Ex 1-22 [c.1A p.Met1] through [c.3328G p.Ser1109 + 1] | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron (NM_000350.2) | Ex 1-22 [c.1A p.Met1] through [c.3328G p.Ser1109 + 1] | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |

TABLE 1-continued

| Gene | Description | Target | Position |
|---|---|---|---|
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |

TABLE 1-continued

| | | | |
|---|---|---|---|
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |

TABLE 1-continued

| | | | |
|---|---|---|---|
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |

TABLE 1-continued

| | | | |
|---|---|---|---|
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |

TABLE 1-continued

| | | | |
|---|---|---|---|
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |

TABLE 1-continued

| | | | |
|---|---|---|---|
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Ex 1-22 [c.1A p.Met1] through [c.3328G p.Ser1109 + 1] (NM_000350.2) | 5' |
| ABCA4 | ~30-250 nts complementary to target intron | Out of Range | |
| ABCA4 | ~30-250 nts complementary to target intron | Out of Range | |
| ABCA4 | ~30-250 nts complementary to target intron | Out of Range | |
| ABCA4 | ~30-250 nts complementary to target intron | Out of Range | |
| ABCA4 | ~30-250 nts complementary to target intron | Out of Range | |
| ABCA4 | ~30-250 nts complementary to target intron | Out of Range | |
| ABCA4 | ~30-250 nts complementary to target intron | Out of Range | |
| ABCA4 | ~30-250 nts complementary to target intron | Out of Range | |
| ABCA4 | ~30-250 nts complementary to target intron | Out of Range | |
| ABCA4 | ~30-250 nts complementary to target intron | Out of Range | |
| ABCA4 | ~30-250 nts complementary to target intron | Out of Range | |
| ABCA4 | ~30-250 nts complementary to target intron | Out of Range | |
| ABCA4 | ~30-250 nts complementary to target intron | Out of Range | |
| ABCA4 | ~30-250 nts complementary to target intron | Out of Range | |

TABLE 1-continued

| | | | |
|---|---|---|---|
| ABCA4 | ~30-250 nts complementary to target intron | Out of Range | |
| ABCA4 | ~30-250 nts complementary to target intron | Out of Range | |
| ABCA4 | ~30-250 nts complementary to target intron | Out of Range | |
| ABCA4 | ~30-250 nts complementary to target intron | Out of Range | |
| ABCA4 | ~30-250 nts complementary to target intron | Out of Range | |
| ABCA4 | ~30-250 nts complementary to target intron | Out of Range | |
| ABCA4 | ~30-250 nts complementary to target intron | Out of Range | |
| ABCA4 | ~30-250 nts complementary to target intron | Out of Range | |
| ABCA4 | ~30-250 nts complementary to target intron | Out of Range | |
| ABCA4 | ~30-250 nts complementary to target intron | Out of Range | |
| ABCA4 | ~30-250 nts complementary to target intron | Out of Range | |
| ABCA4 | ~30-250 nts complementary to target intron | Out of Range | |
| ABCA4 | ~30-250 nts complementary to target intron | Out of Range | |
| ABCA4 | ~30-250 nts complementary to target intron | Out of Range | |
| ABCA4 | ~30-250 nts complementary to target intron | Out of Range | |
| ABCA4 | ~30-250 nts complementary to target intron | Out of Range | |
| ABCA4 | ~30-250 nts complementary to target intron | Out of Range | |
| ABCA4 | ~30-250 nts complementary to target intron | Out of Range | |
| ABCA4 | ~30-250 nts complementary to target intron | Out of Range | |
| ABCA4 | ~30-250 nts complementary to target intron | Out of Range | |
| ABCA4 | ~30-250 nts complementary to target intron | Out of Range | |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |

TABLE 1-continued

| | | | |
|---|---|---|---|
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |

TABLE 1-continued

| | | | |
|---|---|---|---|
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |

TABLE 1-continued

| | | | |
|---|---|---|---|
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |

TABLE 1-continued

| | | | |
|---|---|---|---|
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |

TABLE 1-continued

| | | | |
|---|---|---|---|
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |

TABLE 1-continued

| Gene | Length | Target | End |
|---|---|---|---|
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |

TABLE 1-continued

| | | | |
|---|---|---|---|
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |

TABLE 1-continued

| | | | |
|---|---|---|---|
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |

TABLE 1-continued

| | | | |
|---|---|---|---|
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |

TABLE 1-continued

| | | | |
|---|---|---|---|
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |

TABLE 1-continued

| | | | |
|---|---|---|---|
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |

TABLE 1-continued

| | | | |
|---|---|---|---|
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |

TABLE 1-continued

| | | | |
|---|---|---|---|
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |

TABLE 1-continued

| | | | |
|---|---|---|---|
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |

TABLE 1-continued

| | | | |
|---|---|---|---|
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |
| ABCA4 | ~30-250 nts complementary to target intron | Ex 27-50 [c.3863G p.Gly1289 − 2] through [c.6822A p.Stop2274] (NM_000350.2) | 3' |

TABLE 2

| Target Ocular Gene | Ocular Disease | Mutation | Target Cells | Intron/SEQ | Binding Domain Seq | RTM Exon/Seq | Splice Site Seq |
|---|---|---|---|---|---|---|---|
| CEP290 | Meckel Syndrome | c.3043G > T | Multi-organ | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Meckel Syndrome | c.3104 − 1G > A | multi-organ | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Joubert Syndrome: LCA & Nephronophthisis & CNS anomalies | c.3104 − 2A > G | Photoreceptors, Kidney tubular epithelium; CNS | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Meckel Syndrome | c.3175del | Photoreceptors, Kidney tubular epithelium; CNS | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Joubert Syndrome: LCA & Nephronophthisis & CNS anomalies | c.3175dup | Photoreceptors, Kidney tubular epithelium; CNS | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Joubert Syndrome: LCA & Nephronophthisis & CNS anomalies | c.3176del | Photoreceptors, Kidney tubular epithelium; CNS | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Joubert Syndrome: LCA & Nephronophthisis & CNS anomalies | c.3178delA | Photoreceptors, Kidney tubular epithelium; CNS | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Joubert Syndrome: LCA & Nephronophthisis & CNS anomalies | c.3292G > T | Photoreceptors, Kidney tubular epithelium; CNS | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Joubert Syndrome: LCA & Nephronophthisis & CNS anomalies | c.3310 − 1G > C | Photoreceptors, Kidney tubular epithelium; CNS | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Joubert Syndrome: LCA & Nephronophthisis & CNS anomalies | c.3310 − a_3310delinsAA | Photoreceptors, Kidney tubular epithelium; CNS | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Joubert Syndrome: LCA & Nephronophthisis & CNS anomalies | c.3422dup | Photoreceptors, Kidney tubular epithelium; CNS | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Meckel Syndrome | c.3793C > T | Multi-organ | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Joubert Syndrome: LCA & Nephronophthisis & CNS anomalies | c.3802C > T | Photoreceptors, Kidney tubular epithelium; CNS | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Joubert Syndrome: LCA & Nephronophthisis & CNS anomalies | c.3811C > T | Photoreceptors, Kidney tubular epithelium; CNS | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Joubert Syndrome: LCA & Nephronophthisis & CNS anomalies | c.3814C > T | Photoreceptors, Kidney tubular epithelium; CNS | Int 26 (NG_008417.1) | ~30-250 nts complementary to target intron | Ex 27-54 [c.2992T p.Cys998] through [c.7440A p.Stop2480] (NM_025114.3) | 3' |

TABLE 2-continued

| Target Ocular Gene | Ocular Disease | Mutation | Intron/SEQ | Binding Domain Seq | RTM Exon/Seq | Splice Site Seq |
|---|---|---|---|---|---|---|
| CEP290 | Joubert Syndrome: LCA & Nephronophthisis & CNS anomalies | c.3922C > T | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Joubert Syndrome: LCA & Nephronophthisis & CNS anomalies | c.4001del | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Joubert Syndrome: LCA & Nephronophthisis & CNS anomalies | c.4028del | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Joubert Syndrome: LCA & Nephronophthisis & CNS anomalies | c.4114_4115del | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Meckel Syndrome | c.4115_4116del | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Joubert Syndrome: LCA & Nephronophthisis & CNS anomalies | c.4195 – 1G > A | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Senior Loken Syndrome: LCA & Nephronophthisis | c.4452_4455del AGAA | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Senior Loken Syndrome: LCA & Nephronophthisis | c.4656del | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | LCA | c.4661_4663del | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Joubert Syndrome: LCA & Nephronophthisis & CNS anomalies | c.4723A > T | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Joubert Syndrome: LCA & Nephronophthisis & CNS anomalies | c.4732G > T | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Joubert Syndrome: LCA & Nephronophthisis & CNS anomalies | c.4771C > T | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Joubert Syndrome: LCA & Nephronophthisis & CNS anomalies | c.4791_4794del | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Joubert Syndrome: LCA & Nephronophthisis & CNS anomalies | c.4882C > T | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Joubert Syndrome: LCA & Nephronophthisis & CNS anomalies | c.4962_4963del | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Joubert Syndrome: LCA & Nephronophthisis & CNS anomalies | c.4965_4966del | Int 26 (NG_008417.1) | ~30-250 nts complementary to target intron | Ex 27-54 [c.2992T p.Cys998] through [c.7440A p.Stop2480] (NM_025114.3) | 3' |

Target Cells column (in order): Photoreceptors, Kidney tubular epithelium; CNS; Photoreceptors, Kidney tubular epithelium; CNS; Photoreceptors, Kidney tubular epithelium; CNS; Photoreceptors, Kidney tubular epithelium; CNS; multi-organ; Photoreceptors, Kidney tubular epithelium; CNS; Photoreceptors, Kidney tubular epithelium; Photoreceptors, Kidney tubular epithelium; Photoreceptors; Photoreceptors, Kidney tubular epithelium; CNS; Photoreceptors, Kidney tubular epithelium; CNS; Photoreceptors, Kidney tubular epithelium; CNS; Photoreceptors, Kidney tubular epithelium; CNS; Photoreceptors, Kidney tubular epithelium; CNS; Photoreceptors, Kidney tubular epithelium; CNS; Photoreceptors, Kidney tubular epithelium; CNS.

TABLE 2-continued

| Target Ocular Gene | Ocular Disease | Mutation | Target Cells | Intron/SEQ | Binding Domain Seq | RTM Exon/Seq | Splice Site Seq |
|---|---|---|---|---|---|---|---|
| CEP290 | Joubert Syndrome: LCA & Nephronophthisis & CNS anomalies | c.4966G > T | Photoreceptors, Kidney tubular epithelium; CNS | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Joubert Syndrome: LCA & Nephronophthisis & CNS anomalies | c.5046del | Photoreceptors, Kidney tubular epithelium; CNS | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Joubert Syndrome: LCA & Nephronophthisis & CNS anomalies | c.5163del | Photoreceptors, Kidney tubular epithelium; CNS | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Joubert Syndrome: LCA & Nephronophthisis & CNS anomalies | c.5182G > T | Photoreceptors, Kidney tubular epithelium; CNS | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Joubert Syndrome: LCA & Nephronophthisis & CNS anomalies | c.5218C > T | Photoreceptors, Kidney tubular epithelium; CNS | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Senior Loken Syndrome: LCA & Nephronophthisis | c.5226 + 5_8del GTAA | Photoreceptors, Kidney tubular epithelium | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Senior Loken Syndrome: LCA & Nephronophthisis | c.5256_5257del | Photoreceptors, Kidney tubular epithelium | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Senior Loken Syndrome: LCA & Nephronophthisis | c.5434_5435del | Photoreceptors, Kidney tubular epithelium | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Senior Loken Syndrome: LCA & Nephronophthisis | c.5445 – 8delAACT | Photoreceptors, Kidney tubular epithelium | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Senior Loken Syndrome: LCA & Nephronophthisis | c.5493del | Photoreceptors, Kidney tubular epithelium | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Senior Loken Syndrome: LCA & Nephronophthisis | c.5515_5518del | Photoreceptors, Kidney tubular epithelium | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Senior Loken Syndrome: LCA & Nephronophthisis | c.5519_5537del | Photoreceptors, Kidney tubular epithelium | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Senior Loken Syndrome: LCA & Nephronophthisis | c.5587 – 1G > C | Photoreceptors, Kidney tubular epithelium | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Senior Loken Syndrome: LCA & Nephronophthisis | c.5611_5614del | Photoreceptors, Kidney tubular epithelium | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Meckel Syndrome | c.5649_5650insA | multi-organ | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Senior Loken Syndrome: LCA & Nephronophthisis | c.5649dup | Photoreceptors, Kidney tubular epithelium | Int 26 (NG_008417.1) | ~30-250 nts complementary to target intron | Ex 27-54 [c.2992T p.Cys998] through [c.7440A p.Stop2480] (NM_025114.3) | 3' |

TABLE 2-continued

| Target Ocular Gene | Ocular Disease | Mutation | Target Cells | Intron/SEQ | Binding Domain Seq | Exon/Seq | Splice Site Seq |
|---|---|---|---|---|---|---|---|
| | | | | | RTM | | |
| CEP290 | Joubert Syndrome: LCA & Nephronophthisis & CNS anomalies | c.5722G > T | Photoreceptors, Kidney tubular epitheliuam; CNS | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Joubert Syndrome: LCA & Nephronophthisis & CNS anomalies | c.5734del | Photoreceptors, Kidney tubular epitheliuam; CNS | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Joubert Syndrome: LCA & Nephronophthisis & CNS anomalies | c.5776C > T | Photoreceptors, Kidney tubular epitheliuam; CNS | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Joubert Syndrome: LCA & Nephronophthisis & CNS anomalies | c.5813_5817del | Photoreceptors, Kidney tubular epitheliuam; CNS | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Joubert Syndrome: LCA & Nephronophthisis & CNS anomalies | c.5824C > T | Photoreceptors, Kidney tubular epitheliuam; CNS | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Meckel Syndrome | c.5850del | multi-organ | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Joubert Syndrome: LCA & Nephronophthisis & CNS anomalies | c.5865_5867del insGG | Photoreceptors, Kidney tubular epitheliuam; CNS | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Joubert Syndrome: LCA & Nephronophthisis & CNS anomalies | c.5866G > T | Photoreceptors, Kidney tubular epitheliuam; CNS | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Senior Loken Syndrome: LCA & Nephronophthisis | c.5932C > T | photoreceptors, Kidney tubular epithelium | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Joubert Syndrome: LCA & Nephronophthisis & CNS anomalies | c.6031C > T | Photoreceptors, Kidney tubular epitheliuam; CNS | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Joubert Syndrome: LCA & Nephronophthisis & CNS anomalies | c.6072C > A | Photoreceptors, Kidney tubular epitheliuam; CNS | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Senior Loken Syndrome: LCA & Nephronophthisis | c.6271 – 8T > G | Photoreceptors, Kidney tubular epithelium | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Senior Loken Syndrome: LCA & Nephronophthisis | c.6277del | Photoreceptors, Kidney tubular epithelium | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Joubert Syndrome: LCA & Nephronophthisis & CNS anomalies | c.6604del | Photoreceptors, Kidney tubular epitheliuam | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Joubert Syndrome: LCA & Nephronophthisis & CNS anomalies | c.6869del | Photoreceptors, Kidney tubular epitheliuam; CNS | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Joubert Syndrome: LCA & Nephronophthisis & CNS anomalies | c.6870del | Photoreceptors, Kidney tubular epitheliuam | Int 26 (NG_008417.1) | ~30-250 nts complementary to target intron | Ex 27-54 [c.2992T p.Cys998] through [c.7440A p.Stop2480] (NM_025114.3) | 3' |

TABLE 2-continued

| Target Ocular Gene | Ocular Disease | Mutation | Target Cells | Intron/SEQ | Binding Domain Seq | RTM Exon/Seq | Splice Site Seq |
|---|---|---|---|---|---|---|---|
| CEP290 | Senior Loken Syndrome: LCA & Nephronophthisis | c.7318_7321dup | Photoreceptors, Kidney tubular epithelium | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Senior Loken Syndrome: LCA & Nephronophthisis | c.7341dup | Photoreceptors, Kidney tubular epithelium | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Senior Loken Syndrome: LCA & Nephronophthisis | c.7366_7369del | Photoreceptors, Kidney tubular epithelium | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Senior Loken Syndrome: LCA & Nephronophthisis | c5226 + 1G > A | Photoreceptors, Kidney tubular epithelium | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | LCA | c5777G > C | Photoreceptors | Int 26 (NG_008417.1) | ~30-250 nts complementary to target intron | Ex 27-54 [c.2992T p.Cys998] through [c.7440A p.Stop2480] (NM_025114.3) | 3' |
| CEP290 | Joubert Syndrome: LCA & Nephronophthisis & CNS anomalies | c5941G > T | Photoreceptors, Kidney tubular epithelium; CNS | Int 26 (NG_008417.1) | ~30-250 nts complementary to target intron | Ex 1-26 [c.1A p.Met1] through [c.2991G p.Glu997] (NM_025114.3) | 5' |
| CEP290 | Joubert Syndrome: LCA & Nephronophthisis & CNS anomalies | 1984C | Photoreceptors, Kidney tubular epithelium; CNS | Int 26 (NG_008417.1) | ~30-250 nts complementary to target intron | Ex 1-26 [c.1A p.Met1] through [c.2991G p.Glu997] (NM_025114.3) | 5' |
| CEP290 | Joubert Syndrome: LCA & Nephronophthisis & CNS anomalies | c.103-13_103-18del | Photoreceptors, Kidney tubular epithelium; CNS | Int 26 (NG_008417.1) | ~30-250 nts complementary to target intron | Ex 1-26 [c.1A p.Met1] through [c.2991G p.Glu997] (NM_025114.3) | 5' |
| CEP290 | Joubert Syndrome: LCA & Nephronophthisis & CNS anomalies | c.1066 – 1G > A | Photoreceptors, Kidney tubular epithelium; CNS | Int 26 (NG_008417.1) | ~30-250 nts complementary to target intron | Ex 1-26 [c.1A p.Met1] through [c.2991G p.Glu997] (NM_025114.3) | 5' |
| CEP290 | Joubert Syndrome: LCA & Nephronophthisis & CNS anomalies | c.1189 + 1G > A | Photoreceptors, Kidney tubular epithelium; CNS | Int 26 (NG_008417.1) | ~30-250 nts complementary to target intron | Ex 1-26 [c.1A p.Met1] through [c.2991G p.Glu997] (NM_025114.3) | 5' |
| CEP290 | Meckel Syndrome | c.1219_1220del | multi-organ | Int 26 (NG_008417.1) | ~30-250 nts complementary to target intron | Ex 1-26 [c.1A p.Met1] through [c.2991G p.Glu997] (NM_025114.3) | 5' |
| CEP290 | Joubert Syndrome: LCA & Nephronophthisis & CNS anomalies | c.1260_1264del | Photoreceptors, Kidney tubular epithelium; CNS | Int 26 (NG_008417.1) | ~30-250 nts complementary to target intron | Ex 1-26 [c.1A p.Met1] through [c.2991G p.Glu997] (NM_025114.3) | 5' |
| CEP290 | Joubert Syndrome: LCA & Nephronophthisis & CNS anomalies | c.1361del | Photoreceptors, Kidney tubular epithelium; CNS | Int 26 (NG_008417.1) | ~30-250 nts complementary to target intron | Ex 1-26 [c.1A p.Met1] through [c.2991G p.Glu997] (NM_025114.3) | 5' |
| CEP290 | Senior Loken Syndrome: LCA & Nephronophthisis | c.136G > T | Photoreceptors, Kidney tubular epithelium | Int 26 (NG_008417.1) | ~30-250 nts complementary to target intron | Ex 1-26 [c.1A p.Met1] through [c.2991G p.Glu997] (NM_025114.3) | 5' |
| CEP290 | Senior Loken Syndrome: LCA & Nephronophthisis | c.1419_1423del | Photoreceptors, Kidney tubular epithelium | Int 26 (NG_008417.1) | ~30-250 nts complementary to target intron | Ex 1-26 [c.1A p.Met1] through [c.2991G p.Glu997] (NM_025114.3) | 5' |
| CEP290 | Joubert Syndrome: LCA & Nephronophthisis & CNS anomalies | c.1429T | Photoreceptors, Kidney tubular epithelium; CNS | Int 26 (NG_008417.1) | ~30-250 nts complementary to target intron | Ex 1-26 [c.1A p.Met1] through [c.2991G p.Glu997] (NM_025114.3) | 5' |

TABLE 2-continued

| Target Ocular Gene | Ocular Disease | Mutation | Target Cells | Intron/SEQ | Binding Domain Seq | Exon/Seq | Splice Site Seq |
|---|---|---|---|---|---|---|---|
| | | | | | RTM | | |
| CEP290 | Joubert Syndrome: LCA & Nephronophthisis & CNS anomalies | c.164_167del | Photoreceptors, Kidney tubular epitheliuam; CNS | Int 26 (NG_008417.1) | ~30-250 nts complementary to target intron | Ex 1-26 [c.1A p.Met1] through [c.2991G p.Glu997] (NM_025114.3) | 5' |
| CEP290 | Joubert Syndrome: LCA & Nephronophthisis & CNS anomalies | c.1645C > T | Photoreceptors, Kidney tubular epitheliuam; CNS | Int 26 (NG_008417.1) | ~30-250 nts complementary to target intron | Ex 1-26 [c.1A p.Met1] through [c.2991G p.Glu997] (NM_025114.3) | 5' |
| CEP290 | Joubert Syndrome: LCA & Nephronophthisis & CNS anomalies | c.1666del | Photoreceptors, Kidney tubular epitheliuam; CNS | Int 26 (NG_008417.1) | ~30-250 nts complementary to target intron | Ex 1-26 [c.1A p.Met1] through [c.2991G p.Glu997] (NM_025114.3) | 5' |
| CEP290 | Joubert Syndrome: LCA & Nephronophthisis & CNS anomalies | c.1682_1683del | Photoreceptors, Kidney tubular epitheliuam; CNS | Int 26 (NG_008417.1) | ~30-250 nts complementary to target intron | Ex 1-26 [c.1A p.Met1] through [c.2991G p.Glu997] (NM_025114.3) | 5' |
| CEP290 | Joubert Syndrome: LCA & Nephronophthisis & CNS anomalies | c.1709C > G | Photoreceptors, Kidney tubular epitheliuam; CNS | Int 26 (NG_008417.1) | ~30-250 nts complementary to target intron | Ex 1-26 [c.1A p.Met1] through [c.2991G p.Glu997] (NM_025114.3) | 5' |
| CEP290 | Joubert Syndrome: LCA & Nephronophthisis & CNS anomalies | c.1711 + 5A > G | Photoreceptors, Kidney tubular epitheliuam; CNS | Int 26 (NG_008417.1) | ~30-250 nts complementary to target intron | Ex 1-26 [c.1A p.Met1] through [c.2991G p.Glu997] (NM_025114.3) | 5' |
| CEP290 | Joubert Syndrome: LCA & Nephronophthisis & CNS anomalies | c.180 + 1G > T | Photoreceptors, Kidney tubular epitheliuam; CNS | Int 26 (NG_008417.1) | ~30-250 nts complementary to target intron | Ex 1-26 [c.1A p.Met1] through [c.2991G p.Glu997] (NM_025114.3) | 5' |
| CEP290 | Meckel Syndrome | c.180 + 2T > A | multi-organ | Int 26 (NG_008417.1) | ~30-250 nts complementary to target intron | Ex 1-26 [c.1A p.Met1] through [c.2991G p.Glu997] (NM_025114.3) | 5' |
| CEP290 | Joubert Syndrome: LCA & Nephronophthisis & CNS anomalies | c.1824G > A | Photoreceptors, Kidney tubular epitheliuam; CNS | Int 26 (NG_008417.1) | ~30-250 nts complementary to target intron | Ex 1-26 [c.1A p.Met1] through [c.2991G p.Glu997] (NM_025114.3) | 5' |
| CEP290 | Joubert Syndrome: LCA & Nephronophthisis & CNS anomalies | c.1830delA | Photoreceptors, Kidney tubular epitheliuam; CNS | Int 26 (NG_008417.1) | ~30-250 nts complementary to target intron | Ex 1-26 [c.1A p.Met1] through [c.2991G p.Glu997] (NM_025114.3) | 5' |
| CEP290 | Joubert Syndrome: LCA & Nephronophthisis & CNS anomalies | c.1859_1862del | Photoreceptors, Kidney tubular epitheliuam; CNS | Int 26 (NG_008417.1) | ~30-250 nts complementary to target intron | Ex 1-26 [c.1A p.Met1] through [c.2991G p.Glu997] (NM_025114.3) | 5' |
| CEP290 | Meckel Syndrome | c.1860_1861del | multi-organ | Int 26 (NG_008417.1) | ~30-250 nts complementary to target intron | Ex 1-26 [c.1A p.Met1] through [c.2991G p.Glu997] (NM_025114.3) | 5' |
| CEP290 | Joubert Syndrome: LCA & Nephronophthisis & CNS anomalies | c.1910 − 2A > C | Photoreceptors, Kidney tubular epitheliuam; CNS | Int 26 (NG_008417.1) | ~30-250 nts complementary to target intron | Ex 1-26 [c.1A p.Met1] through [c.2991G p.Glu997] (NM_025114.3) | 5' |
| CEP290 | Joubert Syndrome: LCA & Nephronophthisis & CNS anomalies | c.1936C > T | Photoreceptors, Kidney tubular epitheliuam; CNS | Int 26 (NG_008417.1) | ~30-250 nts complementary to target intron | Ex 1-26 [c.1A p.Met1] through [c.2991G p.Glu997] (NM_025114.3) | 5' |
| CEP290 | Meckel Syndromec kidneys, polydactyly, hepatic fibrosis, LCA) (encephalocele, | c.1984C > T | Multi-organ | Int 26 (NG_008417.1) | ~30-250 nts complementary to target intron | Ex 1-26 [c.1A p.Met1] through [c.2991G p.Glu997] (NM_025114.3) | 5' |

TABLE 2-continued

| Target Ocular Gene | Ocular Disease | Mutation | Target Cells | Intron/SEQ | RTM Binding Domain Seq | RTM Exon/Seq | Splice Site Seq |
|---|---|---|---|---|---|---|---|
| CEP290 | polycyst LCA | c.1985A > T | Photoreceptors | Int 26 (NG_008417.1) | ~30-250 nts complementary to target intron | Ex 1-26 [c.1A p.Met1] through [c.2991G p.Glu997] (NM_025114.3) | 5' |
| CEP290 | Joubert Syndrome: LCA & Nephronophthisis & CNS anomalies | c.1987A > T | Photoreceptors, Kidney tubular epithelium; CNS | Int 26 (NG_008417.1) | ~30-250 nts complementary to target intron | Ex 1-26 [c.1A p.Met1] through [c.2991G p.Glu997] (NM_025114.3) | 5' |
| CEP290 | LCA | c.1991A > G | Photoreceptors | Int 26 (NG_008417.1) | ~30-250 nts complementary to target intron | Ex 1-26 [c.1A p.Met1] through [c.2991G p.Glu997] (NM_025114.3) | 5' |
| CEP290 | Joubert Syndrome: LCA & Nephronophthisis & CNS anomalies | c.1992del | Photoreceptors, Kidney tubular epithelium; CNS | Int 26 (NG_008417.1) | ~30-250 nts complementary to target intron | Ex 1-26 [c.1A p.Met1] through [c.2991G p.Glu997] (NM_025114.3) | 5' |
| CEP290 | LCA | c.1A > G | Photoreceptors | Int 26 (NG_008417.1) | ~30-250 nts complementary to target intron | Ex 1-26 [c.1A p.Met1] through [c.2991G p.Glu997] (NM_025114.3) | 5' |
| CEP290 | Senior Loken Syndrome: LCA & Nephronophthisis | c.2118_2122dup | Photoreceptors, Kidney tubular epithelium | Int 26 (NG_008417.1) | ~30-250 nts complementary to target intron | Ex 1-26 [c.1A p.Met1] through [c.2991G p.Glu997] (NM_025114.3) | 5' |
| CEP290 | LCA | c.21G > T | Photoreceptors | Int 26 (NG_008417.1) | ~30-250 nts complementary to target intron | Ex 1-26 [c.1A p.Met1] through [c.2991G p.Glu997] (NM_025114.3) | 5' |
| CEP290 | Joubert Syndrome: LCA & Nephronophthisis & CNS anomalies | c.2213delT | Photoreceptors, Kidney tubular epithelium; CNS | Int 26 (NG_008417.1) | ~30-250 nts complementary to target intron | Ex 1-26 [c.1A p.Met1] through [c.2991G p.Glu997] (NM_025114.3) | 5' |
| CEP290 | Senior Loken Syndrome: LCA & Nephronophthisis | c.2118-15_2220del | Photoreceptors, Kidney tubular epithelium | Int 26 (NG_008417.1) | ~30-250 nts complementary to target intron | Ex 1-26 [c.1A p.Met1] through [c.2991G p.Glu997] (NM_025114.3) | 5' |
| CEP290 | Senior Loken Syndrome: LCA & Nephronophthisis | c.2218 − 2A > C | Photoreceptors, Kidney tubular epithelium | Int 26 (NG_008417.1) | ~30-250 nts complementary to target intron | Ex 1-26 [c.1A p.Met1] through [c.2991G p.Glu997] (NM_025114.3) | 5' |
| CEP290 | Senior Loken Syndrome: LCA & Nephronophthisis | c.2118-4_2222del | Photoreceptors, Kidney tubular epithelium | Int 26 (NG_008417.1) | ~30-250 nts complementary to target intron | Ex 1-26 [c.1A p.Met1] through [c.2991G p.Glu997] (NM_025114.3) | 5' |
| CEP290 | Joubert Syndrome: LCA & Nephronophthisis & CNS anomalies | c.2505_2506delAG | Photoreceptors, Kidney tubular epithelium; CNS | Int 26 (NG_008417.1) | ~30-250 nts complementary to target intron | Ex 1-26 [c.1A p.Met1] through [c.2991G p.Glu997] (NM_025114.3) | 5' |
| CEP290 | Senior Loken Syndrome: LCA & Nephronophthisis | c.265dup | Photoreceptors, Kidney tubular epithelium | Int 26 (NG_008417.1) | ~30-250 nts complementary to target intron | Ex 1-26 [c.1A p.Met1] through [c.2991G p.Glu997] (NM_025114.3) | 5' |
| CEP290 | Senior Loken Syndrome: LCA & Nephronophthisis | c.270_274delAGTAA | Photoreceptors, Kidney tubular epithelium | Int 26 (NG_008417.1) | ~30-250 nts complementary to target intron | Ex 1-26 [c.1A p.Met1] through [c.2991G p.Glu997] (NM_025114.3) | 5' |
| CEP290 | Senior Loken Syndrome: LCA & Nephronophthisis | c.287del | Photoreceptors, Kidney tubular epithelium | Int 26 (NG_008417.1) | ~30-250 nts complementary to target intron | Ex 1-26 [c.1A p.Met1] through [c.2991G p.Glu997] (NM_025114.3) | 5' |

TABLE 2-continued

| Target Ocular Gene | Ocular Disease | Mutation | Target Cells | Intron/SEQ | Binding Domain Seq | Exon/Seq | Splice Site Seq |
|---|---|---|---|---|---|---|---|
| | | | | | RTM | | |
| CEP290 | Meckel Syndrome | c.2906dupA | multi-organ | Int 26 (NG_008417.1) | ~30-250 nts complementary to target intron | Ex 1-26 [c.1A p.Met1] through [c.2991G p.Glu997] (NM_025114.3) | 5' |
| CEP290 | LCA | c.2915T > G | Photoreceptors | Int 26 (NG_008417.1) | ~30-250 nts complementary to target intron | Ex 1-26 [c.1A p.Met1] through [c.2991G p.Glu997] (NM_025114.3) | 5' |
| CEP290 | LCA | c.2991 + 1655A > G | Photoreceptors | Int 26 (NG_008417.1) | ~30-250 nts complementary to target intron | Ex 1-26 [c.1A p.Met1] through [c.2991G p.Glu997] (NM_025114.3) | 5' |
| CEP290 | LCA | c.2T > G | Photoreceptors | Int 26 (NG_008417.1) | ~30-250 nts complementary to target intron | Ex 1-26 [c.1A p.Met1] through [c.2991G p.Glu997] (NM_025114.3) | 5' |
| CEP290 | Joubert Syndrome: LCA & Nephronophthisis anomalies | c.322C > T | Photoreceptors, Kidney tubular epithelium; CNS | Int 26 (NG_008417.1) | ~30-250 nts complementary to target intron | Ex 1-26 [c.1A p.Met1] through [c.2991G p.Glu997] (NM_025114.3) | 5' |
| CEP290 | Meckel Syndrome | c.381_382delinsT | Multi-organ | Int 26 (NG_008417.1) | ~30-250 nts complementary to target intron | Ex 1-26 [c.1A p.Met1] through [c.2991G p.Glu997] (NM_025114.3) | 5' |
| CEP290 | Senior Loken Syndrome: LCA & Nephronophthisis | c.384_385del | Photoreceptors, Kidney tubular epithelium | Int 26 (NG_008417.1) | ~30-250 nts complementary to target intron | Ex 1-26 [c.1A p.Met1] through [c.2991G p.Glu997] (NM_025114.3) | 5' |
| CEP290 | Meckel Syndrome | c.384_387del | Multi-organ | Int 26 (NG_008417.1) | ~30-250 nts complementary to target intron | Ex 1-26 [c.1A p.Met1] through [c.2991G p.Glu997] (NM_025114.3) | 5' |
| CEP290 | Meckel Syndrome | c.387delTAGA | multi-organ | Int 26 (NG_008417.1) | ~30-250 nts complementary to target intron | Ex 1-26 [c.1A p.Met1] through [c.2991G p.Glu997] (NM_025114.3) | 5' |
| CEP290 | Senior Loken Syndrome: LCA & Nephronophthisis | c.437del | Photoreceptors, Kidney tubular epithelium | Int 26 (NG_008417.1) | ~30-250 nts complementary to target intron | Ex 1-26 [c.1A p.Met1] through [c.2991G p.Glu997] (NM_025114.3) | 5' |
| CEP290 | Joubert Syndrome: LCA & Nephronophthisis anomalies | c.451C > T | Photoreceptors, Kidney tubular epithelium; CNS | Int 26 (NG_008417.1) | ~30-250 nts complementary to target intron | Ex 1-26 [c.1A p.Met1] through [c.2991G p.Glu997] (NM_025114.3) | 5' |
| CEP290 | Joubert Syndrome: LCA & Nephronophthisis anomalies | c.566C > G | Photoreceptors, Kidney tubular epithelium; CNS | Int 26 (NG_008417.1) | ~30-250 nts complementary to target intron | Ex 1-26 [c.1A p.Met1] through [c.2991G p.Glu997] (NM_025114.3) | 5' |
| CEP290 | Meckel Syndrome | c.613C > T | Multi-organ | Int 26 (NG_008417.1) | ~30-250 nts complementary to target intron | Ex 1-26 [c.1A p.Met1] through [c.2991G p.Glu997] (NM_025114.3) | 5' |
| CEP290 | Senior Loken Syndrome: LCA & Nephronophthisis | c.679_680del | Photoreceptors, Kidney tubular epithelium | Int 26 (NG_008417.1) | ~30-250 nts complementary to target intron | Ex 1-26 [c.1A p.Met1] through [c.2991G p.Glu997] (NM_025114.3) | 5' |
| CEP290 | LCA | c.829G > C | Photoreceptors | Int 26 (NG_008417.1) | ~30-250 nts complementary to target intron | Ex 1-26 [c.1A p.Met1] through [c.2991G p.Glu997] (NM_025114.3) | 5' |

TABLE 2-continued

| Target Ocular Gene | Ocular Disease | Mutation | Intron/SEQ | Target Cells | Binding Domain Seq | Exon/Seq | Splice Site Seq |
|---|---|---|---|---|---|---|---|
| | | | | | | RTM | |
| CEP290 | Joubert Syndrome: LCA & Nephronophthisis & CNS anomalies | IVS10 – 11_12insG | Int 26 (NG_008417.1) | Photoreceptors, Kidney tubular epitheliuam; CNS | ~30-250 nts complementary to target intron | Ex 1-26 [c.1A p.Met1] through [c.2991G p.Glu997] (NM_025114.3) | 5' |
| CEP290 | Joubert Syndrome: LCA & Nephronophthisis & CNS anomalies | IVS26 + 1655A > G | Int 26 (NG_008417.1) | Photoreceptors, Kidney tubular epitheliuam; CNS | ~30-250 nts complementary to target intron | Ex 1-26 [c.1A p.Met1] through [c.2991G p.Glu997] (NM_025114.3) | 5' |

TABLE 3

| Target Ocular Gene | Ocular Disease | Mutation | Protein change | Target Cells | Intron/SEQ |
|---|---|---|---|---|---|
| MYO7A | Usher Syndrome | c.4450C > T | p.L1484F | RPE, Photoreceptors, Cochlear hair cells, Olfactory epithelium | Int 32 (NG_009086.1) |
| MYO7A | Usher Syndrome | c.4475C > T | p.A1492V | RPE, Photoreceptors, Cochlear hair cells, Olfactory epithelium | Int 32 (NG_009086.1) |
| MYO7A | Usher Syndrome | c.4697C > T | p.T1566M | RPE, Photoreceptors, Cochlear hair cells, Olfactory epithelium | Int 32 (NG_009086.1) |
| MYO7A | Usher Syndrome | c.4740C > A | p.Y1580X | RPE, Photoreceptors, Cochlear hair cells, Olfactory epithelium | Int 32 (NG_009086.1) |
| MYO7A | Usher Syndrome | c.4805G > A | p.R1602Q | RPE, Photoreceptors, Cochlear hair cells, Olfactory epithelium | Int 32 (NG_009086.1) |
| MYO7A | Usher Syndrome | c.4882G > T | p.A1628S | RPE, Photoreceptors, Cochlear hair cells, Olfactory epithelium | Int 32 (NG_009086.1) |
| MYO7A | Usher Syndrome | c.4996A > T | p.S1666C | RPE, Photoreceptors, Cochlear hair cells, Olfactory epithelium | Int 32 (NG_009086.1) |
| MYO7A | Usher Syndrome | c.5101C > T | p.R1701X | RPE, Photoreceptors, Cochlear hair cells, Olfactory epithelium | Int 32 (NG_009086.1) |
| MYO7A | Usher Syndrome | c.5146G > T | p.E1716X | RPE, Photoreceptors, Cochlear hair cells, Olfactory epithelium | Int 32 (NG_009086.1) |
| MYO7A | Usher Syndrome | c.5156A > G | p.Y1719C | RPE, Photoreceptors, Cochlear hair cells, Olfactory epithelium | Int 32 (NG_009086.1) |
| MYO7A | Usher Syndrome | c.5215C > T | p.R1739X | RPE, Photoreceptors, Cochlear hair cells, Olfactory epithelium | Int 32 (NG_009086.1) |
| MYO7A | Usher Syndrome | c.5227C > T | p.R1743W | RPE, Photoreceptors, Cochlear hair cells, Olfactory epithelium | Int 32 (NG_009086.1) |
| MYO7A | Usher Syndrome | c.5309C > A | p.A1770D | RPE, Photoreceptors, Cochlear hair cells, Olfactory epithelium | Int 32 (NG_009086.1) |
| MYO7A | Usher Syndrome | c.5392C > T | p.Q1798X | RPE, Photoreceptors, Cochlear hair cells, Olfactory epithelium | Int 32 (NG_009086.1) |
| MYO7A | Usher Syndrome | c.5507T > C | p.L1836P | RPE, Photoreceptors, Cochlear hair cells, Olfactory epithelium | Int 32 (NG_009086.1) |
| MYO7A | Usher Syndrome | c.5573T > C | p.L1858P | RPE, Photoreceptors, Cochlear hair cells, Olfactory epithelium | Int 32 (NG_009086.1) |
| MYO7A | Usher Syndrome | c.5581C > T | p.R1861X | RPE, Photoreceptors, Cochlear hair cells, Olfactory epithelium | Int 32 (NG_009086.1) |
| MYO7A | Usher Syndrome | c.5617C > T | p.R1873W | RPE, Photoreceptors, Cochlear hair cells, Olfactory epithelium | Int 32 (NG_009086.1) |
| MYO7A | Usher Syndrome | c.5618G > A | p.R1873Q | RPE, Photoreceptors, Cochlear hair cells, Olfactory epithelium | Int 32 (NG_009086.1) |
| MYO7A | Usher Syndrome | c.5648G > A | p.R1883Q | RPE, Photoreceptors, Cochlear hair cells, Olfactory epithelium | Int 32 (NG_009086.1) |
| MYO7A | Usher Syndrome | c.5660C > T | p.P1887L | RPE, Photoreceptors, Cochlear hair cells, Olfactory epithelium | Int 32 (NG_009086.1) |
| MYO7A | Usher Syndrome | c.5686C > T | p.Q1896X | RPE, Photoreceptors, Cochlear hair cells, Olfactory epithelium | Int 32 (NG_009086.1) |
| MYO7A | Usher Syndrome | c.5749G > T | p.E1917X | RPE, Photoreceptors, Cochlear hair cells, Olfactory epithelium | Int 32 (NG_009086.1) |
| MYO7A | Usher Syndrome | c.5944G > A | p.G1982R | RPE, Photoreceptors, Cochlear hair cells, Olfactory epithelium | Int 32 (NG_009086.1) |
| MYO7A | Usher Syndrome | c.5945G > A | p.G1982E | RPE, Photoreceptors, Cochlear hair cells, Olfactory epithelium | Int 32 (NG_009086.1) |
| MYO7A | Usher Syndrome | c.5968C > T | p.Q1990X | RPE, Photoreceptors, Cochlear hair cells, Olfactory epithelium | Int 32 (NG_009086.1) |
| MYO7A | Usher Syndrome | c.6028G > A | p.D2010N | RPE, Photoreceptors, Cochlear hair cells, Olfactory epithelium | Int 32 (NG_009086.1) |
| MYO7A | Usher Syndrome | c.6043T > C | p.Y2015H | RPE, Photoreceptors, Cochlear hair cells, Olfactory epithelium | Int 32 (NG_009086.1) |
| MYO7A | Usher Syndrome | c.6070C > T | p.R2024X | RPE, Photoreceptors, Cochlear hair cells, Olfactory epithelium | Int 32 (NG_009086.1) |
| MYO7A | Usher Syndrome | c.6410G > A | p.G2137E | RPE, Photoreceptors, Cochlear hair cells, Olfactory epithelium | Int 32 (NG_009086.1) |
| MYO7A | Usher Syndrome | c.6487G > A | p.G2163S | RPE, Photoreceptors, Cochlear hair cells, Olfactory epithelium | Int 32 (NG_009086.1) |
| MYO7A | Usher Syndrome | c.6557T > C | p.L2186P | RPE, Photoreceptors, Cochlear hair cells, Olfactory epithelium | Int 32 (NG_009086.1) |
| MYO7A | Usher Syndrome | c.6560G > A | p.G2187D | RPE, Photoreceptors, Cochlear hair cells, Olfactory epithelium | Int 32 (NG_009086.1) |
| MYO7A | Usher Syndrome | c.6610G > C | p.A2204P | RPE, Photoreceptors, Cochlear hair cells, Olfactory epithelium | Int 32 (NG_009086.1) |
| MYO7A | Usher Syndrome | c.4502_4503delTG | p.Val1501Glysfs*2 | RPE, Photoreceptors, Cochlear hair cells, Olfactory epithelium | Int 32 (NG_009086.1) |
| MYO7A | Usher Syndrome | c.4648_4852 + 668del | p.Pro1550Glnfs*27 | RPE, Photoreceptors, Cochlear hair cells, Olfactory epithelium | Int 32 (NG_009086.1) |
| MYO7A | Usher Syndrome | c.4770dup | p.Arg1591Serfs*2 | RPE, Photoreceptors, Cochlear hair cells, Olfactory epithelium | Int 32 (NG_009086.1) |
| MYO7A | Usher Syndrome | c.4838delA | p.Asp1613Valfs*32 | RPE, Photoreceptors, Cochlear hair cells, Olfactory epithelium | Int 32 (NG_009086.1) |

TABLE 3-continued

| | | | | |
|---|---|---|---|---|
| MYO7A | Usher Syndrome | c.4919delG | p.Gly1640Alafs*5 | RPE, Photoreceptors, Cochlear hair cells, Olfactory epithelium Int 32 (NG_009086.1) |
| MYO7A | Usher Syndrome | c.5004C > G | p.Tyr1668* | RPE, Photoreceptors, Cochlear hair cells, Olfactory epithelium Int 32 (NG_009086.1) |
| MYO7A | Usher Syndrome | c.5146_5148delGAG | p.Glu1716del | RPE, Photoreceptors, Cochlear hair cells, Olfactory epithelium Int 32 (NG_009086.1) |
| MYO7A | Usher Syndrome | c.5227C > T | p.Arg1743Trp | RPE, Photoreceptors, Cochlear hair cells, Olfactory epithelium Int 32 (NG_009086.1) |
| MYO7A | Usher Syndrome | c.5411delT | p.Leu1804Argfs*6 | RPE, Photoreceptors, Cochlear hair cells, Olfactory epithelium Int 32 (NG_009086.1) |
| MYO7A | Usher Syndrome | c.5480 + 1G > A | p.? | RPE, Photoreceptors, Cochlear hair cells, Olfactory epithelium Int 32 (NG_009086.1) |
| MYO7A | Usher Syndrome | c.5502G > A | p.Trp1834* | RPE, Photoreceptors, Cochlear hair cells, Olfactory epithelium Int 32 (NG_009086.1) |
| MYO7A | Usher Syndrome | c.5581C > T | p.Arg1861* | RPE, Photoreceptors, Cochlear hair cells, Olfactory epithelium Int 32 (NG_009086.1) |
| MYO7A | Usher Syndrome | c.5623C > T | p.Gln1875* | RPE, Photoreceptors, Cochlear hair cells, Olfactory epithelium Int 32 (NG_009086.1) |
| MYO7A | Usher Syndrome | c.5632delC | p.Leu1878* | RPE, Photoreceptors, Cochlear hair cells, Olfactory epithelium Int 32 (NG_009086.1) |
| MYO7A | Usher Syndrome | c.5637 − 1G > A | p.? | RPE, Photoreceptors, Cochlear hair cells, Olfactory epithelium Int 32 (NG_009086.1) |
| MYO7A | Usher Syndrome | c.5637 − 1G > T | p.? | RPE, Photoreceptors, Cochlear hair cells, Olfactory epithelium Int 32 (NG_009086.1) |
| MYO7A | Usher Syndrome | c.5750_*2614del | p.Ph1916_Lys2215del | RPE, Photoreceptors, Cochlear hair cells, Olfactory epithelium Int 32 (NG_009086.1) |
| MYO7A | Usher Syndrome | c.5824G > A | p.Fly1942* | RPE, Photoreceptors, Cochlear hair cells, Olfactory epithelium Int 32 (NG_009086.1) |
| MYO7A | Usher Syndrome | c.5835_5838swlCTTT | p.Phe1946Serfs*23 | RPE, Photoreceptors, Cochlear hair cells, Olfactory epithelium Int 32 (NG_009086.1) |
| MYO7A | Usher Syndrome | c.5824G > T | p.Gly1942* | RPE, Photoreceptors, Cochlear hair cells, Olfactory epithelium Int 32 (NG_009086.1) |
| MYO7A | Usher Syndrome | c.5835_5838delCTTT | p.Phe1946Serfs*23 | RPE, Photoreceptors, Cochlear hair cells, Olfactory epithelium Int 32 (NG_009086.1) |
| MYO7A | Usher Syndrome | c.5856G > A | p.Ala1915_lys1952del | RPE, Photoreceptors, Cochlear hair cells, Olfactory epithelium Int 32 (NG_009086.1) |
| MYO7A | Usher Syndrome | c.5856 + 1G > A | p.? | RPE, Photoreceptors, Cochlear hair cells, Olfactory epithelium Int 32 (NG_009086.1) |
| MYO7A | Usher Syndrome | c.5886_5888delCTT | p.Phe1963del | RPE, Photoreceptors, Cochlear hair cells, Olfactory epithelium Int 32 (NG_009086.1) |
| MYO7A | Usher Syndrome | c.6025delG | p.Ala2009Profs*32 | RPE, Photoreceptors, Cochlear hair cells, Olfactory epithelium Int 32 (NG_009086.1) |
| MYO7A | Usher Syndrome | c.6049C > T | p.Gln2017* | RPE, Photoreceptors, Cochlear hair cells, Olfactory epithelium Int 32 (NG_009086.1) |
| MYO7A | Usher Syndrome | c.6051 + 1G > A | p.? | RPE, Photoreceptors, Cochlear hair cells, Olfactory epithelium Int 32 (NG_009086.1) |
| MYO7A | Usher Syndrome | c.6070C > T | p.Arg2024* | RPE, Photoreceptors, Cochlear hair cells, Olfactory epithelium Int 32 (NG_009086.1) |
| MYO7A | Usher Syndrome | c.6193delC | p.Gln2066Argfs*36 | RPE, Photoreceptors, Cochlear hair cells, Olfactory epithelium Int 32 (NG_009086.1) |
| MYO7A | Usher Syndrome | c.6205_6206delAT | p.Ile2069Profs*6 | RPE, Photoreceptors, Cochlear hair cells, Olfactory epithelium Int 32 (NG_009086.1) |
| MYO7A | Usher Syndrome | c.6321G > A | p.Trp2107* | RPE, Photoreceptors, Cochlear hair cells, Olfactory epithelium Int 32 (NG_009086.1) |
| MYO7A | Usher Syndrome | c.6324_6339del | p.Thr2109Serfs*4 | RPE, Photoreceptors, Cochlear hair cells, Olfactory epithelium Int 32 (NG_009086.1) |
| MYO7A | Usher Syndrome | c.6354 + 628_* + 737del | p.Gln2119_Lys2215del | RPE, Photoreceptors, Cochlear hair cells, Olfactory epithelium Int 32 (NG_009086.1) |
| MYO7A | Usher Syndrome | c.6355_6645del | p.Gln2119_Lys2215del | RPE, Photoreceptors, Cochlear hair cells, Olfactory epithelium Int 32 (NG_009086.1) |
| MYO7A | Usher Syndrome | c.6377delC | p.Pro2126Leufs*5 | RPE, Photoreceptors, Cochlear hair cells, Olfactory epithelium Int 32 (NG_009086.1) |
| MYO7A | Usher Syndrome | c.1007G > A | p.R336H | RPE, Photoreceptors, Cochlear hair cells, Olfactory epithelium Int 18 (NG_009086.1) |
| MYO7A | Usher Syndrome | c.1097T > C | p.L366P | RPE, Photoreceptors, Cochlear hair cells, Olfactory epithelium Int 18 (NG_009086.1) |
| MYO7A | Usher Syndrome | c.1132C > A | p.R378S | RPE, Photoreceptors, Cochlear hair cells, Olfactory epithelium Int 18 (NG_009086.1) |
| MYO7A | Usher Syndrome | c.1142C > T | p.T381M | RPE, Photoreceptors, Cochlear hair cells, Olfactory epithelium Int 18 (NG_009086.1) |
| MYO7A | Usher Syndrome | c.1190C > A | p.A397D | RPE, Photoreceptors, Cochlear hair cells, Olfactory epithelium Int 18 (NG_009086.1) |
| MYO7A | Usher Syndrome | c.1258A > T | p.K420X | RPE, Photoreceptors, Cochlear hair cells, Olfactory epithelium Int 18 (NG_009086.1) |
| MYO7A | Usher Syndrome | c.1309G > A | p.D437N | RPE, Photoreceptors, Cochlear hair cells, Olfactory epithelium Int 18 (NG_009086.1) |
| MYO7A | Usher Syndrome | c.1325A > G | p.E442G | RPE, Photoreceptors, Cochlear hair cells, Olfactory epithelium Int 18 (NG_009086.1) |
| MYO7A | Usher Syndrome | c.1348G > C | p.E450Q | RPE, Photoreceptors, Cochlear hair cells, Olfactory epithelium Int 18 (NG_009086.1) |

TABLE 3-continued

| Gene | Disease | Variant | Protein | Tissue | Reference |
|---|---|---|---|---|---|
| MYO7A | Usher Syndrome | c.1370 > T | p.A457V | RPE, Photoreceptors, Cochlear hair cells, Olfactory epithelium | Int 18 (NG_009086.1) |
| MYO7A | Usher Syndrome | c.1373A > T | p.N458I | RPE, Photoreceptors, Cochlear hair cells, Olfactory epithelium | Int 18 (NG_009086.1) |
| MYO7A | Usher Syndrome | c.1478A > C | p.Q493P | RPE, Photoreceptors, Cochlear hair cells, Olfactory epithelium | Int 18 (NG_009086.1) |
| MYO7A | Usher Syndrome | c.1508C > T | p.P503L | RPE, Photoreceptors, Cochlear hair cells, Olfactory epithelium | Int 18 (NG_009086.1) |
| MYO7A | Usher Syndrome | c.1556G > A | p.G519D | RPE, Photoreceptors, Cochlear hair cells, Olfactory epithelium | Int 18 (NG_009086.1) |
| MYO7A | Usher Syndrome | c.1591C > T | p.Q531X | RPE, Photoreceptors, Cochlear hair cells, Olfactory epithelium | Int 18 (NG_009086.1) |
| MYO7A | Usher Syndrome | c.1797G > A | p.M599I | RPE, Photoreceptors, Cochlear hair cells, Olfactory epithelium | Int 18 (NG_009086.1) |
| MYO7A | Usher Syndrome | c.1884C > A | p.C628X | RPE, Photoreceptors, Cochlear hair cells, Olfactory epithelium | Int 18 (NG_009086.1) |
| MYO7A | Usher Syndrome | c.1900C > T | p.R634X | RPE, Photoreceptors, Cochlear hair cells, Olfactory epithelium | Int 18 (NG_009086.1) |
| MYO7A | Usher Syndrome | c.1945C > T | p.R649W | RPE, Photoreceptors, Cochlear hair cells, Olfactory epithelium | Int 18 (NG_009086.1) |
| MYO7A | Usher Syndrome | c.1952T > C | p.L651P | RPE, Photoreceptors, Cochlear hair cells, Olfactory epithelium | Int 18 (NG_009086.1) |
| MYO7A | Usher Syndrome | c.1969C > T | p.R657W | RPE, Photoreceptors, Cochlear hair cells, Olfactory epithelium | Int 18 (NG_009086.1) |
| MYO7A | Usher Syndrome | c.1996C > T | p.R666X | RPE, Photoreceptors, Cochlear hair cells, Olfactory epithelium | Int 18 (NG_009086.1) |
| MYO7A | Usher Syndrome | c.199G > A | p.V67M | RPE, Photoreceptors, Cochlear hair cells, Olfactory epithelium | Int 18 (NG_009086.1) |
| MYO7A | Usher Syndrome | c.2005C > T | p.R669X | RPE, Photoreceptors, Cochlear hair cells, Olfactory epithelium | Int 18 (NG_009086.1) |
| MYO7A | Usher Syndrome | c.2028C > G | p.Y676X | RPE, Photoreceptors, Cochlear hair cells, Olfactory epithelium | Int 18 (NG_009086.1) |
| MYO7A | Usher Syndrome | c.2164G > C | p.G722R | RPE, Photoreceptors, Cochlear hair cells, Olfactory epithelium | Int 18 (NG_009086.1) |
| MYO7A | Usher Syndrome | c.2266C > T | p.R756W | RPE, Photoreceptors, Cochlear hair cells, Olfactory epithelium | Int 18 (NG_009086.1) |
| MYO7A | Usher Syndrome | c.2302A > T | p.K768X | RPE, Photoreceptors, Cochlear hair cells, Olfactory epithelium | Int 18 (NG_009086.1) |
| MYO7A | Usher Syndrome | c.2323C > T | p.Q775X | RPE, Photoreceptors, Cochlear hair cells, Olfactory epithelium | Int 18 (NG_009086.1) |
| MYO7A | Usher Syndrome | c.2461C > T | p.Q821X | RPE, Photoreceptors, Cochlear hair cells, Olfactory epithelium | Int 18 (NG_009086.1) |
| MYO7A | Usher Syndrome | c.2476G > A | p.A826T | RPE, Photoreceptors, Cochlear hair cells, Olfactory epithelium | Int 18 (NG_009086.1) |
| MYO7A | Usher Syndrome | c.2513G > A | p.W838X | RPE, Photoreceptors, Cochlear hair cells, Olfactory epithelium | Int 18 (NG_009086.1) |
| MYO7A | Usher Syndrome | c.252C > G | p.N84K | RPE, Photoreceptors, Cochlear hair cells, Olfactory epithelium | Int 18 (NG_009086.1) |
| MYO7A | Usher Syndrome | c.2557C > T | p.R853C | RPE, Photoreceptors, Cochlear hair cells, Olfactory epithelium | Int 18 (NG_009086.1) |
| MYO7A | Usher Syndrome | c.269G > C | p.R90P | RPE, Photoreceptors, Cochlear hair cells, Olfactory epithelium | Int 18 (NG_009086.1) |
| MYO7A | Usher Syndrome | c.2863G > A | p.G955S | RPE, Photoreceptors, Cochlear hair cells, Olfactory epithelium | Int 18 (NG_009086.1) |
| MYO7A | Usher Syndrome | c.2878G > T | p.E960X | RPE, Photoreceptors, Cochlear hair cells, Olfactory epithelium | Int 18 (NG_009086.1) |
| MYO7A | Usher Syndrome | c.2904G > T | p.E968D | RPE, Photoreceptors, Cochlear hair cells, Olfactory epithelium | Int 18 (NG_009086.1) |
| MYO7A | Usher Syndrome | c.2914C > T | p.R972X | RPE, Photoreceptors, Cochlear hair cells, Olfactory epithelium | Int 18 (NG_009086.1) |
| MYO7A | Usher Syndrome | c.3134T > C | p.I1045T | RPE, Photoreceptors, Cochlear hair cells, Olfactory epithelium | Int 18 (NG_009086.1) |
| MYO7A | Usher Syndrome | c.3171C > G | p.Y1057X | RPE, Photoreceptors, Cochlear hair cells, Olfactory epithelium | Int 18 (NG_009086.1) |
| MYO7A | Usher Syndrome | c.318C > A | p.N106K | RPE, Photoreceptors, Cochlear hair cells, Olfactory epithelium | Int 18 (NG_009086.1) |
| MYO7A | Usher Syndrome | c.3238A > T | p.K1080X | RPE, Photoreceptors, Cochlear hair cells, Olfactory epithelium | Int 18 (NG_009086.1) |
| MYO7A | Usher Syndrome | c.3260T > C | p.L1087P | RPE, Photoreceptors, Cochlear hair cells, Olfactory epithelium | Int 18 (NG_009086.1) |
| MYO7A | Usher Syndrome | c.3503G > C | p.R1168P | RPE, Photoreceptors, Cochlear hair cells, Olfactory epithelium | Int 18 (NG_009086.1) |
| MYO7A | Usher Syndrome | c.3508G > A | p.E1170K | RPE, Photoreceptors, Cochlear hair cells, Olfactory epithelium | Int 18 (NG_009086.1) |
| MYO7A | Usher Syndrome | c.3547C > A | p.P1183T | RPE, Photoreceptors, Cochlear hair cells, Olfactory epithelium | Int 18 (NG_009086.1) |
| MYO7A | Usher Syndrome | c.3652G > A | p.G1218R | RPE, Photoreceptors, Cochlear hair cells, Olfactory epithelium | Int 18 (NG_009086.1) |
| MYO7A | Usher Syndrome | c.3718C > T | p.R1240W | RPE, Photoreceptors, Cochlear hair cells, Olfactory epithelium | Int 18 (NG_009086.1) |

TABLE 3-continued

| | | | | |
|---|---|---|---|---|
| MYO7A | Usher Syndrome | c.3719G > A | p.R1240Q | RPE, Photoreceptors, Cochlear hair cells, Olfactory epithelium Int 18 (NG_009086.1) |
| MYO7A | Usher Syndrome | c.3731C > G | p.P1244R | RPE, Photoreceptors, Cochlear hair cells, Olfactory epithelium Int 18 (NG_009086.1) |
| MYO7A | Usher Syndrome | c.3862G > C | p.A1288P | RPE, Photoreceptors, Cochlear hair cells, Olfactory epithelium Int 18 (NG_009086.1) |
| MYO7A | Usher Syndrome | c.395C > T | p.P132L | RPE, Photoreceptors, Cochlear hair cells, Olfactory epithelium Int 18 (NG_009086.1) |
| MYO7A | Usher Syndrome | c.3979G > A | p.E1327K | RPE, Photoreceptors, Cochlear hair cells, Olfactory epithelium Int 18 (NG_009086.1) |
| MYO7A | Usher Syndrome | c.397C > G | p.H133D | RPE, Photoreceptors, Cochlear hair cells, Olfactory epithelium Int 18 (NG_009086.1) |
| MYO7A | Usher Syndrome | c.4018G > C | p.A1340P | RPE, Photoreceptors, Cochlear hair cells, Olfactory epithelium Int 18 (NG_009086.1) |
| MYO7A | Usher Syndrome | c.401T > A | p.I134N | RPE, Photoreceptors, Cochlear hair cells, Olfactory epithelium Int 18 (NG_009086.1) |
| MYO7A | Usher Syndrome | c.4029G > C | p.R1343S | RPE, Photoreceptors, Cochlear hair cells, Olfactory epithelium Int 18 (NG_009086.1) |
| MYO7A | Usher Syndrome | c.4045G > A | p.E1349K | RPE, Photoreceptors, Cochlear hair cells, Olfactory epithelium Int 18 (NG_009086.1) |
| MYO7A | Usher Syndrome | c.4117C > T | p.R1373X | RPE, Photoreceptors, Cochlear hair cells, Olfactory epithelium Int 18 (NG_009086.1) |
| MYO7A | Usher Syndrome | c.448C > T | p.R150X | RPE, Photoreceptors, Cochlear hair cells, Olfactory epithelium Int 18 (NG_009086.1) |
| MYO7A | Usher Syndrome | c.470G > A | p.S157N | RPE, Photoreceptors, Cochlear hair cells, Olfactory epithelium Int 18 (NG_009086.1) |
| MYO7A | Usher Syndrome | c.47T > A | p.L16X | RPE, Photoreceptors, Cochlear hair cells, Olfactory epithelium Int 18 (NG_009086.1) |
| MYO7A | Usher Syndrome | c.47T > C | p.L16S | RPE, Photoreceptors, Cochlear hair cells, Olfactory epithelium Int 18 (NG_009086.1) |
| MYO7A | Usher Syndrome | c.487G > A | p.G163R | RPE, Photoreceptors, Cochlear hair cells, Olfactory epithelium Int 18 (NG_009086.1) |
| MYO7A | Usher Syndrome | c.487G > C | p.G163R | RPE, Photoreceptors, Cochlear hair cells, Olfactory epithelium Int 18 (NG_009086.1) |
| MYO7A | Usher Syndrome | c.491A > G | p.K164R | RPE, Photoreceptors, Cochlear hair cells, Olfactory epithelium Int 18 (NG_009086.1) |
| MYO7A | Usher Syndrome | c.494C > T | p.T165M | RPE, Photoreceptors, Cochlear hair cells, Olfactory epithelium Int 18 (NG_009086.1) |
| MYO7A | Usher Syndrome | c.52C > T | p.Q18X | RPE, Photoreceptors, Cochlear hair cells, Olfactory epithelium Int 18 (NG_009086.1) |
| MYO7A | Usher Syndrome | c.592G > A | p.A198T | RPE, Photoreceptors, Cochlear hair cells, Olfactory epithelium Int 18 (NG_009086.1) |
| MYO7A | Usher Syndrome | c.610A > G | p.T204A | RPE, Photoreceptors, Cochlear hair cells, Olfactory epithelium Int 18 (NG_009086.1) |
| MYO7A | Usher Syndrome | c.616C > T | p.R206C | RPE, Photoreceptors, Cochlear hair cells, Olfactory epithelium Int 18 (NG_009086.1) |
| MYO7A | Usher Syndrome | c.617G > A | p.R206H | RPE, Photoreceptors, Cochlear hair cells, Olfactory epithelium Int 18 (NG_009086.1) |
| MYO7A | Usher Syndrome | c.629C > G | p.S210X | RPE, Photoreceptors, Cochlear hair cells, Olfactory epithelium Int 18 (NG_009086.1) |
| MYO7A | Usher Syndrome | c.634C > T | p.R212C | RPE, Photoreceptors, Cochlear hair cells, Olfactory epithelium Int 18 (NG_009086.1) |
| MYO7A | Usher Syndrome | c.635G > A | p.R212H | RPE, Photoreceptors, Cochlear hair cells, Olfactory epithelium Int 18 (NG_009086.1) |
| MYO7A | Usher Syndrome | c.640G > A | p.G214R | RPE, Photoreceptors, Cochlear hair cells, Olfactory epithelium Int 18 (NG_009086.1) |
| MYO7A | Usher Syndrome | c.689C > T | p.A230V | RPE, Photoreceptors, Cochlear hair cells, Olfactory epithelium Int 18 (NG_009086.1) |
| MYO7A | Usher Syndrome | c.700C > T | p.Q234X | RPE, Photoreceptors, Cochlear hair cells, Olfactory epithelium Int 18 (NG_009086.1) |
| MYO7A | Usher Syndrome | c.721C > A | p.R241S | RPE, Photoreceptors, Cochlear hair cells, Olfactory epithelium Int 18 (NG_009086.1) |
| MYO7A | Usher Syndrome | c.721C > G | p.R241G | RPE, Photoreceptors, Cochlear hair cells, Olfactory epithelium Int 18 (NG_009086.1) |
| MYO7A | Usher Syndrome | c.721C > T | p.R241C | RPE, Photoreceptors, Cochlear hair cells, Olfactory epithelium Int 18 (NG_009086.1) |
| MYO7A | Usher Syndrome | c.722G > A | p.R241H | RPE, Photoreceptors, Cochlear hair cells, Olfactory epithelium Int 18 (NG_009086.1) |
| MYO7A | Usher Syndrome | c.731G > C | p.R244P | RPE, Photoreceptors, Cochlear hair cells, Olfactory epithelium Int 18 (NG_009086.1) |
| MYO7A | Usher Syndrome | c.73G > A | p.G25R | RPE, Photoreceptors, Cochlear hair cells, Olfactory epithelium Int 18 (NG_009086.1) |
| MYO7A | Usher Syndrome | c.755A > G | p.Y252C | RPE, Photoreceptors, Cochlear hair cells, Olfactory epithelium Int 18 (NG_009086.1) |
| MYO7A | Usher Syndrome | c.77C > A | p.A26E | RPE, Photoreceptors, Cochlear hair cells, Olfactory epithelium Int 18 (NG_009086.1) |
| MYO7A | Usher Syndrome | c.905G > A | p.R302H | RPE, Photoreceptors, Cochlear hair cells, Olfactory epithelium Int 18 (NG_009086.1) |
| MYO7A | Usher Syndrome | c.93C > A | p.C31X | RPE, Photoreceptors, Cochlear hair cells, Olfactory epithelium Int 18 (NG_009086.1) |

TABLE 3-continued

| MYO7A | Usher Syndrome | c.940G > T | p.E314X | RPE, Photoreceptors, Cochlear hair cells, Olfactory epithelium | Int 18 (NG_009086.1) |
| --- | --- | --- | --- | --- | --- |
| MYO7A | Usher Syndrome | c.977T > A | p.L326Q | RPE, Photoreceptors, Cochlear hair cells, Olfactory epithelium | Int 18 (NG_009086.1) |
| MYO7A | Usher Syndrome | c.999T > G | p.Y333X | RPE, Photoreceptors, Cochlear hair cells, Olfactory epithelium | Int 18 (NG_009086.1) |
| MYO7A | Usher Syndrome | c.-272-?_5168 + 213del | p.? | RPE, Photoreceptors, Cochlear hair cells, Olfactory epithelium | Int 18 (NG_009086.1) |
| MYO7A | Usher Syndrome | c.-46 - 2A > G | p.? | RPE, Photoreceptors, Cochlear hair cells, Olfactory epithelium | Int 18 (NG_009086.1) |
| MYO7A | Usher Syndrome | c.6_9dup | p.Leu4Aspfs*39 | RPE, Photoreceptors, Cochlear hair cells, Olfactory epithelium | Int 18 (NG_009086.1) |
| MYO7A | Usher Syndrome | c.19 - 2A > G | p.? | RPE, Photoreceptors, Cochlear hair cells, Olfactory epithelium | Int 18 (NG_009086.1) |
| MYO7A | Usher Syndrome | c.33G > A | p.Trp11* | RPE, Photoreceptors, Cochlear hair cells, Olfactory epithelium | Int 18 (NG_009086.1) |
| MYO7A | Usher Syndrome | c.54G > C | p.Gln18His | RPE, Photoreceptors, Cochlear hair cells, Olfactory epithelium | Int 18 (NG_009086.1) |
| MYO7A | Usher Syndrome | c.133 - 2A > G | p.? | RPE, Photoreceptors, Cochlear hair cells, Olfactory epithelium | Int 18 (NG_009086.1) |
| MYO7A | Usher Syndrome | c.223delG | pAsp75Thrfs*31 | RPE, Photoreceptors, Cochlear hair cells, Olfactory epithelium | Int 18 (NG_009086.1) |
| MYO7A | Usher Syndrome | c.223G > C | p.Asn84Lys | RPE, Photoreceptors, Cochlear hair cells, Olfactory epithelium | Int 18 (NG_009086.1) |
| MYO7A | Usher Syndrome | c.338_348dup | p.Glu117Serfs*33 | RPE, Photoreceptors, Cochlear hair cells, Olfactory epithelium | Int 18 (NG_009086.1) |
| MYO7A | Usher Syndrome | c.358delC | p.Arg120Alafs*26 | RPE, Photoreceptors, Cochlear hair cells, Olfactory epithelium | Int 18 (NG_009086.1) |
| MYO7A | Usher Syndrome | c.360delC | p.Gln121Serfs*25 | RPE, Photoreceptors, Cochlear hair cells, Olfactory epithelium | Int 18 (NG_009086.1) |
| MYO7A | Usher Syndrome | c.397dup | p.His133Profs*7 | RPE, Photoreceptors, Cochlear hair cells, Olfactory epithelium | Int 18 (NG_009086.1) |
| MYO7A | Usher Syndrome | c.397dupC | p.His133Profs*7 | RPE, Photoreceptors, Cochlear hair cells, Olfactory epithelium | Int 18 (NG_009086.1) |
| MYO7A | Usher Syndrome | c.462C > A | p.Cys154* | RPE, Photoreceptors, Cochlear hair cells, Olfactory epithelium | Int 18 (NG_009086.1) |
| MYO7A | Usher Syndrome | c.471 - 1G > A | p.? | RPE, Photoreceptors, Cochlear hair cells, Olfactory epithelium | Int 18 (NG_009086.1) |
| MYO7A | Usher Syndrome | c.490A > T | p.Lys164fs* | RPE, Photoreceptors, Cochlear hair cells, Olfactory epithelium | Int 18 (NG_009086.1) |
| MYO7A | Usher Syndrome | c.496delG | p.Glu166Argfs*5 | RPE, Photoreceptors, Cochlear hair cells, Olfactory epithelium | Int 18 (NG_009086.1) |
| MYO7A | Usher Syndrome | c.581_582delCC | p.Pro194Hisfs*14 | RPE, Photoreceptors, Cochlear hair cells, Olfactory epithelium | Int 18 (NG_009086.1) |
| MYO7A | Usher Syndrome | c.652_657del | pAsp218_Ile219del | RPE, Photoreceptors, Cochlear hair cells, Olfactory epithelium | Int 18 (NG_009086.1) |
| MYO7A | Usher Syndrome | c.722G > C | p.Arg241Pro | RPE, Photoreceptors, Cochlear hair cells, Olfactory epithelium | Int 18 (NG_009086.1) |
| MYO7A | Usher Syndrome | c.726delC | p.Cys243Valfs*20 | RPE, Photoreceptors, Cochlear hair cells, Olfactory epithelium | Int 18 (NG_009086.1) |
| MYO7A | Usher Syndrome | c.834C > A | p.Tyr278* | RPE, Photoreceptors, Cochlear hair cells, Olfactory epithelium | Int 18 (NG_009086.1) |
| MYO7A | Usher Syndrome | c.938delC | p.Glu314Argfs*48 | RPE, Photoreceptors, Cochlear hair cells, Olfactory epithelium | Int 18 (NG_009086.1) |
| MYO7A | Usher Syndrome | c.986dup | p.Asn330Glnfs*5 | RPE, Photoreceptors, Cochlear hair cells, Olfactory epithelium | Int 18 (NG_009086.1) |
| MYO7A | Usher Syndrome | c.1005_1012del | p.Arg336* | RPE, Photoreceptors, Cochlear hair cells, Olfactory epithelium | Int 18 (NG_009086.1) |
| MYO7A | Usher Syndrome | c.1157_1158delTG | p.Leu386Glnfs*56 | RPE, Photoreceptors, Cochlear hair cells, Olfactory epithelium | Int 18 (NG_009086.1) |
| MYO7A | Usher Syndrome | c.1303delC | p.Leu435Serfs*12 | RPE, Photoreceptors, Cochlear hair cells, Olfactory epithelium | Int 18 (NG_009086.1) |
| MYO7A | Usher Syndrome | c.1343 + 1G > A | p.? | RPE, Photoreceptors, Cochlear hair cells, Olfactory epithelium | Int 18 (NG_009086.1) |
| MYO7A | Usher Syndrome | c,1344 - 2A > G | p.? | RPE, Photoreceptors, Cochlear hair cells, Olfactory epithelium | Int 18 (NG_009086.1) |
| MYO7A | Usher Syndrome | c.1454delT | p.Leu485Argfs*14 | RPE, Photoreceptors, Cochlear hair cells, Olfactory epithelium | Int 18 (NG_009086.1) |
| MYO7A | Usher Syndrome | c.1477C > T | p.Gln493* | RPE, Photoreceptors, Cochlear hair cells, Olfactory epithelium | Int 18 (NG_009086.1) |
| MYO7A | Usher Syndrome | c.1555 - 1G > C | p.? | RPE, Photoreceptors, Cochlear hair cells, Olfactory epithelium | Int 18 (NG_009086.1) |
| MYO7A | Usher Syndrome | c.1563delC | p.Asp521Glufs*8 | RPE, Photoreceptors, Cochlear hair cells, Olfactory epithelium | Int 18 (NG_009086.1) |
| MYO7A | Usher Syndrome | c.1591C > T | p.Gln531* | RPE, Photoreceptors, Cochlear hair cells, Olfactory epithelium | Int 18 (NG_009086.1) |
| MYO7A | Usher Syndrome | c.1595delA | p.His532Profs*90 | RPE, Photoreceptors, Cochlear hair cells, Olfactory epithelium | Int 18 (NG_009086.1) |
| MYO7A | Usher Syndrome | c.1623dup | p.Lys542Glnfs*5 | RPE, Photoreceptors, Cochlear hair cells, Olfactory epithelium | Int 18 (NG_009086.1) |

TABLE 3-continued

| Gene | Disease | Variant | Protein | Tissue |
|---|---|---|---|---|
| MYO7A | Usher Syndrome | c.1690 + 1G > A | p.? | RPE, Photoreceptors, Cochlear hair cells, Olfactory epithelium Int 18 (NG_009086.1) |
| MYO7A | Usher Syndrome | c.1708C > T | p.Arg570* | RPE, Photoreceptors, Cochlear hair cells, Olfactory epithelium Int 18 (NG_009086.1) |
| MYO7A | Usher Syndrome | c.1797G > A | p.Met599Ile | RPE, Photoreceptors, Cochlear hair cells, Olfactory epithelium Int 18 (NG_009086.1) |
| MYO7A | Usher Syndrome | c.1884C > A | p.Cys628* | RPE, Photoreceptors, Cochlear hair cells, Olfactory epithelium Int 18 (NG_009086.1) |
| MYO7A | Usher Syndrome | c.1900C > T | p.Arg634* | RPE, Photoreceptors, Cochlear hair cells, Olfactory epithelium Int 18 (NG_009086.1) |
| MYO7A | Usher Syndrome | c.1935G > A | p.Met645Ile | RPE, Photoreceptors, Cochlear hair cells, Olfactory epithelium Int 18 (NG_009086.1) |
| MYO7A | Usher Syndrome | c.1935 + 1G > A | p.? | RPE, Photoreceptors, Cochlear hair cells, Olfactory epithelium Int 18 (NG_009086.1) |
| MYO7A | Usher Syndrome | c.1952_1953insAG | p.Cys652Glyfs*11 | RPE, Photoreceptors, Cochlear hair cells, Olfactory epithelium Int 18 (NG_009086.1) |
| MYO7A | Usher Syndrome | c.1954delT | p.Cys652Alafs*10 | RPE, Photoreceptors, Cochlear hair cells, Olfactory epithelium Int 18 (NG_009086.1) |
| MYO7A | Usher Syndrome | c.2115C > A | p.Cys705* | RPE, Photoreceptors, Cochlear hair cells, Olfactory epithelium Int 18 (NG_009086.1) |
| MYO7A | Usher Syndrome | c.2187 + 1G > A | p.? | RPE, Photoreceptors, Cochlear hair cells, Olfactory epithelium Int 18 (NG_009086.1) |
| MYO7A | Usher Syndrome | c.2241_2242delAG | p.Arg747Serfs*16 | RPE, Photoreceptors, Cochlear hair cells, Olfactory epithelium Int 18 (NG_009086.1) |
| MYO7A | Usher Syndrome | c.2283 − 1G > T | p.Ser762Cysfs*61 | RPE, Photoreceptors, Cochlear hair cells, Olfactory epithelium Int 18 (NG_009086.1) |
| MYO7A | Usher Syndrome | c.2307delC | p.Asn769Lysfs*61 | RPE, Photoreceptors, Cochlear hair cells, Olfactory epithelium Int 18 (NG_009086.1) |
| MYO7A | Usher Syndrome | c.2425delC | p.Gln809Serfs*42 | RPE, Photoreceptors, Cochlear hair cells, Olfactory epithelium Int 18 (NG_009086.1) |
| MYO7A | Usher Syndrome | c.2443C > T | p.Gln821* | RPE, Photoreceptors, Cochlear hair cells, Olfactory epithelium Int 18 (NG_009086.1) |
| MYO7A | Usher Syndrome | c.2500delC | p.Arg834Alafs*17 | RPE, Photoreceptors, Cochlear hair cells, Olfactory epithelium Int 18 (NG_009086.1) |
| MYO7A | Usher Syndrome | c.2513G > A | p.Trp838* | RPE, Photoreceptors, Cochlear hair cells, Olfactory epithelium Int 18 (NG_009086.1) |
| MYO7A | Usher Syndrome | c.2557C > T | p.Arg853Cys | RPE, Photoreceptors, Cochlear hair cells, Olfactory epithelium Int 18 (NG_009086.1) |
| MYO7A | Usher Syndrome | c.2656_2664del | p.Ala886_Lys888del | RPE, Photoreceptors, Cochlear hair cells, Olfactory epithelium Int 18 (NG_009086.1) |
| MYO7A | Usher Syndrome | c.2662dup | p.Ala889Glyfs*19 | RPE, Photoreceptors, Cochlear hair cells, Olfactory epithelium Int 18 (NG_009086.1) |
| MYO7A | Usher Syndrome | c.2766_2779del | p.Lys923Alafs*8 | RPE, Photoreceptors, Cochlear hair cells, Olfactory epithelium Int 18 (NG_009086.1) |
| MYO7A | Usher Syndrome | c.2797delC | p.Arg933Alafs*129 | RPE, Photoreceptors, Cochlear hair cells, Olfactory epithelium Int 18 (NG_009086.1) |
| MYO7A | Usher Syndrome | c.2874_2878delCCAGG | p.Gln959Glysfs*5 | RPE, Photoreceptors, Cochlear hair cells, Olfactory epithelium Int 18 (NG_009086.1) |
| MYO7A | Usher Syndrome | c.3108 + 1G > A | p.? | RPE, Photoreceptors, Cochlear hair cells, Olfactory epithelium Int 18 (NG_009086.1) |
| MYO7A | Usher Syndrome | c.3135dup | p.Leu1046Profs*9 | RPE, Photoreceptors, Cochlear hair cells, Olfactory epithelium Int 18 (NG_009086.1) |
| MYO7A | Usher Syndrome | c.3238A > T | p.Lys1080* | RPE, Photoreceptors, Cochlear hair cells, Olfactory epithelium Int 18 (NG_009086.1) |
| MYO7A | Usher Syndrome | c.3260T > C | p.Leu1087Pro | RPE, Photoreceptors, Cochlear hair cells, Olfactory epithelium Int 18 (NG_009086.1) |
| MYO7A | Usher Syndrome | c.3262C > T | p.Gln1088* | RPE, Photoreceptors, Cochlear hair cells, Olfactory epithelium Int 18 (NG_009086.1) |
| MYO7A | Usher Syndrome | c.3285delG | p.Ala1089Profs*19 | RPE, Photoreceptors, Cochlear hair cells, Olfactory epithelium Int 18 (NG_009086.1) |
| MYO7A | Usher Syndrome | c.3504 − 1G > C | p.? | RPE, Photoreceptors, Cochlear hair cells, Olfactory epithelium Int 18 (NG_009086.1) |
| MYO7A | Usher Syndrome | c.3594C > A | p.Cys1198* | RPE, Photoreceptors, Cochlear hair cells, Olfactory epithelium Int 18 (NG_009086.1) |
| MYO7A | Usher Syndrome | c.3596dup | p.Cys1201Leufs*28 | RPE, Photoreceptors, Cochlear hair cells, Olfactory epithelium Int 18 (NG_009086.1) |
| MYO7A | Usher Syndrome | c.3631delT | p.Tyr1211Thrfs*21 | RPE, Photoreceptors, Cochlear hair cells, Olfactory epithelium Int 18 (NG_009086.1) |
| MYO7A | Usher Syndrome | c.3702delC | p.Phe1235Leufs*28 | RPE, Photoreceptors, Cochlear hair cells, Olfactory epithelium Int 18 (NG_009086.1) |
| MYO7A | Usher Syndrome | c.3719G > A | p.Arg1240Gl | RPE, Photoreceptors, Cochlear hair cells, Olfactory epithelium Int 18 (NG_009086.1) |
| MYO7A | Usher Syndrome | c.3724C > T | p.Gln1242* | RPE, Photoreceptors, Cochlear hair cells, Olfactory epithelium Int 18 (NG_009086.1) |
| MYO7A | Usher Syndrome | c.3750 + 2T > A | p.? | RPE, Photoreceptors, Cochlear hair cells, Olfactory epithelium Int 18 (NG_009086.1) |
| MYO7A | Usher Syndrome | c.3764delA | p.Lys1255Argfs*97 | RPE, Photoreceptors, Cochlear hair cells, Olfactory epithelium Int 18 (NG_009086.1) |
| MYO7A | Usher Syndrome | c.4012delC | p.Arg1338Alafs*61 | RPE, Photoreceptors, Cochlear hair cells, Olfactory epithelium Int 18 (NG_009086.1) |

TABLE 3-continued

| | | | | |
|---|---|---|---|---|
| MYO7A | Usher Syndrome | c.4036_4038delTTC | p.Phe1346del | RPE, Photoreceptors, Cochlear hair Int 18 (NG_009086.1) cells, Olfactory epithelium |
| MYO7A | Usher Syndrome | c.4039_4053del | p.Arg1347_Phe1351del | RPE, Photoreceptors, Cochlear hair Int 18 (NG_009086.1) cells, Olfactory epithelium |
| MYO7A | Usher Syndrome | c.4045G > A | p.Glu1349Lys | RPE, Photoreceptors, Cochlear hair Int 18 (NG_009086.1) cells, Olfactory epithelium |
| MYO7A | Usher Syndrome | c.4065delC | p.His1355Glnfs*44 | RPE, Photoreceptors, Cochlear hair Int 18 (NG_009086.1) cells, Olfactory epithelium |
| MYO7A | Usher Syndrome | c.4117C > T | p.Arg1373* | RPE, Photoreceptors, Cochlear hair Int 18 (NG_009086.1) cells, Olfactory epithelium |
| MYO7A | Usher Syndrome | c.4131dup | p.Gly1378Trpfs*6 | RPE, Photoreceptors, Cochlear hair Int 18 (NG_009086.1) cells, Olfactory epithelium |
| MYO7A | Usher Syndrome | c.4166delC | p.Ala1389Valfs*10 | RPE, Photoreceptors, Cochlear hair Int 18 (NG_009086.1) cells, Olfactory epithelium |
| MYO7A | Usher Syndrome | c.4293G > A | p.Trp1431* | RPE, Photoreceptors, Cochlear hair Int 18 (NG_009086.1) cells, Olfactory epithelium |
| MYO7A | Usher Syndrome | c.4297delC | p.Gln1433Serfs*116 | RPE, Photoreceptors, Cochlear hair Int 18 (NG_009086.1) cells, Olfactory epithelium |
| MYO7A | Usher Syndrome | c.4483_4484dup | p.Trp1495Cysfs*55 | RPE, Photoreceptors, Cochlear hair Int 18 (NG_009086.1) cells, Olfactory epithelium |

| | RTM | | |
|---|---|---|---|
| Target Ocular Gene | Binding Domain Seq | Exon/Seq | Splice Site Seq |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |

TABLE 3-continued

| | | | |
|---|---|---|---|
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |

TABLE 3-continued

| | | | |
|---|---|---|---|
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 33-49 [c.4324G p.Gly1442] through [c.6648A p.Stop2216] (NM_000260.3) | 3' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |

TABLE 3-continued

| | | | |
|---|---|---|---|
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |

TABLE 3-continued

| | | | |
|---|---|---|---|
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |

TABLE 3-continued

| | | | |
|---|---|---|---|
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |

TABLE 3-continued

| | | | |
|---|---|---|---|
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |
| MYO7A | ~30-250 nts complementary to target intron | Ex 1-18 [c.1A p.Met1] through [c.2187G p.Lys729] (NM_000260.3) | 5' |

The Pharmaceutical Carrier and Pharmaceutical Compositions

The compositions described herein containing the recombinant viral vector, e.g., AAV, containing the desired RTM minigene for use in the selected target ocular cells, e.g., photoreceptor cells for treatment of Stargardt Disease, as detailed above, is preferably assessed for contamination by conventional methods and then formulated into a pharmaceutical composition intended for a suitable route of administration. Still other compositions containing the RTM, e.g., naked DNA or as protein, may be formulated similarly with a suitable carrier. Such formulation involves the use of a pharmaceutically and/or physiologically acceptable vehicle or carrier, particularly directed for administration to the target cell. In one embodiment, carriers suitable for administration to the cells of the eye include buffered saline, an isotonic sodium chloride solution, or other buffers, e.g., HEPES, to maintain pH at appropriate physiological levels, and, optionally, other medicinal agents, pharmaceutical agents, stabilizing agents, buffers, carriers, adjuvants, diluents, etc.

For injection, the carrier will typically be a liquid. Exemplary physiologically acceptable carriers include sterile, pyrogen-free water and sterile, pyrogen-free, phosphate buffered saline. A variety of such known carriers are provided in U.S. Pat. No. 7,629,322, incorporated herein by reference. In one embodiment, the carrier is an isotonic sodium chloride solution. In another embodiment, the carrier is balanced salt solution. In one embodiment, the carrier includes tween. If the virus is to be stored long-term, it may be frozen in the presence of glycerol or Tween20.

In other embodiments, e.g., compositions containing RTMs described herein include a surfactant. Useful surfactants, such as Pluronic F68 ((Poloxamer 188), also known as Lutrol® F68) may be included as they prevent AAV from sticking to inert surfaces and thus ensure delivery of the desired dose.

As an example, one illustrative composition designed for the treatment of the ocular diseases described herein comprises a recombinant adeno-associated vector carrying a nucleic acid sequence encoding 3'RTM as described herein, under the control of regulatory sequences which express the RTM in an ocular cell of a mammalian subject, and a pharmaceutically acceptable carrier. The carrier is isotonic sodium chloride solution and includes a surfactant Pluronic F68. In one embodiment, the RTM is that described in the examples. In another embodiment, the RTM contains the binding and coding regions for CEP290 or MYO7A.

In yet another exemplary embodiment, the composition comprises a recombinant AAV2/5 pseudotyped adeno-associated virus carrying a 3' or 5' or RTM for internal ocular gene replacement, the nucleic acid sequence under the control of promoter which directs expression of the RTM in said photoreceptor cells, wherein the composition is formulated with a carrier and additional components suitable for subretinal injection. In still another embodiment, the composition or components for production or assembly of this composition, including carriers, rAAV particles, surfactants, and/or the components for generating the rAAV, as well as suitable laboratory hardware to prepare the composition, may be incorporated into a kit.

Methods of Treating Ocular Disorders

The compositions described above are thus useful in methods of treating one or more of the ocular diseases (e.g., Stargardt Disease, Lebers Congenital Amaurosis, cone rod dystrophy, fundus flavimaculatus, retinitis pigmentosa, age-related macular degeneration, Senior Laken syndrome, Joubert syndrome, or Usher Syndrome, among others) including delaying or ameliorating symptoms associated with the ocular diseases described herein. Such methods involve contacting a target pre-mRNA (e.g., ABCA4, CEP290, MYO7A) with one or more of a 3'RTM, 5' RTM, both 3' and 5' RTM or a double trans-splicing RTM as described herein, under conditions in which a portion of the RTM is spliced to the target pre-mRNA to replace all or a part of the targeted gene carrying one or more defects or mutations, with a "healthy", or normal or wildtype or corrected mRNA of the targeted gene, in order to correct expression of that gene in the ocular cell. Alternatively, a pre-miRNA (see the RTM documents cited herein) can be formed, which is designed to reduce the expression of a target mRNA. Thus, the methods and compositions are used to treat the ocular diseases/pathologies associated with the specific mutations and/or gene expression.

In one embodiment, the contacting involves direct administration to the affected subject; in another embodiment, the contacting may occur ex vivo to the cultured cell and the treated ocular cell reimplanted in the subject. In one embodiment, the method involves administering a rAAV particle carrying a 3' RTM. In another embodiment, the method involves administering a rAAV particle carrying a 5' RTM. In another embodiment, the method involves administering a rAAV particle carrying a double trans-splicing RTM. In still another embodiment, the method involves administering a mixture of rAAV particle carrying a 3' RTM and rAAV particle carrying a 5' RTM. In still another embodiment, the method involves administering a mixture of rAAV particle carrying a 3' RTM and an rAAV particle carrying a double trans-splicing RTM. In still another embodiment, the method involves administering a mixture of rAAV particle carrying a 5' RTM and an rAAV carrying a double trans-splicing RTM. In still another embodiment, the method involves administering a mixture of an rAAV particle carrying a 3' RTM, with an rAAV particle carrying a 5' RTM and an rAAV particle carrying a double trans-splicing RTM.

These methods comprise administering to a subject in need thereof subject an effective concentration of a composition of any of those described herein. In one illustrative embodiment, such a method is provided for preventing, arresting progression of or ameliorating vision loss associated with Stargardt Disease in a subject, said method comprising administering to an ocular cell of a mammalian subject in need thereof an effective concentration of a composition comprising a recombinant adeno-associated virus (AAV) carrying a 3'RTM such as described above and in the examples, under the control of regulatory sequences which permit the RTM to function and cause trans-splicing of the defective targeted gene in an ocular cell, e.g., photoreceptor cell, of a mammalian subject. In still another embodiment, the method involves administering two rAAV particles, one carrying a 5' RTM and the other carrying the 3'RTM, such as those RTMs described in the examples to replace large portions of large genes.

By "administering" as used in the methods means delivering the composition to the target selected cell which is characterized by the disease caused by a mutation or defect in the targeted ocular gene. For example, in one embodiment, the method involves delivering the composition by subretinal injection to the photoreceptor cells or other ocular cells. In another embodiment, intravitreal injection to ocular cells or injection via the palpebral vein to ocular cells may be employed. Still other methods of administration may be selected by one of skill in the art given this disclosure.

Furthermore, in certain embodiments, it is desirable to perform non-invasive retinal imaging and functional studies to identify areas of retained photoreceptors to be targeted for therapy. In these embodiments, clinical diagnostic tests are employed to determine the precise location(s) for one or more subretinal injection(s). These tests may include electroretinography (ERG), perimetry, topographical mapping of the layers of the retina and measurement of the thickness of its layers by means of confocal scanning laser ophthalmoscopy (cSLO) and optical coherence tomography (OCT), topographical mapping of cone density via adaptive optics (AO), functional eye exam, etc. In view of the imaging and functional studies, in some embodiments one or more injections are performed in the same eye in order to target different areas of retained photoreceptors.

For use in these methods, the volume and viral titer of each injection is determined individually, as further described below, and may be the same or different from other injections performed in the same, or contralateral, eye. In another embodiment, a single, larger volume injection is made in order to treat the entire eye. The dosages, administrations and regimens may be determined by the attending physician given the teachings of this specification.

In one embodiment, the volume and concentration of the rAAV composition is selected so that only the certain regions of photoreceptors or other ocular cell is impacted. In another embodiment, the volume and/or concentration of the rAAV composition is a greater amount, in order reach larger portions of the eye. Similarly dosages are adjusted for administration to other organs.

An effective concentration of a recombinant adeno-associated virus carrying a RTM as described herein ranges between about $10^8$ and $10^{13}$ vector genomes per milliliter (vg/mL). The rAAV infectious units are measured as described in S. K. McLaughlin et al, 1988 J. Virol., 62:1963. In another embodiment, the concentration ranges between $10^9$ and $10^{13}$ vector genomes per milliliter (vg/mL). In another embodiment, the effective concentration is about $1.5 \times 10^{11}$ vg/mL. In one embodiment, the effective concentration is about $1.5 \times 10^{10}$ vg/mL. In another embodiment, the effective concentration is about $2.8 \times 10^{11}$ vg/mL. In yet another embodiment, the effective concentration is about $1.5 \times 10^{12}$ vg/mL. In another embodiment, the effective concentration is about $1.5 \times 10^{13}$ vg/mL. It is desirable that the lowest effective concentration of virus be utilized in order to reduce the risk of undesirable effects, such as toxicity, and other issues related to administration to the eye, e.g., retinal dysplasia and detachment. Still other dosages in these ranges or in other units may be selected by the attending physician, taking into account the physical state of the subject, preferably human, being treated, including the age of the subject; the composition being administered and the particular ocular disorder; the targeted cell and the degree to which the disorder, if progressive, has developed.

The composition may be delivered in a volume of from about 50 µL to about 1 mL, including all numbers within the range, depending on the size of the area to be treated, the viral titer used, the route of administration, and the desired effect of the method. In one embodiment, the volume is about 50 µL. In another embodiment, the volume is about 70 µL. In another embodiment, the volume is about 100 µL. In another embodiment, the volume is about 125 µL. In another embodiment, the volume is about 150 µL. In another embodiment, the volume is about 175 µL. In yet another embodiment, the volume is about 200 µL. In another embodiment, the volume is about 250 µL. In another embodiment, the volume is about 300 µL. In another embodiment, the volume is about 450 µL. In another embodiment, the volume is about 500 µL. In another embodiment, the volume is about 600 µL. In another embodiment, the volume is about 750 µL. In another embodiment, the volume is about 850 µL. In another embodiment, the volume is about 1000 µL.

In another embodiment, the invention provides a method to prevent, or arrest photoreceptor function loss, or increase photoreceptor function in the subject. The composition may be administered before disease onset or after initiation of photoreceptor loss. Photoreceptor function may be assessed using the functional studies, e.g., ERG or perimetry, which are conventional in the art. As used herein "photoreceptor function loss" means a decrease in photoreceptor function as compared to a normal, non-diseased eye or the same eye at an earlier time point. As used herein, "increase photoreceptor function" means to improve the function of the photoreceptors or increase the number or percentage of functional photoreceptors as compared to a diseased eye (having the same ocular disease), the same eye at an earlier time point, a non-treated portion of the same eye, or the contralateral eye of the same patient.

For each of the described methods, the treatment may be used to prevent the occurrence of further damage or to rescue tissues or organ, e.g., eyes in a subject with LCA10 or Stargardt Disease or Ushers Syndrome or retinitis pigmentosa, having mild or advanced disease. As used herein, the term "rescue" means to prevent progression of the disease, prevent spread of damage to uninjured ocular cells or to improve damage in injured ocular cells.

Thus, in one embodiment, the composition is administered before disease onset. In another embodiment, the composition is administered prior to the initiation of vision impairment or loss. In another embodiment, the composition is administered after initiation of vision impairment or loss. In yet another embodiment, the composition is administered when less than 90% of the photoreceptors are functioning or remaining, as compared to a non-diseased eye.

In another embodiment, the method includes performing functional and imaging studies to determine the efficacy of the treatment. These studies include ERG and in vivo retinal imaging, as described in U.S. Pat. No. 8,147,823; in co-pending International patent application publication WO 2014/011210 or WO 2014/124282, incorporated by reference. In addition visual field studies, perimetry and microperimetry, mobility testing, visual acuity, color vision testing may be performed.

In yet another embodiment, any of the above described methods is performed in combination with another, or secondary, therapy. The therapy may be any now known, or as yet unknown, therapy which helps prevent, arrest or ameliorate these mutations or defects or any of the effects associated therewith. The secondary therapy can be administered before, concurrent with, or after administration of the rAAVs described above. In one embodiment, a secondary therapy involves non-specific approaches for maintaining the health of the retinal cells, such as administration of neurotrophic factors, anti-oxidants, anti-apoptotic agents. The non-specific approaches are achieved through injection of proteins, recombinant DNA, recombinant viral vectors, stem cells, fetal tissue, or genetically modified cells. The latter could include genetically modified cells that are encapsulated.

The compositions and methods described herein are believed to have many advantages over any currently employed therapies. Firstly, the use of the RTM delivery by rAAV provides efficient and specific delivery of a gene therapy to photoreceptors. Secondly, these compositions and methods permit correction of the genetic defect at the source. Additionally, these compositions and methods provide are useful to treat any type of mutation in ABCA4 (or other large cDNAs/transgene cassettes). Correction of the defect in photoreceptors provides secondary rescue to retinal pigment epithelium cells. Further, the method of gene correction is benign immunologically. As there is currently no other treatment available for ABCA4-mediated disease (or other retinal disease caused by defects in transgenes with large cDNAs, these methods and compositions are clearly valuable. The use of subretinal delivery and other features renders the effect specific to photoreceptors, so that toxicity due to off-target splicing is likely minimal. Finally, RNA repair does not require cell division, whereas DNA repair methodologies (such as CRISPR-Cas9 or zinc fingers) have a requirement for the cell to go through mitosis for homology directed repair to occur, which is a disadvantage in post-mitotic tissues like the retina.

Restoration of cellular function by the method described herein can be assessed in an animal model of the appropriate disease caused by defect or mutation, such as the restoration of visual function in a subject with a CEP290 defect causing LCA in the rd16 mouse LCA model or canine model of LCA. The use of the exemplary rAAV carrying an RTM as described herein can demonstrate that the defect in the mutant dog or other animal model could be corrected by gene delivery. This data allow one of skill in the art to readily anticipate that this method may be similarly used in treatment of other types of retinal disease in other subjects, including humans.

The examples that follow do not limit the scope of the embodiments described herein. One skilled in the art will appreciate that modifications can be made in the following examples which are intended to be encompassed by the spirit and scope of the invention.

Example 1: Splicing Dependent Reporter RTM

A splicing dependent reporter RTM is a molecule comprising a binding domain, spacer, and 3' splice site. The binding domain can be selected from appropriate binding domains for the selected targeted intron, and the 3' splice site can be any of those disclosed herein. A trans-splicing dependent reporter RTM contains the complete coding DNA sequence of green fluorescent protein, but lacking the first three bases, ATG, constituting the start codon. The molecule does not have an open reading frame for GFP. Therefore, GFP is only translated if it is spliced in-frame and 3' to a trans-pre-mRNA. These reagents split the complete coding DNA sequence between two plasmids to reconstitute GFP via trans-splicing. This is a novel reagent with potential commercial use for evaluating the occurrence of trans-splicing with a single plasmid.

Example 2: rAAV—RTM Assembly for Stargardt's Disease

For the structures of the 3' RTM or 5' RTM for ABCA4, see FIG. 1.

A 3' RTM is designed with a binding domain that targets intron 26 (4,696 bp NG_009073.1). The 3' RTM molecule for the ABCA4 trans-splicing comprises:
3' RTM promoter
3' RTM Binding domain sequence: 70-2000 nucleotides complementary to target intron 26;

3' RTM Spacer sequence:
SEQ ID NO: 10
GAGAACATTATTATAGCGTTGCTCGAG

3' RTM Branch point sequence:
TACTAAC;

3' RTM Polypyrimidine tract:
SEQ ID NO: 11
TGGTACCTCTTCTTTTTTTTCTG

3' acceptor splice site: CAGGT; Coding domain of 2,930 bp ABCA4 cDNA encoding exons 27 through the terminal exon 50; and
3'RTM polyA signal sequence.

In another embodiment a 5' RTM molecule for the ABCA4 trans-splicing comprises:
3' RTM promoter:
5'RTM coding domain of 3,328 bp ABCA4 cDNA encoding exons 1 through the exon 22;

5' RTM 5' Splice Site:
AGGT;

5'RTM spacer sequence:
SEQ ID NO: 12
AGAGCTCGTTGCGATATTAT;

Binding domain sequence: 70-2000 nucleotides complementary to target intron 22 (1,358 bp NG_009073.1); and
5' RTM PolyA sequence.

The pair of trans-splicing reagents covers mutations spaced over the entire coding ABCA4 coding sequence. The two cDNA molecules are derived from a mammalian codon optimized sequence of ABCA4.

Each RTM is introduced into a proviral plasmid p618 as referenced above, following the teachings of WO2012/158757. The proviral plasmids are cultured in the host cells which express the cap and/or rep proteins. In the host cells, each minigene consisting of the RTM with flanking AAV ITRs is rescued and packaged into the capsid protein or envelope protein to form an infectious viral particle. Thus two types of recombinant AAV infectious particle are produced and purified from culture: one carrying the 3'RTM and the other carrying the 5'RTM. See, e.g., FIGS. 3A and 3B and TABLE 4, which is the sequence of the RTM of FIG. 3A in GenBank format which delineates features of the sequence.

TABLE 4 pAAV ABCA4 3'RTM CMV CMB chimInt BD 126 3'SS Ex 27_50
synthetic DNA construct - 12513 bp ds-DNA circular
recombinant plasmid
REFERENCE 1 (bases 1 to 12513) SEQ ID NO: 1

| Features | Location/Qualifiers |
|---|---|
| Source | 1 . . . 12513<br>/organism = "recombinant plasmid"<br>/mol_type = "other DNA" |
| Repeat Region | 1 . . . 130<br>/note = "5 ITR" |
| Misc Feature | 113 . . . 130<br>/note = "ITR D segment" |
| Enhancer | 241 . . . 544<br>/note = "CMV enhancer"<br>/note = "human cytomegalovirus immediate early enhancer" |
| Promoter | 546 . . . 823<br>/note = "chicken beta-actin promoter" |
| Intron | 919 . . . 1051<br>/note = "chimeric intron"<br>/note = "chimera between introns from human beta-globin and immunoglobulin heavy chain genes" |
| Intron | complement (1074 . . . 1222)<br>/label = "Intron 26"<br>/note = "ABCA4I26 BD" |
| misc_feature | 1243 . . . 1269<br>/gene = "spacer"<br>/note = "spacer" |
| misc_feature | 1270 . . . 1297<br>/note = "3'SS" |

TABLE 4-continued pAAV ABCA4 3'RTM CMV CMB chimInt BD 126 3'SS Ex 27_50
synthetic DNA construct - 12513 bp ds-DNA circular
recombinant plasmid
REFERENCE 1 (bases 1 to 12513) SEQ ID NO: 1

| Features | Location/Qualifiers |
|---|---|
| gene | 1298 . . . 4257<br>/label = "ABCA4 NM_000350.2" |
| misc_feature | 1298 . . . 1563<br>/label = "Exon 27"<br>/note = "Exon 27" |
| misc_feature | 1564 . . . 1688<br>/label = "Exon 28"<br>/note = "Exon 28" |
| misc_feature | 1689 . . . 1787<br>/label = "Exon 29"<br>/label = "Exon 29"<br>/note = "Exon 29" |
| misc_feature | 1788 . . . 1974<br>/label = "Exon 30"<br>/note = "Exon 30" |
| misc_feature | 1975 . . . 2069<br>/label = "Exon 31"<br>/note = "Exon 31" |
| misc_feature | 2070 . . . 2102<br>/label = " Exon 32"<br>/note = "Exon 32" |
| misc_feature | 2103 . . . 2208<br>/label = " Exon 33"<br>/note = "Exon 33" |
| misc_feature | 2209 . . . 2283<br>/label = " Exon 34"<br>/note = "Exon 34" |
| misc_feature | 2284 . . . 2453<br>/label = " Exon 35"<br>/note = "Exon 35" |
| misc_feature | 2454 . . . 2631<br>/label = " Exon 36"<br>/note = "Exon 36" |
| misc_feature | 2632 . . . 2747<br>/label = " Exon 37"<br>/note = "Exon 37" |
| misc_feature | 2748 . . . 2895<br>/label = " Exon 38"<br>/note = "Exon 38" |
| misc_feature | 2896 . . . 3019<br>/label = " Exon 39"<br>/note = "Exon 39" |
| misc_feature | 3020 . . . 3149<br>/label = " Exon 40"<br>/note = "Exon 40" |
| misc_feature | 3150 . . . 3270<br>/label = " Exon 41"<br>/note = "Exon 41" |
| misc_feature | 3271 . . . 3333<br>/label = "Exon 42"<br>/note = "Exon 42" |
| misc_feature | 3334 . . . 3440<br>/label = "Exon 43"<br>/note = "Exon 43" |

TABLE 4-continued pAAV ABCA4 3'RTM CMV CMB chimInt BD 126 3'SS Ex 27_50
synthetic DNA construct - 12513 bp ds-DNA circular
recombinant plasmid
REFERENCE 1 (bases 1 to 12513) SEQ ID NO: 1

| Features | Location/Qualifiers |
|---|---|
| misc_feature | 3441 . . . 3582<br>/label = "Exon 44"<br>/note = "Exon 44" |
| misc_feature | 3583 . . . 3717<br>/label = "Exon 45"<br>/note = "Exon 45" |
| misc_feature | 3718 . . . 3821<br>/label = "Exon 46"<br>/note = "Exon 46" |
| misc_feature | 3822 . . . 3914<br>/label = "Exon 47"<br>/note = "Exon 47" |
| misc_feature | 3915 . . . 4164<br>/label = "Exon 48"<br>/note = "Exon 48" |
| misc_feature | 4165 . . . 4251<br>/label = "Exon 49"<br>/note = "Exon 49" |
| misc_feature | 4252 . . . 4257<br>/label = "Exon 50"<br>/note = "Exon 50" |
| polyA_signal | 4275 . . . 4482<br>/note = "bGH poly(A) signal"<br>/note = "bovine growth hormone polyadenylation signal" |
| Repeat region | 4532 . . . 4661<br>/note = "3 ITR" |
| misc_feature | 4532 . . . 4549<br>/note = "ITR D segment" |
| protein_bind | complement (4689 . . . 4722)<br>/bound_moiety = "FLP recombinase from the *Saccharomyces cerevisiae* 2u plasmid"<br>/note = "FRT (minimal)"<br>/note = "supports FLP-mediated excision but not integration (Turan and Bode, 2011)" |
| misc_feature | 4755 . . . 5055<br>/product = "bla txn terminator"<br>/note = "bla txn terminator" |
| misc_feature | 4846 . . . 4871<br>/product = "pTF3"<br>/note = "pTF3" |
| misc_feature | 5062 . . . 5175<br>/product = "rpn txn terminator"<br>/note = "rpn txn terminator" |
| misc_feature | 5191 . . . 10257<br>/note = "lambda stuffer" |
| primer_bind | complement (10263 . . . 10279)<br>/note = "M13 fwd"<br>/note = "common sequencing primer, one of multiple similar variants" |
| rep_origin | complement (10549 . . . 11137)<br>/direction = LEFT<br>/note = "ori"<br>/note = "high-copy-number ColE1/pMB1/pBR322/pUC origin of replication" |

TABLE 4-continued pAAV ABCA4 3'RTM CMV CMB chimInt BD 126 3'SS Ex 27_50
synthetic DNA construct - 12513 bp ds-DNA circular
recombinant plasmid
REFERENCE 1 (bases 1 to 12513) SEQ ID NO: 1

| Features | Location/Qualifiers |
|---|---|
| CDS SEQ ID NO: 3 | Complement (11261 . . . 12070)<br>/codon_start = 1<br>/gene = "aph(3')-Ia"<br>/product = "aminoglycoside phosphotransferase"<br>/note = "KanR"<br>/note = "confers resistance to kanamycin in bacteria or G418 (Geneticin(R)) in eukaryotes"<br>/translation = "MSHIQRETSRPRLNSNMDADLYGYKWARDNVGQSGATIYRLYGKPDA<br>PELFLKHGKGSVANDVTDEMVRLNWLTEF<br>MPLPTIKHFIRTPDDAWLLTTAIPGKTAFQVLEEYPDSGE<br>NIVDALAVFLRRLHSIPVCNCPFNSDRVFRLAQAQSRMN<br>NGLVDASDFDDERNGWPVEQVWKEMHKLLPFSPDSVVT<br>HGDFSLDNLIFDEGKLIGCIDVGRVGIADRYQDLAILWNCL<br>GEFSPSLQKRLFQKYGIDNPDMNKLQFHLMLDEFF" |
| promoter | complement(12071 . . . 12162)<br>/gene = "bla"<br>/note = "AmpR promoter" |
| misc_feature | complement(12249 . . . 12423)<br>/product = "rrnB1 B T1 txn terminator"<br>/note = "rrnB1 B2 T1 txn terminator" |
| misc_feature | 12324 . . . 12340<br>/product = "pTR"<br>/note = "pTR" |
| protein_bind | 12455 . . . 12488<br>/bound_moiety = "FLP recombinase from the *Saccharomyces cerevisiae* 2u plasmid"<br>/note = "FRT (minimal)"<br>/note = "supports FLP-mediated excision but not integration (Turan and Bode, 2011)" |

ORIGIN SEQ ID NO: 1

```
    1   ctgcgcgctc gctcgct-
        cac tgaggccgcc cgggcaaagc ccgggcgtcg ggcgaccttt
   61   ggtcgcccgg cctcagtgag cgagcgagcg cgcagagagg gagtggccaa ctccat-
        cact
  121   aggggttcct tgtagttaat gattaacccg ccatgctact tatc-
        tacgta gcaagctagc
  181   tagttattaa tagtaatcaa ttacgggtc attagttcat agcc-
        catata tggagttccg
  241   cgttacataa cttacggtaa atggcccgcc tggctgaccg cccaacgacc cccgcc-
        catt
  301   gacgtcaata atgacgtatg ttcccatagt aacgc-
        caata gggactttcc attgacgtca
  361   atgggtggag tatttacggt aaactgccca cttggcagta cat-
        caagtgt atcatatgcc
  421   aagtacgccc cctattgacg tcaatgacgg taaatggccc gcctgg-
        catt atgcccagta
  481   catgacctta tgggactttc ctacttggca gtacatctac gtattagtca tcgctat-
        taa
  541   catggtcgag gtgagcccca cgttctgctt cactctcccc atctccccc cctccc-
        cacc
  601   cccaattttg tatttattta ttttt-
        taatt attttgtgca gcgatggggg cggggggggg
  661   ggggggcgc gcgccaggcg gggcggggcg gggcgagggg cggggcgggg cgaggcg-
        gag
  721   aggtgcggcg gcagc-
        caatc agagcggcgc gctccgaaag tttccttta tggcgaggcg
```

TABLE 4-continued pAAV ABCA4 3'RTM CMV CMB chimInt BD 126 3'SS Ex 27_50
synthetic DNA construct - 12513 bp ds-DNA circular
recombinant plasmid
REFERENCE 1 (bases 1 to 12513) SEQ ID NO: 1

| Features | Location/Qualifiers |
|---|---|
| 781 | gcggcggcgg cggccctata aaaagcgaag cgcgcggcgg gcggggagtc gctgcgacgc |
| 841 | tgccttcgcc ccgtgccccg ctccgccgcc gcctcgcgcc gcccgccccg gctctgactg |
| 901 | accgcgttac tcccacaggt aagtatcaag gttacaagac aggtttaagg agaccaatag |
| 961 | aaactgggct tgtcgagaca gagaagactc ttgcgtttct gataggcacc tattggtctt |
| 1021 | actgacatcc actttgcctt tctctccaca ggttggtgta cactagcggc cgcaaactct |
| 1081 | gctacactca cacatgcttt gtgtggctgt gggtttgata aaagttcatg gaaggagcta |
| 1141 | gttggtgccc aggctgacac atgtagaaga gagacttcta gaatccacag gaattttggt |
| 1201 | ccccatgttt tcaaagccca tacaagcttc gaattcgata tcgagaacat tattatagcg |
| 1261 | ttgctcgagt actaactggt acctcttctt ttttttcgtg gcgctcagca gaaaagagaa |
| 1321 | aacgtcaacc cccgacaccc ctgcttgggt cccagagaga aggctggaca gacacccag |
| 1381 | gactccaatg tctgctcccc aggggcgccg gctgctcacc cagagggcca gcctccccca |
| 1441 | gagccagagt gcccaggccc gcagctcaac acggggacac agctggtcct ccagcatgtg |
| 1501 | caggcgctgc tggtcaagag attccaacac accatccgca gccacaagga cttcctggcg |
| 1561 | cagatcgtgc tcccggctac ctttgtgttt ttggctctga tgcttttctat tgttatccct |
| 1621 | cctttttggcg aatacccccgc tttgacccctt caccccctgga tatatgggca gcagtacacc |
| 1681 | ttcttcagca tggatgaacc aggcagtgag cagttcacgg tacttgcaga cgtcctcctg |
| 1741 | aataagccag gctttggcaa ccgctgcctg aaggaagggt ggcttccgga gtacccctgt |
| 1801 | ggcaactcaa caccctggaa gactccttct gtgtccccaa acatcaccca gctgttccag |
| 1861 | aagcagaaat ggacacaggt caacccttca ccatcctgca ggtgcagcac cagggagaag |
| 1921 | ctcaccatgc tgccagagtg ccccgagggt gccggggcc tcccgccccc cagagaaca |
| 1981 | cagcgcagca cggaaattct acaagacctg acggacagga acatctccga cttcttggta |
| 2041 | aaaacgtatc ctgctcttat aagaagcagc ttaaagagca aattctgggt caatgaacag |
| 2101 | aggtatggag gaatttccat tggaggaaag ctcccagtcg tccccatcac ggggaagca |
| 2161 | cttgttgggt tttaagcga ccttggccgg atcatgaatg tgagcggggg ccctatcact |
| 2221 | agagaggcct ctaaagaaat acctgatttc cttaaacatc tagaaactga agacaacatt |
| 2281 | aaggtgtggt ttaataacaa aggctggcat gccctggtca gctttctcaa tgtggcccac |

TABLE 4-continued pAAV ABCA4 3'RTM CMV CMB chimInt BD 126 3'SS Ex 27_50
synthetic DNA construct - 12513 bp ds-DNA circular
recombinant plasmid
REFERENCE 1 (bases 1 to 12513) SEQ ID NO: 1

| Features | Location/Qualifiers |
|---|---|
| 2341 | aacgccatct tacgggccag cctgcctaag gacaggagcc ccgaggagta tggaatcacc |
| 2401 | gtcattagcc aacccctgaa cctgaccaag gagcagctct cagagattac agtgctgacc |
| 2461 | acttcagtgg atgctgtggt tgccatctgc gtgattttct ccatgtcctt cgtcccagcc |
| 2521 | agctttgtcc tttatttgat ccaggagcgg gtgaacaaat ccaagcacct ccagtttatc |
| 2581 | agtggagtga gccccaccac ctactgggtg accaacttcc tctgggacat catgaattat |
| 2641 | tccgtgagtg ctgggctggt ggtgggcatc ttcatcgggt tcagaagaa agcctacact |
| 2701 | tctccagaaa accttcctgc ccttgtggca ctgctcctgc tgtatggatg ggcggtcatt |
| 2761 | cccatgatgt acccagcatc cttcctgttt gatgtcccca gcacagccta tgtggcttta |
| 2821 | tcttgtgcta atctgttcat cggcatcaac agcagtgcta ttaccttcat cttggaatta |
| 2881 | tttgagaata accggacgct gctcaggttc aacgccgtgc tgaggaagct gctcattgtc |
| 2941 | ttcccccact tctgcctggg ccggggcctc attgaccttg cactgagcca ggctgtgaca |
| 3001 | gatgtctatg cccggtttgg tgaggagcac tctgcaaatc cgttccactg ggacctgatt |
| 3061 | gggaagaacc tgtttgccat ggtggtggaa gggtggtgt acttcctcct gaccctgctg |
| 3121 | gtccagcgcc acttcttcct ctcccaatgg attgccgagc ccactaagga gcccattgtt |
| 3181 | gatgaagatg atgatgtggc tgaagaaaga caaagaatta ttactggtgg aaataaaact |
| 3241 | gacatcttaa ggctacatga actaaccaag atttatccag gcacctccag cccagcagtg |
| 3301 | gacaggctgt gtgtcggagt tcgccctgga gagtgctttg gcctcctggg agtgaatggt |
| 3361 | gccggcaaaa caaccacatt caagatgctc actggggaca ccacagtgac ctcagggat |
| 3421 | gccaccgtag caggcaagag tattttaacc aatatttctg aagtccatca aaatatgggc |
| 3481 | tactgtcctc agtttgatgc aattgatgag ctgctcacag gacgagaaca tctttaccctt |
| 3541 | tatgcccggc ttcgaggtgt accagcagaa gaaatcgaaa aggttgcaaa ctggagtatt |
| 3601 | aagagcctgg gcctgactgt ctacgccgac tgcctggctg gcacgtacag tgggggcaac |
| 3661 | aagcggaaac tctccacagc catcgcactc attggctgcc caccgctggt gctgctgat |
| 3721 | gagcccacca cagggatgga ccccaggca cgccgcatgc tgtggaacgt catcgtgagc |
| 3781 | atcatcagag aagggaggc tgtggtcctc acatcccaca gcatggaaga atgtgaggca |
| 3841 | ctgtgtaccc ggctggccat catggtaaag ggcgcctttc gatgtatggg caccatcag |

TABLE 4-continued pAAV ABCA4 3'RTM CMV CMB chimInt BD 126 3'SS Ex 27_50
synthetic DNA construct - 12513 bp ds-DNA circular
recombinant plasmid
REFERENCE 1 (bases 1 to 12513) SEQ ID NO: 1

| Features | Location/Qualifiers |
|---|---|
| 3901 | catctcaagt ccaaatttgg agatggctat atcgtcacaa tgaagatcaa atccccgaag |
| 3961 | gacgacctgc ttcctgacct gaaccctgtg gagcagttct tccagggaa cttcccaggc |
| 4021 | agtgtgcaga gggagaggca ctacaacatg ctccagttcc aggtctcctc ctcctccctg |
| 4081 | gcgaggatct tccagctcct cctctcccac aaggacagcc tgctcatcga ggagtactca |
| 4141 | gtcacacaga ccacactgga ccaggtgttt gtaaattttg ctaaacagca gactgaaagt |
| 4201 | catgacctcc ctctgcaccc tcgagctgct ggagccagtc gacaagccca ggactgactg |
| 4261 | cagatctgcc tcgactgtgc cttctagttg ccagccatct gttgtttgcc cctcccccgt |
| 4321 | gccttccttg accctggaag gtgccactcc cactgtcctt tcctaataaa atgaggaaat |
| 4381 | tgcatcgcat tgtctgagta ggtgtcattc tattctgggg ggtggggtgg ggcaggacag |
| 4441 | caaggggag gattgggaag acaatagcag gcatgctggg gactcgagtt ctacgtagat |
| 4501 | aagtagcatg gcgggttaat cattaactac aaggaacccc tagtgatgga gttggccact |
| 4561 | ccctctctgc gcgctcgctc gctcactgag gccgggcgac caaggtcgc ccgacgcccg |
| 4621 | ggctttgccc gggcggcctc agtgagcgag cgagcgcgca gccttaatta acctaaggaa |
| 4681 | aatgaagtga agttcctata ctttctagag aataggaact tctatagtga gtcgaataag |
| 4741 | ggcgacacaa aatttattct aaatgcataa taaatactga taacatctta tagtttgtat |
| 4801 | tatattttgt attatcgttg acatgtataa ttttgatatc aaaaactgat tttcccttta |
| 4861 | ttattttcga gatttatttt cttaattctc tttaacaaac tagaaatatt gtatatacaa |
| 4921 | aaaatcataa ataatagatg aatagtttaa ttataggtgt tcatcaatcg aaaaagcaac |
| 4981 | gtatcttatt taaagtgcgt tgctttttc tcatttataa ggttaaataa ttctcatata |
| 5041 | tcaagcaaag tgacaggcgc cctaaatat tctgacaaat gctctttccc taaactcccc |
| 5101 | ccataaaaaa acccgccgaa gcgggttttt acgttatttg cggattaacg attactcgtt |
| 5161 | atcagaaccg cccaggggc ccgagcttaa ccttttttatt tgggggagag ggaagtcatg |
| 5221 | aaaaaactaa cctttgaaat tcgatctcca gcacatcagc aaaacgctat tcacgcagta |
| 5281 | cagcaaatcc ttccagaccc aaccaaacca atcgtagtaa ccattcagga acgcaaccgc |
| 5341 | agcttagacc aaaacaggaa gctatggggcc tgcttaggtg acgtctctcg tcaggttgaa |
| 5401 | tggcatggtc gctggctgga tgcagaaagc tggaagtgtg tgtttaccgc agcattaaag |

TABLE 4-continued pAAV ABCA4 3'RTM CMV CMB chimInt BD 126 3'SS Ex 27_50
synthetic DNA construct - 12513 bp ds-DNA circular
recombinant plasmid
REFERENCE 1 (bases 1 to 12513) SEQ ID NO: 1

| Features | Location/Qualifiers |
|---|---|
| 5461 | cagcaggatg ttgttcctaa ccttgccggg aatggctttg tggtaatagg ccagtcaacc |
| 5521 | agcaggatgc gtgtaggcga atttgcggag ctattagagc ttatacaggc attcggtaca |
| 5581 | gagcgtggcg ttaagtggtc agacgaagcg agactggctc tggagtggaa agcgagatgg |
| 5641 | ggagacaggg ctgcatgata aatgtcgtta gtttctccgg tggcaggacg tcagcatatt |
| 5701 | tgctctggct aatggagcaa agcgacggg caggtaaaga cgtgcattac gttttcatgg |
| 5761 | atacaggttg tgaacatcca atgacatatc ggtttgtcag ggaagttgtg aagttctggg |
| 5821 | atataccgct caccgtattg caggttgata tcaacccgga gcttggacag ccaaatggtt |
| 5881 | atacggtatg ggaaccaaag gatattcaga cgcgaatgcc tgttctgaag ccatttatcg |
| 5941 | atatggtaaa gaaatatggc actccatacg tcggcggcgc gttctgcact gacagattaa |
| 6001 | aactcgttcc cttcaccaaa tactgtgatg accatttcgg gcgagggaat tacaccacgt |
| 6061 | ggattggcat cagagctgat gaaccgaagc ggctaaagcc aaagcctgga atcagatatc |
| 6121 | ttgctgaact gtcagacttt gagaaggaag atatcctcgc atggtggaag caacaaccat |
| 6181 | tcgatttgca aataccggaa catctcggta actgcatatt ctgcattaaa aaatcaacgc |
| 6241 | aaaaaatcgg acttgcctgc aaagatgagg agggattgca gcgtgttttt aatgaggtca |
| 6301 | tcacgggatc ccatgtgcgt gacggacatc gggaaacgcc aaaggagatt atgtaccgag |
| 6361 | gaagaatgtc gctggacggt atcgcgaaaa tgtattcaga aaatgattat caagccctgt |
| 6421 | atcaggacat ggtacgagct aaaagattcg ataccggctc ttgttctgag tcatgcgaaa |
| 6481 | tatttggagg gcagcttgat ttcgacttcg ggagggaagc tgcatgatgc gatgttatcg |
| 6541 | gtgcggtgaa tgcaaagaag ataaccgctt ccgaccaaat caaccttact ggaatcgatg |
| 6601 | gtgtctccgg tgtgaaagaa caccaacagg ggtgttacca ctaccgcagg aaaaggagga |
| 6661 | cgtgtggcga cagcgacg aagtatcacc gacataatct gcgaaaactg caaataccttt |
| 6721 | ccaacgaaac gcaccagaaa taaacccaag ccaatcccaa aagaatctga cgtaaaaacc |
| 6781 | ttcaactaca cggctcacct gtgggatatc cggtggctaa gacgtcgtgc gaggaaaaca |
| 6841 | aggtgattga ccaaaatcga agttacgaac aagaaagcgt cgagcgagct ttaacgtgcg |
| 6901 | ctaactgcgg tcagaagctg catgtgctgg aagttcacgt gtgtgagcac tgctgcgcag |

TABLE 4-continued pAAV ABCA4 3'RTM CMV CMB chimInt BD 126 3'SS Ex 27_50
synthetic DNA construct - 12513 bp ds-DNA circular
recombinant plasmid
REFERENCE 1 (bases 1 to 12513) SEQ ID NO: 1

| Features | Location/Qualifiers |
|---|---|
| 6961 | aactgatgag cgatccgaat agctcgatgc acgaggaaga agatgatggc taaaccagcg |
| 7021 | cgaagacgat gtaaaaacga tgaatgccgg gaatggtttc accctgcatt cgctaatcag |
| 7081 | tggtggtgct ctccagagtg tggaaccaag atagcactcg aacgacgaag taaagaacgc |
| 7141 | gaaaaagcgg aaaaagcagc agagaagaaa cgacgacgag aggagcagaa acagaaagat |
| 7201 | aaacttaaga ttcgaaaact cgccttaaag ccccgcagtt actggattaa acaagccaa |
| 7261 | caagccgtaa acgccttcat cagagaaaga accgcgact taccatgtat ctcgtgcgga |
| 7321 | acgctcacgt ctgctcagtg ggatgccgga cattaccgga caactgctgc ggcacctcaa |
| 7381 | ctccgattta atgaacgcaa tattcacaag caatgcgtgg tgtgcaacca gcacaaaagc |
| 7441 | ggaaatctcg ttccgtatcg cgtcgaactg attagccgca tcgggcagga agcagtagac |
| 7501 | gaaatcgaat caaaccataa ccgccatcgc tggactatcg aagagtgcaa ggcgatcaag |
| 7561 | gcagagtacc aacagaaact caaagacctg cgaaatagca gaagtgaggc cgcatgacgt |
| 7621 | tctcagtaaa aaccattcca gacatgctcg ttgaagcata cggaaatcag acagaagtag |
| 7681 | cacgcagact gaaatgtagt cgcggtacgg tcagaaaata cgttgatgat aaagacggga |
| 7741 | aaatgcacgc catcgtcaac gacgttctca tggttcatcg cggatggagt gaaagagatg |
| 7801 | cgctattacg aaaaaattga tggcagcaaa taccgaaata tttgggtagt tggcgatctg |
| 7861 | cacggatgct acacgaacct gatgaacaaa ctggatacga ttggattcga caacaaaaaa |
| 7921 | gacctgctta tctcggtggg cgatttggtt gatcgtggtg cagagaacgt tgaatgcctg |
| 7981 | gaattaatca cattcccctg gttcagagct gtacgtggaa accatgagca aatgatgatt |
| 8041 | gatggcttat cagagcgtgg aaacgttaat cactggctgc ttaatggcgg tggctggttc |
| 8101 | tttaatctcg attacgacaa agaaattctg gctaaagctc ttgcccataa agcagatgaa |
| 8161 | cttccgttaa tcatcgaact ggtgagcaaa gataaaaaat atgttatctg ccacgccgat |
| 8221 | tatcccttgt acgaatacga gtttggaaag ccagttgatc atcagcaggt aatctggaac |
| 8281 | cgcgaacgaa tcagcaactc acaaaacggg atcgtgaaag aaatcaaagg cgcggacacg |
| 8341 | ttcatctttg gtcatacgcc agcagtgaaa ccactcaagt ttgccaacca aatgtatatc |
| 8401 | gataccggcg cagtgttctg cggaaaccta acattgattc aggtacaggg agaaggcgca |
| 8461 | tgagactcga aagcgtagct aaatttcatt cgccaaaaag cccgatgatg agcgactcac |

TABLE 4-continued pAAV ABCA4 3'RTM CMV CMB chimInt BD 126 3'SS Ex 27_50
synthetic DNA construct - 12513 bp ds-DNA circular
recombinant plasmid
REFERENCE 1 (bases 1 to 12513) SEQ ID NO: 1

| Features | Location/Qualifiers |
|---|---|
| 8521 | cacgggccac ggcttctgac tctctttccg gtactgatgt gatggctgct atggggatgg |
| 8581 | cgcaatcaca agccggattc ggtatggctg cattctgcgg taagcacgaa ctcagccaga |
| 8641 | acgacaaaca aaaggctatc aactatctga tgcaatttgc acacaaggta tcggggaaat |
| 8701 | accgtggtgt ggcaaagctt gaaggaaata ctaaggcaaa ggtactgcaa gtgctcgcaa |
| 8761 | cattcgctta tgcggattat tgccgtagtg ccgcgacgcc gggggcaaga tgcagagatt |
| 8821 | gccatggtac aggccgtgcg gttgatattg ccaaaacaga gctgtggggg agagttgtcg |
| 8881 | agaaagagtg cggaagatgc aaaggcgtcg gctattcaag gatgccagca agcgcagcat |
| 8941 | atcgcgctgt gacgatgcta atcccaaacc ttacccaacc cacctggtca cgcactgtta |
| 9001 | agccgctgta tgacgctctg gtggtgcaat gccacaaaga agagtcaatc gcagacaaca |
| 9061 | ttttgaatgc ggtcacacgt tagcagcatg attgccacgg atggcaacat attaacggca |
| 9121 | tgatattgac ttattgaata aaattgggta aatttgactc aacgatgggt taattcgctc |
| 9181 | gttgtggtag tgagatgaaa agaggcggcg cttactaccg attccgccta gttggtcact |
| 9241 | tcgacgtatc gtctggaact ccaaccatcg caggcagaga ggtctgcaaa atgcaatccc |
| 9301 | gaaacagttc gcaggtaata gttagagcct gcataacggt ttcggggattt tttatatctg |
| 9361 | cacaacaggt aagagcattg agtcgataat cgtgaagagt cggcgagcct ggttagccag |
| 9421 | tgctctttcc gttgtgctga attaagcgaa taccggaagc agaaccggat caccaaatgc |
| 9481 | gtacaggcgt catcgccgcc cagcaacagc acaacccaaa ctgagccgta gccactgtct |
| 9541 | gtcctgaatt cattagtaat agttacgctg cggccttttta cacatgacct tcgtgaaagc |
| 9601 | gggtggcagg aggtcgcgct aacaacctcc tgccgttttg cccgtgcata tcggtcacga |
| 9661 | acaaatctga ttactaaaca cagtagcctg gatttgttct atcagtaatc gaccttattc |
| 9721 | ctaattaaat agagcaaatc cccttattgg gggtaagaca tgaagatgcc agaaaaacat |
| 9781 | gacctgttgg ccgccattct cgcggcaaag gaacaaggca tcgggcaatc ccttgcgttt |
| 9841 | gcaatggcgt accttcgcgg cagatataat ggcggtgcgt ttacaaaaac agtaatcgac |
| 9901 | gcaacgatgt gcgccattat cgcctggttc attcgtgacc ttctcgactt cgccggacta |
| 9961 | agtagcaatc tcgcttatat aacgagcgtg tttatcggct acatcggtac tgactcgatt |
| 10021 | ggttcgctta tcaaacgctt cgctgctaaa aaagccggag tagaagatgg tagaaatcaa |

TABLE 4-continued pAAV ABCA4 3'RTM CMV CMB chimInt BD 126 3'SS Ex 27_50
synthetic DNA construct - 12513 bp ds-DNA circular
recombinant plasmid
REFERENCE 1 (bases 1 to 12513) SEQ ID NO: 1

| Features | Location/Qualifiers |
|---|---|
| 10081 | taatcaacgt aaggcgttcc tcgatatgct ggcgtggtcg gagggaactg ataacggacg |
| 10141 | tcagaaaacc agaaatcatg gttatgacgt cattgtaggc ggagagctat ttactgatta |
| 10201 | ctccgatcac cctcgcaaac ttgtcacgct aaacccaaaa ctcaaatcaa caggcgctta |
| 10261 | agactggccg tcgttttaca acacagaaag agtttgtaga aacgcaaaaa ggccatccgt |
| 10321 | cagggggcctt ctgcttagtt tgatgcctgg cagttcccta ctctcgcctt ccgcttcctc |
| 10381 | gctcactgac tcgctgcgct cggtcgttcg gctgcggcga gcggtatcag ctcactcaaa |
| 10441 | ggcggtaata cggttatcca cagaatcagg ggataacgca ggaaagaaca tgtgagcaaa |
| 10501 | aggccagcaa aaggccagga accgtaaaaa ggccgcgttg ctggcgtttt tccataggct |
| 10561 | ccgcccccct gacgagcatc acaaaaatcg acgctcaagt cagaggtggc gaaacccgac |
| 10621 | aggactataa agataccagg cgtttccccc tggaagctcc ctcgtgcgct ctcctgttcc |
| 10681 | gaccctgccg cttaccggat acctgtccgc ctttctccct cgggaagcg tggcgctttc |
| 10741 | tcatagctca cgctgtaggt atctcagttc ggtgtaggtc gttcgctcca agctgggctg |
| 10801 | tgtgcacgaa ccccccgttc agcccgaccg ctgcgcctta tccggtaact atcgtcttga |
| 10861 | gtccaacccg gtaagacacg acttatcgcc actggcagca gccactggta acaggattag |
| 10921 | cagagcgagg tatgtaggcg gtgctacaga gttcttgaag tggtgggcta actacggcta |
| 10981 | cactagaaga acagtatttg gtatctgcgc tctgctgaag ccagttacct tcggaaaaag |
| 11041 | agttggtagc tcttgatccg gcaaacaaac caccgctggt agcggtggtt tttttgtttg |
| 11101 | caagcagcag attacgcgca gaaaaaaagg atctcaagaa gatcctttga tcttttctac |
| 11161 | ggggtctgac gctcagtgga acgacgcgcg cgtaactcac gttaagggat tttggtcatg |
| 11221 | agcttgcgcc gtcccgtcaa gtcagcgtaa tgctctgctt ttagaaaaac tcatcgagca |
| 11281 | tcaaatgaaa ctgcaattta ttcatatcag gattatcaat accatatttt tgaaaaagcc |
| 11341 | gtttctgtaa tgaaggagaa aactcaccga gcagttccta ggatggcaa agatcctggt |
| 11401 | atcggtctgc gattccgact cgtccaacat caatacaacc tattaatttc ccctcgtcaa |
| 11461 | aaataaggtt atcaagtgag aaatcaccat gagtgacgac tgaatccggt gagaatggca |
| 11521 | aaagtttatg catttctttc cagacttgtt caacaggcca gccattacgc tcgtcatcaa |

TABLE 4-continued pAAV ABCA4 3'RTM CMV CMB chimInt BD 126 3'SS Ex 27_50
synthetic DNA construct - 12513 bp ds-DNA circular
recombinant plasmid
REFERENCE 1 (bases 1 to 12513) SEQ ID NO: 1

| Features | Location/Qualifiers |
|---|---|
| 11581 | aatcactcgc atcaaccaaa ccgttattca ttcgtgattg cgcct-gagcg aggcgaaata |
| 11641 | cgcgatcgct gttaaaagga caattacaaa caggaatcga gtgcaaccgg cgcag-gaaca |
| 11701 | ctgccagcgc atcaacaata ttttcacctg aatcaggata ttcttctaat acctg-gaacg |
| 11761 | ctgttttttcc ggggatcgca gtggtgagta accatgcatc atcaggagta cgga-taaaat |
| 11821 | gcttgatggt cggaagtggc ataaattccg tcagccagtt tagtctgacc atct-catctg |
| 11881 | taacatcatt ggcaacgcta cctttgc-cat gtttcagaaa caactctggc gcatcgggct |
| 11941 | tcccatacaa gcgatagatt gtcgcacctg attgcccgac attatcgcga gcccatt-tat |
| 12001 | acccatataa atcagcatcc atgttggaat ttaatcgcgg cctcgacgtt tcccgtt-gaa |
| 12061 | tatgctcat attcttcctt tttcaatatt attgaagcat ttatcagggt tat-tgtctca |
| 12121 | tgagcggata catatttgaa tgtatttaga aaaataaaca aatagggggtc agtgtta-caa |
| 12181 | ccaattaacc aattctgaac attatcgcga gcccatttat acctgaatat ggctcat-aac |
| 12241 | acccttgtt tgcctggcgg cagtagcgcg gtggtcccac ctgaccc-cat gccgaactca |
| 12301 | gaagtgaaac gccgtagcgc cgatggtagt gtggggactc cccatgcgag agtagg-gaac |
| 12361 | tgccaggcat caaataaaac gaaaggctca gtcgaaa-gac tgggcctttc gcccgggcta |
| 12421 | attaggggt gtcgcccta ttcgactcta tagtgaagtt cctat-tctct agaaagtata |
| 12481 | ggaacttctg aagtggggtc gacttaatta agg |

These rAAV particles are tested for efficacy in cell culture and then administered to an animal model of an ABCA4-associated ocular disorder.

In the cell, for example, the 5' RTM molecule that is designed to interact with a selected target pre-mRNA, e.g., human ABCA4. The RTM comprises a target binding domain, which is a sequence complementary to a portion of Intron 22 of ABCA4, a splicing domain, and a coding domain, with its sequence encoding wildtype Exon 1-22 of ABCA4. Upon delivery to the ocular cell in a recombinant AAV, the target binding domain, which is a sequence complementary to a portion of Intron 22 of ABCA4, binds to Intron 22 of the targeted defective/mutated gene, and the action of the spliceosome operates to replace the target coding wildtype Exon 1-22 of the 5'RTM for the subject's Exon 1-22, which contains defects resulting in disease. The RTM in vivo reprograms the subject's pre-mRNA in the cell, so that the cell now produces ABCA4 without the defects previously in the mutated gene. The same operation occurs with the delivery of the 3' RTM via the rAAV and the ocular cells now have the ability to produce the normal wildtype or corrected gene.

Example 3: Methods of Evaluating RTM Efficacy

ABCA4 is exclusively expressed in photoreceptors of the retina, and these cells are particularly challenging to culture ex vivo. On method of modeling model molecular correction of ABCA4 involves delivering a mixture of rAAV particles containing the 3'RTM and 5'RTM of Example 1 in normal cell culture of photoreceptors. The cells are permitted to grow in culture for a time sufficient to permit the RTM transgenes delivered by the rAAV to perform the trans-splicing function in the cells. Thereafter the cells will be analyzed by conventional methods for the presence of wildtype (or corrected) ABCA4.

Another method of modeling disease to determine the effect of the rAAV delivery of the RTMs is in personalized models using induced pluripotent stem (iPSC) cells obtained from patients diagnosed with Stargardt's in the clinic.

In still another method to facilitate ABCA4 RTM evaluation, an ABCA4 Intron 26 mini-gene is designed for analysis of trans-splicing. The mini-gene construct is created from a healthy donor genomic DNA pool and modified via polymerase chain reaction (PCR) to include a 5' c-Myc tag and a 3' 3×FLAG tag. Additionally, a 3' IRES followed by a Puromycin resistance gene allows for positive selection of cells containing the mini-gene. One such recombinant construct comprises a Myc protein tag, Exon26-Intron 26-Exon 27 of human ABCA4, a 3×FLAG protein tag, an IRES, and an antibiotic resistance gene, under the control of regulatory sequences which can express the product of said gene in selected mammalian host cell.

This construct is cloned into the pK1 retroviral vector, and recombinant virus is generated by triple transfection. The recombinant virus carrying the minigene is transduced into HEK293T cells. With puromycin selection, a stably selected 293T-ABCA4-Int26 mg cell line is created. This mini-gene design allows bidirectional reporting for both 5' and 3' trans-splicing. This cell line is used for preliminary analysis of the ABCA4 RNA trans-splicing molecules.

In a similar manner, a mini-gene for intron 22 is provided to facilitate evaluation of 5' RTMs for ABCA4.

Example 4—RTM Assembly for LCA10

In another embodiment a 5' RTM is designed with a binding domain targeting intron 26 of CEP290 comprises:
3' RTM promoter
Binding domain sequence: 70-200 nucleotides complementary to target intron 26;

```
3'RTM spacer sequence:
                                    SEQ ID NO: 13
AGAGCTCGTTGCGATATTAT

3'RTM BP:
TACTAAC

3'RTM PPT:
                                    SEQ ID NO: 14
TGGTACCTCTTCTTTTTTTCTG

3' Splice Site:
CAGGT
```

Coding domain of CEP290 cDNA encoding exons 1 through the exon 26; 3' RTM PolyA signal sequence.

Figure 2B:
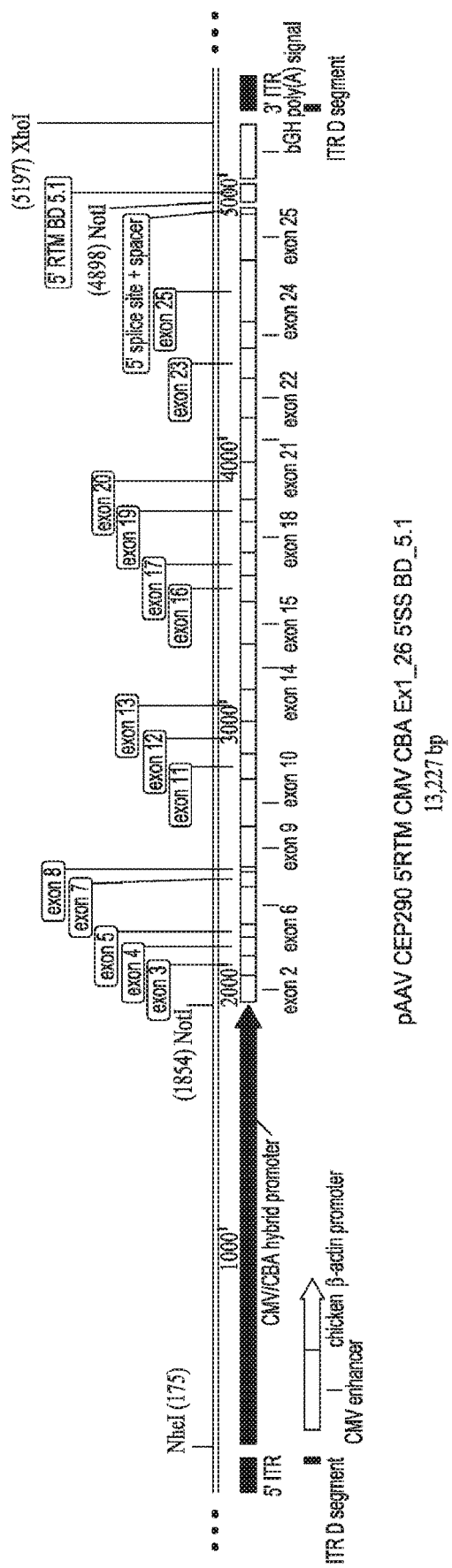
FIG. 2B is a linearized map focusing on the provirus containing the RTM of FIG. 2A, i.e., the plasmid bases only between the 5' and 3' AAV ITRs.

Each RTM is introduced into a proviral plasmid p618 as referenced above, following the teachings of WO2012/158757. The proviral plasmids are cultured in the host cells which express the cap and/or rep proteins. In the host cells, each minigene consisting of the RTM with flanking AAV ITRs is rescued and packaged into the capsid protein or envelope protein to form an infectious viral particle. Thus two types of recombinant AAV infectious particle are produced and purified from culture: one carrying the 3'RTM and the other carrying the 5'RTM. See, e.g., FIGS. 2A and 2B and TABLE 5, which is the sequence of the RTM of FIG. 2A in GenBank format which delineates features of the sequence.

TABLE 5 pAAV CEP290 5'RTM CMV CBA Ex1_26 5'SS BD_5.1
synthetic DNA construct - recombinant plasmid
13227 bp ds-DNA circular
REFERENCE 1 (bases 1 to 13227) SEQ ID NO: 2

| Features | Location/Qualifiers |
|---|---|
| source | 1 . . . 13227<br>/organism = "recombinant plasmid"<br>/mol_type = "other DNA" |
| repeat_region | 1 . . . 130<br>/note = "5' ITR" |
| misc_feature | 113 . . . 130<br>/note = "ITR D segment" |
| promoter | 191 . . . 1852<br>/note = "CMV/CBA hybrid promoter" |
| enhancer | 241 . . . 544<br>/note = "CMV enhancer"<br>/note = "human cytomegalovirus immediate early enhancer" |
| promoter | 546 . . . 823<br>/note = " chicken beta-actin promoter" |
| exon | 1861 . . . 1962<br>/gene = "CEP290"<br>/gene_synonym = "3H11Ag; BBS14; CT87; JBTS5; LCA10; MKS4; NPHP6; POC3; rd16; SLSN6"<br>/note = "exon 2"<br>/inference = "alignmentsame species:1.39.8" |
| exon | 1963 . . . 2040<br>/gene = "CEP290"<br>/gene_synonym = "3H11Ag; BBS14; CT87; JBTS5; LCA10; MKS4; NPHP6; POC3; rd16; SLSN6"<br>/note = "exon 3"<br>/inference = "alignmentsame species:1.39.8" |

TABLE 5-continued pAAV CEP290 5'RTM CMV CBA Ex1_26 5'SS BD_5.1
synthetic DNA construct - recombinant plasmid
13227 bp ds-DNA circular
REFERENCE 1 (bases 1 to 13227) SEQ ID NO: 2

| Features | Location/Qualifiers |
|---|---|
| exon | 2041 . . . 2110<br>/gene = "CEP290"<br>/gene_synonym = "3H11Ag; BBS14; CT87; JBTS5; LCA10; MKS4; NPHP6; POC3; rd16; SLSN6"<br>/note = "exon 4"<br>inference = "alignmentsame species:1.39.8" |
| exon | 2111 . . . 2157<br>/gene = "CEP290"<br>/gene_synonym = "3H11Ag; BBS14; CT87; JBTS5; LCA10; MKS4; NPHP6; POC3; rd16; SLSN6"<br>/note = "exon 5"<br>/inference = "alignmentsame species:1.39.8" |
| exon | 2158 . . . 2301<br>/gene = "CEP290"<br>/gene_synonym = "3H11Ag; BBS14; CT87; JBTS5; LCA10; MKS4; NPHP6; POC3; rd16; SLSN6"<br>/note = "exon 6"<br>/inference = "alignmentsame species:1.39.8" |
| exon | 2302 . . . 2355<br>/gene = "CEP290"<br>/gene_synonym = "3H11Ag; BBS14; CT87; JBTS5; LCA10; MKS4; NPHP6; POC3; rd16; SLSN6"<br>/note = "exon 7"<br>/inference = "alignmentsame species:1.39.8" |
| exon | 2356 . . . 2376<br>/gene = "CEP290"<br>/gene_synonym = "3H11Ag; BBS14; CT87; JBTS5; LCA10; MKS4; NPHP6; POC3; rd16; SLSN6"<br>/note = "exon 8"<br>/inference = "alignmentsame species:1.39.8" |
| exon | 2377 . . . 2529<br>/gene = "CEP290"<br>/gene_synonym = "3H11Ag; BBS14; CT87; JBTS5; LCA10; MKS4; NPHP6; POC3; rd16; SLSN6"<br>/note = "exon 9"<br>/inference = "alignmentsame species:1.39.8" |
| exon | 2530 . . . 2712<br>/gene = "CEP290"<br>/gene_synonym = "3H11Ag; BBS14; CT87; JBTS5; LCA10; MKS4; NPHP6; POC3; rd16; SLSN6"<br>/note = "exon 10"<br>/inference = "alignmentsame species:1.39.8" |
| exon | 2713 . . . 2802<br>/gene = "CEP290"<br>/gene_synonym = "3H11Ag; BBS14; CT87; JBTS5; LCA10; MKS4; NPHP6; POC3; rd16; SLSN6"<br>/note = "exon 11"<br>inference = "alignmentsame species:1.39.8" |
| exon | 2803 . . . 2925<br>/gene = "CEP290"<br>/gene_synonym = "3H11Ag; BBS14; CT87; JBTS5; LCA10; MKS4; NPHP6; POC3; rd16; SLSN6"<br>/note = "exon 12"<br>/inference = "alignmentsame species:1.39.8" |
| exon | 2926 . . . 3049<br>/gene = "CEP290"<br>/gene_synonym = "3H11Ag; BBS14; CT87; JBTS5; LCA10; MKS4; NPHP6; POC3; rd16; SLSN6"<br>/note = "exon 13"<br>/inference = "alignmentsame species:1.39.8" |

TABLE 5-continued pAAV CEP290 5'RTM CMV CBA Ex1_26 5'SS BD_5.1
synthetic DNA construct - recombinant plasmid
13227 bp ds-DNA circular
REFERENCE 1 (bases 1 to 13227) SEQ ID NO: 2

| Features | Location/Qualifiers |
|---|---|
| exon | 3050 . . . 3219<br>/gene = "CEP290"<br>/gene_synonym = "3H11Ag; BBS14; CT87; JBTS5; LCA10; MKS4;<br>NPHP6; POC3; rd16; SLSN6"<br>/note = "exon 14"<br>/inference = "alignmentsame species:1.39.8" |
| exon | 3220 . . . 3382<br>/gene = "CEP290"<br>/gene_synonym = "3H11Ag; BBS14; CT87; JBTS5; LCA10; MKS4;<br>NPHP6; POC3; rd16; SLSN6"<br>/note = "exon 15"<br>/inference = "alignmentsame species:1.39.8" |
| exon | 3383 . . . 3483<br>/gene = "CEP290"<br>/gene_synonym = "3H11Ag; BBS14; CT87; JBTS5; LCA10; MKS4;<br>NPHP6; POC3; rd16; SLSN6"<br>/note = "exon 16"<br>/inference = "alignmentsame species:1.39.8" |
| exon | 3484 . . . 3571<br>/gene = "CEP290"<br>/gene_synonym = "3H11Ag; BBS14; CT87; JBTS5; LCA10; MKS4;<br>NPHP6; POC3; rd16; SLSN6"<br>/note = "exon 17"<br>inference = "alignmentsame species:1.39.8" |
| exon | 3572 . . . 3684<br>/gene = "CEP290"<br>/gene_synonym = "3H11Ag; BBS14; CT87; JBTS5; LCA10; MKS4;<br>NPHP6; POC3; rd16; SLSN6"<br>/note = "exon 18"<br>/inference = "alignmentsame species:1.39.8" |
| exon | 3685 . . . 3769<br>/gene = "CEP290"<br>/gene_synonym = "3H11Ag; BBS14; CT87; JBTS5; LCA10; MKS4;<br>NPHP6; POC3; rd16; SLSN6"<br>/note = "exon 19"<br>/inference = "alignmentsame species:1.39.8" |
| exon | 3770 . . . 3912<br>/gene = "CEP290"<br>/gene_synonym = "3H11Ag; BBS14; CT87; JBTS5; LCA10;<br>MKS4;<br>NPHP6; POC3; rd16; SLSN6"<br>/note = "exon 20"<br>/inference = "alignmentsame species:1.39.8" |
| exon | 3913 . . . 4077<br>/gene = "CEP290"<br>/gene_synonym = "3H11Ag; BBS14; CT87; JBTS5; LCA10;<br>MKS4;<br>NPHP6; POC3; rd16; SLSN6"<br>/note = "exon 21"<br>/inference = "alignmentsame species:1.39.8" |
| exon | 4078 . . . 4227<br>/gene = "CEP290"<br>/gene_synonym = "3H11Ag; BBS14; CT87; JBTS5; LCA10;<br>MKS4;<br>NPHP6; POC3; rd16; SLSN6"<br>/note = "exon 22"<br>/inference = "alignmentsame species:1.39.8" |

TABLE 5-continued pAAV CEP290 5'RTM CMV CBA Ex1_26 5'SS BD_5.1
synthetic DNA construct - recombinant plasmid
13227 bp ds-DNA circular
REFERENCE 1 (bases 1 to 13227) SEQ ID NO: 2

| Features | Location/Qualifiers |
|---|---|
| exon | 4228 . . . 4343<br>/gene = "CEP290"<br>/gene_synonym = "3H11Ag; BBS14; CT87; JBTS5; LCA10; MKS4;<br>NPHP6; POC3; rd16; SLSN6"<br>/note = "exon 23"<br>/inference = "alignmentsame species:1.39.8" |
| exon | 4344 . . . 4446<br>/gene = "CEP290"<br>/gene_synonym = "3H11Ag; BBS14; CT87; JBTS5; LCA10; MKS4;<br>NPHP6; POC3; rd16; SLSN6"<br>/note = "exon 24"<br>/inference = "alignmentsame species:1.39.8" |
| exon | 4447 . . . 4677<br>/gene = "CEP290"<br>/gene_synonym = "3H11Ag; BBS14; CT87; JBTS5; LCA10; MKS4;<br>NPHP6; POC3; rd16; SLSN6"<br>/note = "exon 25"<br>/inference = "alignmentsame species:1.39.8" |
| exon | 4678 . . . 4851<br>/gene = "CEP290"<br>/gene_synonym = "3H11Ag; BBS14; CT87; JBTS5; LCA10; MKS4;<br>NPHP6; POC3; rd16; SLSN6"<br>/note = "exon 26"<br>/inference = "alignmentsame species:1.39.8" |
| misc_feature | 4853 . . . 4876<br>/note = "5' splice site + spacer" |
| misc_feature | 4899 . . . 4967<br>/note = "5' RTM BD 5.1" |
| polyA_signal | 4989 . . . 5196<br>/note = "bGH poly(A) signal"<br>/note = "bovine growth hormone polyadenylation signal" |
| repeat_region | 5246 . . . 5375<br>/note = "3' ITR" |
| misc_feature | 5246 . . . 5263<br>/note = "ITR D segment" |
| protein_bind | complement (5403 . . . 5436)<br>/bound_moiety = "FLP recombinase from the *Saccharomyces cerevisiae* 2u plasmid"<br>/note = "FRT (minimal)"<br>/note = "supports FLP-mediated excision but not integration<br>(Turan and Bode, 2011)" |
| misc_feature | 5469 . . . 5769<br>/product = "bla txn terminator"<br>/note = "bla txn terminator" |
| misc_feature | 5560 . . . 5585<br>/product = "pTF3"<br>/note = "pTF3" |
| misc_feature | 5776 . . . 5889<br>/product = "rpn txn terminator"<br>/note = "rpn txn terminator" |
| misc_feature | 5905 . . . 10971<br>/note = "lambda stuffer" |

TABLE 5-continued pAAV CEP290 5'RTM CMV CBA Ex1_26 5'SS BD_5.1
synthetic DNA construct - recombinant plasmid
13227 bp ds-DNA circular
REFERENCE 1 (bases 1 to 13227) SEQ ID NO: 2

| Features | Location/Qualifiers |
|---|---|
| primer_bind | complement (10977 . . . 10993)<br>/note = "M13 fwd"<br>/note = "common sequencing primer, one of multiple similar variants" |
| rep_origin | complement (11263 . . . 11851)<br>/direction = LEFT<br>/note = "ori"<br>/note = "high-copy-number ColE1/pMB1/pBR322/pUC origin of replication" |
| CDS SEQ<br>ID NO: 4 | complement(11975 . . . 12784)<br>/codon start = 1<br>/gene = "aph(3')-Ia"<br>/product = " aminoglycoside phosphotransferase"<br>/note = "KanR"<br>/note = "confers resistance to kanamycin in bacteria or G418 (Geneticin(R)) in eukaryotes"<br>/translation = "MSHIQRETSRPRLNSNMDADLYGYKWAR DNVGQSGATIYRLYGKPDAPELFLKHGKGSVANDVTD EMVRLNWLTEFMPLPTIKHFIRTPDDAWLLTTAIPGKT AFQVLEEYPDSGENIVDALAVFLRRLHSIPVCNCPFNS DRVFRLAQAQSRMNNGLVDASDFDDERNGWPVEQV WKEMHKLLPFSPDSVVTHGDFSLDNLIFDEGKLIGCIDV GRVGIADRYQDLAILWNCLGEFSPSLQKRLFQKYGIDN PDMNKLQFHLMLDEFF" |
| promoter | complement (12785 . . . 12876)<br>/gene = "bla"<br>/note = "AmpR promoter" |
| misc feature | complement (12963 . . . 13137)<br>/product = "rrnB1 B2 T1 txn terminator"<br>/note = "rrnB1 B2 T1 txn terminator" |
| misc feature | 13038 . . . 13054<br>/product = "pTR"<br>/note = "pTR" |
| protein_bind | 13169 . . . 13202<br>/bound_moiety = "FLP recombinase from the Saccharomyces cerevisiae 2u plasmid"<br>/note = "FRT (minimal)"<br>/note = "supports FLP-mediated excision but not integration (Turan and Bode, 2011)" |

ORIGIN SEQ ID NO: 2

```
    1    ctgcgcgctc gctcgctcac tgaggccgcc cgggcaaagc ccgggcgtcg ggcgaccttt
   61    ggtcgcccgg cctcagtgag cgagcgagcg cgcagagagg gagtggccaa ctccatcact
  121    aggggttcct tgtagttaat gattaacccg ccatgctact tatctacgta gcaagctagc
  181    tagttattaa tagtaatcaa ttacggggtc attagttcat agcccatata tggagttccg
  241    cgttacataa cttacggtaa atggcccgcc tggctgaccg cccaacgacc cccgcccatt
  301    gacgtcaata atgacgtatg ttcccatagt aacgccaata gggactttcc attgacgtca
  361    atgggtggag tatttacggt aaactgccca cttggcagta catcaagtgt atcatatgcc
  421    aagtacgccc cctattgacg tcaatgacgg taaatggccc gcctggcatt atgcccagta
  481    catgacctta tgggactttc ctacttggca gtacatctac gtattagtca tcgctattaa
  541    catggtcgag gtgagcccca cgttctgctt cactctcccc atctcccccc cctccccacc
  601    cccaattttg tatttattta ttttttaatt attttgtgca gcgatggggg cggggggggg
  661    ggggggcgc gcgccaggcg gggcggggcg gggcgagggg cggggcgggg cgaggcggag
  721    aggtgcggcg gcagccaatc agagcggcgc gctccgaaag tttccttta tggcgaggcg
```

TABLE 5-continued pAAV CEP290 5'RTM CMV CBA Ex1_26 5'SS BD_5.1
synthetic DNA construct - recombinant plasmid
13227 bp ds-DNA circular
REFERENCE 1 (bases 1 to 13227) SEQ ID NO: 2

| Features | Location/Qualifiers |
|---|---|
| 781 | gcggcggcgg cggccctata aaaagcgaag cgcgcggcgg gcggggagtc gctgcgacgc |
| 841 | tgccttcgcc ccgtgccccg ctccgccgcc gcctcgcgcc gcccgccccg gctctgactg |
| 901 | accgcgttac tcccacaggt gagcgggcgg gacggccctt ctcctccggg ctgtaattag |
| 961 | cgcttggttt aatgacggct tgtttctttt ctgtggctgc gtgaaagcct tgagggggctc |
| 1021 | cgggagggcc ctttgtgcgg gggagcggc tcgggggggtg cgtgcgtgtg tgtgtgcgtg |
| 1081 | gggagcgccg cgtgcggctc cgcgctgccc ggcggctgtg agcgctgcgg gcgcggcgcg |
| 1141 | gggctttgtg cgctccgcag tgtgcgcgag gggagcgcgg ccggggggcgg tgccccgcgg |
| 1201 | tgcggggggg gctgcgaggg aacaaaggc tgcgtgcggg gtgtgtgcgt ggggggggtga |
| 1261 | gcagggggtg tgggcgcgtc ggtcgggctg caacccccc tgcaccccc tccccgagtt |
| 1321 | gctgagcacg gcccggcttc gggtgcgggg ctccgtacgg ggcgtggcgc ggggctcgcc |
| 1381 | gtgccgggcg gggggtggcg gcaggtgggg gtgccgggcg gggcggggcc gcctcgggcc |
| 1441 | ggggagggct cggggggaggg gcgcggcggc ccccggagcg ccggcggctg tcgaggcgcg |
| 1501 | gcgagccgca gccattgcct tttatggtaa tcgtgcgaga gggcgcaggg acttcctttg |
| 1561 | tcccaaatct gtgcggagcc gaaatctggg aggcgccgcc gcacccctc tagcgggcgc |
| 1621 | ggggcgaagc ggtgcggcgc cggcaggaag gaaatgggcg gggagggcct tcgtgcgtcg |
| 1681 | ccgcgccgcc gtccccttct ccctctccag cctcggggct gtccgcgggg gacggctgc |
| 1741 | cttcgggggg gacggggcag ggcgggttc ggcttctggc gtgtgaccgg cggctctaga |
| 1801 | caattgtact aaccttcttc tctttcctct cctgacaggt tggtgtacac tagcggccgc |
| 1861 | atgccaccta atataaactg gaaagaaata atgaaagttg acccagatga cctgccccgt |
| 1921 | caagaagaac tggcagataa tttattgatt tccttatcca aggtggaagt aaatgagcta |
| 1981 | aaaagtgaaa agcaagaaaa tgtgatacac cttttcagaa ttactcagtc actaatgaag |
| 2041 | atgaaagctc aagaagtgga gctggctttg gaagaagtag aaaaagctgg agaagaacaa |
| 2101 | gcaaaatttg aaaatcaatt aaaaactaaa gtaatgaaac tggaaaatga actggagatg |
| 2161 | gctcagcagt ctgcaggtgg acgagatact cggttttac gtaatgaaat ttgccaactt |
| 2221 | gaaaaacaat tagaacaaaa agatagagaa ttggaggaca tggaaaagga gttggagaaa |
| 2281 | gagaagaaag ttaatgagca attggctctt cgaaatgagg aggcagaaaa tgaaaacagc |
| 2341 | aaattaagaa gagagaacaa acgtctaaag aaaaagaatg aacaactttg tcaggatatt |
| 2401 | attgactacc agaaacaaat agattcacag aaagaaacac ttttatcaag aagagggaa |
| 2461 | gacagtgact accgatcaca gttgtctaaa aaaactatg agcttatcca atatcttgat |
| 2521 | gaaattcaga ctttaacaga agctaatgag aaaattgaag ttcagaatca agaaatgaga |
| 2581 | aaaaatttag aagagtctgt acaggaaatg gagaagatga ctgatgaata taatagaatg |
| 2641 | aaagctattg tgcatcagac agataatgta atagatcagt taaaaaaga aaacgatcat |
| 2701 | tatcaacttc aagtgcagga gcttacagat cttctgaaat caaaaaatga agaagatgat |
| 2761 | ccaattatgg tagctgtcaa tgcaaaagta gaagaatgga agctaatttt gtcttctaaa |
| 2821 | gatgatgaaa ttattgagta tcagcaaatg ttacataacc taagggagaa acttaagaat |
| 2881 | gctcagcttg atgctgataa aagtaatgtt atggctctac agcagggtat acaggaacga |

TABLE 5-continued pAAV CEP290 5'RTM CMV CBA Ex1_26 5'SS BD_5.1
synthetic DNA construct - recombinant plasmid
13227 bp ds-DNA circular
REFERENCE 1 (bases 1 to 13227) SEQ ID NO: 2

| Features | Location/Qualifiers |
|---|---|
| 2941 | gacagtcaaa ttaagatgct caccgaacaa gtagaacaat atacaaaaga aatggaaaag |
| 3001 | aatacttgta ttattgaaga tttgaaaaat gagctccaaa gaaacaaagg tgcttcaacc |
| 3061 | ctttctcaac agactcatat gaaaattcag tcaacgttag acattttaaa agagaaaact |
| 3121 | aaagaggctg agagaacagc tgaactggct gaggctgatg ctagggaaaa ggataaagaa |
| 3181 | ttagttgagg ctctgaagag gttaaaagat tatgaatcgg gagtatatgg tttagaagat |
| 3241 | gctgtcgttg aaataaagaa ttgtaaaaac caaattaaaa taagagatcg agagattgaa |
| 3301 | atattaacaa aggaaatcaa taaacttgaa ttgaagatca gtgatttcct tgatgaaaat |
| 3361 | gaggcactta gagagcgtgt gggccttgaa ccaaagacaa tgattgattt aactgaattt |
| 3421 | agaaatagca aacacttaaa acagcagcag tacagagctg aaaaccagat tcttttgaaa |
| 3481 | gagattgaaa gtctagagga agaacgactt gatctgaaaa aaaaaattcg tcaaatggct |
| 3541 | caagaaagag gaaaaagaag tgcaacttca ggattaacca ctgaggacct gaacctaact |
| 3601 | gaaaacattt ctcaaggaga tagaataagt gaaagaaaat tggatttatt gagcctcaaa |
| 3661 | aatatgagtg aagcacaatc aaagaatgaa tttctttcaa gagaactaat tgaaaagaa |
| 3721 | agagatttag aaaggagtag gacagtgata gccaaatttc agaataaatt aaaagaatta |
| 3781 | gttgaagaaa ataagcaact tgaagaaggt atgaaagaaa tattgcaagc aattaaggaa |
| 3841 | atgcagaaag atcctgatgt taaaggagga gaaacatctc taattatccc tagccttgaa |
| 3901 | agactagtta atgctataga atcaaagaat gcagaaggaa tctttgatgc gagtctgcat |
| 3961 | ttgaaagccc aagttgatca gcttaccgga agaaatgaag aattaagaca ggagctcagg |
| 4021 | gaatctcgga aagaggctat aaattattca cagcagttgg caaaagctaa tttaaagata |
| 4081 | gaccatcttg aaaaagaaac tagtcttttta cgacaatcag aaggatcgaa tgttgttttt |
| 4141 | aaaggaattg acttacctga tgggatagca ccatctagtg ccagtatcat taattctcag |
| 4201 | aatgaatatt taatacattt gttacaggaa ctagaaaata agaaaaaaaa gttaaagaat |
| 4261 | ttagaagatt ctcttgaaga ttacaacaga aaatttgctg taattcgtca tcaacaaagt |
| 4321 | ttgttgtata aagaatacct aagtgaaaag gagacctgga aaacagaatc taaaacaata |
| 4381 | aaagaggaaa agagaaaact tgaggatcaa gtccaacaag atgctataaa agtaaaagaa |
| 4441 | tataataatt tgctcaatgc tcttcagatg gattcggatg aaatgaaaaa aatacttgca |
| 4501 | gaaaatagta ggaaaattac tgttttgcaa gtgaatgaaa aatcacttat aaggcaatat |
| 4561 | acaaccttag tagaattgga gcgacaactt agaaaagaaa atgagaagca aaagaatgaa |
| 4621 | ttgttgtcaa tggaggctga agtttgtgaa aaaattgggt gtttgcaaag atttaaggaa |
| 4681 | atggccattt tcaagattgc agctctccaa aaagttgtag ataatagtgt ttctttgtct |
| 4741 | gaactagaac tggctaataa acagtacaat gaactgactg ctaagtacag ggacatcttg |
| 4801 | caaaaagata atatgcttgt tcaaagaaca agtaacttgg aacacctgga ggtaagagag |
| 4861 | ctcgttgcga tattattaca gatatccagc acagtggcgg ccgctgtaat cccagcactt |
| 4921 | taggaggccg aggcgggtgg atcacgagtt caggagatcg acccgcgt tcgaaagatc |
| 4981 | tgcctcgact gtgccttcta gttgccagcc atctgttgtt tgcccctccc ccgtgccttc |
| 5041 | cttgaccctg gaaggtgcca ctcccactgt cctttcctaa taaaatgagg aaattgcatc |
| 5101 | gcattgtctg agtaggtgtc attctattct ggggggtggg gtggggcagg acagcaaggg |

TABLE 5-continued pAAV CEP290 5'RTM CMV CBA Ex1_26 5'SS BD_5.1
synthetic DNA construct - recombinant plasmid
13227 bp ds-DNA circular
REFERENCE 1 (bases 1 to 13227) SEQ ID NO: 2

| Features | Location/Qualifiers |
|---|---|
| 5161 | ggaggattgg gaagacaata gcaggcatgc tgggactcg agttctacgt agataagtag |
| 5221 | catggcgggt taatcattaa ctacaaggaa ccctagtga tggagttggc cactccctct |
| 5281 | ctgcgcgctc gctcgctcac tgaggccggg cgaccaaagg tcgcccgacg cccgggcttt |
| 5341 | gcccgggcgg cctcagtgag cgagcgagcg cgcagcctta attaacctaa ggaaaatgaa |
| 5401 | gtgaagttcc tatactttct agagaatagg aacttctata gtgagtcgaa taagggcgac |
| 5461 | acaaaattta ttctaaatgc ataataaata ctgataacat cttatagttt gtattatatt |
| 5521 | ttgtattatc gttgacatgt ataattttga tatcaaaaac tgattttccc tttattattt |
| 5581 | tcgagattta ttttcttaat tctctttaac aaactagaaa tattgtatat acaaaaaatc |
| 5641 | ataataata gatgaatagt ttaattatag gtgttcatca atcgaaaaag caacgtatct |
| 5701 | tatttaaagt gcgttgcttt tttctcattt ataaggttaa ataattctca tatatcaagc |
| 5761 | aaagtgacag gcgcccttaa atattctgac aaatgctctt tccctaaact cccccataa |
| 5821 | aaaaacccgc cgaagcgggt ttaacgtttt tttgcggatt aacgattact cgttatcaga |
| 5881 | accgcccagg gggcccgagc ttaacctttt tatttgggg agagggaagt catgaaaaaa |
| 5941 | ctaacctttg aaattcgatc tccagcacat cagcaaaacg ctattcacgc agtacagcaa |
| 6001 | atccttccag acccaaccaa accaatcgta gtaaccattc aggaacgcaa ccgcagctta |
| 6061 | gaccaaaaca ggaagctatg gcctgctta ggtgacgtct ctcgtcaggt tgaatggcat |
| 6121 | ggtcgctggc tggatgcaga aagctggaag tgtgtgttta ccgcagcatt aaagcagcag |
| 6181 | gatgttgttc ctaaccttgc cgggaatggc tttgtggtaa taggccagtc aaccagcagg |
| 6241 | atgcgtgtag gcgaatttgc ggagctatta gagcttatac aggcattcgg tacagagcgt |
| 6301 | ggcgttaagt ggtcagacga agcgagactg gctctggagt ggaaagcgag atggggagac |
| 6361 | agggctgcat gataaatgtc gttagtttct ccggtggcag gacgtcagca tatttgctct |
| 6421 | ggctaatgga gcaaaagcga cgggcaggta aagacgtgca ttacgttttc atggatacag |
| 6481 | gttgtgaaca tccaatgaca tatcggtttg tcaggaagt tgtgaagttc tgggatatac |
| 6541 | cgctcaccgt attgcaggtt gatatcaacc cggagcttgg acagccaaat ggttatacgg |
| 6601 | tatgggaacc aaaggatatt cagacgcgaa tgcctgttct gaagccattt atcgatatgg |
| 6661 | taaagaaata tggcactcca tacgtcggcg gcgcgttctg cactgacaga ttaaaactcg |
| 6721 | ttcccttcac caaatactgt gatgaccatt cgggcgagg aattacacc acgtggattg |
| 6781 | gcatcagagc tgatgaaccg aagcggctaa agccaaagcc tggaatcaga tatcttgctg |
| 6841 | aactgtcaga ctttgagaag gaagatatcc tcgcatggtg aagcaacaa ccattcgatt |
| 6901 | tgcaaatacc ggaacatctc ggtaactgca tattctgcat taaaaaatca acgcaaaaaa |
| 6961 | tcggacttgc ctgcaaagat gaggagggat tgcagcgtgt ttttaatgag gtcatcacgg |
| 7021 | gatcccatgt gcgtgacgga catcgggaaa cgccaaagga gattatgtac cgaggaagaa |
| 7081 | tgtcgctgga cggtatcgcg aaaatgtatt cagaaaatga ttatcaagcc ctgtatcagg |
| 7141 | acatggtacg agctaaaaga ttcgataccg ctcttgttc tgagtcatgc gaaatatttg |
| 7201 | gagggcagct tgatttcgac ttcggggg aagctgcatg atgcgatgtt atcggtgcgg |
| 7261 | tgaatgcaaa gaagataacc gcttccgacc aaatcaacct tactggaatc gatggtgtct |

TABLE 5-continued pAAV CEP290 5'RTM CMV CBA Ex1_26 5'SS BD_5.1
synthetic DNA construct - recombinant plasmid
13227 bp ds-DNA circular
REFERENCE 1 (bases 1 to 13227) SEQ ID NO: 2

| Features | Location/Qualifiers |
|---|---|
| 7321 | ccggtgtgaa agaacaccaa caggggtgtt accactaccg caggaaaagg aggacgtgtg |
| 7381 | gcgagacagc gacgaagtat caccgacata atctgcgaaa actgcaaata ccttccaacg |
| 7441 | aaacgcacca gaaataaacc caagccaatc ccaaaagaat ctgacgtaaa aaccttcaac |
| 7501 | tacacggctc acctgtggga tatccggtgg ctaagacgtc gtgcgaggaa acaaggtga |
| 7561 | ttgaccaaaa tcgaagttac gaacaagaaa gcgtcgagcg agctttaacg tgcgctaact |
| 7621 | gcggtcagaa gctgcatgtg ctggaagttc acgtgtgtga gcactgctgc gcagaactga |
| 7681 | tgagcgatcc gaatagctcg atgcacgagg aagaagatga tggctaaacc agcgcgaaga |
| 7741 | cgatgtaaaa acgatgaatg ccgggaatgg tttcaccctg cattcgctaa tcagtggtgg |
| 7801 | tgctctccag agtgtggaac caagatagca ctcgaacgac gaagtaaaga acgcgaaaaa |
| 7861 | gcggaaaaag cagcagagaa gaaacgacga cgagaggagc agaaacagaa agataaactt |
| 7921 | aagattcgaa aactcgcctt aaagccccgc agttactgga ttaaacaagc ccaacaagcc |
| 7981 | gtaaacgcct tcatcagaga aagagaccgc gacttaccat gtatctcgtg cggaacgctc |
| 8041 | acgtctgctc agtgggatgc cggacattac cggacaactg ctgcggcacc tcaactccga |
| 8101 | tttaatgaac gcaatattca caagcaatgc gtggtgtgca accagcacaa aagcggaaat |
| 8161 | ctcgttccgt atcgcgtcga actgattagc cgcatcgggc aggaagcagt agacgaaatc |
| 8221 | gaatcaaacc ataaccgcca tcgctggact atcgaagagt gcaaggcgat caaggcagag |
| 8281 | taccaacaga aactcaaaga cctgcgaaat agcagaagtg aggccgcatg acgttctcag |
| 8341 | taaaaaccat tccagacatg ctcgttgaag catacggaaa tcagacagaa gtagcacgca |
| 8401 | gactgaaatg tagtcgcggt acggtcagaa aatacgttga tgataaagac gggaaaatgc |
| 8461 | acgccatcgt caacgacgtt ctcatggttc atcgcggatg gagtgaaaga gatgcgctat |
| 8521 | tacgaaaaaa ttgatgcag caaataccga aatatttggg tagttggcga tctgcacgga |
| 8581 | tgctacacga acctgatgaa caaactggat acgattggat tcgacaacaa aaaagacctg |
| 8641 | cttatctcgg tgggcgattt ggttgatcgt ggtgcagaga acgttgaatg cctggaatta |
| 8701 | atcacattcc cctggttcag agctgtacgt ggaaaccatg agcaaatgat gattgatggc |
| 8761 | ttatcagagc gtggaaacgt taatcactgg ctgcttaatg gcggtggctg gttctttaat |
| 8821 | ctcgattacg acaaagaaat tctggctaaa gctcttgccc ataaagcaga tgaacttccg |
| 8881 | ttaatcatcg aactggtgag caaagataaa aaatatgtta tctgccacgc cgattatccc |
| 8941 | tttgacgaat acgagtttgg aaagccagtt gatcatcagc aggtaatctg gaaccgcgaa |
| 9001 | cgaatcagca actcacaaaa cgggatcgtg aaagaaatca aaggcgcgga cacgttcatc |
| 9061 | tttggtcata cgccagcagt gaaaccactc aagtttgcca accaaatgta tatcgatacc |
| 9121 | ggcgcagtgt tctgcggaaa cctaacattg attcaggtac agggagaagg cgcatgagac |
| 9181 | tcgaaagcgt agctaaattt cattcgccaa aaagcccgat gatgagcgac tcaccacggg |
| 9241 | ccacggcttc tgactctctt tccggtactg atgtgatggc tgctatgggg atggcgcaat |
| 9301 | cacaagccgg attcggtatg gctgcattct gcggtaagca cgaactcagc cagaacgaca |
| 9361 | aacaaaaggc tatcaactat ctgatgcaat tgcacacaa ggtatcgggg aaataccgtg |
| 9421 | gtgtggcaaa gcttgaagga aatactaagg caaaggtact gcaagtgctc gcaacattcg |
| 9481 | cttatgcgga ttattgccgt agtgccgcga cgccggggc aagatgcaga gattgccatg |

TABLE 5-continued pAAV CEP290 5'RTM CMV CBA Ex1_26 5'SS BD_5.1
synthetic DNA construct - recombinant plasmid
13227 bp ds-DNA circular
REFERENCE 1 (bases 1 to 13227) SEQ ID NO: 2

| Features | Location/Qualifiers |
|---|---|
| 9541 | gtacaggccg tgcggttgat attgccaaaa cagagctgtg ggggagagtt gtcgagaaag |
| 9601 | agtgcggaag atgcaaaggc gtcggctatt caaggatgcc agcaagcgca gcatatcgcg |
| 9661 | ctgtgacgat gctaatccca aaccttaccc aacccacctg gtcacgcact gttaagccgc |
| 9721 | tgtatgacgc tctggtggtg caatgccaca agaagagtc aatcgcagac aacattttga |
| 9781 | atgcggtcac acgttagcag catgattgcc acggatggca acatattaac ggcatgatat |
| 9841 | tgacttattg aataaaattg ggtaaatttg actcaacgat gggttaattc gctcgttgtg |
| 9901 | gtagtgagat gaaaagaggc ggcgcttact accgattccg cctagttggt cacttcgacg |
| 9961 | tatcgtctgg aactccaacc atcgcaggca gagaggtctg caaaatgcaa tcccgaaaca |
| 10021 | gttcgcaggt aatagttaga gcctgcataa cggtttcggg attttttata tctgcacaac |
| 10081 | aggtaagagc attgagtcga taatcgtgaa gagtcggcga gcctggttag ccagtgctct |
| 10141 | ttccgttgtg ctgaattaag cgaataccgg aagcagaacc ggatcaccaa atgcgtacag |
| 10201 | gcgtcatcgc cgcccagcaa cagcacaacc caaactgagc cgtagccact gtctgtcctg |
| 10261 | aattcattag taatagttac gctgcggcct tttacacatg accttcgtga aagcgggtgg |
| 10321 | caggaggtcg cgctaacaac ctcctgccgt tttgcccgtg catatcggtc acgaacaaat |
| 10381 | ctgattacta aacacagtag cctggatttg ttctatcagt aatcgacctt attcctaatt |
| 10441 | aaatagagca aatccccttta ttgggggtaa gacatgaaga tgccagaaaa acatgacctg |
| 10501 | ttggccgcca ttctcgcggc aaaggaacaa ggcatcgggg caatccttgc gtttgcaatg |
| 10561 | gcgtaccttc gcggcagata taatgcggt gcgtttacaa aaacagtaat cgacgcaacg |
| 10621 | atgtgcgcca ttatcgcctg gttcattcgt gaccttctcg acttcgccgg actaagtagc |
| 10681 | aatctcgctt atataacgag cgtgtttatc ggctacatcg gtactgactc gattggttcg |
| 10741 | cttatcaaac gcttcgctgc taaaaaagcc ggagtagaag atggtagaaa tcaataatca |
| 10801 | acgtaaggcg ttcctcgata tgctggcgtg gtcggaggga actgataacg gacgtcagaa |
| 10861 | aaccagaaat catggttatg acgtcattgt aggcggagag ctatttactg attactccga |
| 10921 | tcaccctcgc aaacttgtca cgctaaaccc aaaactcaaa tcaacaggcg cttaagactg |
| 10981 | gccgtcgttt tacaacacag aaagagtttg tagaaacgca aaaaggccat ccgtcagggg |
| 11041 | ccttctgctt agtttgatgc ctggcagttc cctactctcg ccttccgctt cctcgctcac |
| 11101 | tgactcgctg cgctcggtcg ttcggctgcg gcgagcggta tcagctcact caaaggcggt |
| 11161 | aatacggtta tccacagaat caggggataa cgcaggaaag aacatgtgag caaaaggcca |
| 11221 | gcaaaaggcc aggaaccgta aaaaggccgc gttgctggcg ttttccata ggctccgccc |
| 11281 | ccctgacgag catcacaaaa atcgacgctc aagtcagagg tggcgaaacc cgacaggact |
| 11341 | ataaagatac caggcgtttc ccctggaag ctccctcgtg cgctctcctg ttccgaccct |
| 11401 | gccgcttacc ggatacctgt ccgcctttct cccttcggga agcgtggcgc tttctcatag |
| 11461 | ctcacgctgt aggtatctca gttcggtgta ggtcgttcgc tccaagctgg gctgtgtgca |
| 11521 | cgaaccccc gttcagcccg accgctgcgc cttatccggt aactatcgtc ttgagtccaa |
| 11581 | cccggtaaga cacgacttat cgccactggc agcagccact ggtaacagga ttagcagagc |
| 11641 | gaggtatgta ggcggtgcta cagagttctt gaagtggtgg gctaactacg gctacactag |

TABLE 5-continued pAAV CEP290 5'RTM CMV CBA Ex1_26 5'SS BD_5.1
synthetic DNA construct - recombinant plasmid
13227 bp ds-DNA circular
REFERENCE 1 (bases 1 to 13227) SEQ ID NO: 2

| Features | Location/Qualifiers |
|---|---|
| 11701 | aagaacagta tttggtatct gcgctctgct gaagccagtt accttcggaa aaagagttgg |
| 11761 | tagctcttga tccggcaaac aaaccaccgc tggtagcggt ggttttttg tttgcaagca |
| 11821 | gcagattacg cgcagaaaaa aaggatctca agaagatcct ttgatctttt ctacggggtc |
| 11881 | tgacgctcag tggaacgacg cgcgcgtaac tcacgttaag ggattttggt catgagcttg |
| 11941 | cgccgtcccg tcaagtcagc gtaatgctct gcttttagaa aaactcatcg agcatcaaat |
| 12001 | gaaactgcaa tttattcata tcaggattat caataccata tttttgaaaa agccgtttct |
| 12061 | gtaatgaagg agaaaactca ccgaggcagt tccataggat ggcaagatcc tggtatcggt |
| 12121 | ctgcgattcc gactcgtcca acatcaatac aacctattaa tttcccctcg tcaaaaataa |
| 12181 | ggttatcaag tgagaaatca ccatgagtga cgactgaatc cggtgagaat ggcaaaagtt |
| 12241 | tatgcatttc tttccagact tgttcaacag gccagccatt acgctcgtca tcaaaatcac |
| 12301 | tcgcatcaac caaaccgtta ttcattcgtg attgcgcctg agcgaggcga atacgcgat |
| 12361 | cgctgttaaa aggacaatta caaacaggaa tcgagtgcaa ccggcgcagg aacactgcca |
| 12421 | gcgcatcaac aatattttca cctgaatcag gatattcttc taatacctgg aacgctgttt |
| 12481 | ttccggggat cgcagtggtg agtaaccatg catcatcagg agtacggata aaatgcttga |
| 12541 | tggtcggaag tggcataaat tccgtcagcc agtttagtct gaccatctca tctgtaacat |
| 12601 | cattggcaac gctacctttg ccatgtttca gaaacaactc tggcgcatcg gcttcccat |
| 12661 | acaagcgata gattgtcgca cctgattgcc cgacattatc gcgagcccat ttatacccat |
| 12721 | ataaatcagc atccatgttg gaatttaatc gcggcctcga cgtttcccgt tgaatatggc |
| 12781 | tcatattctt cctttttcaa tattattgaa gcatttatca gggttattgt ctcatgagcg |
| 12841 | gatacatatt tgaatgtatt tagaaaaata aacaaatagg ggtcagtgtt acaaccaatt |
| 12901 | aaccaattct gaacattatc gcgagcccat ttatacctga atatggctca taccccct |
| 12961 | tgtttgcctg gcggcagtag cgcggtggtc ccacctgacc ccatgccgaa ctcagaagtg |
| 13021 | aaacgccgta gcgccgatgg tagtgtgggg actccccatg cgagagtagg gaactgccag |
| 13081 | gcatcaaata aaacgaaagg ctcagtcgaa agactgggcc tttcgcccgg gctaattagg |
| 13141 | gggtgtcgcc cttattcgac tctatagtga agttcctatt ctctagaaag tataggaact |
| 13201 | tctgaagtgg ggtcgactta attaagg |

These rAAV particles are tested for efficacy in cell culture and then administered to an animal model of LCA10.

TABLE 6

(Sequence Listing Free Text)
The following information is provided for sequences containing free text under numeric identifier <223>.

| SEQ ID NO: (containing free text) | Free text under <223> |
|---|---|
| 1 | pAAV ABCA4 3"RTM CMV synthetic construct |
| 2 | pAAV CEP290 5'RTM CMV CBA synthetic construct |
| 5 | 5' splice site with spacer |
| 6 | Splice site for 3' RTM |
| 7 | Polypyrimidine tract for 3' RTM |
| 8 | Spacer for 5' RTM |
| 9 | Spacer for 3' RTM |
| 10 | Spacer for 3' RTM |

TABLE 6-continued (Sequence Listing Free Text)
The following information is provided for sequences containing free text under numeric identifier <223>.

| SEQ ID NO: (containing free text) | Free text under <223> |
|---|---|
| 11 | Polypyrimidine tract for 3' RTM |
| 12 | Spacer for 5' RTM |
| 13 | Spacer for 3' RTM |
| 14 | Polypyrimidine tract for 3' RTM |

All documents listed in this specification, and U.S. provisional application No. 62/257,500, are incorporated herein by reference. While the invention has been described with reference to specific embodiments, it is appreciated that modifications can be made without departing from the spirit of the invention. Such modifications are intended to fall within the scope of the appended claims.

The invention claimed is:

1. A nucleic acid trans-splicing molecule comprising
   (a) a binding domain (BD) that binds a target intron of a mammalian ABCA4 pre-mRNA carrying a defect or mutation causing an ocular disease,
   (b) a splice site, and
   (c) an exon sequence that encodes one more exons of an ABCA4 gene without the defect or mutation.

2. The molecule according to claim 1, wherein the exon sequence comprises exons 1-22.

3. The molecule according to claim 1, wherein the exon sequence comprises exons 27-50.

4. The molecule according to claim 1, comprising:
   (a) a BD that binds a target intron of an ABCA4 pre-mRNA 5' to the defect or mutation in the ABCA4 pre-mRNA;
   (b) an optional spacer;
   (c) a 3' splice site, and
   (d) an exon sequence that encodes one or all exons of the mammalian ABCA4 gene that are 3' to the target intron.

5. The molecule according to claim 4, further comprising:
   (e) a second BD that binds a target the ABCA4 pre-mRNA to the defect or mutation; and
   (f) a 5' splice site.

6. The molecule according to claim 4, wherein the BD binds to a portion of intron 26 and the coding sequence encodes exons 27-50 of the ABCA4 gene.

7. The molecule according to claim 1, comprising in sequential order:
   (a) a BD that binds a target pre-mRNA of the ABCA4 gene 3' to the defect or mutation in the ABCA4 pre-mRNA;
   (b) a 5' splice site;
   (c) an optional spacer; and
   (d) a sequence that encodes all exons of the ABCA4 gene that are 5' to the target pre-mRNA intron.

8. The molecule according to claim 7, wherein the BD binds to a portion of intron 22 and the coding sequence encodes exons 1-22 of the ABCA4 gene.

9. The molecule according to claim 1, which is a nucleic acid sequence of up to 3000 bp in length.

10. A proviral plasmid comprising a wildtype 5' AAV ITR sequence, a promoter comprising an ocular cell-specific promoter/enhancer, a multi-cloning polylinker sequence having inserted therein a nucleic acid sequence of the molecule of claim 1, operatively linked to, and under the regulatory control of, the promoter; and a wildtype 3' AAV ITR sequence.

11. The plasmid according to claim 10, which is p618 comprising the nucleic acid sequence.

12. A recombinant adeno-associated virus comprising a nucleic acid trans-splicing molecule of claim 1.

13. A method of treating an ocular disease caused by a defect or mutation in a mammalian ABCA4 gene comprising: administering to the ocular cells of a subject having an ocular disease a composition comprising the nucleic acid trans-splicing molecule of claim 1.

14. The method according to claim 13, wherein the disease is Stargardt Disease, cone rod dystrophy, fundus flavimaculatus, retinitis pigmentosa, or age-related macular degeneration.

15. The method according to claim 14, wherein the disease is Stargardt Disease, the cells are photoreceptor cells, and the corrected exon sequence is Exons 1-22 or Exons 27-50.

16. The method according to claim 13 comprising administering a 5' nucleic acid trans-splicing molecule or administering a 3' nucleic acid trans-splicing molecule or administering a double nucleic acid trans-splicing molecule.

17. The method according to claim 13, wherein the composition is administered by subretinal injection.

* * * * *

SEQUENCE LISTING

```
<160> NUMBER OF SEQ ID NOS: 14

<210> SEQ ID NO 1
<211> LENGTH: 12513
<212> TYPE: DNA
<213> ORGANISM: Artificial Sequence
<220> FEATURE:
<223> OTHER INFORMATION: pAAV ABCA4 3'RTM CMV synthetic construct

<400> SEQUENCE: 1
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tgtagttaat gattaacccg ccatgctact tatctacgta gcaagctagc     180
tagttattaa tagtaatcaa ttacggggtc attagttcat agcccatata tggagttccg     240
cgttacataa cttacggtaa atggcccgcc tggctgaccg cccaacgacc cccgcccatt     300
gacgtcaata atgacgtatg ttcccatagt aacgccaata gggactttcc attgacgtca     360
atgggtggag tatttacggt aaactgccca cttggcagta catcaagtgt atcatatgcc     420
aagtacgccc cctattgacg tcaatgacgg taaatggccc gcctggcatt atgcccagta     480
catgacctta tgggactttc ctacttggca gtacatctac gtattagtca tcgctattaa     540
catggtcgag gtgagcccca cgttctgctt cactctcccc atctcccccc cctccccacc     600
cccaattttg tatttattta ttttttaatt attttgtgca gcgatggggg cggggggggg     660 ggggggcgc gcgccaggcg gggcggggcg gggcgagggg cggggcgggg cgaggcggag     720
aggtgcggcg gcagccaatc agagcggcgc gctccgaaag tttccttta tggcgaggcg     780 gcggcggcg cggccctata aaaagcgaag cgcgcggcg gcggggagtc gctgcgacgc     840
tgccttcgcc ccgtgccccg ctccgccgcc gcctcgcgcc gcccgccccg gctctgactg     900
accgcgttac tcccacaggt aagtatcaag gttacaagac aggtttaagg agaccaatag     960
aaactgggct tgtcgagaca gagaagactc ttgcgtttct gataggcacc tattggtctt    1020
actgacatcc actttgcctt tctctccaca ggttggtgta cactagcggc cgcaaactct    1080
gctacactca cacatgcttt gtgtggctgt gggtttgata aaagttcatg gaaggagcta    1140
gttggtgccc aggctgacac atgtagaaga gagacttcta gaatccacag gaattttggt    1200
ccccatgttt tcaaagccca tacaagcttc gaattcgata tcgagaacat tattatagcg    1260
```

-continued

```
ttgctcgagt actaactggt acctcttctt tttttttcgtg gcgctcagca gaaaagagaa      1320
aacgtcaacc cccgacaccc ctgcttgggt cccagagaga aggctggaca gacaccccag      1380
gactccaatg tctgctcccc aggggcgccg gctgctcacc cagagggcca gcctccccca      1440
gagccagagt gcccaggccc gcagctcaac acggggacac agctggtcct ccagcatgtg      1500
caggcgctgc tggtcaagag attccaacac accatccgca gccacaagga cttcctggcg      1560
cagatcgtgc tcccggctac ctttgtgttt ttggctctga tgctttctat tgttatccct      1620
ccttttggcg aatacccgc tttgacccctt caccctgga tatatgggca gcagtacacc      1680
ttcttcagca tggatgaacc aggcagtgag cagttcacgg tacttgcaga cgtcctcctg      1740
aataagccag gctttggcaa ccgctgcctg aaggaagggt ggcttccgga gtaccctgt       1800
ggcaactcaa cacctggaa gactccttct gtgtccccaa acatcaccca gctgttccag      1860
aagcagaaat ggacacaggt caaccttca ccatcctgca ggtgcagcac cagggagaag      1920
ctcaccatgc tgccagagtg ccccgagggt gccggggcc tccgcccccc cagagaaca       1980
cagcgcagca cggaaattct acaagacctg acggacagga acatctccga cttcttggta     2040
aaaacgtatc ctgctcttat aagaagcagc ttaaagagca aattctgggt caatgaacag     2100
aggtatggag gaatttccat tggaggaaag ctcccagtcg tccccatcac ggggaagca      2160
cttgttgggt ttttaagcga ccttggccgg atcatgaatg tgagcggggg ccctatcact     2220
agagaggcct ctaaagaaat acctgatttc cttaaacatc tagaaactga agacaacatt     2280
aaggtgtggt ttaataacaa aggctggcat gccctggtca gctttctcaa tgtggcccac     2340
aacgccatct tacgggccag cctgcctaag gacaggagcc ccgaggagta tggaatcacc     2400
gtcattagcc aaccctgaa cctgaccaag gagcagctct cagagattac agtgctgacc     2460
acttcagtgg atgctgtggt tgccatctgc gtgattttct ccatgtcctt cgtcccagcc     2520
agctttgtcc tttatttgat ccaggagcgg gtgaacaaat ccaagcacct ccagtttatc     2580
agtggagtga gccccaccac ctactgggtg accaacttcc tctgggacat catgaattat     2640
tccgtgagtg ctgggctggt ggtgggcatc ttcatcgggt tcagaagaa agcctacact      2700
tctccagaaa accttcctgc ccttgtggca ctgctcctgc tgtatggatg ggcggtcatt     2760
cccatgatgt acccagcatc cttcctgttt gatgtcccca gcacagccta tgtggcttta     2820
tcttgtgcta atctgttcat cggcatcaac agcagtgcta ttaccttcat cttggaatta     2880
tttgagaata ccggacgct gctcaggttc aacgccgtgc tgaggaagct gctcattgtc     2940
ttcccccact tctgcctggg ccggggcctc attgaccttg cactgagcca ggctgtgaca     3000
gatgtctatg cccggtttgg tgaggagcac tctgcaaatc cgttccactg ggacctgatt     3060
gggaagaacc tgtttgccat ggtggtggaa ggggtggtgt acttcctcct gacccctgctg    3120
gtccagcgcc acttcttcct ctcccaatgg attgccgagc ccactaagga gcccattgtt     3180
gatgaagatg atgatgtggc tgaagaaga caaagaatta ttactggtgg aaataaaact     3240
gacatcttaa ggctacatga actaaccaag atttatccag gcacctccag cccagcagtg    3300
gacaggctgt gtgtcggagt tcgccctgga gagtgctttg gcctcctggg agtgaatggt    3360
gccggcaaaa caaccacatt caagatgctc actggggaca ccacagtgac ctcagggggat   3420
gccaccgtag caggcaagag tattttaacc aatatttctg aagtccatca aatatgggc    3480
tactgtcctc agtttgatgc aattgatgag ctgctcacag acgagaaca tctttacctt    3540
tatgcccggc ttcgaggtgt accagcagaa gaaatcgaaa aggttgcaaa ctggagtatt    3600
aagagcctgg gcctgactgt ctacgccgac tgcctggctg gcacgtacag tggggggcaac  3660
```

```
aagcggaaac tctccacagc catcgcactc attggctgcc caccgctggt gctgctggat    3720
gagcccacca cagggatgga cccccaggca cgccgcatgc tgtggaacgt catcgtgagc    3780
atcatcagag aagggagggc tgtggtcctc acatcccaca gcatggaaga atgtgaggca    3840
ctgtgtaccc ggctggccat catggtaaag ggcgcctttc gatgtatggg caccattcag    3900
catctcaagt ccaaatttgg agatggctat atcgtcacaa tgaagatcaa atccccgaag    3960
gacgacctgc ttcctgacct gaaccctgtg gagcagttct tccaggggaa cttcccaggc    4020
agtgtgcaga gggagaggca ctacaacatg ctccagttcc aggtctcctc ctcctccctg    4080
gcgaggatct tccagctcct cctctcccac aaggacagcc tgctcatcga ggagtactca    4140
gtcacacaga ccacactgga ccaggtgttt gtaaattttg ctaaacagca gactgaaagt    4200
catgacctcc ctctgcaccc tcgagctgct ggagccagtc gacaagccca ggactgactg    4260
cagatctgcc tcgactgtgc cttctagttg ccagccatct gttgtttgcc cctcccccgt    4320
gccttccttg accctggaag gtgccactcc cactgtcctt tcctaataaa atgaggaaat    4380
tgcatcgcat tgtctgagta ggtgtcattc tattctgggg ggtggggtgg ggcaggacag    4440
caagggggag gattggaag  acaatagcag gcatgctggg gactcgagtt ctacgtagat    4500
aagtagcatg gcgggttaat cattaactac aaggaacccc tagtgatgga gttggccact    4560
ccctctctgc gcgctcgctc gctcactgag gccgggcgac caaggtcgc ccgacgcccg    4620 ggctttgccc gggcggcctc agtgagcgag cgagcgcgca gccttaatta acctaaggaa    4680
aatgaagtga agttcctata ctttctagag aataggaact tctatagtga gtcgaataag    4740
ggcgacacaa aatttattct aaatgcataa taaatactga taacatctta tagtttgtat    4800
tatattttgt attatcgttg acatgtataa ttttgatatc aaaaactgat tttcccttta    4860
ttattttcga gatttatttt cttaattctc tttaacaaac tagaaatatt gtatatacaa    4920
aaaatcataa ataatagatg aatagtttaa ttataggtgt tcatcaatcg aaaaagcaac    4980
gtatcttatt taaagtgcgt tgcttttttc tcatttataa ggttaaataa ttctcatata    5040
tcaagcaaag tgacaggcgc ccttaaatat tctgacaaat gctctttccc taaactcccc    5100
ccataaaaaa acccgccgaa gcgggttttt acgttatttg cggattaacg attactcgtt    5160
atcagaaccg cccaggggc  ccgagcttaa ccttttttatt tggggagag  ggaagtcatg    5220 aaaaaactaa cctttgaaat tcgatctcca gcacatcagc aaaacgctat tcacgcagta    5280
cagcaaatcc ttccagaccc aaccaaacca atcgtagtaa ccattcagga acgcaaccgc    5340
agcttagacc aaaacaggaa gctatgggcc tgcttaggtg acgtctctcg tcaggttgaa    5400
tggcatggtc gctggctgga tgcagaaagc tggaagtgtg tgtttaccgc agcattaaag    5460
cagcaggatg ttgttcctaa ccttgccggg aatggctttg tggtaatagg ccagtcaacc    5520
agcaggatgc gtgtaggcga atttgcggag ctattagagc ttatacaggc attcggtaca    5580
gagcgtggcg ttaagtggtc agacgaagcg agactggctc tggagtggaa agcgagatgg    5640
ggagacaggg ctgcatgata aatgtcgtta gtttctccgg tggcaggacg tcagcatatt    5700
tgctctggct aatggagcaa aagcgacggg caggtaaaga cgtgcattac gttttcatgg    5760
atacaggttg tgaacatcca atgacatatc ggttgtcag  ggaagttgtg aagttctggg    5820
atataccgct caccgtattg caggttgata tcaacccgga gcttggacag ccaaatggtt    5880
atacggtatg ggaaccaaag gatattcaga cgcgaatgcc tgttctgaag ccatttatcg    5940
atatggtaaa gaaatatggc actccatacg tcggcggcgc gttctgcact gacagattaa    6000
```

```
aactcgttcc cttcaccaaa tactgtgatg accatttcgg gcgagggaat tacaccacgt    6060
ggattggcat cagagctgat gaaccgaagc ggctaaagcc aaagcctgga atcagatatc    6120
ttgctgaact gtcagacttt gagaaggaag atatcctcgc atggtggaag caacaaccat    6180
tcgatttgca ataccggaa catctcggta actgcatatt ctgcattaaa aaatcaacgc     6240
aaaaaatcgg acttgcctgc aaagatgagg agggattgca gcgtgttttt aatgaggtca    6300
tcacgggatc ccatgtgcgt gacggacatc gggaaacgcc aaaggagatt atgtaccgag    6360
gaagaatgtc gctggacggt atcgcgaaaa tgtattcaga aaatgattat caagccctgt    6420
atcaggacat ggtacgagct aaaagattcg ataccggctc ttgttctgag tcatgcgaaa    6480
tatttggagg gcagcttgat ttcgacttcg ggagggaagc tgcatgatgc gatgttatcg    6540
gtgcggtgaa tgcaaagaag ataaccgctt ccgaccaaat caaccttact ggaatcgatg    6600
gtgtctccgg tgtgaaagaa caccaacagg ggtgttacca ctaccgcagg aaaaggagga    6660
cgtgtggcga gacagcgacg aagtatcacc gacataatct gcgaaaactg caaatacctt    6720
ccaacgaaac gcaccagaaa taaacccaag ccaatcccaa aagaatctga cgtaaaaacc    6780
ttcaactaca cggctcacct gtgggatatc cggtggctaa gacgtcgtgc gaggaaaaca    6840
aggtgattga ccaaaatcga agttacgaac aagaaagcgt cgagcgagct ttaacgtgcg    6900
ctaactgcgg tcagaagctg catgtgctgg aagttcacgt gtgtgagcac tgctgcgcag    6960
aactgatgag cgatccgaat agctcgatgc acgaggaaga agatgatggc taaaccagcg    7020
cgaagacgat gtaaaaacga tgaatgccgg gaatggtttc accctgcatt cgctaatcag    7080
tggtggtgct ctccagagtg tggaaccaag atagcactcg aacgacgaag taagaacgc     7140 gaaaaagcgg aaaaagcagc agagaagaaa cgacgacgag aggagcagaa acagaaagat    7200
aaacttaaga ttcgaaaact cgccttaaag ccccgcagtt actggattaa caagcccaa     7260 caagccgtaa acgccttcat cagagaaaga gaccgcgact taccatgtat ctcgtgcgga    7320
acgctcacgt ctgctcagtg ggatgccgga cattaccgga caactgctgc ggcacctcaa    7380
ctccgattta atgaacgcaa tattcacaag caatgcgtgg tgtgcaacca gcacaaaagc    7440
ggaaatctcg ttccgtatcg cgtcgaactg attagccgca tcgggcagga agcagtagac    7500
gaaatcgaat caaaccataa ccgccatcgc tggactatcg aagagtgcaa ggcgatcaag    7560
gcagagtacc aacagaaact caaagacctg cgaaatagca gaagtgaggc cgcatgacgt    7620
tctcagtaaa aaccattcca gacatgctcg ttgaagcata cggaaatcag acagaagtag    7680
cacgcagact gaaatgtagt cgcggtacgg tcagaaaata cgttgatgat aaagacggga    7740
aaatgcacgc catcgtcaac gacgttctca tggttcatcg cggatggagt gaaagagatg    7800
cgctattacg aaaaaattga tggcagcaaa taccgaaata tttgggtagt tggcgatctg    7860
cacggatgct acacgaacct gatgaacaaa ctggatacga ttggattcga caacaaaaaa    7920
gacctgctta tctcggtggg cgatttggtt gatcgtggtg cagagaacgt tgaatgcctg    7980
gaattaatca cattcccctg gttcagagct gtacgtggaa accatgagca atgatgatt     8040 gatggcttat cagagcgtgg aaacgttaat cactggctgc ttaatggcgg tggctggttc    8100
tttaatctcg attacgacaa agaaattctg gctaaagctc ttgcccataa agcagatgaa    8160
cttccgttaa tcatcgaact ggtgagcaaa gataaaaaat atgttatctg ccacgccgat    8220 tatcccttg acgaatacga gtttggaaag ccagttgatc atcagcaggt aatctggaac    8280
cgcgaacgaa tcagcaactc acaaaacggg atcgtgaaaa aaatcaaagg cgcggacacg    8340
ttcatctttg gtcatacgcc agcagtgaaa ccactcaagt ttgccaacca aatgtatatc    8400
```

```
gataccggcg cagtgttctg cggaaaccta acattgattc aggtacaggg agaaggcgca   8460
tgagactcga aagcgtagct aaatttcatt cgccaaaaag cccgatgatg agcgactcac   8520
cacgggccac ggcttctgac tctctttccg gtactgatgt gatggctgct atggggatgg   8580
cgcaatcaca agccggattc ggtatggctg cattctgcgg taagcacgaa ctcagccaga   8640
acgacaaaca aaaggctatc aactatctga tgcaatttgc acacaaggta tcggggaaat   8700
accgtggtgt ggcaaagctt gaaggaaata ctaaggcaaa ggtactgcaa gtgctcgcaa   8760
cattcgctta tgcggattat tgccgtagtg ccgcgacgcc gggggcaaga tgcagagatt   8820
gccatggtac aggccgtgcg gttgatattg ccaaaacaga gctgtggggg agagttgtcg   8880
agaaagagtg cggaagatgc aaaggcgtcg gctattcaag gatgccagca agcgcagcat   8940
atcgcgctgt gacgatgcta atcccaaacc ttacccaacc cacctggtca cgcactgtta   9000
agccgctgta tgacgctctg gtggtgcaat gccacaaaga agagtcaatc gcagacaaca   9060
ttttgaatgc ggtcacacgt tagcagcatg attgccacgg atggcaacat attaacggca   9120
tgatattgac ttattgaata aaattgggta aatttgactc aacgatgggt taattcgctc   9180
gttgtggtag tgagatgaaa agaggcgcg cttactaccg attccgccta gttggtcact   9240
tcgacgtatc gtctggaact ccaaccatcg caggcagaga ggtctgcaaa atgcaatccc   9300
gaaacagttc gcaggtaata gttagagcct gcataacggt ttcgggattt tttatatctg   9360
cacaacaggt aagagcattg agtcgataat cgtgaagagt cggcgagcct ggttagccag   9420 tgctcttttcc gttgtgctga attaagcgaa taccggaagc agaaccggat caccaaatgc   9480
gtacaggcgt catcgccgcc cagcaacagc acaacccaaa ctgagccgta gccactgtct   9540
gtcctgaatt cattagtaat agttacgctg cggccttta cacatgacct tcgtgaaagc   9600
gggtggcagg aggtcgcgct aacaacctcc tgccgttttg cccgtgcata tcggtcacga   9660
acaaatctga ttactaaaca cagtagcctg gatttgttct atcagtaatc gaccttattc   9720
ctaattaaat agagcaaatc cccttattgg gggtaagaca tgaagatgcc agaaaaacat   9780
gacctgttgg ccgccattct cgcggcaaag gaacaaggca tcgggcaat ccttgcgttt   9840 gcaatggcgt accttcgcgg cagatataat ggcggtgcgt ttacaaaaac agtaatcgac   9900
gcaacgatgt gcgccattat cgcctggttc attcgtgacc ttctcgactt cgccggacta   9960
agtagcaatc tcgcttatat aacgagcgtg tttatcggct acatcggtac tgactcgatt  10020
ggttcgctta tcaaacgctt cgctgctaaa aaagccggag tagaagatgg tagaaatcaa  10080
taatcaacgt aaggcgttcc tcgatatgct ggcgtggtcg gagggaactg ataacgacg   10140 tcagaaaacc agaaatcatg gttatgacgt cattgtaggc ggagagctat ttactgatta  10200
ctccgatcac cctcgcaaac ttgtcacgct aaacccaaaa ctcaaatcaa caggcgctta  10260
agactggccg tcgttttaca acacagaaag agtttgtaga acgcaaaaa ggccatccgt  10320 caggggcctt ctgcttagtt tgatgcctgg cagttcccta ctctcgcctt ccgcttcctc  10380
gctcactgac tcgctgcgct cggtcgttcg gctgcggcga gcggtatcag ctcactcaaa  10440
ggcggtaata cggttatcca cagaatcagg ggataacgca ggaaagaaca tgtgagcaaa  10500
aggccagcaa aaggccagga accgtaaaaa ggccgcgttg ctggcgtttt tccataggct  10560
ccgcccccct gacgagcatc acaaaaatcg acgctcaagt cagaggtggc gaaacccgac  10620
aggactataa agataccagg cgtttccccc tggaagctcc ctcgtgcgct ctcctgttcc  10680
gaccctgccg cttaccggat acctgtccgc ctttctccct tcgggaagcg tggcgctttc  10740
```

```
tcatagctca cgctgtaggt atctcagttc ggtgtaggtc gttcgctcca agctgggctg    10800
tgtgcacgaa ccccccgttc agcccgaccg ctgcgcctta ccggtaact atcgtcttga    10860 gtccaacccg gtaagacacg acttatcgcc actggcagca gccactggta acaggattag    10920
cagagcgagg tatgtaggcg gtgctacaga gttcttgaag tggtgggcta actacggcta    10980
cactagaaga acagtatttg gtatctgcgc tctgctgaag ccagttacct tcggaaaaag    11040
agttggtagc tcttgatccg gcaaacaaac caccgctggt agcggtggtt tttttgtttg    11100
caagcagcag attacgcgca gaaaaaagg atctcaagaa gatcctttga tcttttctac    11160
ggggtctgac gctcagtgga acgacgcgcg cgtaactcac gttaagggat tttggtcatg    11220
agcttgcgcc gtcccgtcaa gtcagcgtaa tgctctgctt ttagaaaaac tcatcgagca    11280
tcaaatgaaa ctgcaattta ttcatatcag gattatcaat accatatttt tgaaaaagcc    11340
gtttctgtaa tgaaggagaa aactcaccga ggcagttcca taggatggca agatcctggt    11400
atcggtctgc gattccgact cgtccaacat caatacaacc tattaattc ccctcgtcaa    11460 aaataaggtt atcaagtgag aaatcaccat gagtgacgac tgaatccggt gagaatggca    11520
aaagtttatg catttctttc cagacttgtt caacaggcca gccattacgc tcgtcatcaa    11580
aatcactcgc atcaaccaaa ccgttattca ttcgtgattg cgcctgagcg aggcgaaata    11640
cgcgatcgct gttaaaagga caattacaaa caggaatcga gtgcaaccgg cgcaggaaca    11700
ctgccagcgc atcaacaata ttttcacctg aatcaggata ttcttctaat acctggaacg    11760
ctgtttttcc ggggatcgca gtggtgagta accatgcatc atcaggagta cggataaaat    11820
gcttgatggt cggaagtggc ataaattccg tcagccagtt tagtctgacc atctcatctg    11880
taacatcatt ggcaacgcta cctttgccat gtttcagaaa caactctggc gcatcgggct    11940
tcccatacaa gcgatagatt gtcgcacctg attgcccgac attatcgcga gcccatttat    12000
acccatataa atcagcatcc atgttggaat ttaatcgcgg cctcgacgtt tcccgttgaa    12060 tatgctcat attcttcctt tttcaatatt attgaagcat ttatcagggt tattgtctca    12120
tgagcggata catatttgaa tgtatttaga aaaataaaca aatagggtc agtgttacaa    12180 ccaattaacc aattctgaac attatcgcga gcccatttat acctgaatat ggctcataac    12240
accccttgtt tgcctggcgg cagtagcgcg gtggtcccac ctgaccccat gccgaactca    12300
gaagtgaaac gccgtagcgc cgatggtagt gtggggactc cccatgcgag gtagggaac    12360 tgccaggcat caaataaaac gaaaggctca gtcgaaagac tgggcctttc gcccgggcta    12420 attaggggt gtcgcccta ttcgactcta gtgaagtt cctattctct agaaagtata    12480
ggaacttctg aagtggggtc gacttaatta agg                                 12513
```

<210> SEQ ID NO 2
<211> LENGTH: 13227
<212> TYPE: DNA
<213> ORGANISM: Artificial Sequence
<220> FEATURE:
<223> OTHER INFORMATION: pAAV CEP290 5'RTM CMV CBA Ex1_26 5'SS BD_5.1
      synthetic DNA construct recombinant plasmid

<400> SEQUENCE: 2

```
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
agggggtcct tgtagttaat gattaacccg ccatgctact tatctacgta gcaagctagc     180
tagttattaa tagtaatcaa ttacggggtc attagttcat agcccatata tggagttccg     240
```

```
cgttacataa cttacggtaa atggcccgcc tggctgaccg cccaacgacc cccgcccatt    300
gacgtcaata atgacgtatg ttcccatagt aacgccaata gggactttcc attgacgtca    360
atgggtggag tatttacggt aaactgccca cttggcagta catcaagtgt atcatatgcc    420
aagtacgccc cctattgacg tcaatgacgg taaatggccc gcctggcatt atgcccagta    480
catgacctta tgggactttc ctacttggca gtacatctac gtattagtca tcgctattaa    540
catggtcgag gtgagcccca cgttctgctt cactctcccc atctcccccc ctccccacc     600 cccaattttg tatttattta ttttttaatt attttgtgca gcgatggggg cgggggggg     660 gggggggcgc gcgccaggcg gggcggggcg gggcgagggg cggggcgggg cgaggcggag    720
aggtgcggcg gcagccaatc agagcggcgc gctccgaaag tttccttttta tggcgaggcg    780 gcggcggcgg cggccctata aaaagcgaag cgcgcggcgg gcggggagtc gctgcgacgc    840
tgccttcgcc ccgtgccccg ctccgccgcc gcctcgcgcc gcccgccccg gctctgactg    900
accgcgttac tcccacaggt gagcgggcgg gacggccctt ctcctcccggg ctgtaattag    960 cgcttggttt aatgacggct tgtttctttt ctgtggctgc gtgaaagcct tgaggggctc    1020
cgggagggcc ctttgtgcgg ggggagcggc tcgggggtg cgtgcgtgtg tgtgtgcgtg    1080
gggagcgccg cgtgcggctc cgcgctgccc ggcggctgtg agcgctgcgg gcgcggcgcg    1140
gggctttgtg cgctccgcag tgtgcgcgag gggagcgcgg ccggggcgg tgccccgcgg    1200 tgcgggggg gctgcgaggg gaacaaaggc tgcgtgcggg gtgtgtgcgt ggggggtga    1260 gcagggggtg tgggcgcgtc ggtcgggctg caaccccccc tgcacccccc tccccgagtt    1320
gctgagcacg gccggcttc gggtgcgggg ctccgtacgg ggcgtggcgc ggggctcgcc    1380
gtgccgggcg gggggtggcg gcaggtgggg gtgccgggcg gggcggggcc gcctcgggcc    1440
ggggagggct cggggaggg gcgcggcggc ccccggagcg ccggcggctg tcgaggcgcg    1500
gcgagccgca gccattgcct tttatggtaa tcgtgcgaga gggcgcaggg acttcctttg    1560
tcccaaatct gtgcggagcc gaaatctggg aggcgccgcc gcacccctc tagcgggcgc    1620 ggggcgaagc ggtgcggcgc cggcaggaag gaaatgggcg gggagggcct tcgtgcgtcg    1680
ccgcgccgcc gtccccttct ccctctccag cctcggggct gtccgcgggg gacggctgc    1740 cttcgggggg gacggggcag ggcggggttc ggcttctggc gtgtgaccgg cggctctaga    1800
caattgtact aaccttcttc tctttcctct cctgacaggt tggtgtacac tagcggccgc    1860
atgccaccta atataaactg gaaagaaata atgaaagttg acccagatga cctgccccgt    1920
caagaagaac tggcagataa tttattgatt tccttatcca aggtggaagt aaatgagcta    1980
aaaagtgaaa agcaagaaaa tgtgatacac ctttttcagaa ttactcagtc actaatgaag    2040
atgaaagctc aagaagtgga gctggctttg gaagaagtag aaaaagctgg agaagaacaa    2100
gcaaaatttg aaaatcaatt aaaaactaaa gtaatgaaac tggaaaatga actggagatg    2160
gctcagcagt ctgcaggtgg acgagatact cggttttac gtaatgaaat ttgccaactt    2220
gaaaaacaat tagaacaaaa agatagagaa ttggaggaca tggaaaagga gttggagaaa    2280
gagaagaaag ttaatgagca attggctctt cgaaatgagg aggcagaaaa tgaaaacagc    2340
aaattaagaa gagagaacaa acgtctaaag aaaaagaatg aacaactttg tcaggatatt    2400
attgactacc agaaacaaat agattcacag aaagaaacac ttttatcaag aagagggaa    2460 gacagtgact accgatcaca gttgtctaaa aaaactatg agcttatcca atatcttgat    2520
gaaattcaga ctttaacaga agctaatgag aaaattgaag ttcagaatca agaaatgaga    2580
aaaaatttag aagagtctgt acaggaaatg gagaagatga ctgatgaata aatagaatg    2640
```

```
aaagctattg tgcatcagac agataatgta atagatcagt taaaaaaaga aaacgatcat   2700
tatcaacttc aagtgcagga gcttacagat cttctgaaat caaaaaatga agaagatgat   2760
ccaattatgg tagctgtcaa tgcaaaagta gaagaatgga agctaatttt gtcttctaaa   2820
gatgatgaaa ttattgagta tcagcaaatg ttacataacc taaggagaaa acttaagaat   2880
gctcagcttg atgctgataa aagtaatgtt atggctctac agcagggtat acaggaacga   2940
gacagtcaaa ttaagatgct caccgaacaa gtagaacaat atacaaaaga aatgaaaaag   3000
aatacttgta ttattgaaga tttgaaaaat gagctccaaa gaaacaaagg tgcttcaacc   3060
ctttctcaac agactcatat gaaaattcag tcaacgttag acattttaaa agagaaaact   3120
aaagaggctg agagaacagc tgaactggct gaggctgatg ctagggaaaa ggataaagaa   3180
ttagttgagg ctctgaagag gttaaaagat tatgaatcgg gagtatatgg tttagaagat   3240
gctgtcgttg aaataaagaa ttgtaaaaac caaattaaaa taagagatcg agagattgaa   3300
atattaacaa aggaaatcaa taaacttgaa ttgaagatca gtgatttcct tgatgaaaat   3360
gaggcactta gagagcgtgt gggccttgaa ccaaagacaa tgattgattt aactgaattt   3420
agaaatagca acacttaaa acagcagcag tacagagctg aaaaccagat tcttttgaaa    3480
gagattgaaa gtctagagga agaacgactt gatctgaaaa aaaaaattcg tcaaatggct   3540
caagaaagag gaaaagaag tgcaacttca ggattaacca ctgaggacct gaacctaact    3600
gaaaacattt ctcaaggaga tagaataagt gaaagaaaat tggatttatt gagcctcaaa   3660
aatatgagtg aagcacaatc aaagaatgaa tttctttcaa gagaactaat tgaaaaagaa   3720
agagatttag aaaggagtag gacagtgata gccaaatttc agaataaatt aaaagaatta   3780
gttgaagaaa ataagcaact tgaagaaggt atgaaagaaa tattgcaagc aattaaggaa   3840
atgcagaaag atcctgatgt taaggagga gaaacatctc taattatccc tagccttgaa    3900
agactagtta atgctataga atcaaagaat gcagaaggaa tctttgatgc gagtctgcat   3960
ttgaaagccc aagttgatca gcttaccgga agaaatgaag aattaagaca ggagctcagg   4020
gaatctcgga aagaggctat aaattattca cagcagttgg caaaagctaa tttaaagata   4080
gaccatcttg aaaaagaaac tagtctttta cgacaatcag aaggatcgaa tgttgttttt   4140
aaaggaattg acttacctga tgggatagca ccatctagtg ccagtatcat taattctcag   4200
aatgaatatt taatacattt gttacaggaa ctagaaaata agaaaaaaa gttaaagaat    4260 ttagaagatt ctcttgaaga ttacaacaga aaatttgctg taattcgtca tcaacaaagt   4320
ttgttgtata aagaatacct aagtgaaaag gagacctgga aaacagaatc taaaacaata   4380
aaagaggaaa agagaaaact tgaggatcaa gtccaacaag atgctataaa agtaaaagaa   4440
tataataatt tgctcaatgc tcttcagatg gattcggatg aaatgaaaaa atacttgca    4500 gaaaatagta ggaaaattac tgttttgcaa gtgaatgaaa aatcacttat aaggcaatat   4560
acaaccttag tagaattgga gcgacaactt agaaagaaa atgagaagca aaagaatgaa    4620 tgttgtcaa tggaggctga agtttgtgaa aaaattgggt gtttgcaaag atttaaggaa    4680
atggccattt tcaagattgc agctctccaa aaagttgtag ataatagtgt ttctttgtct   4740
gaactagaac tggctaataa acagtacaat gaactgactg ctaagtacag ggacatcttg   4800
caaaaagata atatgcttgt tcaaagaaca agtaacttgg aacacctgga ggtaagagag   4860
ctcgttgcga tattattaca gatatccagc acagtggcgg ccgctgtaat cccagcactt   4920
taggaggccg aggcgggtgg atcacgagtt caggagatcg acaccgcggt tcgaaagatc   4980
```

```
tgcctcgact gtgccttcta gttgccagcc atctgttgtt tgcccctccc ccgtgccttc   5040
cttgaccctg gaaggtgcca ctcccactgt cctttcctaa taaaatgagg aaattgcatc   5100
gcattgtctg agtaggtgtc attctattct gggggtggg gtggggcagg acagcaaggg   5160
ggaggattgg gaagacaata gcaggcatgc tggggactcg agttctacgt agataagtag   5220
catggcgggt taatcattaa ctacaaggaa ccctagtga tggagttggc cactccctct   5280
ctgcgcgctc gctcgctcac tgaggccggg cgaccaaagg tcgcccgacg cccgggcttt   5340
gcccgggcgg cctcagtgag cgagcgagcg cgcagcctta attaacctaa ggaaaatgaa   5400
gtgaagttcc tatactttct agagaatagg aacttctata gtgagtcgaa taagggcgac   5460
acaaaattta ttctaaatgc ataataaata ctgataacat cttatagttt gtattatatt   5520
ttgtattatc gttgacatgt ataatttga tatcaaaaac tgattttccc tttattattt   5580
tcgagattta ttttcttaat tctctttaac aaactagaaa tattgtatat acaaaaaatc   5640
ataaataata gatgaatagt ttaattatag gtgttcatca atcgaaaaag caacgtatct   5700
tatttaaagt gcgttgcttt tttctcattt ataaggttaa ataattctca tatatcaagc   5760
aaagtgacag gcgcccttaa atattctgac aaatgctctt tccctaaaact cccccataa    5820 aaaaaccgc cgaagcgggt ttttacgtta tttgcggatt aacgattact cgttatcaga   5880 accgccagg gggcccgagc ttaaccttt tatttggggg agaggaagt catgaaaaaa   5940 ctaacctttg aaattcgatc tccagcacat cagcaaaacg ctattcacgc agtacagcaa   6000
atccttccag acccaaccaa accaatcgta gtaaccattc aggaacgcaa ccgcagctta   6060
gaccaaaaca ggaagctatg ggcctgctta ggtgacgtct ctcgtcaggt tgaatggcat   6120
ggtcgctggc tggatgcaga aagctggaag tgtgtgttta ccgcagcatt aaagcagcag   6180
gatgttgttc ctaaccttgc cgggaatggc tttgtggtaa taggccagtc aaccagcagg   6240
atgcgtgtag gcgaatttgc ggagctatta gagcttatac aggcattcgg tacagagcgt   6300
ggcgttaagt ggtcagacga agcgagactg gctctggagt ggaaagcgag atggggagac   6360
agggctgcat gataaatgtc gttagttct ccggtggcag gacgtcagca tatttgctct   6420
ggctaatgga gcaaaagcga cgggcaggta aagacgtgca ttacgttttc atggatacag   6480
gttgtgaaca tccaatgaca tatcggtttg tcagggaagt tgtgaagttc tgggatatac   6540
cgctcaccgt attgcaggtt gatatcaacc cggagcttgg acagccaaat ggttatacgg   6600
tatgggaacc aaaggatatt cagacgcgaa tgcctgttct gaagccattt atcgatatgg   6660
taaagaaata tggcactcca tacgtcgcg gcgcgttctg cactgacaga ttaaaactcg   6720
ttcccttcac caaatactgt gatgaccatt tcgggcgagg gaattacacc acgtggattg   6780
gcatcagagc tgatgaaccg aagcggctaa agccaaagcc tggaatcaga tatcttgctg   6840
aactgtcaga ctttgagaag gaagatatcc tcgcatggtg gaagcaacaa ccattcgatt   6900
tgcaaatacc ggaacatctc ggtaactgca tattctgcat taaaaaatca acgcaaaaaa   6960
tcggacttgc ctgcaaagat gaggagggat tgcagcgtgt ttttaatgag gtcatcacgg   7020
gatcccatgt gcgtgacgga catcgggaaa cgccaaagga gattatgtac cgaggaagaa   7080
tgtcgctgga cggtatcgcg aaaatgtatt cagaaaatga ttatcaagcc ctgtatcagg   7140
acatggtacg agctaaaaga ttcgataccg gctcttgttc tgagtcatgc gaaatatttg   7200
gagggcagct tgatttcgac ttcggggagg aagctgcatg atgcgatgtt atcggtgcgg   7260
tgaatgcaaa aagataacc gcttccgacc aaatcaacct tactgaatc gatggtgtct   7320 ccggtgtgaa agaacaccaa cagggggtgtt accactaccg caggaaaagg aggacgtgtg   7380
```

```
gcgagacagc gacgaagtat caccgacata atctgcgaaa actgcaaata ccttccaacg   7440
aaacgcacca gaaataaacc caagccaatc ccaaaagaat ctgacgtaaa aaccttcaac   7500
tacacggctc acctgtggga tatccggtgg ctaagacgtc gtgcgaggaa aacaaggtga   7560
ttgaccaaaa tcgaagttac gaacaagaaa gcgtcgagcg agctttaacg tgcgctaact   7620
gcggtcagaa gctgcatgtg ctggaagttc acgtgtgtga gcactgctgc gcagaactga   7680
tgagcgatcc gaatagctcg atgcacgagg aagaagatga tggctaaacc agcgcgaaga   7740
cgatgtaaaa acgatgaatg ccgggaatgg tttcaccctg cattcgctaa tcagtggtgg   7800
tgctctccag agtgtggaac caagatagca ctcgaacgac gaagtaaaga acgcgaaaaa   7860
gcggaaaaag cagcagagaa gaaacgacga cgagaggagc agaaacagaa agataaactt   7920
aagattcgaa aactcgcctt aaagcccgc agttactgga ttaaacaagc ccaacaagcc     7980
gtaaacgcct tcatcagaga aagagaccgc gacttaccat gtatctcgtg cggaacgctc   8040
acgtctgctc agtgggatgc cggacattac cggacaactg ctgcggcacc tcaactccga   8100
tttaatgaac gcaatattca caagcaatgc gtggtgtgca accagcacaa agcggaaat    8160 ctcgttccgt atcgcgtcga actgattagc cgcatcgggc aggaagcagt agacgaaatc   8220
gaatcaaacc ataaccgcca tcgctggact atcgaagagt gcaaggcgat caaggcagag   8280
taccaacaga aactcaaaga cctgcgaaat agcagaagtg aggccgcatg acgttctcag   8340
taaaaaccat tccagacatg ctcgttgaag catacgaaaa tcagacagaa gtagcacgca   8400
gactgaaatg tagtcgcggt acggtcagaa aatacgttga tgataaagac gggaaaatgc   8460
acgccatcgt caacgacgtt ctcatggttc atcgcggatg gagtgaaaga gatgcgctat   8520
tacgaaaaaa ttgatggcag caaataccga aatatttggg tagttggcga tctgcacgga   8580
tgctacacga acctgatgaa caaactggat acgattggat tcgacaacaa aaaagacctg   8640
cttatctcgg tgggcgattt ggttgatcgt ggtgcagaga acgttgaatg cctggaatta   8700
atcacattcc cctggttcag agctgtacgt ggaaaccatg agcaaatgat gattgatggc   8760
ttatcagagc gtggaaacgt taatcactgg ctgcttaatg gcggtggctg gttctttaat   8820
ctcgattacg acaaagaaat tctggctaaa gctcttgccc ataaagcaga tgaacttccg   8880
ttaatcatcg aactggtgag caaagataaa aaatatgtta tctgccacgc cgattatccc   8940
tttgacgaat acgagtttgg aaagccagtt gatcatcagc aggtaatctg gaaccgcgaa   9000
cgaatcagca actcacaaaa cgggatcgtg aaagaaatca aaggcgcgga cacgttcatc   9060
tttggtcata cgccagcagt gaaaccactc aagtttgcca accaaatgta tatcgatacc   9120
ggcgcagtgt tctgcggaaa cctaacattg attcaggtac agggagaagg cgcatgagac   9180
tcgaaagcgt agctaaattt cattcgccaa aaagcccgat gatgagcgac tcaccacggg   9240
ccacggcttc tgactctctt tccggtactg atgtgatggc tgctatgggg atggcgcaat   9300
cacaagccgg attcggtatg gctgcattct gcggtaagca cgaactcagc cagaacgaca   9360
aacaaaaggc tatcaactat ctgatgcaat ttgcacacaa ggtatcgggg aaataccgtg   9420
gtgtggcaaa gcttgaagga aatactaagg caaaggtact gcaagtgctc gcaacattcg   9480
cttatgcgga ttattccgt agtgccgcga cgccgggggc aagatgcaga gattgccatg     9540
gtacaggccg tgcggttgat attgccaaaa cagagctgtg ggggagagtt gtcgagaaag   9600
agtgcggaag atgcaaaggc gtcggctatt caaggatgcc agcaagcgca gcatatcgcg   9660
ctgtgacgat gctaatccca aaccttaccc aacccacctg gtcacgcact gttaagccgc   9720
```

```
tgtatgacgc tctggtggtg caatgccaca agaagagtc aatcgcagac aacatttga    9780
atgcggtcac acgttagcag catgattgcc acggatggca acatattaac ggcatgatat   9840
tgacttattg aataaaattg ggtaaatttg actcaacgat gggttaattc gctcgttgtg   9900
gtagtgagat gaaagagagc ggcgcttact accgattccg cctagttggt cacttcgacg   9960
tatcgtctgg aactccaacc atcgcaggca gagaggtctg caaaatgcaa tcccgaaaca  10020
gttcgcaggt aatagttaga gcctgcataa cggtttcggg atttttttata tctgcacaac  10080
aggtaagagc attgagtcga taatcgtgaa gagtcggcga gcctggttag ccagtgctct  10140
ttccgttgtg ctgaattaag cgaataccgg aagcagaacc ggatcaccaa atgcgtacag  10200
gcgtcatcgc cgcccagcaa cagcacaacc caaactgagc cgtagccact gtctgtcctg  10260
aattcattag taatagttac gctgcggcct tttacacatg accttcgtga aagcgggtgg  10320
caggaggtcg cgctaacaac ctcctgccgt tttgcccgtg catatcggtc acgaacaaat  10380
ctgattacta aacacagtag cctggatttg ttctatcagt aatcgacctt attcctaatt  10440
aaatagagca atccccctta ttgggggtaa acatgaaga tgccagaaaa acatgacctg   10500
ttggccgcca ttctcgcggc aaaggaacaa ggcatcgggg caatccttgc gtttgcaatg  10560
gcgtaccttc gcggcagata taatggcggt gcgtttacaa aaacagtaat cgacgcaacg  10620
atgtgcgcca ttatcgcctg gttcattcgt gaccttctcg acttcgccgg actaagtagc  10680
aatctcgctt atataacgag cgtgtttatc ggctacatcg gtactgactc gattggttcg  10740
cttatcaaac gcttcgctgc taaaaaagcc ggagtagaag atggtagaaa tcaataatca  10800
acgtaaggcg ttcctcgata tgctggcgtg gtcggaggga actgataacg gacgtcagaa  10860
aaccagaaat catggttatg acgtcattgt aggcggagag ctatttactg attactccga  10920
tcaccctcgc aaacttgtca cgctaaaccc aaaactcaaa tcaacaggcg cttaagactg  10980
gccgtcgttt tacaacacag aaagagtttg tagaaacgca aaaaggccat ccgtcagggg  11040
ccttctgctt agtttgatgc ctggcagttc cctactctcg ccttccgctt cctcgctcac  11100
tgactcgctg cgctcggtcg ttcggctgcg gcgagcggta tcagctcact caaaggcggt  11160
aatacggtta tccacagaat cagggggataa cgcaggaaag aacatgtgag caaaaggcca  11220
gcaaaaggcc aggaaccgta aaaaggccgc gttgctggcg ttttttccata ggctccgccc  11280
ccctgacgag catcacaaaa atcgacgctc aagtcagagg tggcgaaacc cgacaggact  11340
ataaagatac caggcgtttc ccctggaag ctccctcgtg cgctctcctg ttccgaccct   11400
gccgcttacc ggatacctgt ccgcctttct cccttcggga agcgtggcgc tttctcatag  11460
ctcacgctgt aggtatctca gttcggtgta ggtcgttcgc tccaagctgg gctgtgtgca  11520
cgaacccccc gttcagcccg accgctgcgc cttatccggt aactatcgtc ttgagtccaa  11580
cccggtaaga cacgacttat cgccactggc agcagccact ggtaacagga ttagcagagc  11640
gaggtatgta ggcggtgcta cagagttctt gaagtggtgg gctaactacg gctacactag  11700
aagaacagta tttggtatct gcgctctgct gaagccagtt accttcggaa aaagagttgg  11760
tagctcttga tccggcaaac aaaccaccgc tggtagcggt ggtttttttg tttgcaagca  11820
gcagattacg cgcagaaaaa aaggatctca agaagatcct ttgatctttt ctacgggtc   11880
tgacgctcag tggaacgacg cgcgcgtaac tcacgttaag ggattttggt catgagcttg  11940
cgccgtcccg tcaagtcagc gtaatgctct gcttttagaa aaactcatcg agcatcaaat  12000
gaaactgcaa tttattcata tcaggattat caataccata ttttttgaaaa agccgtttct  12060
gtaatgaagg agaaaactca ccgaggcagt tccataggat ggcaagatcc tggtatcggt  12120
```

```
ctgcgattcc gactcgtcca acatcaatac aacctattaa tttcccctcg tcaaaaataa    12180
ggttatcaag tgagaaatca ccatgagtga cgactgaatc cggtgagaat ggcaaaagtt    12240
tatgcatttc tttccagact tgttcaacag gccagccatt acgctcgtca tcaaaatcac    12300
tcgcatcaac caaaccgtta ttcattcgtg attgcgcctg agcgaggcga atacgcgat     12360 cgctgttaaa aggacaatta caaacaggaa tcgagtgcaa ccggcgcagg aacactgcca    12420
gcgcatcaac aatattttca cctgaatcag gatattcttc taatacctgg aacgctgttt    12480
ttccggggat cgcagtggtg agtaaccatg catcatcagg agtacggata aaatgcttga    12540
tggtcggaag tggcataaat tccgtcagcc agtttagtct gaccatctca tctgtaacat    12600
cattggcaac gctacctttg ccatgtttca gaaacaactc tggcgcatcg gcttcccat     12660 acaagcgata gattgtcgca cctgattgcc cgacattatc gcgagcccat ttatacccat    12720
ataaatcagc atccatgttg gaatttaatc gcggcctcga cgtttcccgt tgaatatggc    12780
tcatattctt ccttttttcaa tattattgaa gcatttatca gggttattgt ctcatgagcg    12840
gatacatatt tgaatgtatt tagaaaaata aacaaatagg ggtcagtgtt acaaccaatt    12900
aaccaattct gaacattatc gcgagcccat ttatacctga atatggctca taacaccct     12960 tgtttgcctg gcggcagtag cgcggtggtc ccacctgacc ccatgccgaa ctcagaagtg    13020
aaacgccgta gcgccgatgg tagtgtgggg actccccatg cgagagtagg gaactgccag    13080
gcatcaaata aaacgaaagg ctcagtcgaa agactgggcc tttcgcccgg gctaattagg    13140
gggtgtcgcc cttattcgac tctatagtga agttcctatt ctctagaaag tataggaact    13200
tctgaagtgg ggtcgactta attaagg                                        13227

<210> SEQ ID NO 3
<211> LENGTH: 269
<212> TYPE: PRT
<213> ORGANISM: Saccharomyces cerevisiae

<400> SEQUENCE: 3

Met Ser His Ile Gln Arg Glu Thr Ser Arg Pro Arg Leu Asn Ser Asn
1               5                   10                  15

Met Asp Ala Asp Leu Tyr Gly Tyr Lys Trp Ala Arg Asp Asn Val Gly
            20                  25                  30

Gln Ser Gly Ala Thr Ile Tyr Arg Leu Tyr Gly Lys Pro Asp Ala Pro
        35                  40                  45

Glu Leu Phe Leu Lys His Gly Lys Gly Ser Val Ala Asn Asp Val Thr
    50                  55                  60

Asp Glu Met Val Arg Leu Asn Trp Leu Thr Glu Phe Met Pro Leu Pro
65                  70                  75                  80

Thr Ile Lys His Phe Ile Arg Thr Pro Asp Asp Ala Trp Leu Leu Thr
                85                  90                  95

Thr Ala Ile Pro Gly Lys Thr Ala Phe Gln Val Leu Glu Glu Tyr Pro
            100                 105                 110

Asp Ser Gly Glu Asn Ile Val Asp Ala Leu Ala Val Phe Leu Arg Arg
        115                 120                 125

Leu His Ser Ile Pro Val Cys Asn Cys Pro Phe Asn Ser Asp Arg Val
    130                 135                 140

Phe Arg Leu Ala Gln Ala Gln Ser Arg Met Asn Asn Gly Leu Val Asp
145                 150                 155                 160

Ala Ser Asp Phe Asp Asp Glu Arg Asn Gly Trp Pro Val Glu Gln Val
                165                 170                 175
```

Trp Lys Glu Met His Lys Leu Leu Pro Phe Ser Pro Asp Ser Val Val
            180                 185                 190

Thr His Gly Asp Phe Ser Leu Asp Asn Leu Ile Phe Asp Glu Gly Lys
            195                 200                 205

Leu Ile Gly Cys Ile Asp Val Gly Arg Val Gly Ile Ala Asp Arg Tyr
            210                 215                 220

Gln Asp Leu Ala Ile Leu Trp Asn Cys Leu Gly Glu Phe Ser Pro Ser
225                 230                 235                 240

Leu Gln Lys Arg Leu Phe Gln Lys Tyr Gly Ile Asp Asn Pro Asp Met
            245                 250                 255

Asn Lys Leu Gln Phe His Leu Met Leu Asp Glu Phe Phe
            260                 265

<210> SEQ ID NO 4
<211> LENGTH: 269
<212> TYPE: PRT
<213> ORGANISM: Saccharomyces cerevisiae

<400> SEQUENCE: 4

Met Ser His Ile Gln Arg Glu Thr Ser Arg Pro Arg Leu Asn Ser Asn
1               5                   10                  15

Met Asp Ala Asp Leu Tyr Gly Tyr Lys Trp Ala Arg Asp Asn Val Gly
            20                  25                  30

Gln Ser Gly Ala Thr Ile Tyr Arg Leu Tyr Gly Lys Pro Asp Ala Pro
            35                  40                  45

Glu Leu Phe Leu Lys His Gly Lys Gly Ser Val Ala Asn Asp Val Thr
50                  55                  60

Asp Glu Met Val Arg Leu Asn Trp Leu Thr Glu Phe Met Pro Leu Pro
65                  70                  75                  80

Thr Ile Lys His Phe Ile Arg Thr Pro Asp Asp Ala Trp Leu Leu Thr
            85                  90                  95

Thr Ala Ile Pro Gly Lys Thr Ala Phe Gln Val Leu Glu Glu Tyr Pro
            100                 105                 110

Asp Ser Gly Glu Asn Ile Val Asp Ala Leu Ala Val Phe Leu Arg Arg
            115                 120                 125

Leu His Ser Ile Pro Val Cys Asn Cys Pro Phe Asn Ser Asp Arg Val
            130                 135                 140

Phe Arg Leu Ala Gln Ala Gln Ser Arg Met Asn Asn Gly Leu Val Asp
145                 150                 155                 160

Ala Ser Asp Phe Asp Asp Glu Arg Asn Gly Trp Pro Val Glu Gln Val
            165                 170                 175

Trp Lys Glu Met His Lys Leu Leu Pro Phe Ser Pro Asp Ser Val Val
            180                 185                 190

Thr His Gly Asp Phe Ser Leu Asp Asn Leu Ile Phe Asp Glu Gly Lys
            195                 200                 205

Leu Ile Gly Cys Ile Asp Val Gly Arg Val Gly Ile Ala Asp Arg Tyr
            210                 215                 220

Gln Asp Leu Ala Ile Leu Trp Asn Cys Leu Gly Glu Phe Ser Pro Ser
225                 230                 235                 240

Leu Gln Lys Arg Leu Phe Gln Lys Tyr Gly Ile Asp Asn Pro Asp Met
            245                 250                 255

Asn Lys Leu Gln Phe His Leu Met Leu Asp Glu Phe Phe
            260                 265

```
<210> SEQ ID NO 5
<211> LENGTH: 25
<212> TYPE: DNA
<213> ORGANISM: Artificial Sequence
<220> FEATURE:
<223> OTHER INFORMATION: 5' splice site with spacer

<400> SEQUENCE: 5
gtaagagagc tcgttgcgat attat                                            25

<210> SEQ ID NO 6
<211> LENGTH: 33
<212> TYPE: DNA
<213> ORGANISM: Artificial Sequence
<220> FEATURE:
<223> OTHER INFORMATION: splice site for a 3'RTM

<400> SEQUENCE: 6
tactaactgg tacctcttct tttttttctg cag                                   33

<210> SEQ ID NO 7
<211> LENGTH: 23
<212> TYPE: DNA
<213> ORGANISM: Artificial Sequence
<220> FEATURE:
<223> OTHER INFORMATION: polypyrrimidine tract for the 3' RTM

<400> SEQUENCE: 7
tggtacctct tcttttttttt ctg                                             23

<210> SEQ ID NO 8
<211> LENGTH: 20
<212> TYPE: DNA
<213> ORGANISM: Artificial Sequence
<220> FEATURE:
<223> OTHER INFORMATION: Spacer for a 5' RTM

<400> SEQUENCE: 8
agatctcgtt gcgatattat                                                  20

<210> SEQ ID NO 9
<211> LENGTH: 27
<212> TYPE: DNA
<213> ORGANISM: Artificial Sequence
<220> FEATURE:
<223> OTHER INFORMATION: Spacer for a 3' RTM

<400> SEQUENCE: 9
gagaacatta ttatagcgtt gctcgag                                          27

<210> SEQ ID NO 10
<211> LENGTH: 27
<212> TYPE: DNA
<213> ORGANISM: Artificial Sequence
<220> FEATURE:
<223> OTHER INFORMATION: 3' RTM Spacer sequence

<400> SEQUENCE: 10
gagaacatta ttatagcgtt gctcgag                                          27

<210> SEQ ID NO 11
<211> LENGTH: 23
<212> TYPE: DNA
<213> ORGANISM: Artificial Sequence
<220> FEATURE:
<223> OTHER INFORMATION: 3' RTM Polypyrimidine tract
```

```
<400> SEQUENCE: 11
tggtacctct tcttttttttt ctg                                          23

<210> SEQ ID NO 12
<211> LENGTH: 20
<212> TYPE: DNA
<213> ORGANISM: Artificial Sequence
<220> FEATURE:
<223> OTHER INFORMATION: 5'RTM spacer sequence

<400> SEQUENCE: 12
agagctcgtt gcgatattat                                               20

<210> SEQ ID NO 13
<211> LENGTH: 20
<212> TYPE: DNA
<213> ORGANISM: Artificial Sequence
<220> FEATURE:
<223> OTHER INFORMATION: 3'RTM spacer sequence

<400> SEQUENCE: 13
agagctcgtt gcgatattat                                               20

<210> SEQ ID NO 14
<211> LENGTH: 23
<212> TYPE: DNA
<213> ORGANISM: Artificial Sequence
<220> FEATURE:
<223> OTHER INFORMATION: 3 'RTM Polypyrrimidine tract

<400> SEQUENCE: 14
tggtacctct tcttttttttt ctg                                          23
```